US007452964B2

(12) United States Patent
Pasqualini et al.

(10) Patent No.: US 7,452,964 B2
(45) Date of Patent: Nov. 18, 2008

(54) COMPOSITIONS AND METHODS OF USE OF TARGETING PEPTIDES AGAINST PLACENTA AND ADIPOSE TISSUES

(75) Inventors: Renata Pasqualini, Houston, TX (US); Wadih Arap, Houston, TX (US); Mikhail G. Kolonin, Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 246 days.

(21) Appl. No.: 10/489,071

(22) PCT Filed: Aug. 30, 2002

(86) PCT No.: PCT/US02/27836

§ 371 (c)(1),
(2), (4) Date: Oct. 13, 2004

(87) PCT Pub. No.: WO03/022991

PCT Pub. Date: Mar. 20, 2003

(65) Prior Publication Data

US 2006/0094672 A1    May 4, 2006

Related U.S. Application Data

(63) Continuation-in-part of application No. PCT/US01/27692, filed on Sep. 7, 2001.

(51) Int. Cl.
*C07K 5/00* (2006.01)
*A61K 48/00* (2006.01)

(52) U.S. Cl. .................... 530/300; 530/326.1; 424/93.1

(58) Field of Classification Search .................. 530/300
See application file for complete search history.

(56) References Cited

U.S. PATENT DOCUMENTS

| 4,472,509 A | 9/1984 | Gansow et al. .............. 436/548 |
| 4,912,040 A | 3/1990 | Kaufman et al. ............ 435/69.6 |
| 4,931,053 A | 6/1990 | L'Esperance, Jr. ............. 606/2 |
| 5,021,236 A | 6/1991 | Gries et al. ..................... 424/9 |
| 5,081,034 A | 1/1992 | Bevilasqua et al. ..... 435/252.33 |
| 5,098,833 A | 3/1992 | Lasky et al. ................ 435/69.1 |
| 5,188,964 A | 2/1993 | McGuire et al. .............. 436/64 |
| 5,206,347 A | 4/1993 | Ruoslahti et al. ............ 530/413 |
| 5,216,131 A | 6/1993 | Lasky et al. ................ 435/69.1 |
| 5,223,409 A | 6/1993 | Ladner et al. ............... 435/69.7 |
| 5,225,538 A | 7/1993 | Capon et al. ............. 530/387.3 |
| 5,259,380 A | 11/1993 | Mendes et al. .............. 607/115 |
| 5,270,163 A | 12/1993 | Gold et al. ...................... 435/6 |
| 5,288,846 A | 2/1994 | Quertermous et al. ..... 435/172.3 |
| 5,304,640 A | 4/1994 | Asky et al. ................. 536/23.5 |
| 5,415,874 A | 5/1995 | Bender et al. ................ 424/520 |
| 5,428,130 A | 6/1995 | Capon et al. ................ 530/350 |
| 5,453,362 A | 9/1995 | Lamarco et al. ............ 435/69.1 |
| 5,463,026 A | 10/1995 | Nakamura et al. ....... 530/387.3 |
| 5,464,436 A | 11/1995 | Smith ........................... 607/89 |
| 5,492,807 A | 2/1996 | Santi .............................. 435/5 |
| 5,506,126 A | 4/1996 | Seed et al. ................ 435/172.3 |
| 5,536,814 A | 7/1996 | Ruoslahti et al. ............. 530/329 |
| 5,585,277 A | 12/1996 | Bowie et al. ................. 436/518 |
| 5,622,699 A | 4/1997 | Ruoslahti et al. ........... 424/93.6 |
| 5,670,312 A | 9/1997 | Santi .............................. 435/5 |
| 5,688,692 A | 11/1997 | Jat et al. ...................... 435/354 |
| 5,688,935 A | 11/1997 | Stephens et al. ........... 536/23.1 |
| 5,705,610 A | 1/1998 | Zuckerman et al. ......... 530/338 |
| 5,750,344 A | 5/1998 | Doyle ............................. 435/6 |
| 5,840,841 A | 11/1998 | Zuckerman et al. ......... 530/338 |
| 5,866,759 A | 2/1999 | Jat et al. ......................... 800/3 |
| 5,902,598 A | 5/1999 | Chen et al. ................... 424/423 |

(Continued)

FOREIGN PATENT DOCUMENTS

DE        19605175        8/1997

(Continued)

OTHER PUBLICATIONS

Kolonin et al., "Targeting physiological and pathological blood vessel formation with in vivo phage display," *Proc. Am. Assoc. Cancer Res.*, 42:822-823, 2001.

St. Hilaire et al., "The Substrate specificity of a recombinant cystein protease from *Leishmania mexicana*: application of a combinatorial peptide library approach," *Chembiochem: A European Journal of Chemical Biology*, 1:115-122, 2000.

Alonso and Maroto, "Plants as 'chemical factories' for the production of polyunsaturated fatty acids," *Biotechnology Advances*, 18:481-497, 200.

Arap et al., "Cell surface expression of the stress response chaperone GRP78 enables tumor targeting by circulating ligands," *Cancer Cell*, 6:275-284, 2004.

David et al., "Investigation of subsite preferences in aminopeptidase A (EC 3.4.11.7) led to the design of the first highly potent and selective inhibitors of this enzyme," *J. Med. Chem.*, 42:5197-5211, 1999.

(Continued)

*Primary Examiner*—Bruce Campell
*Assistant Examiner*—Bao Qun Li
(74) *Attorney, Agent, or Firm*—Fulbright & Jaworski L.L.P.

(57) ABSTRACT

The present invention concerns compositions comprising and methods of identification and use of targeting peptides for placenta or adipose tissue. In certain embodiments, the targeting peptides comprise part or all of SEQ ID NO:5-11, SEQ ID NO:13-22 OR SEQ ID NO:144. The peptides may be attached to various therapeutic agents for targeted delivery. Adipose-targeting peptides may be used in methods for weight control, inducing weight loss and treating lipodystrophy syndrome. Adipose-targeting may also be accomplished using other binding moieties selectively targeted to adipose receptors, such as a prohibitin receptor protein complex. Placenta-targeting peptides may be used to interfere with pregnancy, induce labor and/or for targeted delivery of therapeutic agents to placenta and/or fetus. In other embodiments, receptors identified by binding to placenta-targeting peptides may be used to screen compounds for potential teratogenicity. An exemplary placental receptor is FcRn/$\beta_2$M, and compounds that bind to FcRn/$\beta_2$M are potential teratogens.

16 Claims, 40 Drawing Sheets

U.S. PATENT DOCUMENTS

| | | | | |
|---|---|---|---|---|
| 5,955,572 | A | 9/1999 | Ruoslahti et al. | 530/317 |
| 6,057,098 | A | 5/2000 | Buechler et al. | 435/6 |
| 6,068,829 | A | 5/2000 | Ruoslahti et al. | 242/9.1 |
| 6,174,861 | B1 | 1/2001 | O'Reilly | 514/12 |
| 6,184,973 | B1 | 2/2001 | Baer et al. | 356/36 |
| 6,215,550 | B1 | 4/2001 | Baer et al. | 356/36 |
| 6,232,440 | B1 | 5/2001 | Hillman et al. | 530/350 |
| 6,271,196 | B1 | 8/2001 | O'Brien | 514/2 |
| 6,300,064 | B1 | 10/2001 | Knappik et al. | 435/6 |
| 6,350,855 | B1 | 2/2002 | Tobin | 530/350 |
| 6,399,384 | B1 | 6/2002 | Jat | 435/456 |
| 6,458,381 | B1 | 10/2002 | Sourovoi et al. | 424/450 |
| 6,528,281 | B1 | 3/2003 | Tobin | 435/69.1 |
| 6,576,239 | B1 | 6/2003 | Ruoslahti et al. | 424/185.1 |
| 6,881,825 | B1 | 4/2005 | Robbins et al. | 530/327 |
| 2001/0046498 | A1 | 11/2001 | Rouslahti et al. | 424/178.1 |
| 2003/0113320 | A1 | 6/2003 | Ruoslahti et al. | 424/143.1 |
| 2005/0191294 | A1 | 9/2005 | Arap et al. | 424/143.1 |

FOREIGN PATENT DOCUMENTS

| | | |
|---|---|---|
| EP | 0639584 | 4/1998 |
| JP | 4026631 | 1/1992 |
| WO | WO 92/00091 | 1/1992 |
| WO | WO 92/03461 | 3/1992 |
| WO | WO 92/06191 | 4/1992 |
| WO | WO 94/28424 | 12/1994 |
| WO | WO 95/14714 | 6/1995 |
| WO | WO 96/34874 | 11/1996 |
| WO | WO 96/34875 | 11/1996 |
| WO | WO 97/10507 | 3/1997 |
| WO | WO 97/19954 | 5/1997 |
| WO | WO 97/39021 | 10/1997 |
| WO | WO 98/10795 | 3/1998 |
| WO | WO 98/39469 | 9/1998 |
| WO | WO 99/04813 | 2/1999 |
| WO | WO 97/30024 | 9/1999 |
| WO | WO 99/46284 | 9/1999 |
| WO | WO 99/57311 | 11/1999 |
| WO | WO 00/14215 | 3/2000 |
| WO | WO 01/13114 | 2/2001 |
| WO | WO 01/42276 | 6/2001 |
| WO | WO 01/53342 | 7/2001 |
| WO | WO 02/02055 | 1/2002 |
| WO | WO 02/20722 | 3/2002 |
| WO | WO 02/20723 | 3/2002 |
| WO | WO 02/20769 | 3/2002 |
| WO | WO 02/20822 | 3/2002 |
| WO | WO 03/022991 | 3/2003 |

OTHER PUBLICATIONS

De Rosa et al., "Poly(lactide-co-glycolide) microspheres for the controlled release of oligonucleotide/polyethylenimine complexes," *J Pharm Sci*, 91(3):790-799, 2002.

Fairbrother et al., "Novel Peptides Selected to Bind Vascular Endothelial Growth Factor Target Receptor-Binding Site," *Biochemistry*, 37:17754-17764, 1998.

Georgiadis et al., "Potent and Selective Inhibition of Zinc Aminopeptidase A (EC 3.4.11.7, APA) by Glutamyl Aminophosphinic Peptides: Importance of Glutamyl Aminophosphinic Residue in the P1 Position," *Biochemistry*, 39:1152-1155, 2000.

Gong et al., "Prostrate-specific membrane antigen (PMSA)-specific monoclonal antibodies in the treatment of prostrate and other cancers," *Cancer and Metastasis Reviews*, 18:483-490, 1999.

Johnson et al., In: *Biotechnology and Pharmacy*, Pezzuto et al. eds., Chapman and Hall, NY, 1993.

Kolonin et al., "Reversal of obesity by targeted ablation of adipose tissue," *Nature Medicine*, 10: 625-632, 2004.

Mintz et al., "Fingerprinting the circulating repertoire of antibodies from cancer patients," *Nature Biotechnology*, 21:57-63, 2003.

Napier and Michaelson, "Genomic and Functional Characterization of Polyunsaturated Fatty Acid Biosynthesis in *Caenorhabditis elegans*," *Lipids*, 36:761-766, 2001.

Nicklin et al., "Selective argeting of gene transfer to vascular endothelial cells by use of peptides isolated by phage display," *Circulation*, 102:231-237, 2000.

Oike et al., "Angiopoietin-related growth factors antagonizes obesity and insulin resistence," *Nature Medicine*, 11:400-408, 2005.

Ozata et al., "Human Leptin Deficiency caused by a missense Mutation: Multiple Endocrine Defects, Decreased sympathetic tone, and immune system dysfunction indicate new targets for leptin action, greater centralthan peripheral resistance to the effects of leptin, and spontaneous correction of leptin-mediated defec," *Jounral of Clinical Endocrinology and Metabolism*, 84:3686-3695, 1999.

Polgren et al., "Identification of muscle homing sequences by using phage display libraries of peptides," *Tumor Biology*, 18:77, 1997.

Quirk et al., "Amastatin and bestatin-induced dipsogenicity in the Sprague-Dawley rat," *Brain Res. Bull.*, 19:145-147, 1987.

Schindler, "Select, microdissect, adneject." *Nature Biotechnology*, 16:719-720,1998.

Wang et al., "Rapid antibody responses by low-dose, single-step, dendritic cell-target immunization," *Proceedings of the National Academy of Sciences of the United States of America*, 97:847-852, 2000.

Yao et al. "Targeting pancreatic islets with phage display assisted by laser pressure catapult microdissection," *The American Journal of Pathology*, 166:625-636, 2005.

Aiello et al., "Suppression of retinal neovascularization in vivo by inhibition of vascular endothelial growth factor (VEGF) using soluble VEGF-receptor chimeric proteins," *Proc. Natl. Acad. Sci., USA*, 92(23):10457-10461, 1995.

Aiello et al., "Vascular endothelial growth factor in ocular fluid of patients with diabetic retinopathy and other retinal disorders," *N. Eng. J. Med.*, 331(22):1480-1487, 1994.

Alliot et al., "Brain parenchyma vessels and the angiotensin system," *Brain Res.*, 830:101-112, 1999.

Alliot et al., "Pericytes and periendothelial cells of brain parenchyma vessels co-express aminopeptidase N, aminopeptidase A, and nestin," *J. Neurosci. Res.*, 58:367-378, 1999.

Alon et al., "Vascular endothelial growth factor acts as a survival factor for newly formed retinal vessels and has implications for retinopathy of prematurity," *Nat. Med.*, 1:1024-1028, 1995.

Andrade et al., "Angiotensin-II-induced angiogenesis in sponge implants in mice," *Int. J. Microcirc. Clin. Exp.*, 16(6):302-307, 1996.

Arap et al., Steps toward mapping the human vasculature by phage display, *Nature Med.*, 8(2):121-127, 2002.

Arap et al., "Cancer treatment by targeted drug delivery to tumor vasculature in a mouse model," *Science*, 279:377-380, 1998.

Arap et al., "Chemotherapy targeted to tumor vasculature," *Curr. Opin. Onclol.*, 10(6):560-565, 1998.

Arap et al., "Targeting the prostate for destruction through a vascular address," *Proc. Natl. Acad. Sci., USA*, 99:1527-1531, 2002.

Arden, "The absence of diabetic retinopathy in patients with retinitis pigmentosa: implications for pathophysiology and possible treatment.," *Br. J. Ophthalmol.*, 85:366-370, 2001.

Asako et al., "Organic solvent tolerance and antibiotic resistance increased by overexpression of marA in *Escherichia coli*," *Applied Environmental Microbiology*, 63(4):1428-1433, 1997.

Assmann et al., "A nephritogenic rat monoclonal antibody to mouse aminopeptidase A. Induction of massive albuminuria after a single intravenous injection," *J. Exp. Med.*, 175:623-635, 1992.

Atkins et al., "Coordinated cytokine expression by stromal and hematopoietic cells during human osteoclast formation," *Bone*, 26(6):653-661, 2000.

Baillie et al., "Tumor vasculature-A potential therapeutic target," *British J. Cancer*, 72:257-267, 1995.

Baringa, "Peptide-guided cancer drugs show promise in mice," *Science*, 279:323-324, 1998.

Baumann et al., "Complex of the soluble IL-11 receptor and IL-11 acts as IL-6-type cytokine in hepatic and nonhepatic cells," *J. Immunol.*, 157(1):284-290, 1996.

Beckman et al., "Experimental manipulation of the rodent visceral yolk sac," *Teratology*, 41(4):395-404, 1990.

Behm et al., "Human homologue of the rat chondroitin sulfate proteoglycan, NG2, detected by monoclonal antibody 7.1, identifies childhood acute lymphoblastic leukemias with t(4;11)(q21;q23) or t(11;19)(q23;13) and MLL gene rearrangements," *Blood*, 87:1134-1139, 1996.

Bergelson et al., "Isolation of a common receptor for Coxsackie B viruses and adenoviruses 2 and 5," *Science*, 275:1320-1322, 1997.

Bergers et al., "Benefits of targeting both pericytes and endothelial cells in the tumor vasculature with kinase inhibitors," *J. Clin. Invest.*, 111(9):1287-1295, 2003.

Bicknell, "Vascular targeting and the inhibition of angiogenesis," *Annals of Oncology*, 5(Suppl 4):S45-S50, 1994.

Bigner et al., "Phase I studies of treatment of malignant gliomas and neoplastic meningitis with 131I-radiolabeled monoclonal antibodies anti-tenascin 81C6 and anti-chondrotin sulfate proteoglycan Mel-14F(ab1)2-a preliminary report," *J. Neuro-Oncol.*, 24:109-122, 1995.

Bogenreider et al., "Expression and localization of aminopeptidase A, aminopeptidase N, and dipeptidyl peptidase IV in benign and malignant human prostate tissue," *Prostate*, 33:225-232, 1997.

Brooks et al., "Anti integrin alpha v beta 3 blocks human breast cancer growth and angiogenesis in human skin," *J. Clin. Invest.*, 96:1815-1822, 1995.

Brooks et al., "Integrin alpha v beta 3 antagonists promote tumor regression by inducing apoptosis of angiogenic blood vessels," *Cell*, 79(7):1157-1164, 1994.

Brooks et al., "Requirement of vascular integrin $\alpha\rho\beta3$ for angiogenesis," *Science*, 264:569-571, 1994.

Bumol et al., "Monoclonal antibody and antibody-toxin conjugate to a cell surface proteoglycan of melanoma cells suppress in vivo tumor growth," *Proc. Natl. Acad. Sci., USA*, 80:529-533, 1983.

Burg et al., "A central segment of the NG2 proteoglycan is critical for the ability of glioma cells to bind and migrate toward type VI collagen," *Exp. Cell. Res.*, 235:254-264, 1997.

Burg et al., "Binding of the NG2 proteoglycan to type VI collagen and other extracellular matrix molecules," *J. Biol. Chem.*, 271(42):26110-26116, 1996.

Burg et al., "Expression of the NG2 proteoglycan enhances the growth and metastatic properties of melanoma cells," *J. Cell. Physiol.*, 177:299-312, 1998.

Burg et al., "NG2 proteoglycan-binding peptides target tumor neovasculature," *Cancer Res.*, 59(12):2869-2874, 1999.

Burioni et al., "Recombinant human Fab to glycoprotein D neutralizes infectivity and prevents cell-to-cell transmission of herpes simplex viruses 1 and 2 in vitro," *Proc. Natl. Acad. Sci., USA*, 91:355-359, 1994.

Burrows and Thorpe, "Vascular targeting—A new approach to the therapy of solid tumors," *Pharmac. Ther.*, 64:155-174, 1994.

Burton et al., "A large array of human monoclonal antibodies to type 1 human immunodeficiency virus from combinatorial libraries of asymptomatic seropositive individuals," *Proc. Natl. Acad. Sci., USA*, 88:10134-10137, 1991.

Butner, "Retinitis pigmentosa and retinal neovascularization: a case report," *Ann. Ophthalmol.*, 16:861-865, 1984.

Cai et al., "Induction of glucose regulated proteins during growth of a murine tumor," *J. Cell Physiol.*, 154(2):229-237, 1993.

Campbell et al., "Prohibitin 3' untranslated region polymorphism and breast cancer risk," *Cancer Epidemiol. Biomarkers Prev.*, 12(11 pt1):1273-1274, 2003.

Campfield and Smith, "Overview: neurobiology of OB protein (leptin)," Proceedings of the Nutrition Society, 57:429-440, 1998.

Campfield et al., "Strategies and potential molecular targets for obesity treatment," *Science*, 280:1383-1387, 1998.

Cao et al., "Expression of angiostatin cDNA in a murine fibrosarcoma suppresses primary tumor growth and produces long-term dormancy of metastases," *J. Clin. Invest.*, 101:1055-1063, 1998.

Cattani et al., "Cloning and characterization of human recombinant antibody Fab fragments specific for types 1 and 2 herpes simplex virus," *Microbiologica*, 18:135-142, 1995.

Chaveroche et al., "A rapid method for efficient gene replacement in the filamentous fungus *Aspergillus nidulans*," *Nucleic Acids Research*, 28(22):E97, 2000.

Chen et al., "Thapsigargin-induced grp78 expression is mediated by the increase of cytosolic free calcium in 9L rat brain tumor cells," *J. Cell. Biochem.*, 78:404-416, 2000.

Chinni et al., "Humoral immune responses to cathepsin D and glucose-regulated protein 78 in ovarian cancer patients," *Clin. Cancer Res.*, 3:1557-1564, 1997.

Choongkittaworn et al., "Expression of prohibitin in rat seminiferous epithelium," *Biol. Reprod.*, 49(2):300-310, 1993.

Curnis et al., "Enhancement of tumor necrosis factor alpha antitumor immunotherapeutic properties by targeted delivery to aminopeptidase N (CD13)," *Nat Biotechnol.*, (11):1185-90, 2000.

D'Amato et al., "Thalidomide is an inhibitor of angiogenesis," *Proc. Natl. Acad. Sci., USA*, 91:4082-4085, 1994.

Davis et al., "Use of a high affinity DNA ligand in flow cytometry," *Nucleic Acids Research*, 24:702-706, 1996.

Delpino et al., "Cell surface localization of the 78 kD glucose regulated protein (GRP 78) induced by thapsigargin," *Mol. Membr. Biol.*, 15(1):21-26, 1998.

Deo et al., "Bispecific molecules directed to the Fc receptor for IgA (FcαRI, CD89) and tumor antigens efficiently promote cell-mediated cytotoxicity of tumor targets in whole blood," J. Immunology, 160:1677-1686, 1998.

Dmitriev et al., "An adenovirus vector with genetically modified fibers demonstrates expanded tropism via utilization of a coxsackievirus and adenovirus receptor-independent cell entry mechanism," *J. Virol.*, 72(12):9706-9713, 1998.

Douglas et al., "Targeted gene delivery by tropism-modified adenoviral vectors," *Nature Biotech.*, 14:1574-1578, 1996.

Drolet et al., "An enzyme-linked oligonucleotide assay," *Nat. Biotech.*, 14:1021-1025, 1996.

Duh et al., "Vascular endothelial growth factor and diabetes," *Diabetes*, 48:1899-1906, 1997.

Dvorak et al., "Structure of solid tumors and their vasculature: implications for therapy with monoclonal antibodies," *Cancer Cells*, 3:77-85, 1991.

Egeblad and Werb, "New functions for the matrix metalloproteinases in cancer progression," *Nat. Rev. Cancer*, 2:161-174, 2002.

Ellerby et al., "Anti-cancer activity of targeted pro-apoptotic peptides," *Nature Med.*, 5(9):1032-8, 1999.

Finnell, "Teratology: general considerations and principles," *J. Allergy Clin. Immunol.*, 103(2 Pt 2):S337-42, 1999.

Folkman, "Addressing tumor blood vessels," *Nature Biotechnology*, 15:510, 1997.

Folkman, "Angiogenesis in cancer, vascular, rheumatoid and other disease," *Nature Biotechnol.*, 1:27-31, 1995.

Fujimura et al., "Aminopeptidase A expression in cervical neoplasia and its relationship to neoplastic transformation and progression," *Oncology*, 58:342-352, 2000.

Furuya et al., "The role of calcium, pH, and cell proliferation in the programmed (apoptotic) death of androgen-independent prostatic cancer cells induced by thapsigargin," *Cancer Res.*, 54(23):6167-6175, 1994.

Fusaro et al., "Prohibitin induces the transcription acivity of p53 and is exported from the nucleus upon apoptotic signaling," *J. Biol. Chem.*, 278(48):47853-47861, 2003.

Geng et al., "Expression of the kidney-associated differentiation glycoprotein gp160 and resistance to the antitumor effects of interferon alpha in renal cell carcinomas," *Anticancer Res.*, 18:1-7, 1998.

Giordano et al., "Biopanning and rapid analysis of selective interactive ligands," *Nat. Med.*, 7(11):1249-1253, 2001.

Girod et al., "Genetic capsid modifications allow efficient re-targeting of adeno-associated virus type 2," *Nature Med.*, 5:1052-1056, 1999.

Goetz et al., "Lu-ECAM-1-mediated adhesion of melanoma cells to endothelium under conditions of flow," *Int. J. Cancer*, 65:192-199, 1996.

Gold et al., "Diversity of oligonucleotide functions," *Annu. Rev. Biochem.*, 64:763-797, 1995.

Goldman et al., "Targeted gene delivery to Kaposi's sarcoma cells via the fibroblast growth factor receptor," *Cancer Res.*, 57(8):1447-51, 1997.

Goodson et al., "High-affinity urokinase receptor antagonists identified with bacteriophage peptide display," *Proc. Natl. Acad. Sci., USA*, 91:7129-7133, 1994.

Grako and Stallcup, "Participation of the NG2 proteoglycan in rat aortic smooth muscle cell responses to platelet-derived growth factor," *Exp. Cell Res.*, 221:231-240, 1995.

Grasso et al., "In vivo effects of leptin-related synthetic peptides on body weight and food intake in female ob/ob mice: localization of leptin activity to domains between amino acid residues 106-140," *Endocrinology*, 138(4):1413-1418, 1997.

Grifman et al., "Incorporation of tumor-targeting peptides into recombinant adeno-associated virus capsids," *Mol. Ther.*, 3(6):964-75, 2001.

Griscelli et al., "Angiostatin gene transfer: inhibition of tumor growth in vivo by blockage of endothelial cell proliferation associated with a mitosis arrest," *Proc. Natl. Acad. Sci., USA*, 95:6367-6372, 1998.

Hadigan et al., "Metformin in the treatment of HIV lipodystrophy syndrome: A randomized controlled trial," *J. Amer. Med. Assn.*, 284:472-477, 2000.

Hammes et al., "Subcutaneous injection of a cyclic peptide antagonist of vitronectin receptor-type integrins inhibits retinal neovascularization," *Nature Med.*, 2:529-533, 1996.

Hanahan, "Signaling vascular morphogenesis and maintenance," *Science*, 277:48-50, 1997.

Harper and Reisfeld, "Cell-associated proteoglycans in human malignant melanoma," *Biology of Proteoglycans*, Acad. Press, 345-366, 1987.

Harper and Reisfeld, "Inhibition of anchorage independent growth of human melanoma cells by a monoclonal antibody to a chondrotin sulfate proteoglycan," *J. Natl. Cancer Inst.*, 71:259-263, 1983.

Hart et al., "Cell binding and internalization by filamentous phage displaying a cyclic Arg-Gly-Asp-containing peptide," *J. Biol. Chem.*, 269:12468-12474, 1994.

Hashizume et al., "Openings between defective endothelial cells explain tumor vessel leakiness," *Am. J. Pathol.*, 156(4):1363-1380, 2000.

Hayakawa et al., "Clinical features of autosomal dominant retinitis pigmentosa with rhodopsin gene codon 17 mutation and retinal neovascularization in a Japanese patient," *Am. J. Ophthalmol.*, 115:168-173, 1993.

Hicke et al., "DNA aptamers block L-selectin function in vivo," *J. Clin. Invest.*, 98:2688-2692, 1996.

Hong et al., "Adenovirus type 5 fiber knob binds to MHC class I alpha2 domain at the surface of human epithelial and B lymphoblastoid cells," *EMBO J.*, 16:2294-2306, 1997.

Huang et al., "Tumor infarction in mice by antibody-directed targeting of tissue factor to tumor vasculature," *Science*, 275:547-550, 1997.

Iida et al., "Spreading and focal contact formation of human melanoma cells in response to the stimulation of both NG2 $\alpha 4\beta 1$ integrin," *Cancer. Res.*, 55:2177-2185, 1995.

Ikonen et al., "Prohibitin, an antiproliferative protein, is localized to mitochondria," *FEBS Letters*, 358(3):273-277, 1995.

Ino et al., "Expression of aminopeptidase A in human gestational choriocarcinoma cell lines and tissues," *Placenta*, 21:63-72, 2000.

Jackson, In: *Goodman and Gilman's The Pharmacological Basis of Therapeutics*, Hardman (eds.), McGraw-Hill Medical Publishing Division, 809-841, 2001.

Jain et al., "Metabolic complications associated with antiretroviral therapy," *Antiviral Res.*, 51:151-177, 2001.

Joliot et al., "alpha-2,8-Polysialic acid is the neuronal surface receptor of antenna pedia homeobox peptide," *New Biol.*, 3:1121-1131, 1991.

Joliot et al., "Antenna pedia homeobox peptide regulates neural morphogenesis," *Proc. Natl. Acad. Sci., USA*, 88:1864-1868, 1991.

Juillerat-Jeanneret et al., "Regulation of aminopeptidase A in human brain tumor vasculature: evidence for a role of transforming growth factor-beta," *Lab. Invest.*, 80(6):973-980, 2000.

Juillerat-Jeanneret et al., "Regulation of peptidase activity in a three-dimensional aggregate model of brain tumor vasculature," *Cell Tissue Res.*, 311:53-59, 2003.

Jupe et al., "The 3' untranslated region of prohibitin and cellular immortalization," *Exp. Cell Res.*, 224(1):128-135, 1996.

Kahler et al., "Chronic administration of OB protein decreases food intake by selectively reducing meal size in male rats," *Am J Physiol*, 275(1 Pt 2):R180-R185, 1998.

Kerbel, "Inhibition of tumor angiogenesis as a strategy to circumvent acquired resistance to anti-cancer therapeutic agents," *BioEssays*, 13(1):31-36, 1991.

Kiang et al., "17 beta-estradiol-induced increases in glucose-related protein 78kD and 94kD protect human breast cancer T47-D cells from thermal injury," *Chin. J. Physiol.*, 40(4):213-219, 1997.

Kifor and Dzau, "Endothelial renin-angiotensin pathway: evidence for intracellular synthesis and secretion of angiotensins," *Circ. Res.*, 60:422-428, 1987.

Kiovunen et al., "Identification of receptor ligands with phage display peptide libraries," *J. Nuclear Medicine*, 40(5):883-888, 1999.

Koivunen et al., "Integrin-binding peptides derived from phage display libraries," *Methods Mol. Biol.*, 129:3-17, 1999.

Koivunen et al., "Phage libraries displaying cyclic peptides with different ring sizes: ligand specificities of the RGD-directed integrins," *Biotechnology*, 13(3):265-270, 1995.

Koivunen et al., "Selection of peptides binding to the alpha5 beta 1 integrin from phage display library," *J. Biol. Chem.*, 268:20205-20210, 1993.

Koivunen et al., "Tumor targeting with a selective gelatinase inhibitor," *Nat. Biotechnol.*, 17:768-774, 1999.

Kolonin et al., "Molecular addresses in blood vessels as targets for therapy," *Curr. Opin. Chem. Biol.*, 5:308-313, 2001.

Kolonin et al., "Teratogenicity induced by targeting a placental immunoglobulin transporter," *Proc. Natl. Acad. Sci., USA*, 99(20):13055-13060, 2002.

Lahdenranta et al., "An anti-angiogenic state in mice and humans with retinal photoreceptor cell degeneration," *Proc. Natl. Acad. Sci., USA*, 98(18):10368-10373, 2001.

Lamers and Bacher, "Prohibitin and prohibitone, ubiquitous and abundant proteins that are reluctant to reveal their identity," *Int. Arch. Allergy Immunol.*, 113(1-3):146-149, 1997.

Lappi, "Tumor targeting through fibroblast growth factor receptors," *Cancer Biology*, 6:279-288, 1995.

Larocca et al., "Gene transfer to mammalian cells using genetically targeted filamentous bacteriophage," *FEBS J.*, 13:727-734, 1999.

Le Noble et al., "The role of angiotensin II and prostaglandins in arcade formation in a developing microvascular network," *J. Vasc. Res.*, 33(6):480-488, 1996.

Le Roux et al., "Neurotrophic activity of the Antenna pedia homeodomain depends on its specific DNA-binding properties," *Proc. Natl. Acad. Sci., USA*, 90:9120-9124, 1993.

Leff, "NeXstar previews 'PASS' for downstream synthesis of therapeutic oligos," *Bioworld Today*, 8:2&4, 1997.

Leger et al., "The chondroitin sulfate proteoglycan NG2 is a tumor specific antigen on the chemically induced rat chondrosarcoma HSN," *Int. J. Cancer*, 58:700-705, 1994.

Li et al., "Widespread tissue distribution of aminopeptidase A, an evolutionarily conserved ectoenzyme recognized by the BP-1 antibody," *Tissue Antigens*, 42:488-496, 1993.

Lin et al., "T and B cell development in BP-1/6C3/aminopeptidase A-deficient mice," *J. Immunol.*, 160(10):4681-4687, 1998.

Look et al., "Human myeloid plasma membrane glycoprotein CD13 (gp150) is identical to aminopeptidase N," *J. Clin. Invest.*, 83:1299-1307, 1999.

Makinen et al., "Differential binding of vascular endothelial growth factor B splice and proteolytic isoforms to neuropilin-1," 274(30):21217-22, 1999.

Mandecki et al., "A mathematical model for biopanning (affinity selection) using peptide libraries on filamentous phage," J. Theor. Biol., 176:523-530, 1995.

Manjeshwar et al., "Tumor suppression by the prohibitin gene 3'untranslated region RNA in human breast cancer," *Cancer Res.*, 63(17):5251-5256, 2003.

Maranghi et al., "Evaluation of the placenta: suggestions for a greater role in developmental toxicology," *Adv. Exp. Med. Biol.*, 444:129-136, 1998.

Martin et al., "Retrovirus targeting by tropism restriction to melanoma cells," *J. Virol.*, 73:6923-6929, 1999.

Martiny-Baron and Marmé, VEGF-mediated tumor angiogenesis: a new target for cancer therapy, *Curr. Opin. Biotech.*, 6:675-680, 1995.

McCarty et al., "Quantitive and qualitative in vivo angiogenesis assay," *Int. J. Oncol.*, 21(1):5-10, 2002.

McClung et al., "Prohibitin: potential role in senescence, development, and tumor suppression," *Exp. Gerontol.*, 30(2):99-124, 1995.

McConnell et al., "Biopanning phage display libraries using magnetic beads vs. polystyrene plates," BioTechniques, 26(2):208-209, 1999.

Mentzel et al., "Induction of albuminuria in mice: synergistic effect of two monoclonal antibodies directed to different domains of aminopeptidase A," *Kidney Int.*, 55(4):1335-1347, 1999.

Miller et al., "Differential susceptibility of primary and established human glioma cells to adenovirus infection: targeting via the epidermal growth factor receptor achieves fiber receptor-independent gene transfer," *Cancer Res.*, 58:5738, 5748, 1998.

Miner et al., "Clonal drift of cell surface, melanogenic and experimental metastatic properties of in vivo-selected, brain meninges-colonizing murine B16 melanoma," *Cancer Research*, 42:4631-4638, 1982.

Misra et al., "The role of Grp 78 in alpha 2-macroglobulin-induced signal transduction. Evidence from RNA interference that the low density lipoprotein receptor-related protein is associated with, but not necessary for, GRP 78-mediated signal transduction," *J Biol Chem.*, 277(44):42082-7, 2002.

Monton et al., "Effects of angiotensin II on endothelial cell growth: role of AT-1 and AT-2 receptors," *J. Am. Soc. Nephrol.*, 9(6):969-974, 1998.

Morikawa et al., "Abnormalities in pericytes on blood vessels and endothelial sprouts in tumors," *Am. J. Pathol.*, 160(3):985-1000, 2002.

Murphy et al., "Tissue inhibitor of metalloproteinases-2 inhibits bFGF-induced human microvascular endothelial cell proliferation," *J. Cell Physiol.*, 157(2):351-358, 1993.

Mustonen and Alitalo, "Endothelial receptor tyrosine kinases involved in angiogenesis," *J. Cell Biol.*, 129:895-898, 1995.

Nadal et al., "Angiotensin II stimulates migration of retinal microvascular pericytes: involvement of TGF-β and BDGF-BB," *Am. J. Physiol. Heart Circ. Physiol.*, 282:739-748, 2002.

Nagy et al., "Cytotoxic analogs of luteinizing hormone-releasing hormone containing doxorubicin or 2-pyrrolinodoxorubicin, a derivative 500-1000 times more potent," *Proc. Natl. Acad. Sci., USA*, 93:7269-7273, 1996.

Nagy et al., "Synthesis and biological evaluation of cytotoxic analogs of somatostatin containing doxorubicin or its intesely potent derivative, 2-pyrrolinodoxorubicin," *Proc. Natl. Acad. Sci., USA*, 95:1794-1799, 1998.

Nanus et al., "Molecular cloning of the human kidney differentiation antigen gp160: human aminopeptidase A," *Proc. Natl. Acad. Sci., USA*, 90:7069-7073, 1993.

Nelson, "Parenting of therapeutics for obesity and nutritional disease," Exp Opin Ther Patents, 9(9):1185-1196, 1999.

Nishiyama and Stallcup, "Expression of NG2 proteoglycan causes retention of type VI collagen on the cell surface," *Mol. Biol. Cell*, 4:1097-1108, 1993.

Nishiyama et al., "Interaction between NG2 proteoglycan and PDGF α receptor is required for optimal response to PDGF," *J. Neurosci. Res.*, 43:315-330, 1996.

Nishiyama et al., "The primary structure of NG2, a novel membrane-spanning proteoglycan," *J. Cell. Biol.*, 114:359-371, 1991.

Nuell et al., "Prohibitin, an evolutionary conserved intracellular protein that blocks DNA synthesis in normal fibroblasts and HeLa cells," *Mol. Cell Biol.*, 11(3):1372-1381, 1991.

Okamoto et al., "Transgenic mice with increased expression of vascular endothelial growth factor in the retina," *Am. J. Pathol.*, 151(1):281-291, 1997.

Oloffson et al., "Phage viability in organic media: insights into phage stability," *J Mol Recognit*, 11(1-6):91-93, abstract, 1998.

Olofsson et al., "Current biology of VEGF-B and VEGF-C," *Curr. Op. Biotechnol.*, 10:528-535, 1999.

Owens et al., "Cloning the antibody response in humans with chronic inflammatory disease: immunopanning of subacute sclerosing panencephalitis (SSPE) brain sections with antibody phage libraries prepared from SSPE brain enriches for antibody recognizing measles virus antigens in situ," *J. Virol.*, 74(3):1533-1537, 2000.

Pasqualini and Ruoslahti, "Organ targeting in vivo using phage display peptide libraries," *Nature*, 380:364-366, 1996.

Pasqualini et al., "A peptide isolated from phage display libraries is a structural and functional mimic of an RGD-binding site on integrins," *J. Cell Biol.*, 130:1189-1196, 1995.

Pasqualini et al., "Aminopeptidase N is a receptor for tumor-homing peptides and a target for inhibiting angiogenesis," *Cancer Res.*, 60(3):722-727, 2000.

Pasqualini et al., "αv integrins as receptors for tumor targeting by circulating ligands," *Nature Biotechnology*, 15:542-546, 1997.

Pasqualini et al., In: *Phage Display: A Laboratory Manual*, eds. Barbas et al., Cold Spring Harbor Laboratory Press, New York, NY, 22.1-24, 2000.

Pasqualini, "Vascular targeting with phage peptide libraries," *J. Nucl. Med.*, 43(2):159-162, 1999.

Pauli et al., "Organ-preference of metastasis," *Cancer and Metastasis Reviews*, 9:175-189, 1990.

Pereboeva et al., "Hepatitis C epitopes from phage-displayed cDNA libraries and improved diagnosis with a chimeric antigen," *J. Med. Virol.*, 60:144-151, 2000.

Pereboeva et al., "Identification of antigenic sites on three hepatitis C virus proteins using phage-displayed peptide libraries," *J. Med. Virol.*, 56:105-111, 1998.

Pierce et al., "Regulation of vascular endothelial growth factor by oxygen in a model of retinopathy of prematurity," *Arch. Ohpthlamol.*, 114:1219-1228, 1996.

Pierce et al., "Vascular endothelial growth factor/vascular permeability factor expression in a mouse model of retinal neovascularization.," *Proc. Natl. Acad. Sci., USA*, 92(3):905-909, 1995.

Pluschke et al., "Molecular cloning of a human melanoma-associated chondroitin sulfate proteoglycan," *Proc. Natl. Acad. Sci., USA*, 93:9710-9715, 1996.

Prezzi et al., "Selection of antigenic and immunogenic mimics of hepatitis C virus using sera from patients," *J. Immunol.*, 156:4504-4513, 1996.

Pruett, "Retinitis pigmentosa: clinical observations and correlations," *Trans. Am. Ophthamol. Soc.*, 81:693-735, 1983.

Rajotte and Ruoslahti, "Membrane dipeptidase is the receptor for a lung -targeting peptide identified by in vivo phage display," *J. Biol. Chem.*, 274:11593-11598, 1999.

Rajotte et al., "Membrane dipeptidase is the receptor for a lung-targeting peptide identified by in vivo phage display," *J. Biol. Chem.*, 274(17):11593-11598, 1999.

Rajotte et al., "Molecular heterogeneity of the vascular endothelium revealed by in vivo phage display," *J. Clin. Invest.*, 102(2):430-437, 1998.

Rak et al., "Consequences of angiogenesis for tumor progression, metastasis and cancer therapy," *Anti-Cancer Drugs*, 6:3-18, 1995.

Raulin et al., "Human immunodeficiency virus and host cell lipid. Interesting pathways in research for a new HIV therapy," *Prog. Lipid Res.*, 41:27-65, 2002.

Real et al., "Surface antigens of melanomas and melanocytes defined by mouse monoclonal antibodies: specificity, analysis, and comparison of antigen expression in cultured cells and tissues," *Cancer Res.*, 45:4401-4411, 1985.

Riordan, "Patents," *The New York Times*, Monday, Sep. 15, 1997.

Roof and Makino, "Structure and function of retinal photoreceptors," *Principles and Practice of Ophthalmology*, W.B. Saunders Company, Philadelphia, 2000.

Roux et al., "Human cord blood monocytes undergo terminal osteoclast differentiation in vitro in the presence of culture medium conditioned by giant cell tumor of bone," *J. Cell Physiol.*, 168(3):489-498, 1996.

Rugh, *The Mouse: Its Reproduction and Development*, Oxford Science Publications, Oxford, 1990.

Sang, "Complex role of matrix metalloproteinase in angiogenesis," *Cell Res.*, 8(3):171-177, 1998.

Schlingemann et al., "Aminopeptidase a is a constituent of activated pericytes in angiogenesis," *J. Pathol.*, 179(4):436-442, 1996.

Schlingemann et al., "Differential expression of markers for endothelial cells, pericytes, and basal lamina in the microvasculature of tumors and granulation tissues," *Amer. J. Path.*, 138:1335-1347, 1991.

Schlingemann et al., "Expression of the high molecular weight melanoma-associated antigen by pericytes during angiogenesis in tumors and in healing wounds," *Amer. J. Path.*, 136:1393-1405, 1990.

Schrappe et al., "Correlation of chondroitin sulfate proteoglycan expression on proliferating brain capillary endothelial cells with the malignant phenotype of astroglial cells," *Cancer Res.*, 51:4986-4993, 1991.

Scott and Smith, "Searching for peptide ligands with an epitope library," *Science*, 249:386-390, 1990.

Smith and Scott, "Libraries of peptides and proteins displayed in filamentous phage," *Meth. Enzymol.*, 21:228-257, 1993.

Smith et al., "Oxygen-induced retinopathy in the mouse," *Invest. Ohpthlamol.*, 35(1):101-111, 1994.

Smith, "Filamentous fusion phage: novel expression vectors that display cloned antigens on the virion surface," *Science*, 228:1315-1317, 1985.

Spitler et al., "Therapy of patients with malignant melanoma using a monoclonal anti-melanoma antibody-ricin immunotoxin," *Cancer Res.*, 47:1717-1723, 1987.

Spurdle et al., "The prohibitin 3'untranslated region polymorphism is not associated with risk of ovarian cancer," *Gynecol. Oncol.*, 90(1):145-149, 2003.

St. Croix et al., "Genes expressed in human tumor endothelium," *Science*, 289(5482):1197-1202, 2000.

Stone et al., "Development of retinal vasculature is mediated by hypoxia-induced vascular endothelial growth factor (VEGF) expression by neuroglia," *J. Neurosci.*, 15(7):4738-4747, 1995.

Tanaka et al., "Viral vector-targeted antiangiogenic gene therapy utilizing an angiostatin complementary DNA," *Cancer Res.*, 58(15):3362-9, 1998.

Tillet et al., "The membrane-spanning proteoglycan NG2 binds to collagen V and VI through central non-helical portion of the ectodomain," *J. Biol. Chem.*, 272:10769-10776, 1997.

Trepel et al., "Molecular adaptors for vascular-targeted adenoviral gene delivery," *Hum Gene Ther.*, 11(14):1971-81, 2000.

Triantafilou et al., "Major histocompatibility class one molecule associates with glucose regulated protein (GRP) 78 on the cell surface," *Hum. Immunol.*, 62(8):764-770, 2001.

Tsimanis et al., "Over-expression of the functional interleukin-11 alpha receptor in the development of B-cell chronic lymphocytic leukemia," *Leuk. Lymphoma*, 42(1-2):195-205, 2001.

Uliss et al., "Retinitis pigmentosa and retinal neovascularization," *Ophthalmology*, 93:1599-1603, 1986.

Verma and Somia, "Gene therapy-promises, problems, and prospects," *Nature*, 389:239-242, 1997.

Volpert et al., "Captopril inhibits angiogenesis and slows the growth of experimental tumors in rats," *J. Clin. Invest.*, 98(3):671-679, 1996.

Walsh et al., "Sequential development of angiotensin receptors and angiotensin I converting enzyme during angiogenesis in the rat subcutaneous sponge granuloma," *Br. J. Pharmacol.*, 120(7):1302-1311, 1997.

Wang et al., "Prohibitin, a potential tumor suppressor, interacts with RB and regulates E2F function," *Oncogene*, 18(23):3501-3510, 1999.

Watkins et al., "The 'adenobody' approach to viral targeting: specific and enhanced adenoviral gene delivery," *Gene Ther.*, 4:1004-1012, 1997.

Watson et al., "Variability among human umbilical vein endothelial cultures," *Science*, 268:447-448, 1995.

Weitzman et al., "Adenovirus vectors in cancer gene therapy," In: *Gene Therapy Technology and Vector Systems*, 2:17-25, 1997.

Whaley et al., "Selection of peptides with semiconductor binding specificity for directed nanocrystal assembly," *Nature*, 405:665-668, 2000.

Wickham et al., "Targeted adenovirus gene transfer to endothelial and smooth muscle cells by using bispecific antibodies," *J. Virol.*, 70:6831-6838, 1996.

Wickham et al., "Targeted adenovirus-mediated gene delivery to T cells via CD3," *J. Virol.*, 71(10):7663-7669, 1997.

Wickham et al., "Targeting adenovirus," *Gene Ther.*, 7:110-114, 2000.

Wickham et al., "Targeting endothelium for gene therapy via receptors up-regulated during angiogenesis and inflammation," *Cancer Immunol. Immunother.*, 45:149-151, 1997.

Costantini et al., "Mitochondrion as a novel target of anticancer chemotherapy," *J. Natl. Cancer Inst.*, 92(13):1042-1053, 2000.

Daniels and Lane, "Phage Peptide Libraries," *Methods*, 9:494-507, 1996.

Hussain et al., "Nasal mucosal metabolism and absorption of pentapeptide enkephalin analogs having varying N-terminal amino acids," *J. Pharm. Sci.*, 84(1):62-64, 1995.

Javadpour et al., "De novo antimicrobial peptides with low mammalian cell toxicity," *J. Med. Chem.*, 39:3107-3113, 1996.

Marchio et al., "Aminopeptidase A-Binding Peptides Regulate Endothelial Cell Function and Inhibit Angiogenesis," *Tumori*, 86:13, 2000.

Muller et al., "Effect of concentration on the cytotoxic mechanism of doxorubicin—apoptosis and oxidative DNA damage," *Biochem. Biophys. Res. Comm.*, 23:254-257, 1997.

Nagan et al., "Modulation of lysyl oxidase activity toward peptidyl lysine by vicinal dicarboxylic amino acid residues. Implications for collagen cross-linking," *J. Biol. Chem.*, 269(35):22366-22371, 1994.

Nomizu et al., "Cell binding sequences in mouse laminin alpha1 chain," *J. Biol. Chem.*, 273(46):32491-32499, 1998.

European Office Action, issued in European Application No. 02 757 531.5, dated Mar. 27, 2008.

Wu et al., "Molecular cloning of the murine BP-1/6C3 antigen: a member of the zinc-dependent metallopeptidase family," *Proc. Natl. Acad. Sci., USA*, 87(3):993-997, 1990.

Wu, "In vivo veritas: live phage display panning," *Nature Biotechnology*, 14:429-431, 1996.

Yang and Reisfeld, "Doxorubicin conjugated with a monoclonal antibody directed to a human melanoma-associated proteoglycan suppresses the growth of established tumor xenografts in nude mice," *Proc. Natl. Acad. Sci., USA*, 85:1189-1193, 1988.

Yanovski et al., "Endocrine and metabolic evaluation of human immunodeficiency virus-infected patients with evidence of protease inhibitor-associated lipodystrophy," *J. Clin. Endocrin. Metab.*, 84(6):1925-1931, 1999.

Yoshiji et al., "The angiotensin-I-converting enzyme inhibitor perindopril suppresses tumor growth and angiogenesis: possible role of the vascular endothelial growth factor," *Clin. Cancer Res.*, 7(4):1073-1078, 2001.

Zempo et al., "Regulation of vascular smooth muscle cell migration and proliferation in vitro and in injured rat arteries by a synthetic matrix metalloproteinase inhibitor," *Arterioscler. Thromb. Vasc. Biol.*, 16:28-33, 1996.

Zhang et al., "Crystal structure of the obese protein leptin-E100," *Nature*, 387:206-209, 1997.

Zhang et al., "Development and application of adenoviral vectors for gene therapy of cancer," *Cancer Gene Therapy*, 6:113-138, 1999.

Zhang et al., "Inhibition of adipocyte differentiation by HIV protease inhibitors," *J. Clin. Endocrin. Metab.*, 84:4274-4277, 1999.

Zhang et al., "Positional cloning of the mouse obese gene and its human homologue," *Nature*, 372:425-432, 1994.

Zhu et al., "Mediation of lung metastasis of murine melanomas by a lung-specific endothelial cell adhesion molecule," *Proc. Natl. Acad. Sci., USA*, 88:9568-9572, 1991.

Phage and Phage DNA Recovery Schemes from PALM Catapulted Material

K91 Infection

- Catapult 90-120 islets and control sections into 30 μl protease cocktail in PBS within 48 hours. Protease cocktail: AEBSF, aprotinin, leupeptin, TPCK, elastase inhibitor, pepstatin A.
- Pool thawed samples and adjust final volume to 200 μl with PBS.
- Infect with 1 ml K91 for 2 hours at RT.
- Add LB/kanamycin/tetracycline 1:1 where the final [tetracycline] = 0.2 μg/ml. Let samples recover in the dark for 40 minutes to 1 hour.
- Increase [tetracycline] to 40 μg/ml and incubate overnight at 37 °C with agitation.
- Plate onto LB/kanamycin/tetracycline plates the following day.
- Pick single colonies to PCR amplify with fUSE5 primers for sequencing.

DNA Amplifications/Subcloning

- Catapult 90-120 islets into 30 μl 1 mM EDTA, pH 8.
- Pool thawed samples and concentrate.
- PCR1: PCR amplify peptide coding sequence with fUSE5 primers.
- PCR2: PCR amplify peptide coding sequence with nested primers.
- Sequence PCR2 products with M13 reverse primer.
- PCR3: PCR amplify peptide coding sequence with library primers containing SfiI sites.
- Digest gel-purified PCR products with SfiI. Also digest fUSE5 with SfiI/CIAP. Clean up products with Qiagen Qiaquick and Nucleotide Cleanup Kits.
- Ligate, electroporate into MC1061, and plate onto LB/streptomycin/tetracycline plates.
- Pick single colonies to PCR amplify with fUSE5 primers for sequencing.

Fig. 36

Islet Homing Peptide Sequence Homology

| Peptide Sequence | Homologous Protein | Sequence | Amino Acid Residue | Sequence Identity | Expected Value |
|---|---|---|---|---|---|
| CVSNPRWKC | putative mouse protein (cloned from full length mouse gene encyclopedia project) | VSNPRW | 123-128 | 100% (6/6) | 6.7 |
| | PI3-kinase p110 subunit | SNPRW | 379-383 | 100% (5/5) | 53 |
| | rat endothelin-converting protein | PRWK | 422-425 | 100% (4/4) | 90 |
| | TNF Receptor p60 homologue 1 | VSNPRW | 130-136 | 85% (6/7) | 127 |
| | 121 kDa protein isolated from rat adipocytes containing insulin-regulated glucose transporter GLUT4 | NPRW | 293-296 | 100% (4/4) | 308 |
| | Reg2 (present in regenerating pancreatic islets and normal exocrine pancreas) | SNRRW | 114-118 | 80% (4/5) | 391 |
| | ephrin-related receptor tyrosine kinase ligand 4 (LERK 4) | SNPR | 35-38 | 100 (4/4) | 524 |
| CVPRRWDVC | laminin β-2 chain | PRRWD | 197-201 | 100 (5/5) | 6.4 |
| CQHTSGRGC | dihydropyridine sensing L-type Ca2+ channel, β3-subunit laminin β-2 chain | QHTSG | 442-446 | 100 (5/5) | 90 |
| | | TSGRG | 1088-1092 | 100 (5/5) | 218 |
| CRARGWLLC | α3 integrin | RAPGWLL | 10-16 | 85 (6/7) | 12 |

Fig. 37

Islet Homing Peptide Sequence Homology

| Peptide Sequence | Homologous Protein | Sequence | Amino Acid Residues | Sequence Identity | Expected Value |
|---|---|---|---|---|---|
| CGGVHALRC | Ret receptor | VHALR | 53-57 | 100 (5/5) | 309 |
| | putative mouse protein | GGVHSL GVDALR | 432-437 248-253 | 99 (6/6) 83 (5/6) | 556 2416 |
| | RIKEN cDNA | GVHAL | 58-62 | 100 (5/5) | 556 |
| CFNRTWIGC | chloride channel protein | NRTWV | 411-415 | 100 (5/5) | 50 |
| | tyrosine protein kinase receptor FLK-2 | FHRTW | 711-715 | 100 (5/5) | 67 |
| CSRGPAWGC | Bone morphogenic protein 3B, growth differentiation factor 10 (TGF-β family member) | RGPSW | 32-36 | 100 (5/5) | 121 |
| | 5-HT 6 receptor | GPAW | 13-16 | 100 (4/4) | 218 |
| | Reticulon 1, neuroendocrine specific protein | PAWG | 45-48 | 100 (4/4) | 218 |
| CWSRGQGGC (25% I vs. 2.2%C) | SOX1 SOX2 SOX3 SOX14 | WSRGQ | 61-65 53-57 79-83 3-7 | 100 (5/5) | 21 21 21 21 |
| | endothelin-1 receptor | WSRVQG | 92-97 | 83 (5/6) | 90 |
| | DAP 12, tyrosine kinase binding protein | SRGQG | 71-75 | 100 (5/5) | 163 |
| | excitatory AA symporter (L-E, L, D-D/Na+) | SRGRGG | 551-556 | 99 (6/6) | 527 |

Fig. 38

Islet Homing Peptide Sequence Homology

| Peptide Sequence | Homologous Protein | Sequence | Amino Acid Residues | Sequence Identity | Expected Value |
|---|---|---|---|---|---|
| CLASGMDAC (9.5%) | TNF-α | LANGMD | 116-121 | 99 (6/6) | 50 |
| CHDERTGRC (8%) | SOX6 | HDQRT | 274-278 | 99 (6/6) | 218 |
| CAHHALMEC (6%) | PI3 kinase p85 subunit | HEERT | 611-615 | 100 (5/5) | 163 |
|  | APC Protein | ALMEC | 569-573 | 100 (5/5) | 15 |
| CMQGARTSC (6%) | cathespsin W (thiol protease) | ARTSC | 365-369 | 100 (5/5) | 67 |
|  | α2 adrenergic receptor | QGART | 326-330 | 100 (5/5) | 121 |
|  | Pancreatitis-associated protein Reg 3α | RTSC | 37-40 | 100 (4/4) | 393 |

Islet Homing Peptide Sequence Homology

| Peptide Sequence | Homologous Protein | Sequence | Amino Acid Residues | Sequence Identity | Expected Value |
|---|---|---|---|---|---|
| CHVLWSTRC (13% I vs. 2.2%C) | integrin linked protein kinase | VLKVRDWSTR | 220-230 | 60 (6/10) | 122 |
| | Ephrin-A2 receptor tyrosine kinase ligand 6 (LERK 6) | VLWS | 202-205 | 100 (4/4) | 220 |
| | α3a integrin | VLWS | 147-150 | 100 (4/4) | 220 |
| CMSSPGVAC (10.7% I vs 3.2%C) | insulin receptor substrate 1 | MSPGVA MASP | 611-616 1-4 | 67 4/4 | 164 2308 |
| | laminin α5 chain | SSPGV | 467-471 | 100 (5/5) | 220 |
| | angiopoietin-2 receptor | MSSP | 262-265 | 100 (4/4) | 265 |
| | SOX17 | MSSP | 1-4 | 100 (4/4) | 396 |
| | citron protein (rho/rac binding protein-GTP form) | MNSPG | 998-1002 | 100 (5/5) | 396 |
| | glucocorticoid receptor | SSPSVA SSPG | 45-50 402-405 | 83 (5/6) 100 (4/4) | 396 1720 |
| CLGLLMAGC (13% I vs. 4.3%C) | chloride channel protein 2 | LGLLMA | 105-110 | 100 (6/6) | 8.7 |
| | tumor necrosis factor receptor 2 | LGLLM | 272-276 | 100 (5/5) | 51 |
| | histidine-rich membrane protein Ke4 | LGLLVAG | 21-27 | 99 (7/7) | 51 |
| | vascular endothelial-cadherin receptor | LGLLAVAAMAG | 15-25 | 63 (7/11) | 68 |
| | endothelial protein C receptor | LGILM_GC LLLPGC | 217-223 12-16 | 81 (7/8) 82 (5/6) | 91 82 |
| | Wnt-3 proto-oncogene | LGLLLSG | 6-10 | 99 (7/7) | 164 |

COMPOSITIONS AND METHODS OF USE OF TARGETING PEPTIDES AGAINST PLACENTA AND ADIPOSE TISSUES

This application is a U.S. nationalization of PCT application PCT/US02/27836, which is a continuation in part of PCT application PCT/US01/27692, filed on Sep. 7, 2001, the entire text of which is incorporated herein by reference.

This invention was made with U.S. government support under grants grants CA90270, 1R1CA90810-01 and 1R01CA82976-01 from the National Institutes of Health. The U.S. government has certain rights in this invention.

BACKGROUND OF THE INVENTION

1. Field of the Invention

The present invention concerns the fields of molecular medicine and targeted delivery of therapeutic agents. More specifically, the present invention relates to compositions and methods for identification and use of peptides that selectively target white adipose tissue and placenta in vivo or in vitro. In other embodiments, the invention concerns compositions and methods for screening potential teratogenic agents.

2. Description of Related Art

Phage display is a technique in which a phage library expresses, for example, a set of random peptide sequences of defined length, incorporated into a phage coat protein (e.g., Smith and Scott, Science 228:1315-17, 1985; Smith and Scott, Meth. Enzymol. 21:228-57, 1993). Peptide sequences that bind to a target molecule, cell, tissue or organ may be identified by incubating a phage display library with the target and selecting for bound peptides (biopanning) (e.g., Pasqualini and Ruoslahti, Nature 380:364-66, 1996; Arap et al., Science 279:377-80, 1998a). Unbound phage may be washed away and bound phage eluted and collected. The collected phage may be amplified and taken through further binding/amplification cycles to enrich the pool of peptides for those that selectively and/or specifically bind to the target. With each cycle, the proportion of phage in the pool that contain targeting peptides for the target of interest is enriched. After several cycles, individual phage clones may be characterized by DNA sequencing to identify the targeting peptide sequences.

Targeting peptides that exhibit selective and/or specific binding for placenta or adipose tissues have not been previously reported in the literature. Targeting peptides against placenta or adipose tissues would have a variety of potential uses. Targeting peptides against adipose tissue could be used to control obesity and related conditions. Adipose-targeting peptides would also be of potential use to treat HIV related adipose malformations such as lipodystrophia and/or hyperlipidemia (see, e.g., Zhang et al., J. Clin. Endocrin. Metab. 84:4274-77, 1999; Jain et al., Antiviral Res. 51:151-177, 2001; Raolin et al., Prog. Lipid Res. 41:27-65, 2002). Targeting peptides against placental tissue could be used to reduce harmful effects by tetragenic agents, to deliver therapeutic agents to the placenta and/or the fetus and to induce labor or spontaneous abortion. Placental receptors identified through the use of placental targeting peptides could be used to screen for potential teratogens.

Presently available methods for control of weight include dieting and surgical procedures. These often exhibit adverse effects and may not result in long-term weight loss. Dieting includes both popular (fad) diets and the use of weight loss and appetite supplements. Fad diets are only good for short-term weight loss and do not achieve long-term weight control. They are often unhealthy, since many important nutrients are missing from the diet. In addition, rapid weight loss can result in dehydration. After losing weight, the dieters typically return to their original eating habits. This often results in weight gain that can exceed the subject's weight before dieting (yo yo effect).

Appetite suppressants such as Phentermen HCl, Meridia, Xernical, Adipex-P, Bontril and Ionomin may have adverse effects, such as addiction, dry mouth, nausea, irritability, and constipation. These supplements can also lead to more serious problems like eating disorders. Weight control through use of such supplements is ineffective, with only limited weight loss achieved. Effective drugs for controlling weight, such as fenfluramine, were withdrawn from the market due to cardiotoxicity.

Surgical methods for weight reduction, such as liposuction and gastric bypass surgery, have many risks. Liposuction removes subcutaneous fat through a suction tube inserted into a small incision in the skin. Risks and complications may include scarring, bleeding, infection, change in skin sensation, pulmonary complications, skin loss, chronic pain, etc. In gastric bypass surgery, the patient has to go through the rest of his or her life with a drastically altered stomach that can hold just two or three ounces of food. Side effects may include nausea, diarrhea, bleeding, infection, bowel blockage caused by scar tissue, hernia and adverse reactions to general anesthesia. The most serious potential risk is leakage of fluid from the stomach or intestines, which may result in abdominal infection and the need for a second surgery. None of the presently available methods for weight control is satisfactory and a need exists for improved methods of weight loss and control.

Another adipose related disease state is lipodystrophy syndrome(s) related to HIV infection (e.g., Jain et al., Antiviral Res. 51:151-177, 2001). Mortality rates from HIV infection have decreased substantially following use of highly active antiretroviral therapy (HAART) (Id.) However, treatment with protease inhibitors as part of the HAART protocol appears to result in a number of lipid-related symptoms, such as hyperlipidemia, fat redistribution with accumulation of abdominal and cervical fat, diabetes mellitus and insulin resistance (Jain et al., 2001; Yanovski et al., J. Clin. Endocrin. Metab. 84:1925-1931; Raulin et al., Prog. Lipid Res. 41:27-65, 2002). Although of minor significance compared to the underlying HIV infection and possible development of AIDS related complex (ARC) and/or AIDS, lipodystrophy syndrome adversely affects quality of life and may be associated with increased risk of coronary artery disease, heart attack, stroke and other adverse side affects of increased blood lipids. While treatment with metformin, an insulin-sensitizing aget, has been reported to provide some alleviation of symptoms (Hadigan et al., J. Amer. Med. Assn. 284:472-477, 2000), a need exists for more effective methods of treating HIV related lypodystrophy.

Teratogens fall into two classes. The first class includes compounds that are actively or passively transferred through the materno-fetal barrier. Those target fetal development by altering cell-signaling pathways that control essential processes in the developing embryo, such as angiogenesis (D'Amato, R. J., et al 1994. Proc. Natl. Acad. Sci. USA 91: 4082-4085; Finnell, R. H. 1999. J. Allergy Clin. Immunol. 103:337-342).

Teratogens of the second class interfere with fetal development by affecting the delivery of nutrients to the embryo through the placenta (Maranghi, F., et al. 1998. Adv. Exp. Med. Biol. 444: 129-136; Rugh, R. 1990. The Mouse: Its Reproduction and Development, Oxford Science Publications, Oxford). Materno-fetal molecule exchange occurs by filtration of blood from the maternal to the fetal side of the placenta through several distinct cell layers. Teratogens that target the placenta are thought to function by blocking receptors required for transport of nutrients to the fetus (Beckman, D. A., et al. 1990. *Teratology* 41: 395-404). Present methods of treatment primarily involve avoiding exposure of the pregnant woman to teratogens. Such methods are ineffective where the mother is unaware of her pregnancy, or for novel teratogens whose effect on fetal development have not yet been characterized. Because teratogens are identified by in vivo animal testing, differences in placental receptors between humans and test animals, such as mice, may result in the failure to identify teratogenic effects until multiple birth defects are reported, such as in the thalidomide tragedy. A need exists for methods of identifying the placental receptors for teratogens, in order to allow more accurate teratogen screening procedures.

SUMMARY OF THE INVENTION

The present invention solves a long-standing need in the art by providing compositions and methods of preparation and use of targeting peptides that are selective and/or specific for white adipose tissue or placenta. In some embodiments, the invention concerns particular targeting peptides selective or specific for adipose or placental tissue, including but not limited to SEQ ID NO:5-11, SEQ ID NO:13-22 and SEQ ID NO:144. Other embodiments concern such targeting peptides attached to therapeutic agents. In other embodiments, placental, adipose or other targeting peptides may be used to selectively or specifically deliver therapeutic agents to target tissues, such as white adipose tissue, placenta or fetal tissue. In certain embodiments, the subject methods concern the preparation and identification of targeting peptides selective or specific for a given target cell, tissue or organ, such as adipose or placenta.

One embodiment of the invention concerns isolated peptides of 100 amino acids or less in size, comprising at least 3 contiguous amino acids of a targeting peptide sequence, selected from any of SEQ ID NO:5-11, SEQ ID NO:13-22 and SEQ ID NO:144. In a preferred embodiment, the isolated peptide is 50 amino acids or less, more preferably 30 amino acids or less, more preferably 20 amino acids or less, more preferably 10 amino acids or less, or even more preferably 5 amino acids or less in size. In other preferred embodiments, the isolated peptide may comprise at least 4, 5, 6, 7, 8 or 9 contiguous amino acids of a targeting peptide sequence, selected from any of SEQ ID NO:5-11, SEQ ID NO:13-22 and SEQ ID NO:144.

In certain embodiments, the isolated peptide may be attached to a molecule. In preferred embodiments, the attachment is a covalent attachment. In various embodiments, the molecule is a drug, a chemotherapeutic agent, a radioisotope, a pro-apoptosis agent, an anti-angiogenic agent, a hormone, a cytokine, a growth factor, a cytotoxic agent, a peptide, a protein, an antibiotic, an antibody, a Fab fragment of an antibody, a survival factor, an anti-apoptotic factor, a hormone antagonist, an imaging agent, a nucleic acid or an antigen. Those molecules are representative only and virtually any molecule may be attached to a targeting peptide and/or administered to a subject within the scope of the invention. In preferred embodiments, the pro-aptoptosis agent is gramicidin, magainin, mellitin, defensin, cecropin, (KLAKLAK)$_2$ (SEQ ID NO:1), (KLAKKLA)$_2$ (SEQ ID NO:2), (KAAKKAA)$_2$ (SEQ ID NO:3) or (KLGKKLG)$_3$ (SEQ ID NO:4). In other preferred embodiments, the anti-angiogenic agent is angiostatin5, pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP-470, endostatin, paclitaxel, docetaxel, polyamines, a proteasome inhibitor, a kinase inhibitor, a signaling inhibitor (SU5416, SU6668, Sugen, South San Francisco, Calif.), accutin, cidofovir, vincristine, bleomycin, AGM-1470, platelet factor 4 or minocycline. In further preferred embodiments, the cytokine is interleukin 1 (IL-1), IL-2, IL-5, IL-10, IL-11, IL-12, IL-18, interferon-γ (IF-γ), IF-α, IF-β, tumor necrosis factor-α (TNF-α), or GM-CSF (granulocyte macrophage colony stimulating factor). Such examples are representative only and are not intended to exclude other pro-apoptosis agents, anti-angiogenic agents or cytokines known in the art.

In various embodiments, targeting peptides attached to one or more therapeutic agents may be administered to a subject, such as an animal, mammal, cat, dog, cow, pig, horse, sheep or human subject. Such administration may be of use for the treatment of various disease states. In certain embodiments, adipose-targeting peptides attached to a cytocidal, pro-apoptotic, anti-angiogenic or other therapeutic agent may be of use in methods to treat obesity, induce weight loss and/or to treat highly active antiretroviral therapy (HAART) associated lipodystrophy syndrome. In other embodiments, placenta-targeting peptides attached to such agents may be used, for example, to induce labor or to terminate pregnancy.

In other embodiments of the invention, the isolated peptide may be attached to a macromolecular complex. In preferred embodiments, the macromolecular complex is a virus, a bacteriophage, a bacterium, a liposome, a microparticle, a magnetic bead, a yeast cell, a mammalian cell, a cell or a microdevice. These are representative examples only and macromolecular complexes within the scope of the present invention may include virtually any complex that may be attached to a targeting peptide and administered to a subject. In other preferred embodiments, the isolated peptide may be attached to a eukaryotic expression vector, more preferably a gene therapy vector.

In another embodiment, the isolated peptide may be attached to a solid support, preferably magnetic beads, Sepharose beads, agarose beads, a nitrocellulose membrane, a nylon membrane, a column chromatography matrix, a high performance liquid chromatography (HPLC) matrix or a fast performance liquid chromatography (FPLC) matrix.

Additional embodiments of the present invention concern fusion proteins comprising at least 3 contiguous amino acids of a sequence selected from any of SEQ ID NO:5-11, SEQ ID NO:13-22 and SEQ ID NO:144. In some embodiments, larger contiguous sequences, up to a full-length sequence selected from any of SEQ ID NO:5-11, SEQ ID NO:13-22 and SEQ ID NO:144 may be used.

Certain other embodiments concern compositions comprising the claimed isolated peptides or fusion proteins in a pharmaceutically acceptable carrier. Further embodiments concern kits comprising the claimed isolated peptides or fusion proteins in one or more containers.

Other embodiments concern methods of targeted delivery comprising selecting a targeting peptide for a desired organ, tissue or cell type, attaching said targeting peptide to a molecule, macromolecular complex or gene therapy vector, and providing said peptide attached to said molecule, complex or vector to a subject. Preferably, the targeting peptide is selected to include at least 3 contiguous amino acids from any of selected from any of SEQ ID NO:5-11, SEQ ID NO:13-22 and SEQ ID NO:144. In certain preferred embodiments, the organ, tissue or cell type is white adipose or placenta. In other preferred embodiments, the molecule attached to the targeting peptide is a chemotherapeutic agent, an antigen or an imaging agent.

Other embodiments of the present invention concern isolated nucleic acids of 300 nucleotides or less in size, encoding a targeting peptide. In preferred embodiments, the isolated nucleic acid is 250, 225, 200, 175, 150, 125, 100, 75, 50, 40, 30, 20 or even 10 nucleotides or less in size. In other preferred embodiments, the isolated nucleic acid is incorporated into a eukaryotic or a prokaryotic expression vector. In even more preferred embodiments, the vector is a plasmid, a cosmid, a yeast artificial chromosome (YAC), a bacterial artificial chromosome (BAC), a virus or a bacteriophage. In other preferred embodiments, the isolated nucleic acid is operatively linked to a leader sequence that localizes the expressed peptide to the extracellular surface of a host cell.

Additional embodiments of the present invention concern methods of treating a disease state comprising selecting a targeting peptide that targets cells associated with the disease state, attaching one or more molecules effective to treat the disease state to the peptide, and administering the peptide to a subject with the disease state. Preferably, the targeting peptide includes at least three contiguous amino acids selected from any of selected from any of SEQ ID NO:5-11, SEQ ID NO:13-22 and SEQ ID NO:144. In preferred embodiments the disease state is obesity, lipodystrophy or a related condition.

In certain embodiments, the methods concern Biopanning and Rapid Analysis of Selective Interactive ligands (BRASIL), a novel method for phage display that results in decreased background of non-specific phage binding, while retaining selective binding of phage to cell receptors. In preferred embodiments, targeting peptides are identified by exposing a subject to a phage display library, collecting samples of one or more organs, tissues or cell types, separating the samples into isolated cells or small clumps of cells suspended in an aqueous phase, layering the aqueous phase over an organic phase, centrifuging the two phases so that the cells are pelleted at the bottom of a centrifuge tube and collecting phage from the pellet. In an even more preferred embodiment, the organic phase is dibutylphtalate.

In other embodiments, phage that bind to a target organ, tissue or cell type, for example to adipose tissue or placenta, may be pre-screened or post-screened against a subject lacking that organ, tissue or cell type. Phage that bind to the subject lacking the target organ, tissue or cell type are removed from the library prior to screening in subjects possessing the organ, tissue or cell type.

In preferred embodiments, targeting phage may be recovered from specific cell types or sub-types present in an organ or tissue after selection of the cell type by PALM (Positioning and Ablation with Laser Microbeams). PALM allows specific cell types to be selected from, for example, a thin section of an organ or tissue. Phage may be recovered from the selected sample.

In another embodiment, a phage display library displaying the antigen binding portions of antibodies from a subject is prepared, the library is screened against one or more antigens and phage that bind to the antigens are collected. In more preferred embodiments, the antigen is a targeting peptide.

In certain embodiments, the methods and compositions may be used to identify one or more receptors for a targeting peptide. In alternative embodiments, the compositions and methods may be used to identify naturally occurring ligands for known or newly identified receptors. In preferred embodiments, the receptor may be a placental receptor for teratogens. In some embodiments, the placental teratogen receptor(s) identified may be used for screening of potential teratogens for receptor binding.

In some embodiments, the methods may comprise contacting a targeting peptide to an organ, tissue or cell containing a receptor of interest, allowing the peptide to bind to the receptor, and identifying the receptor by its binding to the peptide. In preferred embodiments, the targeting peptide contains at least three contiguous amino acids selected from any of selected from any of SEQ D NO:5-11, SEQ ID NO:13-22 and SEQ ID NO:144. In other preferred embodiments, the targeting peptide may comprise a portion of an antibody against the receptor.

In alternative embodiments, the targeting peptide may contain a random amino acid sequence. The skilled artisan will realize that the contacting step can utilize intact organs, tissues or cells, or may alternatively utilize homogenates or detergent extracts of the organs, tissues or cells. In certain embodiments, the cells to be contacted may be genetically engineered to express a suspected receptor for the targeting peptide. In a preferred embodiment, the targeting peptide is modified with a reactive moiety that allows its covalent attachment to the receptor. In a more preferred embodiment, the reactive moiety is a photoreactive group that becomes covalently attached to the receptor when activated by light. In another preferred embodiment, the peptide is attached to a solid support and the receptor is purified by affinity chromatography. In other preferred embodiments, the solid support comprises magnetic beads, Sepharose beads, agarose beads, a nitrocellulose membrane, a nylon membrane, a column chromatography matrix, a high performance liquid chromatography (HPLC) matrix or a fast performance liquid chromatography (FPLC) matrix.

In certain embodiments, the targeting peptide may inhibit the activity of a receptor upon binding to the receptor. The skilled artisan will realize that receptor activity can be assayed by a variety of methods known in the art, including but not limited to catalytic activity and binding activity. In other embodiments, binding of a targeting peptide to a receptor may inhibit a transport activity of the receptor.

In alternative embodiments, one or more ligands for a receptor of interest may be identified by the disclosed methods and compositions. One or more targeting peptides that mimic part or all of a naturally occurring ligand may be identified by phage display and biopanning in vivo or in vitro. A naturally occurring ligand may be identified by homology with a single targeting peptide that binds to the receptor, or a consensus motif of sequences that bind to the receptor. In other alternative embodiments, an antibody may be prepared against one or more targeting peptides that bind to a receptor of interest. Such antibodies may be used for identification or immunoaffinity purification of the native ligand.

In certain embodiments, the targeting peptides of the present invention are of use for the selective delivery of therapeutic agents, including but not limited to gene therapy vectors and fusion proteins, to specific organs, tissues or cell types. The skilled artisan will realize that the scope of the claimed methods of use include any disease state that can be treated by targeted delivery of a therapeutic agent to a desired organ, tissue or cell type. Although such disease states include those where the diseased cells are confined to a specific organ, tissue or cell type, other disease states may be treated by an organ, tissue or cell type-targeting approach. In particular embodiments, the organ, tissue or cell type may comprise white adipose tissue or placenta.

Certain embodiments concern methods of obtaining antibodies against an antigen. In preferred embodiments, the antigen comprises one or more targeting peptides. The targeting peptides are prepared and immobilized on a solid support, serum-containing antibodies is added and antibodies that bind to the targeting peptides are collected.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

(A) Arrows show homing of the CKGGRAKDC (SEQ ID NO:22) peptide to fat endothelium. Bar: 10 μm.

Figure 10:
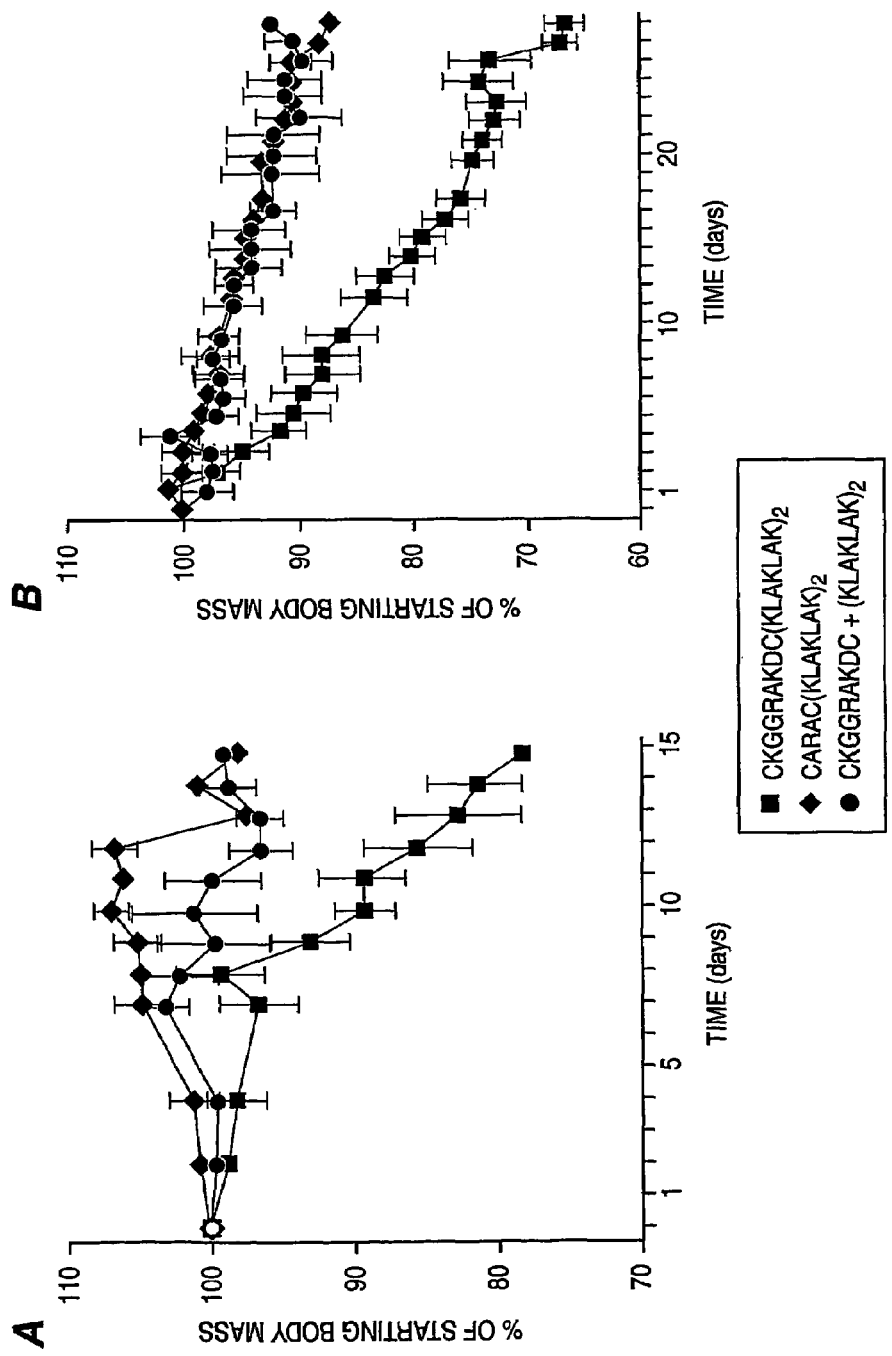

FIG. 10. Treatment of mouse obesity with fat vasculature-targeted apoptosis. Three cohorts (n=3) of (A) high-fat cafeteria diet-fed obese c57bl/6 mice; or (B) regular diet-fed old (~1 year) c57bl/6 mice were each subcutaneously injected daily with equimolar amounts of the indicated peptides. Mouse body mass measurement was taken on days when injections were performed (injections were skipped on days for which body mass measurement is not shown). Error bars are SEM for the measurements in three mice.

Figure 11:
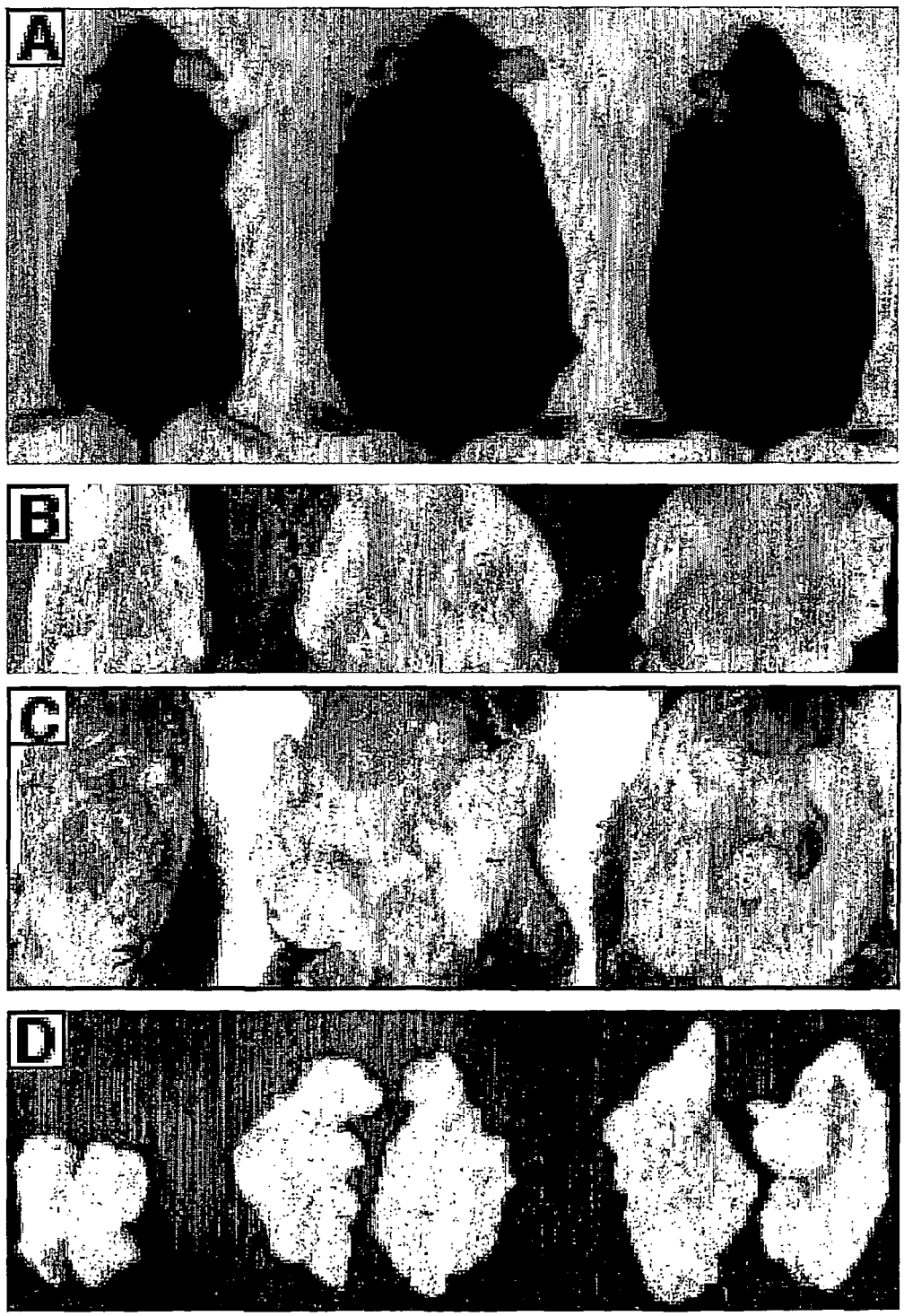

FIG. 11. Fat resorption induced by fat vasculature-targeted apoptosis. (A) Representative high-fat cafeteria diet-fed obese c57bl/6 mice; (B) and (C) representative regular diet-fed old (~1 year) c57bl/6 mice; or (D) epididymal fat from representative regular diet-fed old c57bl/6 mice from the experiment described in FIG. 10. Whole mice (A), subcutaneous fat (B), peritoneal fat (C) and total epididymal fat (D) from the corresponding indicated treatments were photographed 1 week (A) or 3 weeks (B), (C) and (D) after the beginning of subcutaneous injections. The injected peptides were CKGGRAKDC (SEQ ID NO:22) linked to (KLAKLAK)$_2$ (SEQ ID NO:1) (left column), CARAC (SEQ ID NO:12) linked to (KLAKLAK)$_2$ (SEQ ID NO:1) (middle column), and CKGGRAKDC (SEQ ID NO:22) co-administered with (KLAKLAK)$_2$ (SEQ ID NO:1) (right column).

Figure 12:
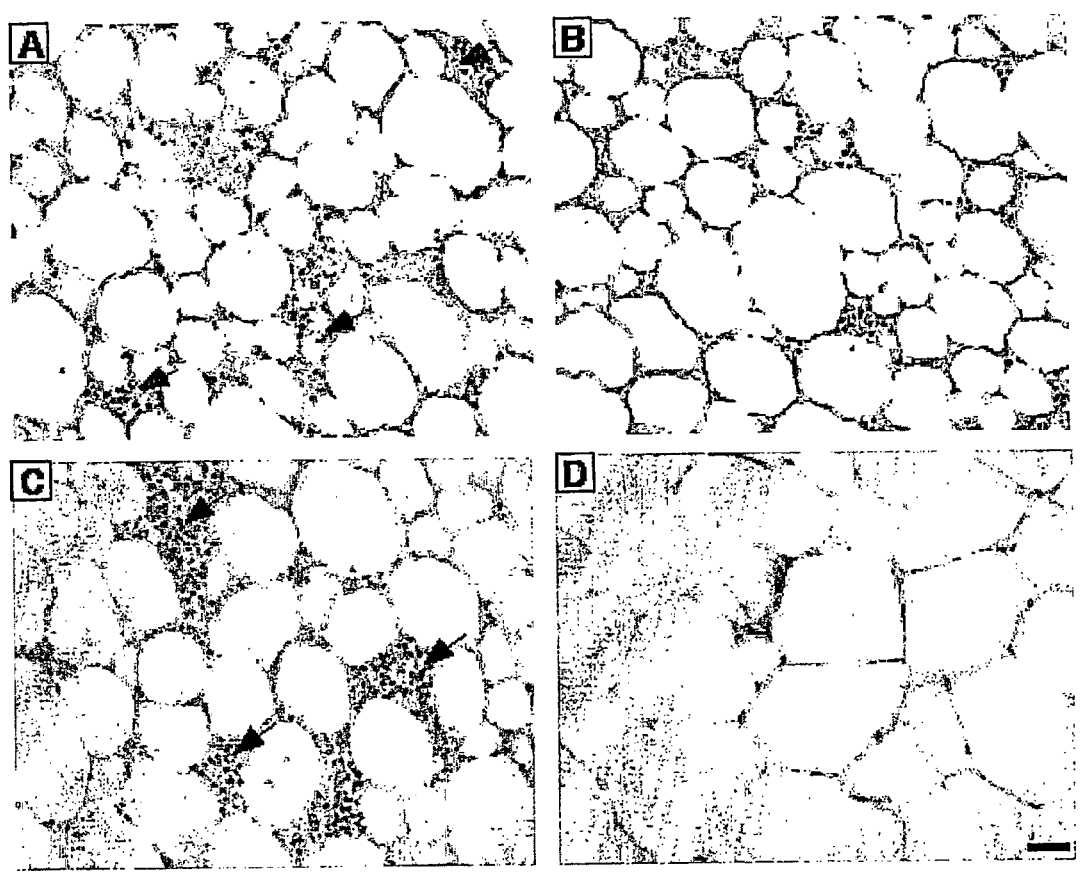

FIG. 12. Destruction of fat blood vessels as a result of targeted apoptosis. (A) Tunnel immunohistochemistry, (B) secondary antibody only negative tunnel staining control and (C) and (D) hematoxylin/eosin staining of white fat of mice. (A), (B) and (C) Mice were treated with CKGGRAKDC (SEQ ID NO:22) linked to (KLAKLAK)$_2$ (SEQ ID NO:1). (D) Mice were treated with CARAC (SEQ ID NO:12) linked to (KLAKLAK)$_2$ (SEQ ID NO:1). Apoptosis (arrows, (A)) and necrosis/lymphocyte infiltration (arrows, (C)) in response to CKGGRAKDC (SEQ ID NO:22) linked to (KLAKLAK)$_2$ (SEQ ID NO:1) treatment are indicated. Bar: 10 μm.

Figure 13:
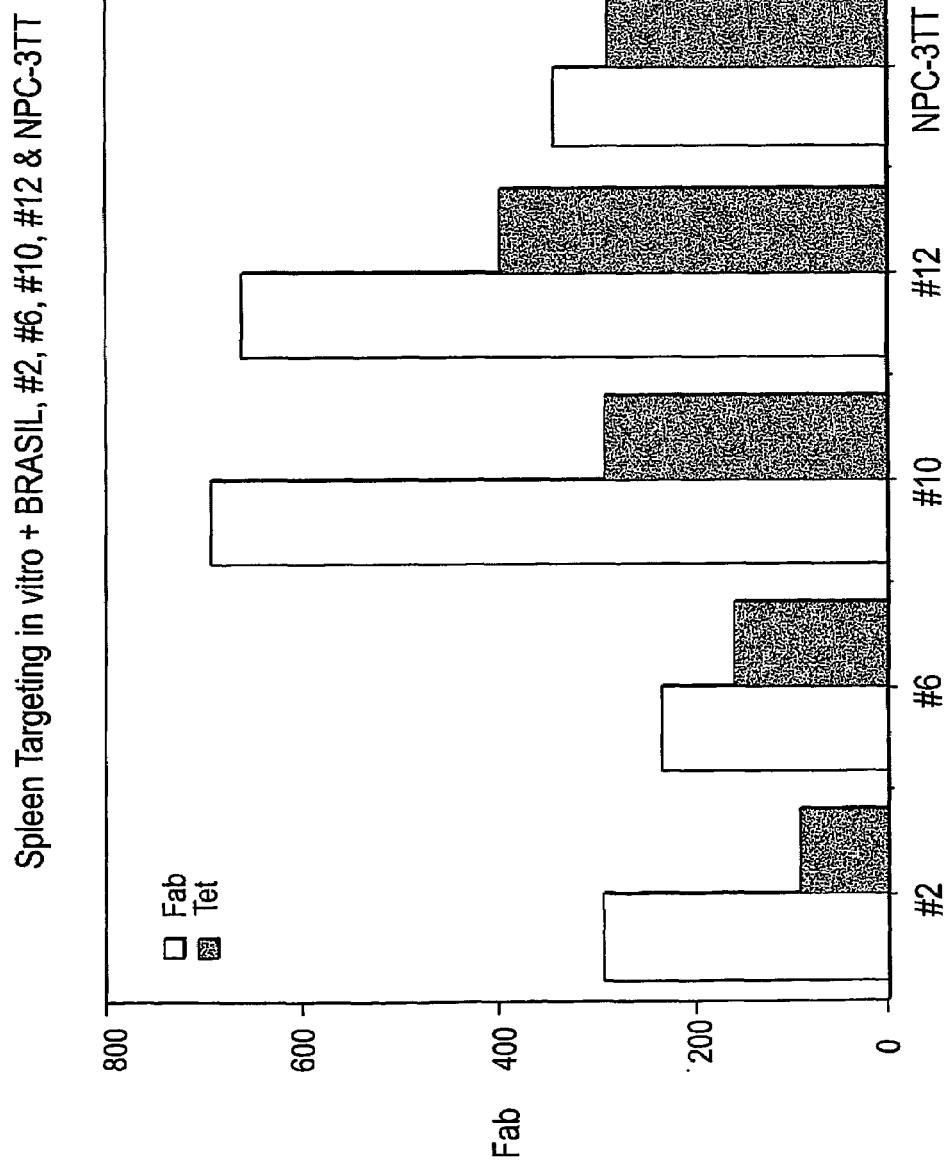

FIG. 13. Spleen targeting in vitro using BRASIL. Binding of Fab clones #2, #6, #10, #12 and control Fab clone NPC-3TT were directly compared to each other.

Figure 14:
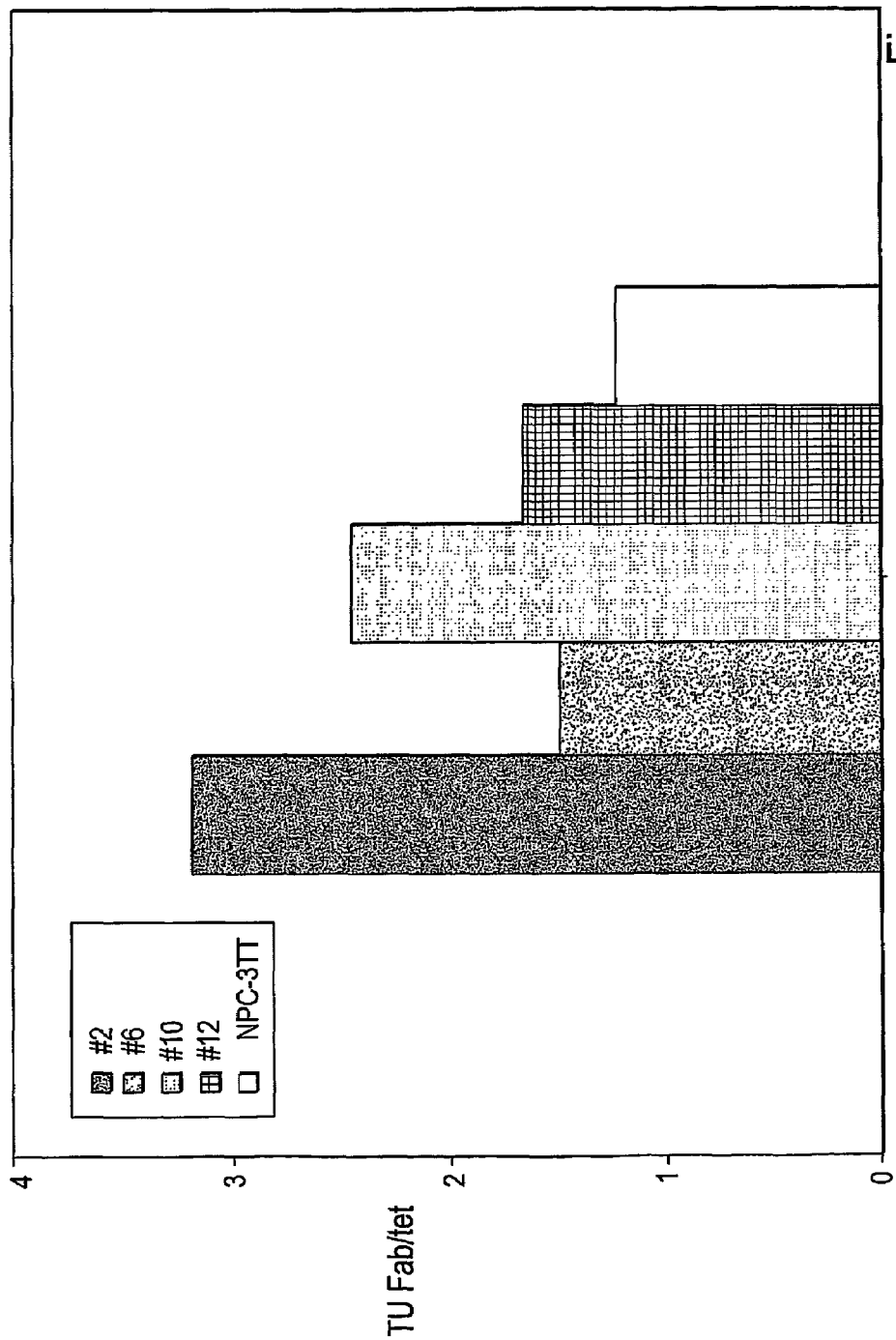

FIG. 14. Spleen targeting in vivo using BRASIL. Binding of Fab clones #2, #6, #10 and #12 to spleen tissue was compared to binding of Fab control clone NPC-3TT.

Figure 15:
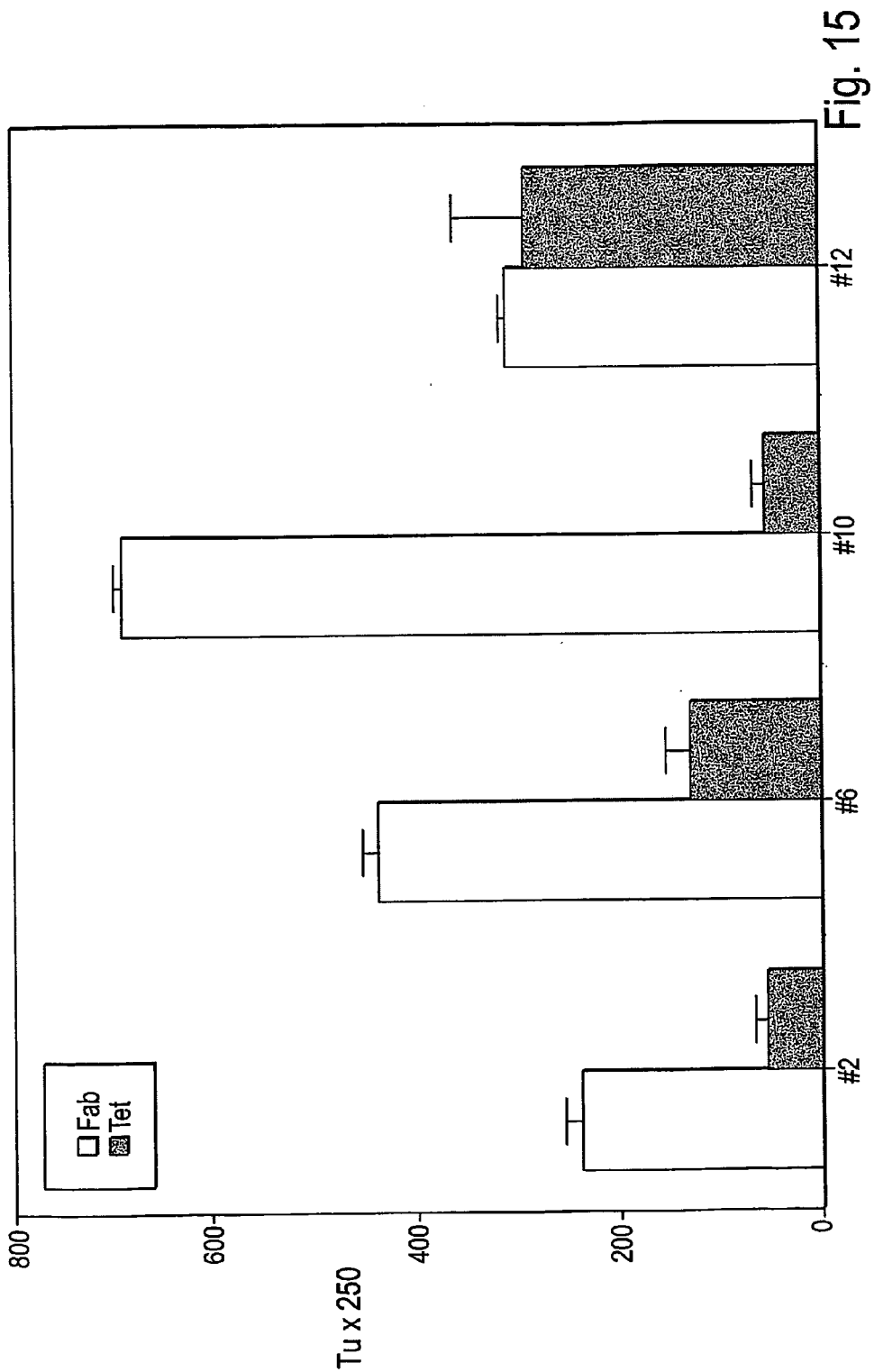

FIG. 15. Spleen targeting in vivo using BRASIL. Binding of Fab clones #2, #6, #10, #12 was compared to binding of Fd-tet phage.

Figure 16:
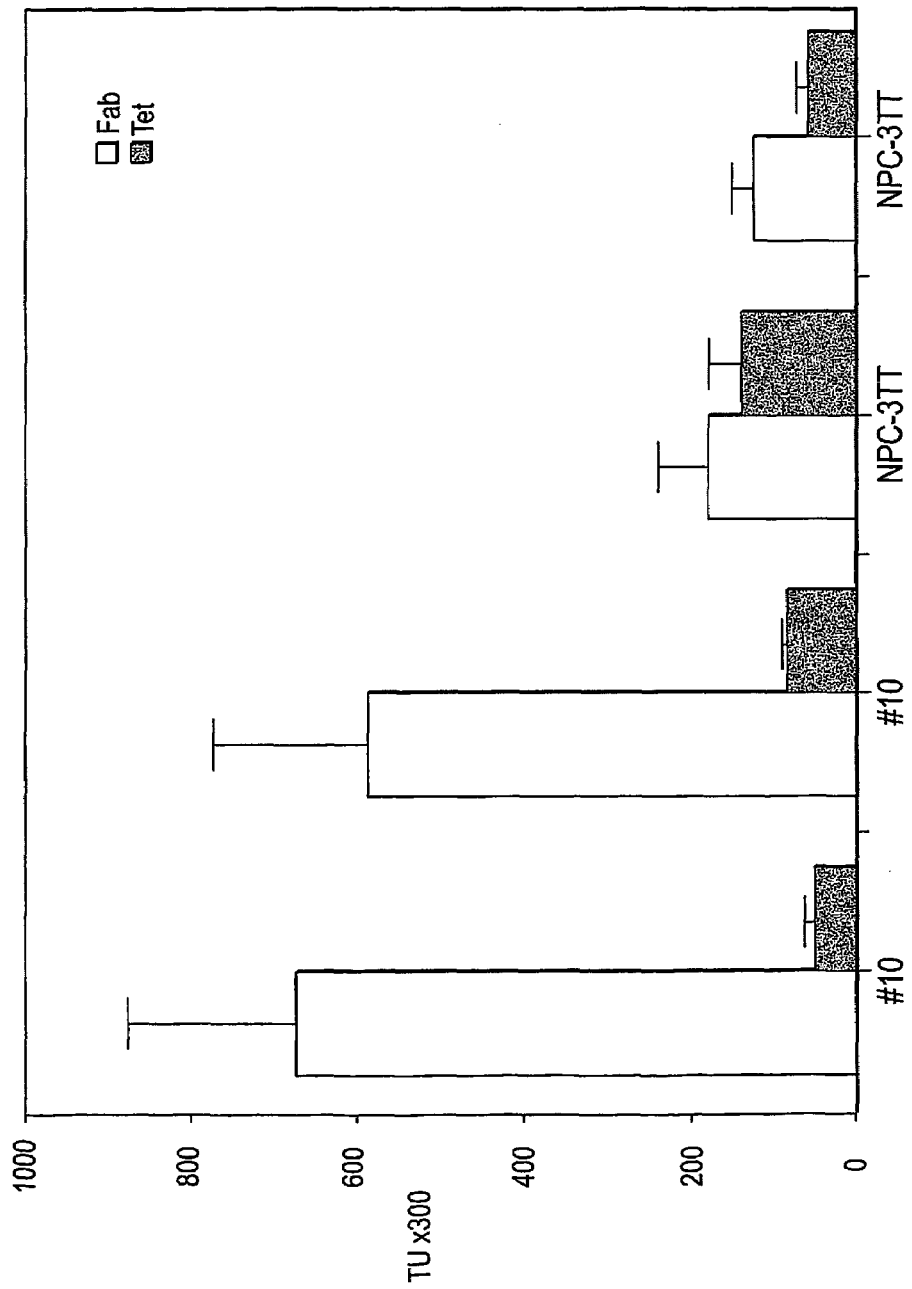

FIG. 16. Spleen targeting in vivo using BRASIL. Binding of Fab clone #10 to spleen tissue was compared to binding of Fab control clone NPC-3TT and Fd-tet phage.

Figure 17:
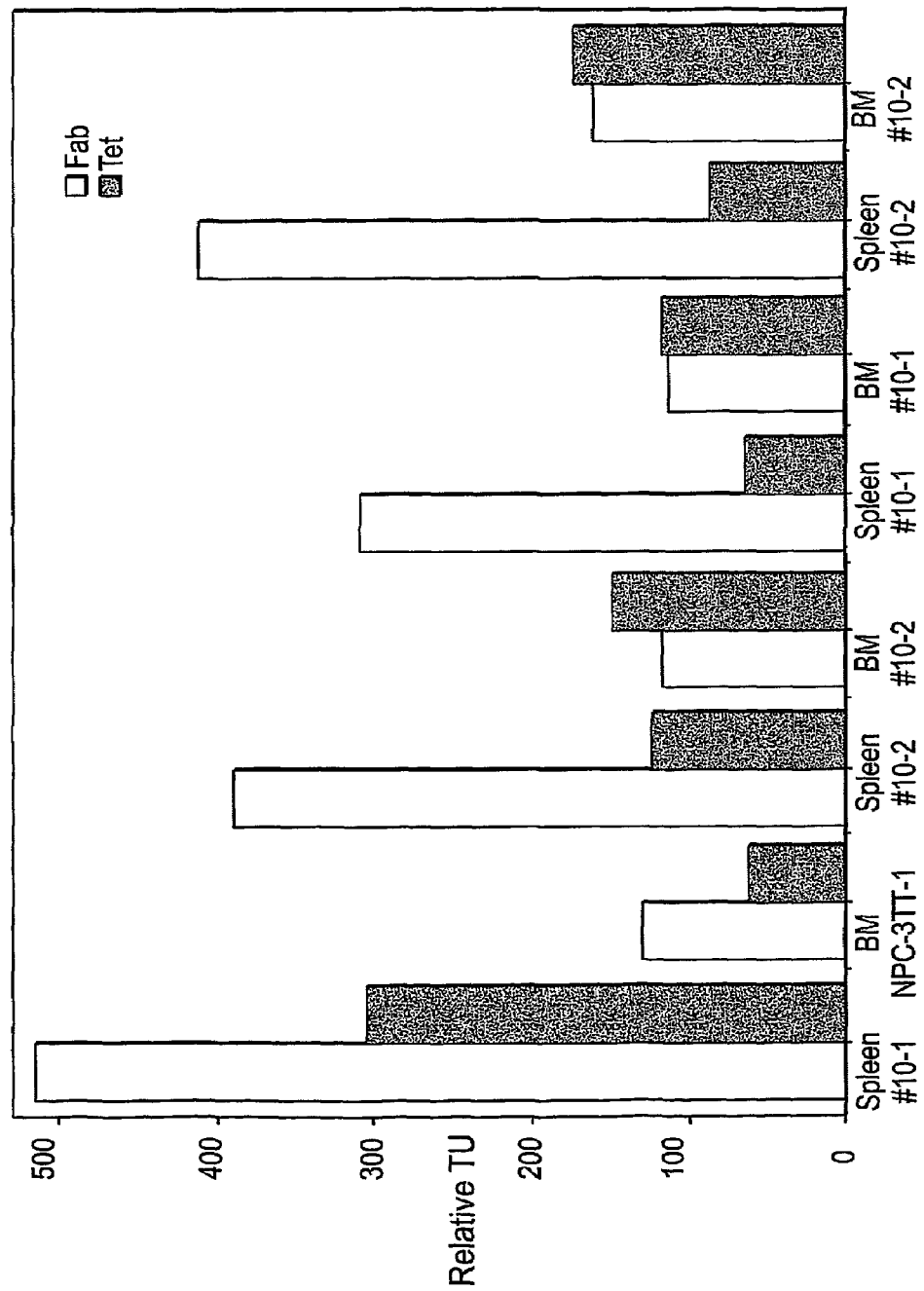

FIG. 17. Binding of Fab clone #10 to spleen versus bone marrow in comparison to Fd-tet phage.

Figure 18:

FIG. 18. Binding of β3 cytoplasmic domain-selected phage to immobilized proteins. GST fusion proteins or GST alone were coated on microtiter wells at 10 μg/ml and used to bind phage-expressing endostatin targeting peptides. Each phage is identified by the peptide sequence it displayed: GLDTYRGSP (SEQ ID NO:30); YDWWYPWSW (SEQ ID NO:29); CLRQSYSYNC (SEQ ID NO:38); SDNRYIGSW (SEQ ID NO:31); CEQRQTQEGC (SEQ ID NO:27); CFQNRC (SEQ ID NO:36). The data represent the mean colony counts from triplicate wells, with standard error of less than 10% of the mean.

Figure 19:
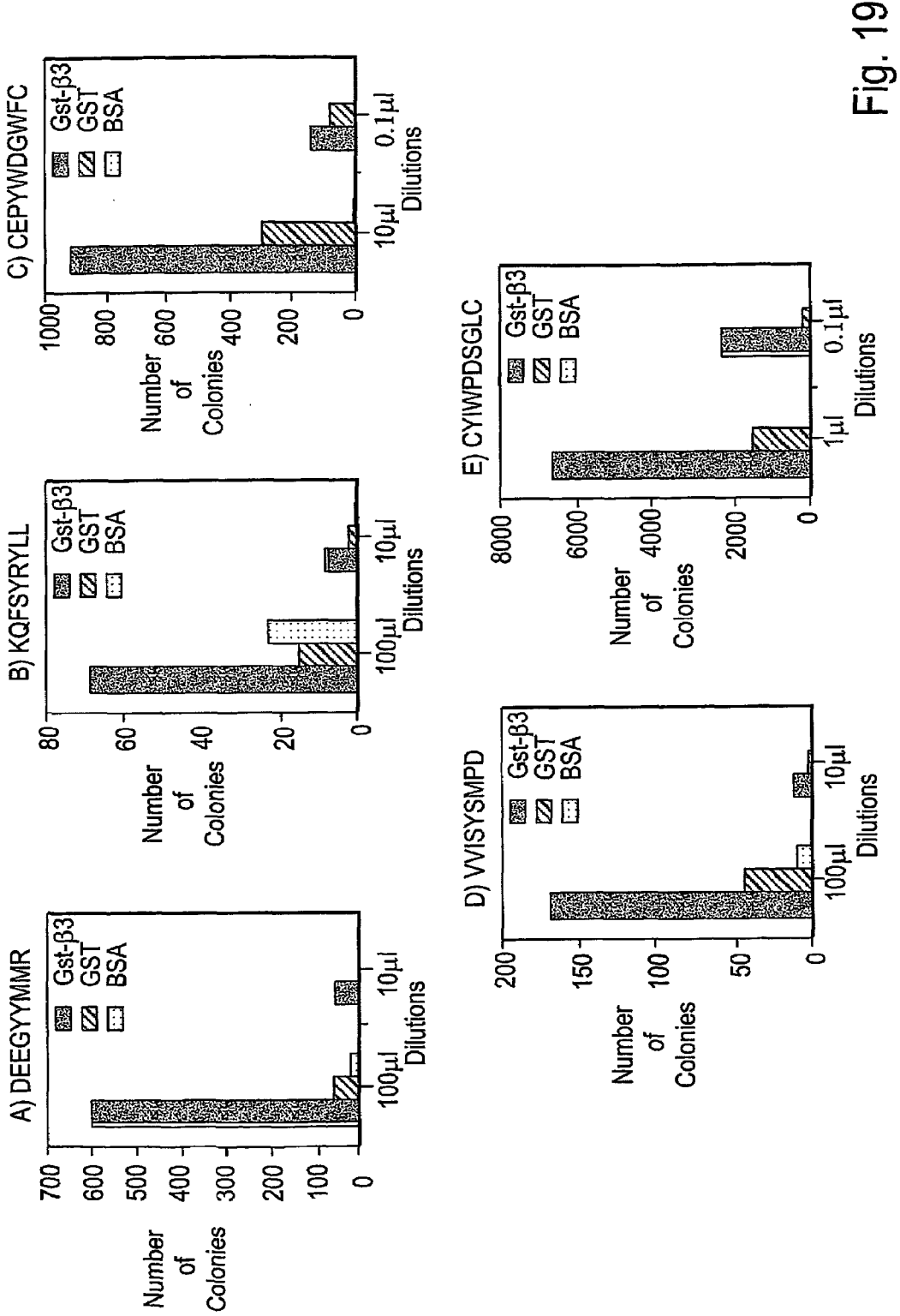

FIG. 19. Binding of β5 cytoplasmic domain-selected phage to immobilized proteins. GST fusion proteins or GST alone were coated on microtiter wells at 10 μg/ml and used to bind phage-expressing endostatin binding peptides. Each phage is identified by the peptide sequence it displayed: (A) DEEGYYMMR (SEQ ID NO:44); (B) KQFSYRYLL (SEQ ID NO:45); (C) CEPYWDGWFC (SEQ ID NO:40); (D) VVISYSMPD (SEQ ID NO:46); and (E) CYIWPDSGLC (SEQ ID NO:39). The data represent the mean colony counts from triplicate wells, with standard error less than 10% of the mean.

Figure 20:
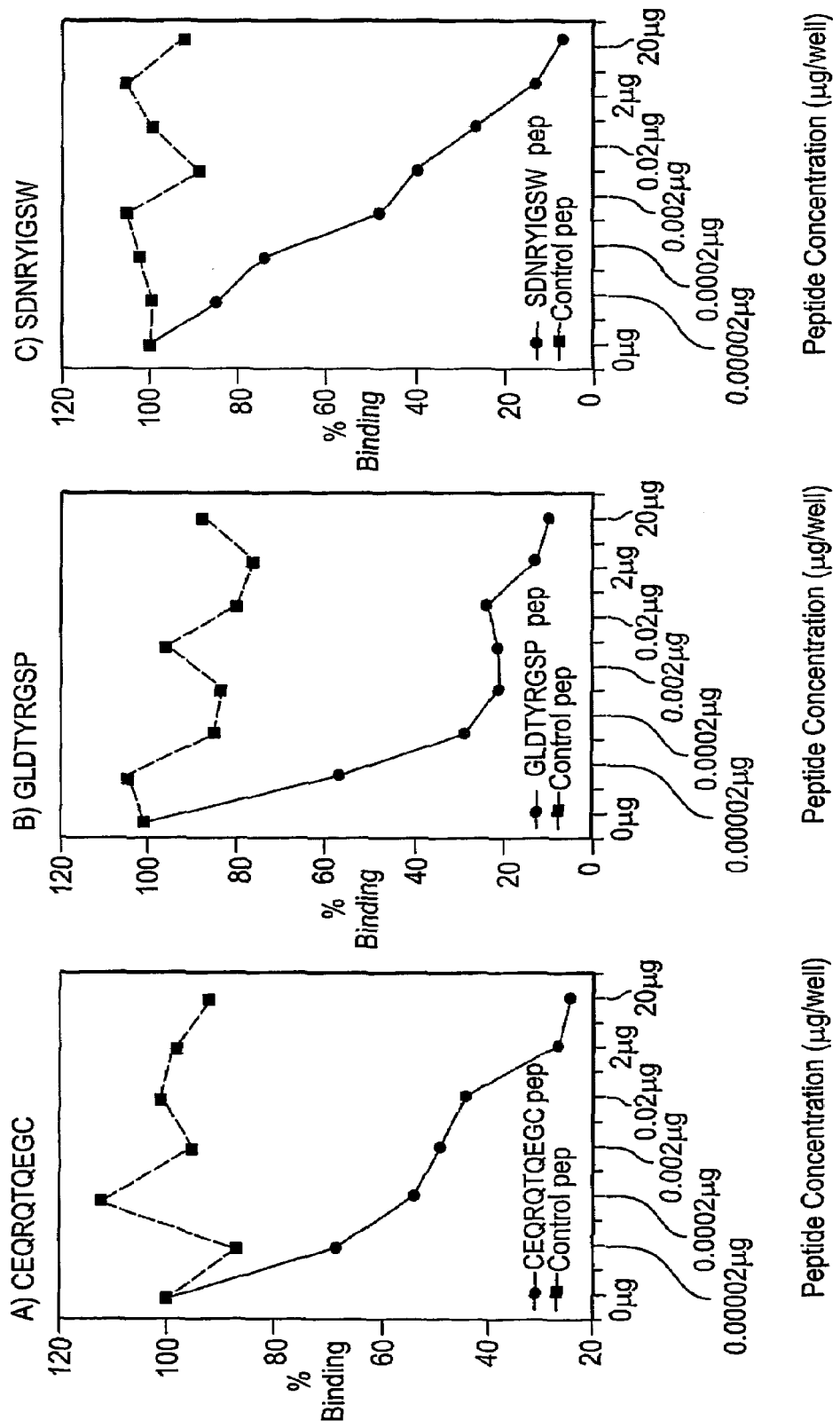

FIG. 20. Binding of the cytoplasmic-domain binding phage to β3 immobilized protein and inhibition with the synthetic peptide. Phage were incubated on wells coated with GST-β3cyto in the presence of increasing concentrations of the corresponding synthetic peptide or a control peptide. The data represent the mean colony counts from triplicate wells, with standard error less than 10% of the mean.

Figure 21:
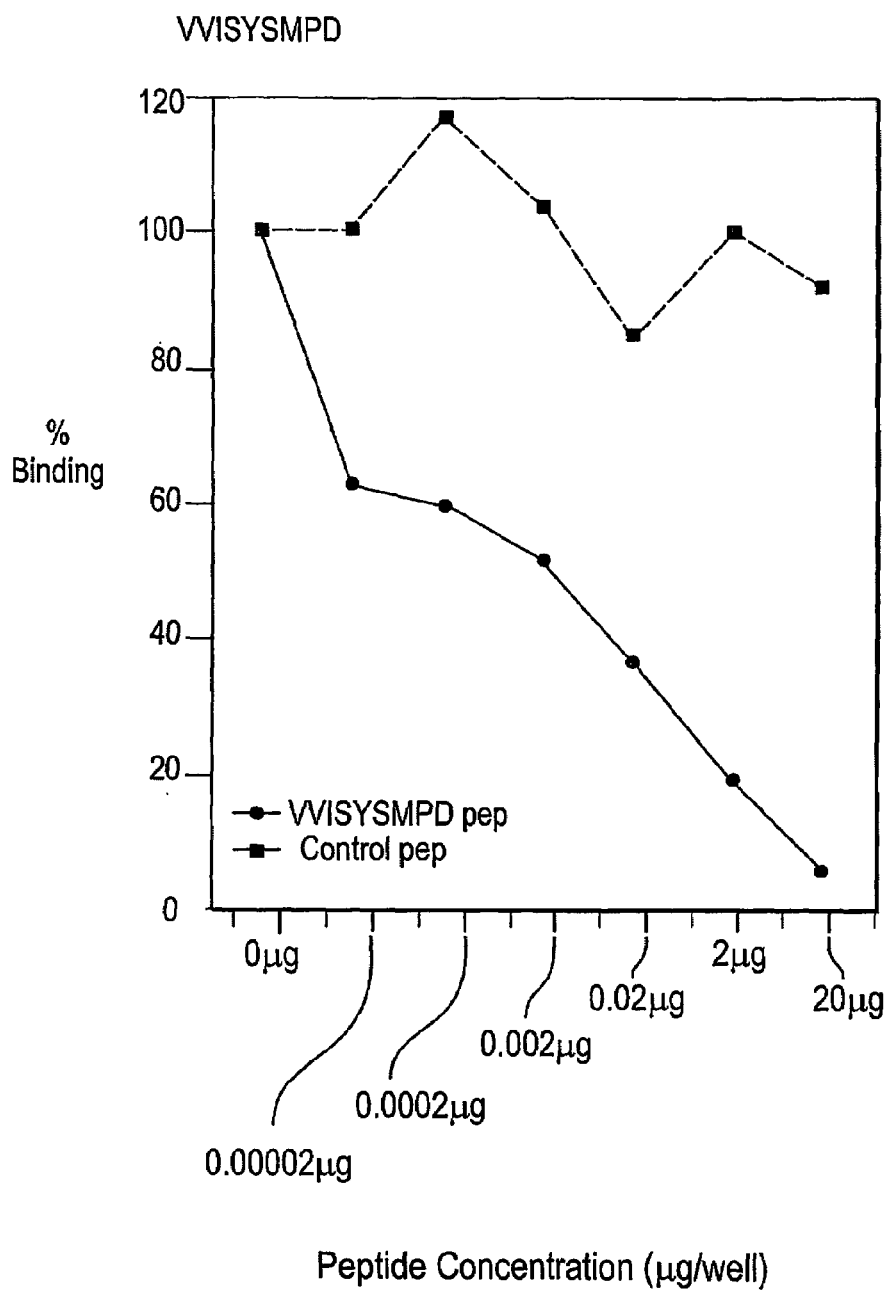

FIG. 21. Binding of the cytoplasmic-domain binding phage to β5 immobilized protein and inhibition with the synthetic peptide. Phage were incubated on wells coated with GST-β5cyto in the presence of increasing concentrations of the corresponding synthetic peptide or a control peptide. The data represent the mean colony counts from triplicate wells, with standard error less than 10% of the mean.

Figure 22:
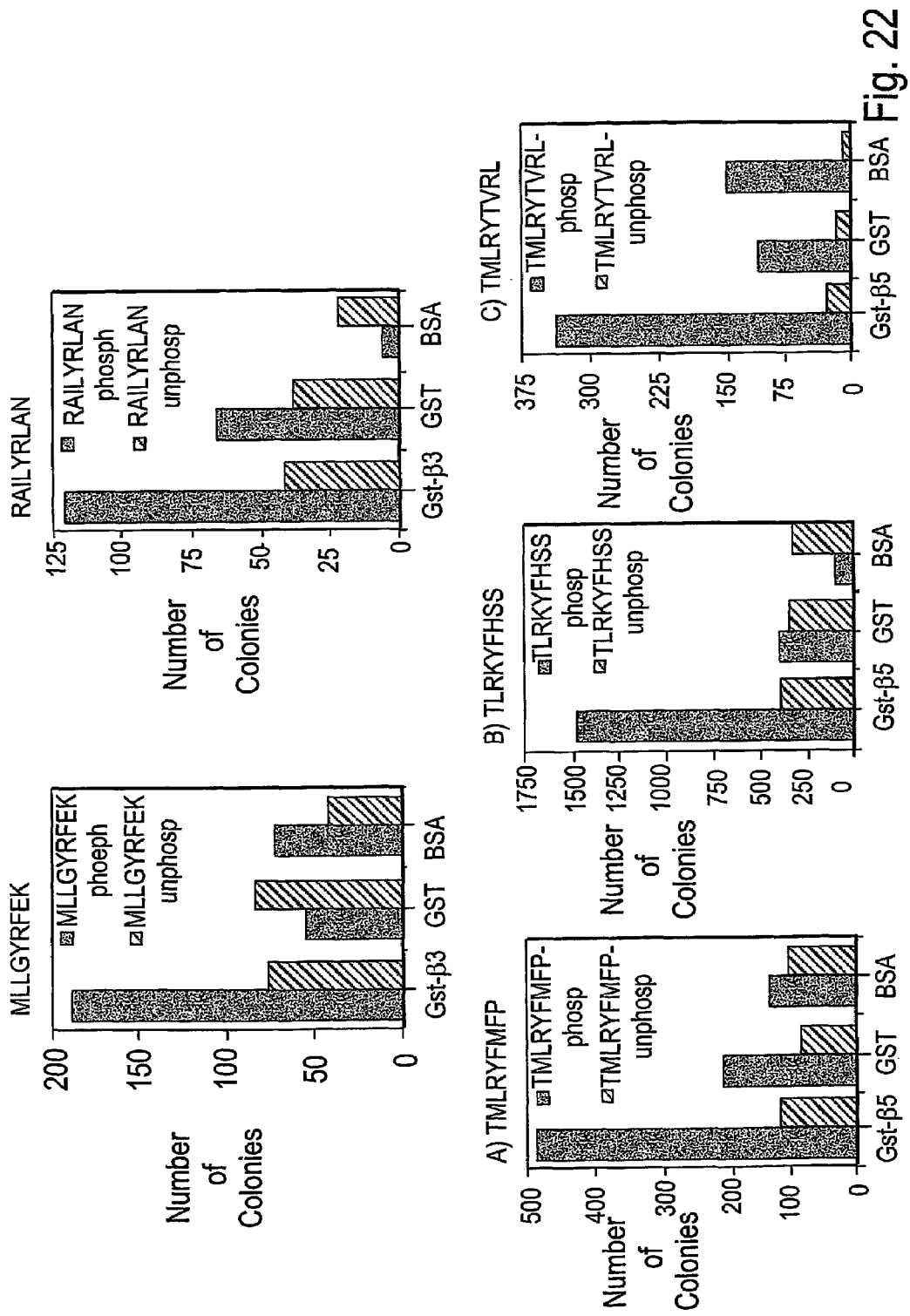

FIG. 22. Binding of phage to immobilized β3-GST and β5-GST after phosphorylation. Phage were phosphorylated with Fyn kinase. Insertless phage were used as a control. Phage were incubated on wells coated with GST-β3cyto or GST-β3cyto. The data represent the mean colony counts from triplicate wells, with standard error less than 10% of the mean.

Figure 23:
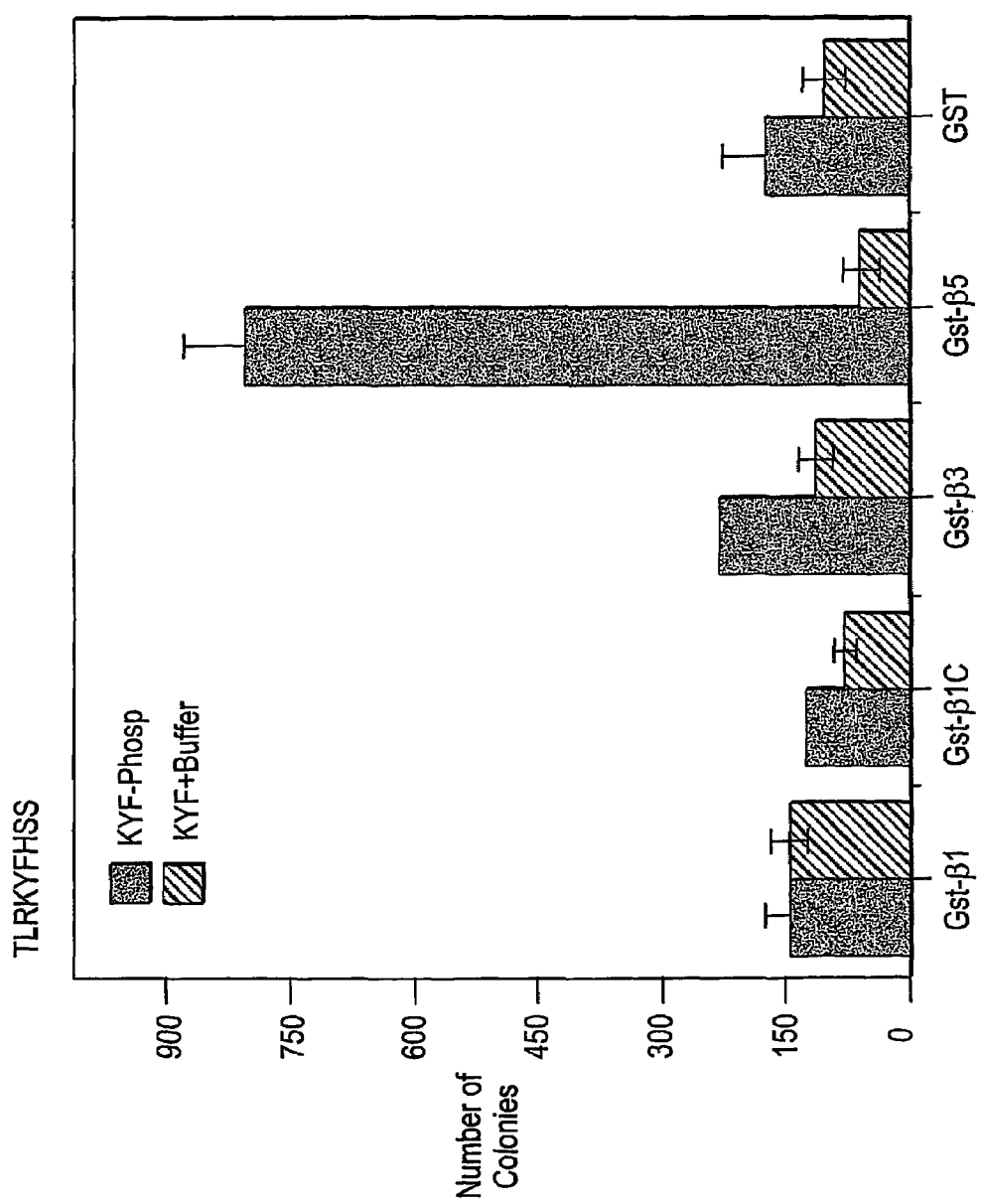

FIG. 23. Binding of phage to immobilized GST fusion proteins after phosphorylation. Phages were phosphorylated with Fyn kinase. Insertless phage was used as a control. Phage were incubated on wells coated with GST-cytoplasmic domains. The data represent the mean of colony counts from triplicate wells, with standard error less than 10% of the mean.

Figure 24:
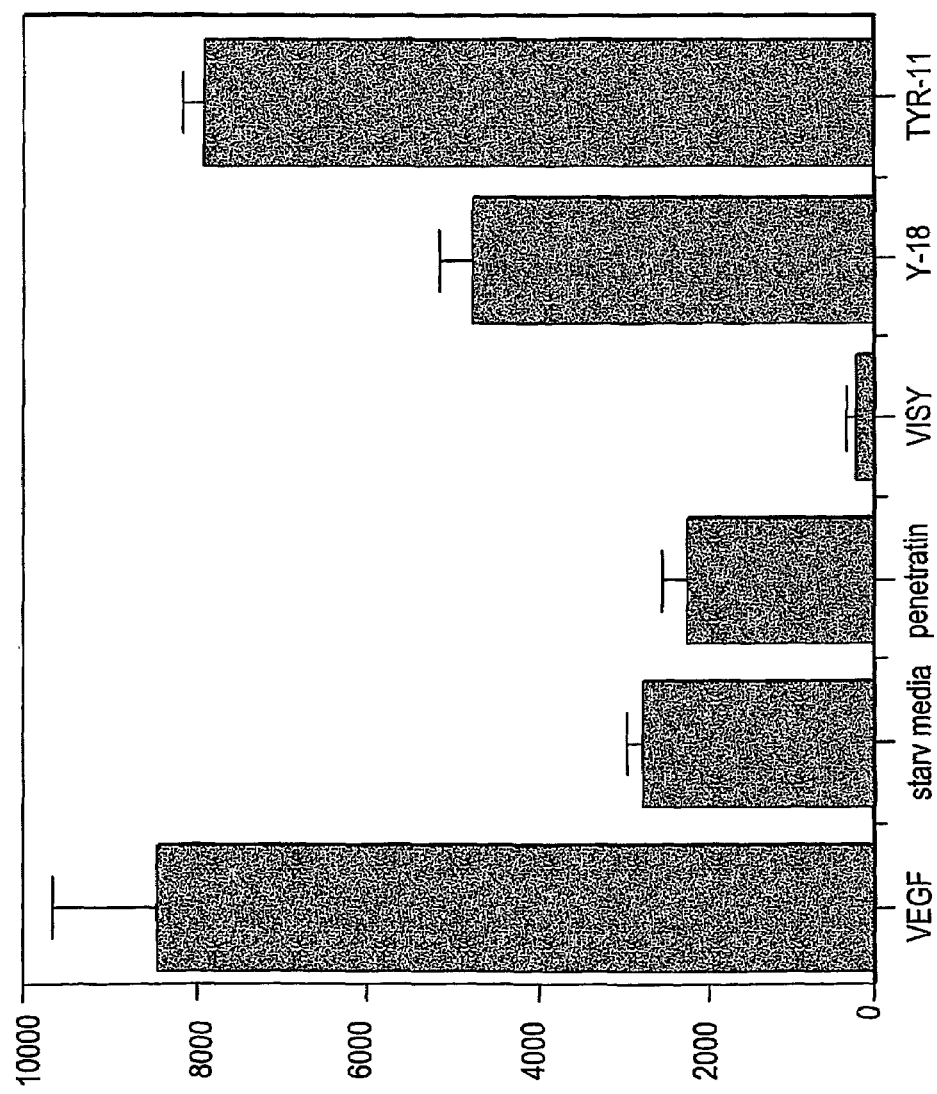

FIG. 24. Effect of integrin cytoplasmic domain binding peptides on cell proliferation. Serum-deprived cells were cultured for 24 h. and the proliferation was determined by [$^3$H] thymidine (1 μCi/ml) uptake measurements. In a positive control, VEGF was added back to serum-starved cells. Each experiment was performed three times with triplicates, and the results were expressed as the mean +/−SD.

Figure 25:
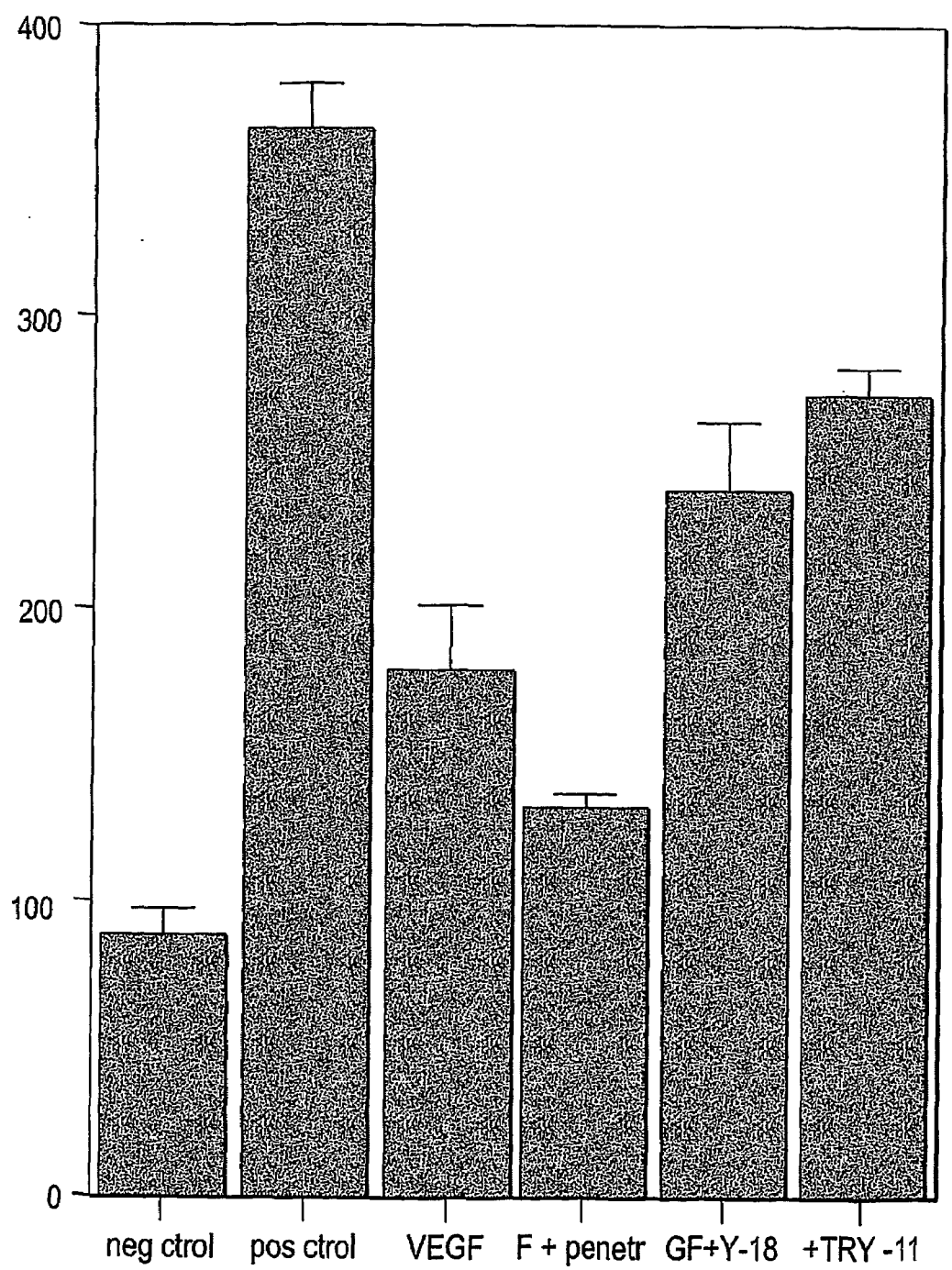

FIG. 25. Effect of penetratin peptide chimeras on endothelial cell migration. Cell migration assay were performed in a 48-well microchemotaxis chamber. Five random high-power fields (magnitude 40×) were counted in each well. The results show that both β3-integrin cytoplasmic domain-binding peptides (Y-18 and TYR-11) increase cell migration while penetratin does not affect the cells.

Figure 26:
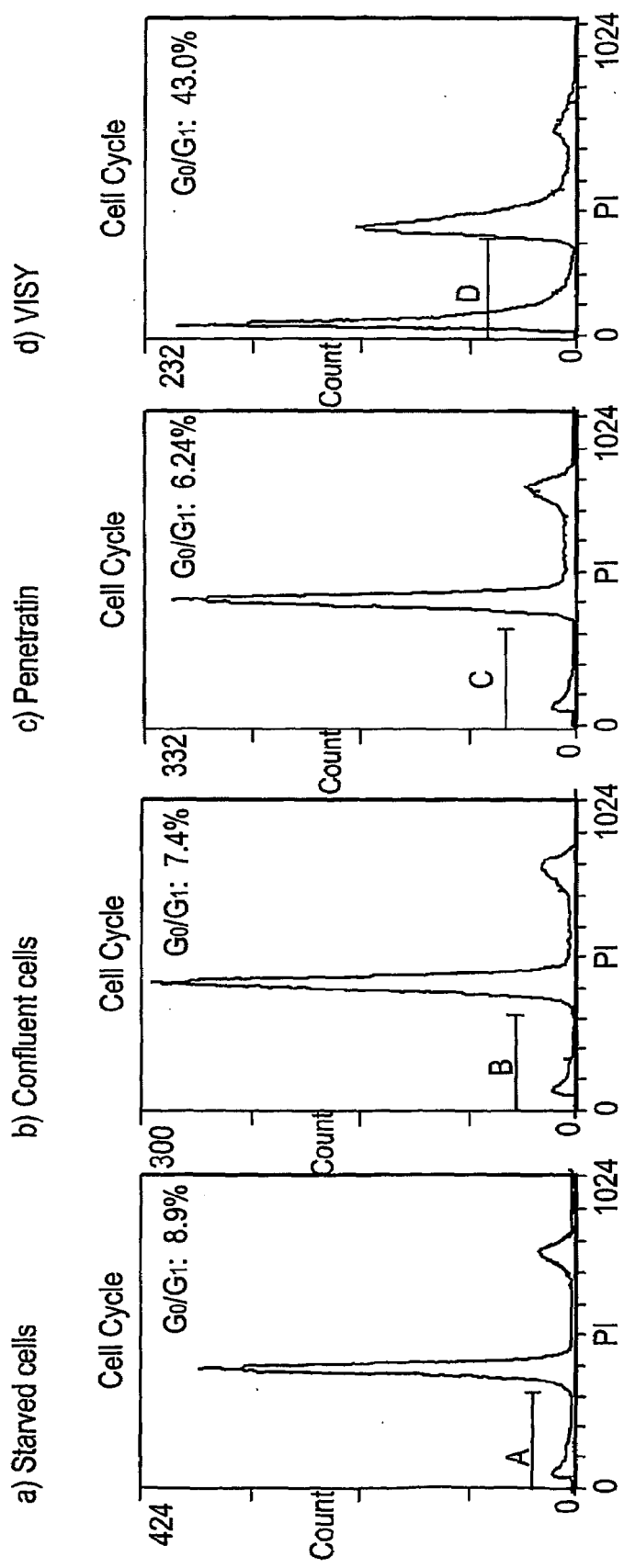

FIG. 26. Penetratin peptide chimera binding to the β5 cytoplasmic domain induces programmed cell death. $10^6$ HUVEC cells were harvested in complete media and 15 μM penetratin peptide chimeras were added to the cells. After four, eight and twelve hours the cells were stained with Propidium Iodide (PI) and induction of apoptosis was analyzed by cytometric analysis. (a) Profile obtained with starved cells after 24 h. (b) Confluent cells in complete media. (c) 15 μM of penetratin after four hours. (d) 15 μM of VISY-penetratin chimera after four hours. Cells analyzed after eight and twelve hours showed similar profiles for the percentage of $G_0/G_1$.

Figure 27:
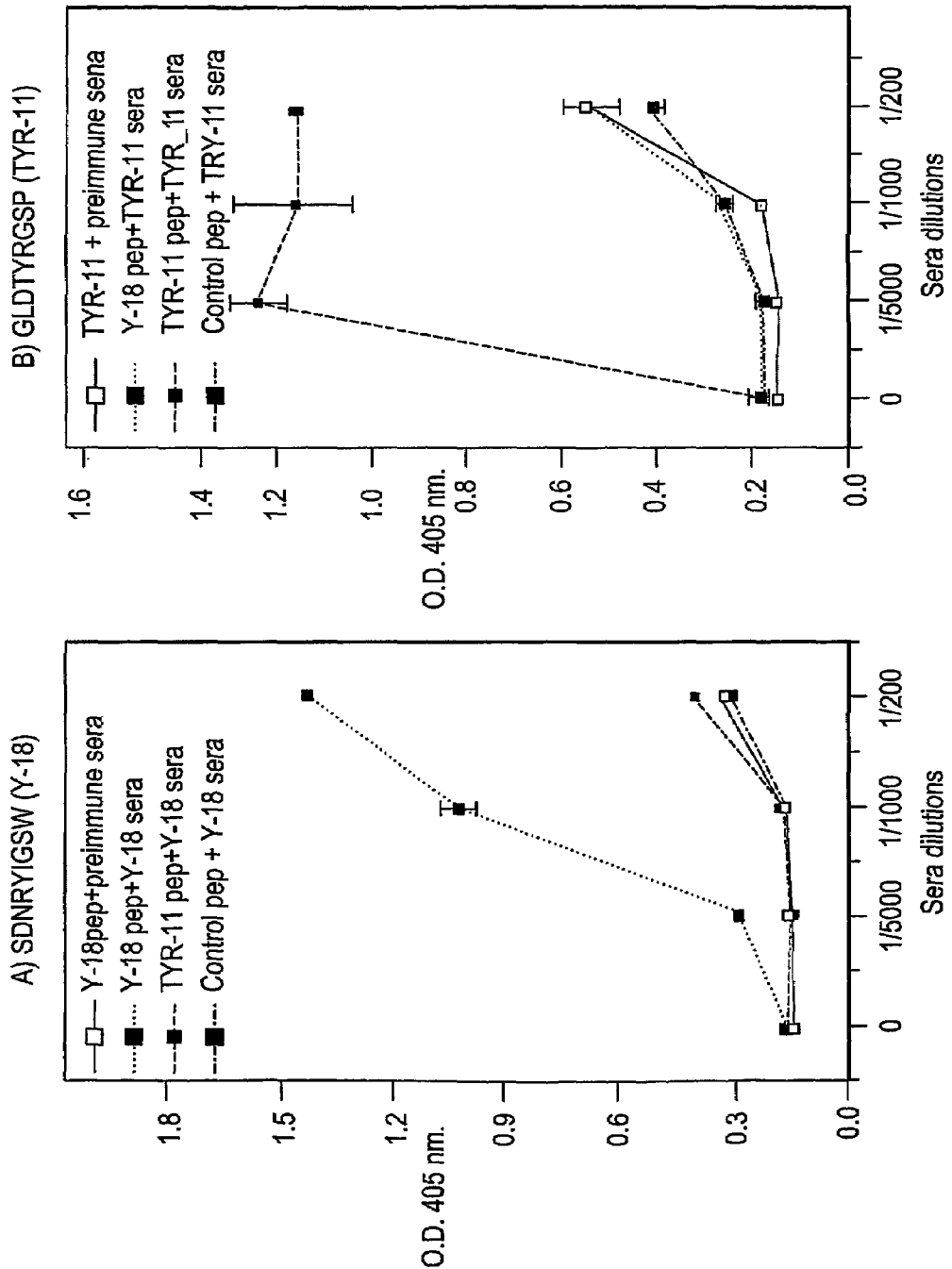

FIG. 27. Specificity of the antibodies raised against β3- or β5-selected phage (ELISA). Increasing dilutions of sera obtained after three immunizations with GLDTYRGSP (SEQ ID NO:30) or SDNRYIGSW (SEQ ID NO:31) conjugated to KLH were incubated on microtiter wells coated with 10 μg of SDNRYIGSW (SEQ ID NO:31, Y-18), GLD- TYRGSP (SEQ ID NO:30, TYR-11) or control peptides. Preimmune sera were used as controls. After incubation with HRP-goat anti-rabbit, OD was measured at 405 nm. The data represent the means from triplicate wells, with standard error less than 10%.

Figure 28:
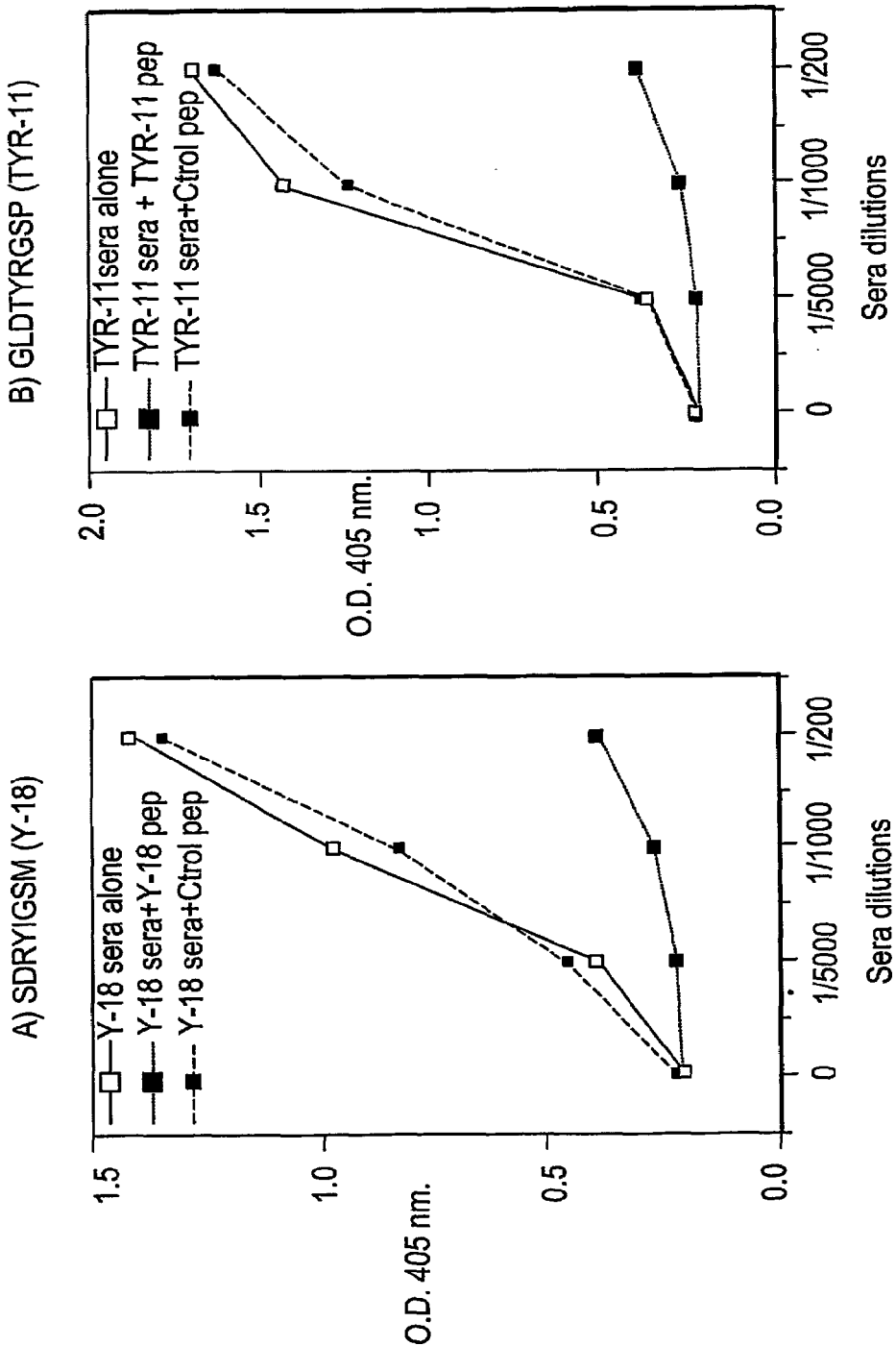

FIG. 28. Specificity of the antibodies raised against β3- or β5-selected phage (ELISA). Sera obtained after three immunizations with SDNRYIGSW (SEQ ID NO:31, Y-18) or GLDTYRGSP (SEQ ID NO:30, TYR-11) conjugated to KLH were incubated in microtiter wells coated with 10 μg of TYR-11 or Y-18. GLDTYRGSP (SEQ ID NO:30) or SDNRYIGSW (SEQ ID NO:31) and control peptides were added in solution. After incubation with HRP goat anti-rabbit, OD was measured at 405 nm. The data represent the means from triplicate wells, with standard error less than 10%. Peptides added in solution specifically block the reactivity with the immobilized peptides.

Figure 29:
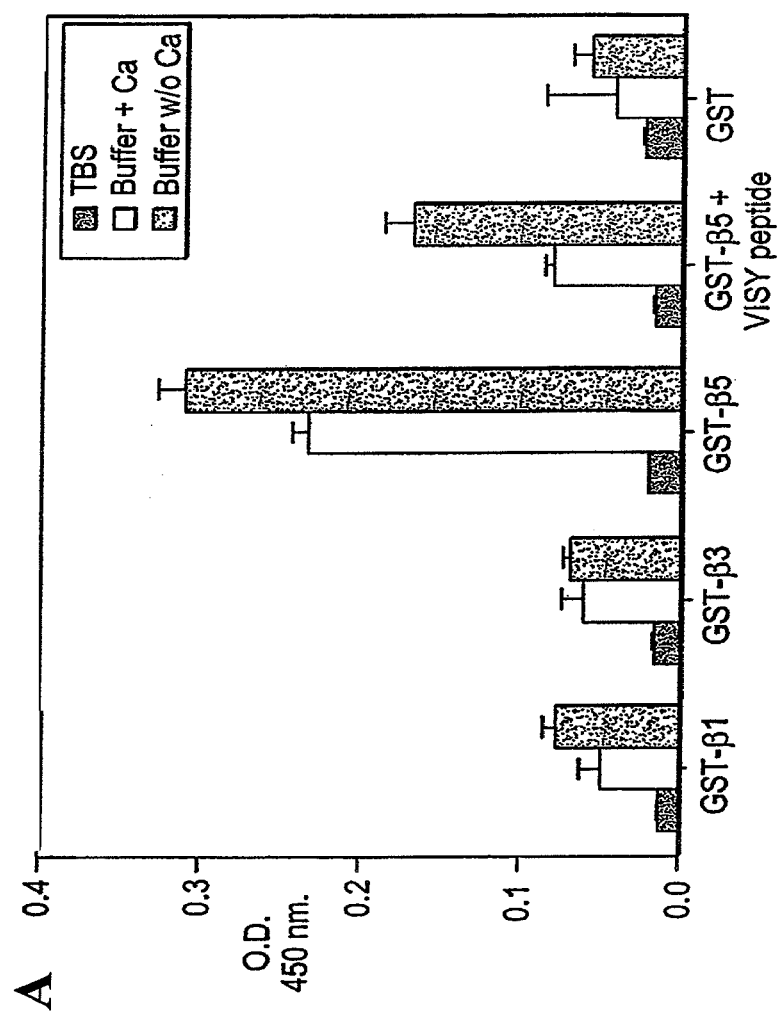

FIG. 29A. Competitive binding of Annexin V to β5 integrin with VISY peptide. Binding assays were performed by ELISA.

FIG. 29B. Relative levels of binding of anti-Annexin V antibody to purified Annexin V protein and VISY peptide.

Figure 30:
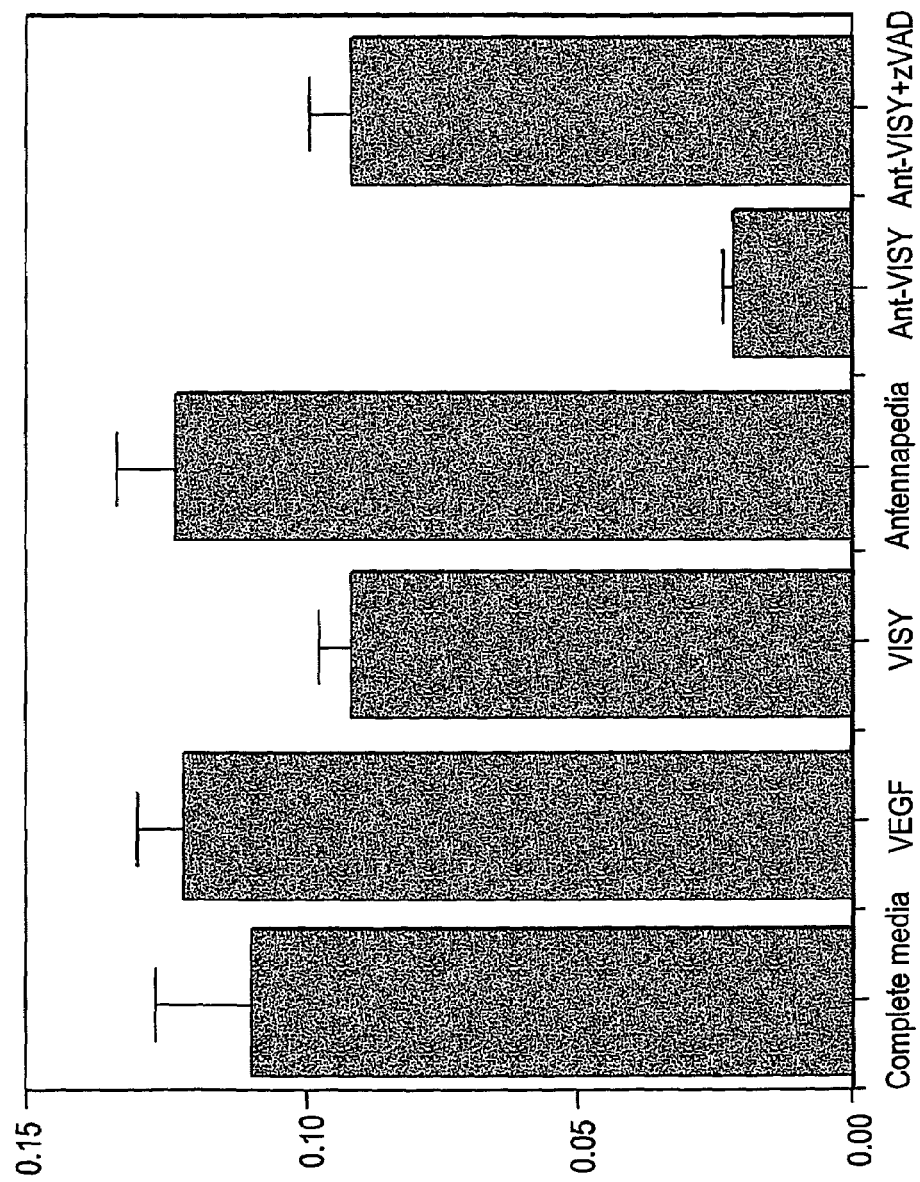

FIG. 30. Chimeric peptide containing VISY peptide linked to penetratin (antennapedia) induces apoptosis. VISY induced apoptosis was inhibited by addition of a caspase inhibitor (zVAD).

Figure 31:
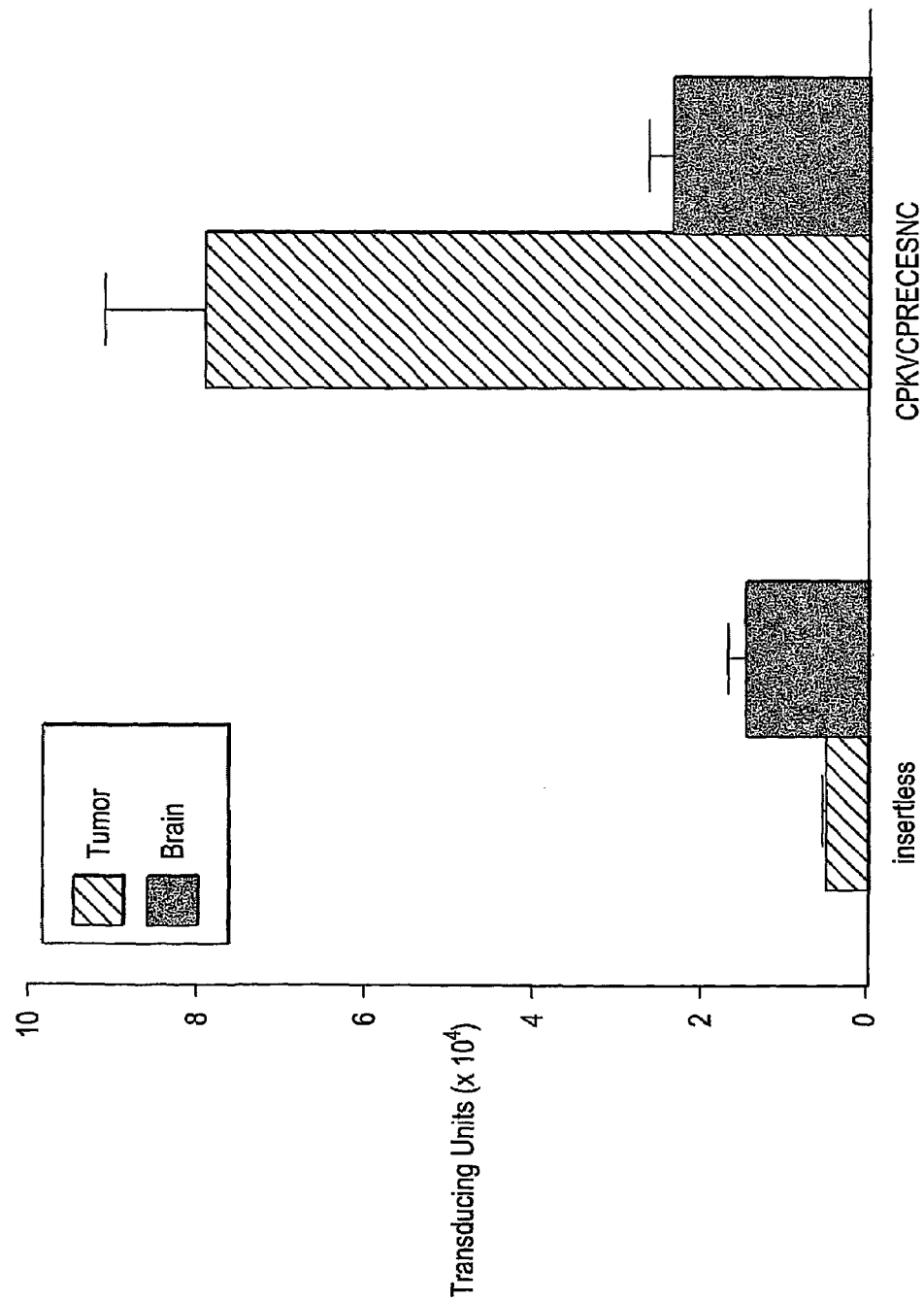

FIG. 31. APA-binding phage specifically bind tumors. Equal amounts of phage were injected into the tail veins of mice bearing MDA-MB-435-derived tumors and phage were recovered after perfusion. Mean values for phage recovered from the tumor or control tissue (brain) and the standard error from triplicate platings are shown.

Figure 32:
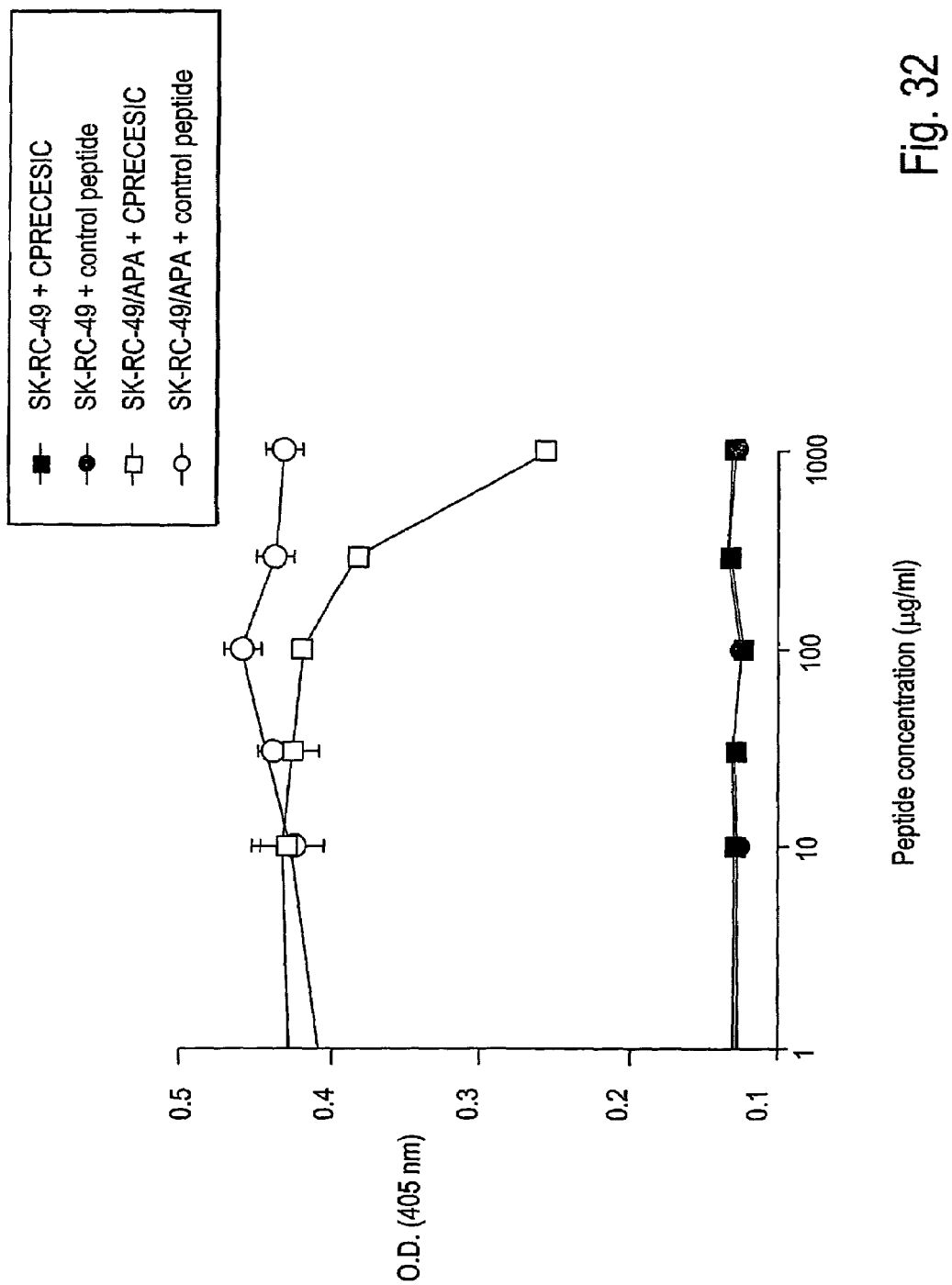

FIG. 32. CPRECESIC (SEQ ID NO:56) is a specific inhibitor of APA activity. APA enzyme activity was assayed in the presence of increasing concentrations of either GACVRLSACGA (SEQ ID NO:57) (control) or CPRECESIC (SEQ ID NO:56) peptide. The $IC_{50}$ for APA inhibition by CPRECESIC (SEQ ID NO:56) was estimated at 800 μM. Error bars are the standard error of the means of triplicate wells. The experiment was repeated three times with similar results.

Figure 33:
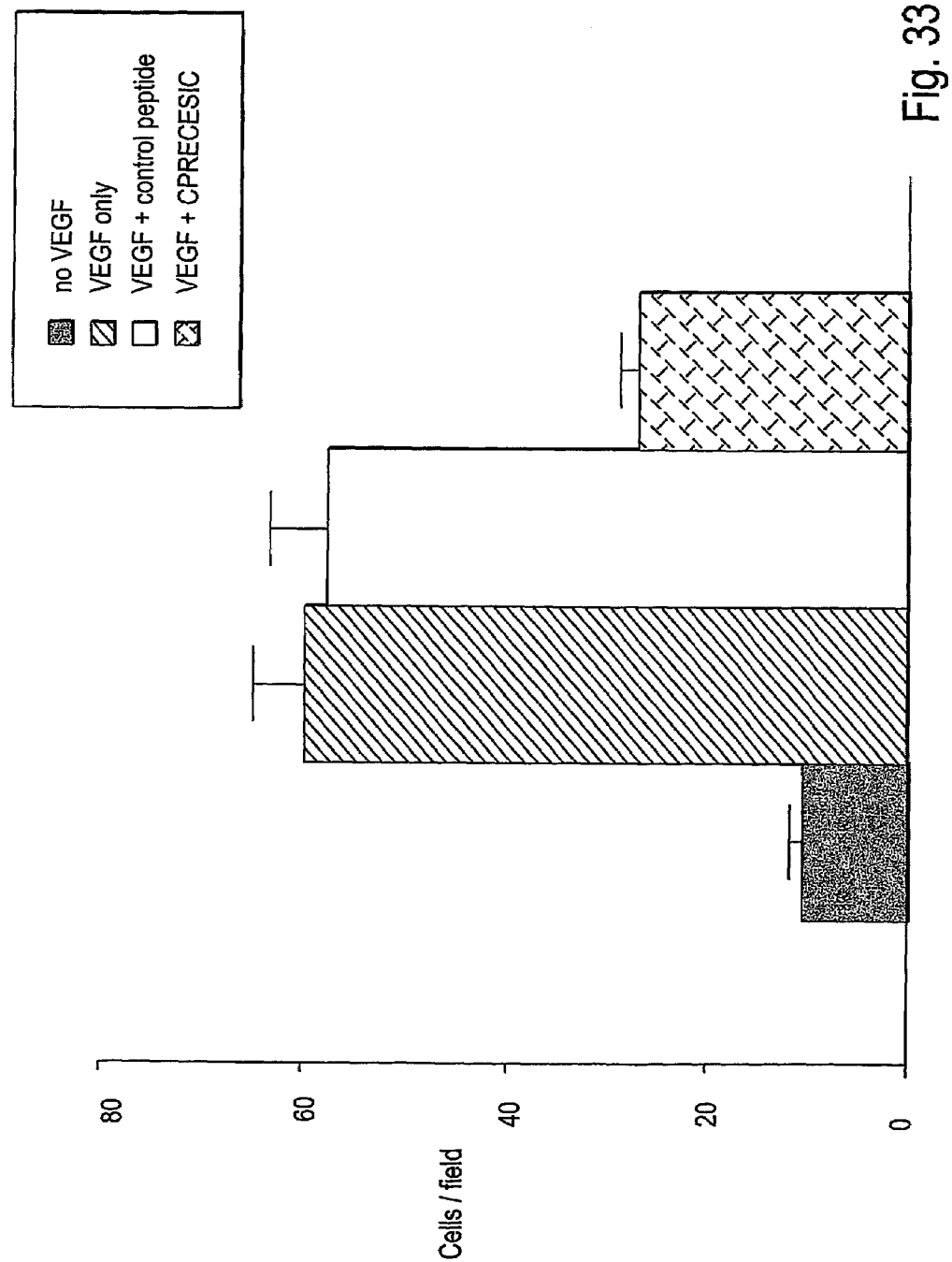

FIG. 33. CPRECESIC (SEQ ID NO:56) inhibits HUVEC migration. HUVECs were stimulated with VEGF-A (10 ng/ml). The assay was performed in a Boyden microchemotaxis chamber, and cells were allowed to migrate through an 8-μm pore filter for 5 h at 37° C. GACVRLSACGA (SEQ ID NO:57) (control) and CPRECESIC (SEQ ID NO:56) peptides were tested at 1 mM concentration. Migrated cells were stained and five high-power fields (magnitude 100×) for each microwell were counted. Error bars are the standard error of the means of triplicate microwells.

Figure 34:
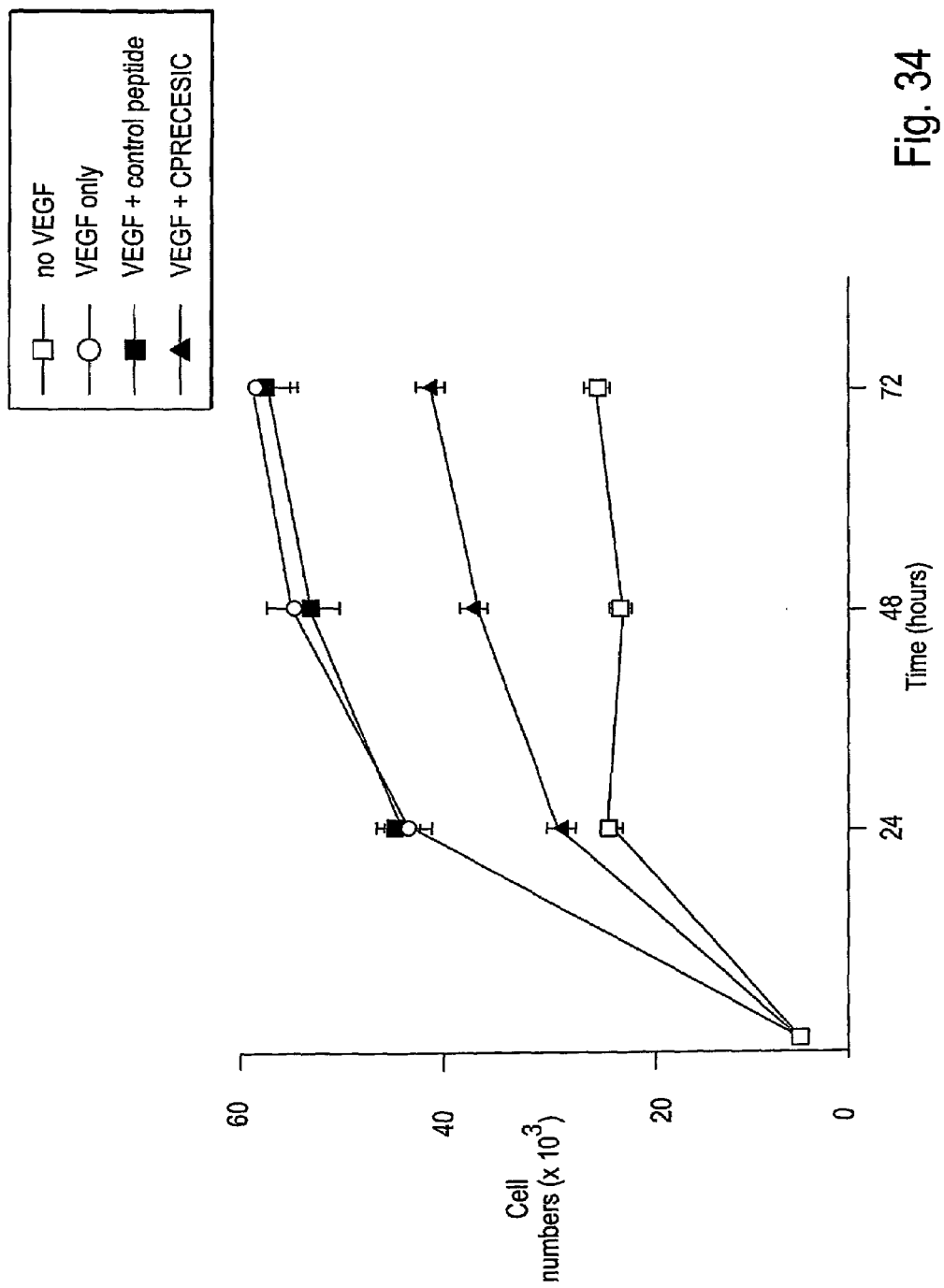

FIG. 34. CPRECESIC (SEQ ID NO:56) inhibits HUVEC proliferation. Cells were stimulated with VEGF-A (10 ng/ml), and growth was evaluated at the indicated times by a colorimetric assay based on crystal violet staining. Error bars are the standard error of the means of triplicate wells. Each experiment was repeated at least twice with similar results.

Figure 35:
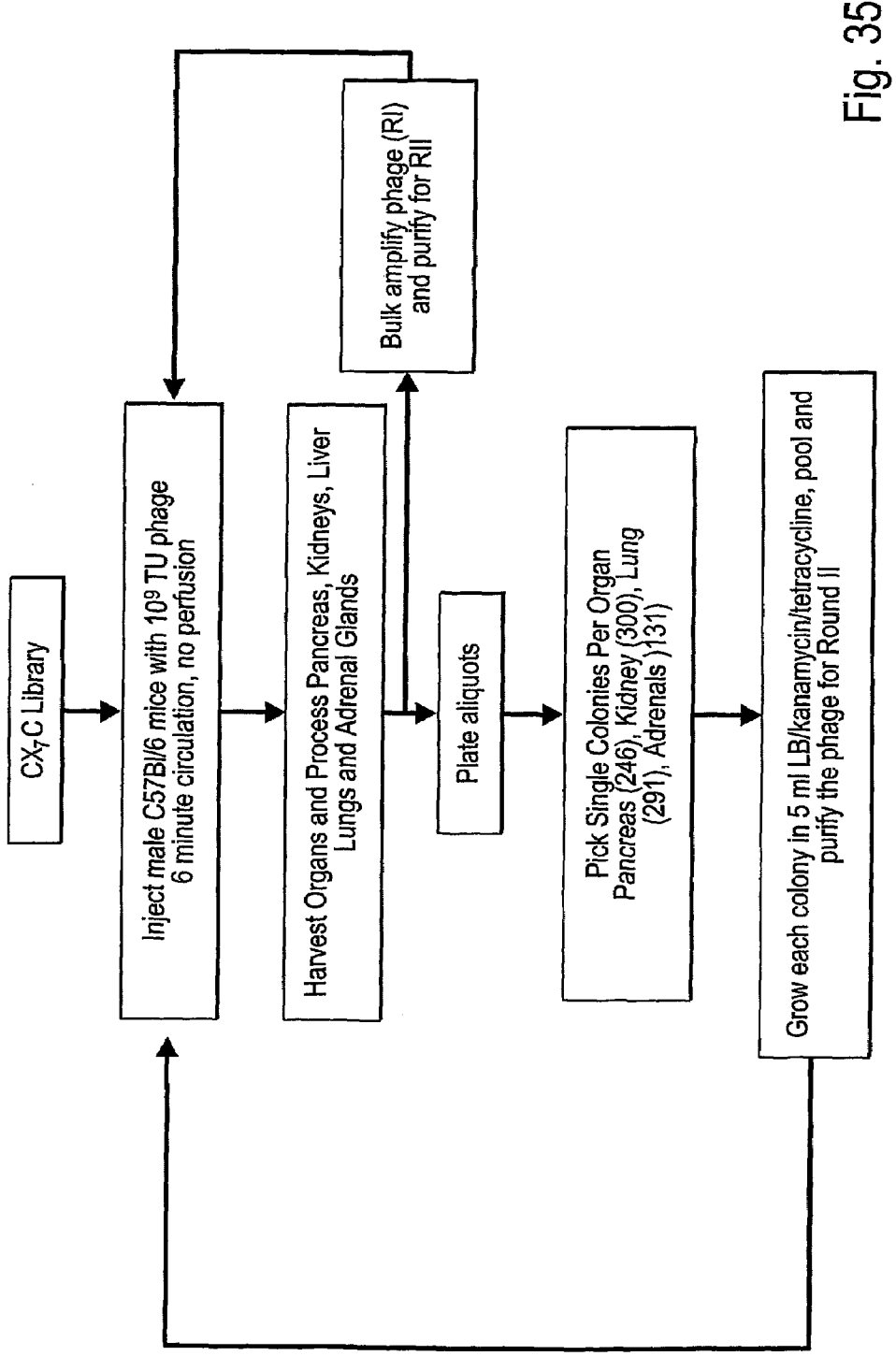

FIG. 35. Protocol for in vivo biopanning for phage targeted in mouse pancreas, kidneys, liver, lungs and adrenal gland.

FIG. 36. Protocol for recovery of phage by infection of *E. coli* or recovery of phage DNA by amplification and subcloning.

FIG. 37. Pancreatic islet targeting peptides and homologous proteins. Candidate endogenous proteins mimicked by the pancreatic islet targeting peptides CVSNPRWKC (SEQ ID NO:131), CVPRRWDVC (SEQ ID NO:128), CQHTSGRGC (SEQ ID NO:129) and CRARGWLLC (SEQ ID NO:130), identified by standard homology searches.

FIG. 38. Pancreatic islet targeting peptides and homologous proteins. Candidate endogenous proteins mimicked by the pancreatic islet targeting peptides CGGVHALRC (SEQ ID NO:98), CFNRTWIGC (SEQ ID NO:132) and CWSRQGGC (SEQ ID NO:134), identified by standard homology searches.

FIG. 39. Pancreatic islet targeting peptides and homologous proteins. Candidate endogenous proteins mimicked by the pancreatic islet targeting peptides CLASGMDAC (SEQ ID NO:138), CHDERTGRC (SEQ ID NO:139), CAHHALMEC (SEQ ID NO:140) and CMQGARTSC (SEQ ID NO:142), identified by standard homology searches.

FIG. 40. Pancreatic islet targeting peptides and homologous proteins. Candidate endogenous proteins mimicked by the pancreatic islet targeting peptides CHVLWSTRC (SEQ ID NO:135), CMSSPGVAC (SEQ ID NO:137) and CLGLLMAGC (SEQ ID NO:136), identified by standard homology searches.

DESCRIPTION OF ILLUSTRATIVE EMBODIMENTS

As used herein in the specification, "a" or "an" may mean one or more. As used herein in the claim(s), in conjunction with the word "comprising," the words "a" or "an" may mean one or more than one. As used herein "another" may mean at least a second or more of an item.

A "targeting peptide" is a peptide comprising a contiguous sequence of amino acids, which is characterized by selective localization to an organ, tissue or cell type. Selective localization may be determined, for example, by methods disclosed below, wherein the putative targeting peptide sequence is incorporated into a protein that is displayed on the outer surface of a phage. Administration to a subject of a library of such phage that have been genetically engineered to express a multitude of such targeting peptides of different amino acid sequence is followed by collection of one or more organs, tissues or cell types from the subject and identification of phage found in that organ, tissue or cell type. A phage expressing a targeting peptide sequence is considered to be selectively localized to a tissue or organ if it exhibits greater binding in that tissue or organ compared to a control tissue or organ. Preferably, selective localization of a targeting peptide should result in a two-fold or higher enrichment of the phage in the target organ, tissue or cell type, compared to a control organ, tissue or cell type. Selective localization resulting in at least a three-fold, four-fold, five-fold, six-fold, seven-fold, eight-fold, nine-fold, ten-fold or higher enrichment in the target organ compared to a control organ, tissue or cell type is more preferred. Alternatively, a phage expressing a targeting peptide sequence that exhibits selective localization preferably shows an increased enrichment in the target organ compared to a control organ when phage recovered from the target organ are reinjected into a second host for another round of screening. Further enrichment may be exhibited following a third round of screening. Another alternative means to determine selective localization is that phage expressing the putative target peptide preferably exhibit a two-fold, more preferably a three-fold or higher enrichment in the target organ compared to control phage that express a non-specific peptide or that have not been genetically engineered to express any putative target peptides. Another means to determine selective localization is that localization to the target organ of phage expressing the target peptide is at least partially blocked by the co-administration of a synthetic peptide containing the target peptide sequence. "Targeting peptide" and "homing peptide" are used synonymously herein.

A "phage display library" means a collection of phage that have been genetically engineered to express a set of putative targeting peptides on their outer surface. In preferred embodiments, DNA sequences encoding the putative targeting peptides are inserted in frame into a gene encoding a phage capsule protein. In other preferred embodiments, the putative targeting peptide sequences are in part random mixtures of all twenty amino acids and in part non-random. In certain preferred embodiments the putative targeting peptides of the phage display library exhibit one or more cysteine residues at fixed locations within the targeting peptide sequence. Cysteines may be used, for example, to create a cyclic peptide.

A "macromolecular complex" refers to a collection of molecules that may be random, ordered or partially ordered in their arrangement. The term encompasses biological organisms such as bacteriophage, viruses, bacteria, unicellular pathogenic organisms, multicellular pathogenic organisms and prokaryotic or eukaryotic cells. The term also encompasses non-living assemblages of molecules, such as liposomes, microcapsules, microparticles, magnetic beads and microdevices. The only requirement is that the complex contains more than one molecule. The molecules may be identical, or may differ from each other.

A "receptor" for a targeting peptide includes but is not limited to any molecule or macromolecular complex that binds to a targeting peptide. Non-limiting examples of receptors include peptides, proteins, glycoproteins, lipoproteins, epitopes, lipids, carbohydrates, multi-molecular structures, a specific conformation of one or more molecules and a morphoanatomic entity. In preferred embodiments, a "receptor" is a naturally occurring molecule or complex of molecules that is present on the lumenal surface of cells forming blood vessels within a target organ, tissue or cell type.

A "subject" refers generally to a mammal. In certain preferred embodiments, the subject is a mouse or rabbit. In even more preferred embodiments, the subject is a human.

Phage Display

Recently, an in vivo selection system was developed using phage display libraries to identify organ, tissue or cell type-targeting peptides in a mouse model system. Phage display libraries expressing transgenic peptides on the surface of bacteriophage were initially developed to map epitope binding sites of immunoglobulins (Smith, G P and Scott, J K, 1985. *Science*, 228:1315-1317, Smith, G P and Scott, J K, 1993. *Meth. Enzymol.* 21:228-257). Such libraries can be generated by inserting random oligonucleotides into cDNAs encoding a phage surface protein, generating collections of phage particles displaying unique peptides in as many as $10^9$ permutations. (Pasqualini, R. and Ruoslahti, E. 1996, *Nature*, 380: 364-366; Arap et al, 1998a; Arap et al., 1998b, Curr. Opin. Oncol. 10:560-565).

Intravenous administration of phage display libraries to mice was followed by the recovery of phage from individual organs (Pasqualini and Ruoslahti, 1996). Phage were recovered that were capable of selective homing to the vascular beds of different mouse organs, tissues or cell types, based on the specific targeting peptide sequences expressed on the outer surface of the phage (Pasqualini and Ruoslahti, 1996). A variety of organ and tumor-homing peptides have been identified by this method (Rajotte et al., 1998, *J. Clin. Invest.* 102:430-437; Rajotte et al, 1999, *J. Biol. Chem.* 274:11593-11598; Koivunen et al., 1999a, *Nature Biotechnol.* 17: 768-774; Burg M, et al., 1999, *Cancer Res.* 58:2869-2874; Pasqualini, 1999, *Quart. J. Nucl. Med.* 43:159-162). Each of those targeting peptides bound to different receptors that were selectively expressed on the vasculature of the mouse target tissue (Pasqualini, 1999; Pasqualini et al., 2000; Folkman J. *Nature Biotechnol.* 15:510, 1997; Folkman J. *Nature Med* 1:27-31, 1995). Tumor-homing peptides bound to receptors that were upregulated in the tumor angiogenic vasculature of mice (Brooks, P. C., et al. *Cell* 79:1157-1164, 1994b; Pasqualini et al., 2000). In addition to identifying individual targeting peptides selective for an organ, tissue or cell type (Pasqualini and Ruoslahti, 1996; Arap et al, 1998a; Koivunen et al., *Methods Mol. Biol.* 129: 3-17, 1999b), this system has been used to identify endothelial cell surface markers that are expressed in mice in vivo (Rajotte and Ruoslahti, 1999).

Attachment of therapeutic agents to targeting peptides resulted in the selective delivery of the agent to a desired organ, tissue or cell type in the mouse model system. Targeted delivery of chemotherapeutic agents and proapoptotic peptides to receptors located in tumor angiogenic vasculature resulted in a marked increase in therapeutic efficacy and a decrease in systemic toxicity in tumor bearing mouse models (Arap et al., 1998a, 1998b; Ellerby et al., *Nature Med* 9:1032-1038, 1999).

The methods described herein for identification of targeting peptides involve the in vivo administration of phage display libraries. Various methods of phage display and methods for producing diverse populations of peptides are well known in the art. For example, U.S. Pat. Nos. 5,223,409; 5,622,699 and 6,068,829 disclose methods for preparing a phage library. The phage display technique involves genetically manipulating bacteriophage so that small peptides can be expressed on their surface (Smith and Scott, 1985, 1993). The potential range of applications for this technique is quite broad, and the past decade has seen considerable progress in the construction of phage-displayed peptide libraries and in the development of screening methods in which the libraries are used to isolate peptide ligands. For example, the use of peptide libraries has made it possible to characterize interacting sites and receptor-ligand binding motifs within many proteins, such as antibodies involved in inflammatory reactions or integrins that mediate cellular adherence. This method has also been used to identify novel peptide ligands that serve as leads to the development of peptidomimetic drugs or imaging agents (Arap et al., 1998a). In addition to peptides, larger protein domains such as single-chain antibodies can also be displayed on the surface of phage particles (Arap et al., 1998a).

Targeting peptides selective for a given organ, tissue or cell type can be isolated by "biopanning" (Pasqualini and Ruoslahti, 1996; Pasqualini, 1999). In brief, a library of phage containing putative targeting peptides is administered to an animal or human and samples of organs, tissues or cell types containing phage are collected. In preferred embodiments utilizing filamentous phage, the phage may be propagated in vitro between rounds of biopanning in pilus-positive bacteria. The bacteria are not lysed by the phage but rather secrete multiple copies of phage that display a particular insert. Phage that bind to a target molecule can be eluted from the target organ, tissue or cell type and then amplified by growing them in host bacteria. If desired, the amplified phage can be administered to a host and samples of organs, tissues or cell types again collected. Multiple rounds of biopanning can be performed until a population of selective binders is obtained. The amino acid sequence of the peptides is determined by sequencing the DNA corresponding to the targeting peptide insert in the phage genome. The identified targeting peptide can then be produced as a synthetic peptide by standard protein chemistry techniques (Arap et al., 1998a, Smith and Scott, 1985). This approach allows circulating targeting peptides to be detected in an unbiased functional assay, without any preconceived notions about the nature of their target. Once a candidate target is identified as the receptor of a targeting peptide, it can be isolated, purified and cloned by using standard biochemical methods (Pasqualini, 1999; Rajotte and Ruoslahti, 1999).

In certain embodiments, a subtraction protocol is used with to further reduce background phage binding. The purpose of subtraction is to remove phage from the library that bind to cells other than the cell of interest, or that bind to inactivated cells. In alternative embodiments, the phage library may be prescreened against a subject who does not possess the targeted cell, tissue or organ. For example, placenta-binding peptides may be identified after prescreening a library against a male or non-pregnant female subject After subtraction the library may be screened against the cell, tissue or organ of interest. In another alternative embodiment, an unstimulated, quiescent cell type, tissue or organ may be screened against the library and binding phage removed. The cell line, tissue or organ is then activated, for example by administration of a hormone, growth factor, cytokine or chemokine and the activated cell type, tissue or organ screened against the subtracted phage library.

Other methods of subtraction protocols are known and may be used in the practice of the present invention, for example as disclosed in U.S. Pat. Nos. 5,840,841, 5,705,610, 5,670,312 and 5,492,807.

Choice of Phage Display System.

Previous in vivo selection studies performed in mice preferentially employed libraries of random peptides expressed as fusion proteins with the gene III capsule protein in the fUSE5 vector (Pasqualini and Ruoslahti, 1996). The number and diversity of individual clones present in a given library is a significant factor for the success of in vivo selection. It is preferred to use primary libraries, which are less likely to have an over-representation of defective phage clones (Koivunen et al., 1999b). The preparation of a library should be optimized to between $10^8$-$10^9$ transducing units (T.U.)/ml. In certain embodiments, a bulk amplification strategy is applied between each round of selection.

Phage libraries displaying linear, cyclic, or double cyclic peptides may be used within the scope of the present invention. However, phage libraries displaying 3 to 10 random residues in a cyclic insert ($CX_{3-10}C$) are preferred, since single cyclic peptides tend to have a higher affinity for the target organ than linear peptides. Libraries displaying double-cyclic peptides (such as $CX_3C$ $X_3CX_3C$; Rojotte et al., 1998) have been successfully used. However, the production of the cognate synthetic peptides, although possible, can be complex due to the multiple conformers with different disulfide bridge arrangements.

Identification of Homing Peptides and Receptors by in vivo Phage Display in Mice.

In vivo selection of peptides from phage-display peptide libraries administered to mice has been used to identify targeting peptides selective for normal mouse brain, kidney, lung, skin, pancreas, retina, intestine, uterus, prostate, and adrenal gland (Pasqualini and Ruoslahti, 1996; Pasqualini, 1999; Rajotte et al., 1998). These results show that the vascular endothelium of normal organs is sufficiently heterogeneous to allow differential targeting with peptide probes (Pasqualini and Ruoslahti, 1996; Rajotte et al., 1998). A means of identifying peptides that home to the angiogenic vasculature of tumors has been devised, as described below. A panel of peptide motifs that target the blood vessels of tumor xenografts in nude mice has been assembled (Arap et al., 1998a; reviewed in Pasqualini, 1999). These motifs include the sequences RGD-4C, NGR, and GSL. The RGD-4C peptide has previously been identified as selectively binding $\alpha v$ integrins and has been shown to home to the vasculature of tumor xenografts in nude mice (Arap et al., 1998a, 1998b; Pasqualini et al., Nature Biotechnol 15: 542-546, 1997).

The receptors for the tumor homing RGD4C targeting peptide has been identified as $\alpha v$ integrins (Pasqualini et al., 1997). The $\alpha v$ integrins play an important role in angiogenesis. The $\alpha v \beta 3$ and $\alpha v \beta 5$ integrins are absent or expressed at low levels in normal endothelial cells but are induced in angiogenic vasculature of tumors (Brooks P C, Clark R A, Cheresh D A. Science, 264: 569-571, 1994, 1994; Hammes H P, Brownlee M, Jonczyk A, Sutter A, and Preissner K T. Nature Med. 2: 529-533, 1996.). Aminopeptidase N/CD13 has recently been identified as an angiogenic receptor for the NGR motif (Burg, M. A., et al. Cancer Res. 59, 2869-2874, 1999.). Aminopeptidase N/CD13 is strongly expressed not only in the angiogenic blood vessels of prostate cancer in TRAMP mice but also in the normal epithelial prostate tissue.

Tumor-homing phage co-localize with their receptors in the angiogenic vasculature of tumors but not in non-angiogenic blood vessels in normal tissues (Arap et al., 1998b). Immunohistochemical evidence shows that vascular targeting phage bind to human tumor blood vessels in tissue sections (Pasqualini et al., 2000) but not to normal blood vessels. A negative control phage with no insert (fd phage) did not bind to normal or tumor tissue sections. The expression of the angiogenic receptors was evaluated in cell lines, in non-proliferating blood vessels and in activated blood vessels of tumors and other angiogenic tissues such as corpus luteum. Flow cytometry and immunohistochemistry showed that these receptors are expressed in a number of tumor cells and in activated HUVECs (data not shown). The angiogenic receptors were not detected in the vasculature of normal organs of mouse or human tissues.

The distribution of these receptors was analyzed by immunohistochemistry in tumor cells, tumor vasculature, and normal vasculature. Alpha v integrins, CD13, aminopeptidase A, NG2, and MMP-2/MMP-9—the known receptors in tumor blood vessels—are specifically expressed in angiogenic endothelial cells and pericytes of both human and murine origin. Angiogenic neovasculature expresses markers that are either expressed at very low levels or not at all in non-proliferating endothelial cells (not shown).

The markers of angiogenic endothelium include receptors for vascular growth factors, such as specific subtypes of VEGF and basic FGF receptors, and $\alpha v$ integrins, among many others (Mustonen T and Alitalo K. J. Cell Biol. 129: 895-898, 1995.). Thus far, identification and isolation of novel molecules characteristic of angiogenic vasculature has been slow, mainly because endothelial cells undergo dramatic phenotypic changes when grown in culture (Watson et al., Science, 268:447-448, 1995).

Many of these tumor vascular markers are proteases and some of the markers also serve as viral receptors. Alpha v integrins are receptors for adenoviruses (Wickham et al., Cancer Immunol. Immunother. 45:149-151, 1997c) and CD13 is a receptor for coronaviruses (Look et al. N. J. Clin. Invest. 83:1299-1307, 1989.). MMP-2 and MMP-9 are receptors for echoviruses (Koivunen et al., 1999a). Aminopeptidase A also appears to be a viral receptor. Bacteriophage may use the same cellular receptors as eukaryotic viruses. These findings suggest that receptors isolated by in vivo phage display will have cell internalization capability, a key feature for utilizing the identified peptide motifs as targeted gene therapy carriers.

Targeted Delivery

Peptides that home to tumor vasculature have been coupled to cytotoxic drugs or proapoptotic peptides to yield compounds that were more effective and less toxic than the parental compounds in experimental models of mice bearing tumor xenografts (Arap et al., 1998a; Ellerby et al, 1999). The insertion of the RGD-4C peptide into a surface protein of an adenovirus has produced an adenoviral vector that may be used for tumor targeted gene therapy (Arap et al., 1998b).

BRASIL

In preferred embodiments, separation of phage bound to the cells of a target organ, tissue or cell type from unbound phage is achieved using the BRASIL technique (PCT Patent Application PCT/US01/28124 entitled, "Biopanning and Rapid Analysis of Selective Interactive Ligands (BRASIL)" by Arap et al., filed Sep. 7, 2001, incorporated herein by reference in its entirety). In BRASIL (Biopanning and Rapid Analysis of Soluble Interactive Ligands), an organ, tissue or cell type is gently separated into cells or small clumps of cells that are suspended in an aqueous phase. The aqueous phase is layered over an organic phase of appropriate density and centrifuged. Cells attached to bound phage are pelleted at the bottom of the centrifuge tube, while unbound phage remain in the aqueous phase. This allows a more efficient separation of bound from unbound phage, while maintaining the binding interaction between phage and cell. BRASIL may be performed in an in vivo protocol, in which organs, tissues or cell types are exposed to a phage display library by intravenous administration, or by an ex vivo protocol, where the cells are exposed to the phage library in the aqueous phase before centrifugation.

Preparation of Large Scale Primary Libraries

In certain embodiments, primary phage libraries are amplified before injection into a human subject. A phage library is prepared by ligating targeting peptide-encoding sequences into a phage vector, such as fUSE5. The vector is transformed into pilus negative host *E. coli* such as strain MC1061. The bacteria are grown overnight and then aliquots are frozen to provide stock for library production. Use of pilus negative bacteria avoids the bias in libraries that arises from differential infection of pilus positive bacteria by different targeting peptide sequences.

To freeze, bacteria are pelleted from two thirds of a primary library culture (5 liters) at 4000×g for 10 min. Bacteria are resuspended and washed twice with 500 ml of 10% glycerol in water, then frozen in an ethanol/dry ice bath and stored at −80° C.

For amplification, 1.5 ml of frozen bacteria are inoculated into 5 liters of LB medium with 20 µg/ml tetracycline and grown overnight. Thirty minutes after inoculation, a serial dilution is plated on LB/tet plates to verify the viability of the culture. If the number of viable bacteria is less than 5-10 times the number of individual clones in the library ($1-2\times10^8$) the culture is discarded.

After growing the bacterial culture overnight, phage are precipitated. About ¼ to ⅓ of the bacterial culture is kept growing overnight in 5 liters of fresh medium and the cycle is repeated up to 5 times. Phage are pooled from all cycles and used for injection into human subjects.

Human Subjects

The methods used for phage display biopanning in the mouse model system require substantial improvements for use with humans. Techniques for biopanning in human subjects are disclosed in PCT Patent Application PCT/US01/28044, filed Sep. 7, 2001, the entire text of which is incorporated herein by reference. In general, humans suitable for use with phage display are either brain dead or terminal wean patients. The amount of phage library (preferably primary library) required for administration must be significantly increased, preferably to $10^{14}$ TU or higher, preferably administered intravenously in approximately 200 ml of Ringer lactate solution over about a 10 minute period.

The amount of phage required for use in humans has required substantial improvement of the mouse protocol, increasing the amount of phage available for injection by five orders of magnitude. To produce such large phage libraries, the transformed bacterial pellets recovered from up to 500 to 1000 transformations are amplified up to 10 times in the bacterial host, recovering the phage from each round of amplification and adding LB Tet medium to the bacterial pellet for collection of additional phage. The phage inserts remain stable under these conditions and phage may be pooled to form the large phage display library required for humans.

Samples of various organs and tissues are collected starting approximately 15 minutes after injection of the phage library. Samples are processed as described below and phage collected from each organ, tissue or cell type of interest for DNA sequencing to determine the amino acid sequences of targeting peptides.

With humans, the opportunities for enrichment by multiple rounds of biopanning are severely restricted, compared to the mouse model system. A substantial improvement in the biopanning technique involves polyorgan targeting.

Polyorgan Targeting

In the standard protocol for phage display biopanning, phage from a single organ are collected, amplified and injected into a new host, where tissue from the same organ is collected for phage rescue and a new round of biopanning. This protocol is feasible in animal subjects. However, the limited availability and expense of processing samples from humans requires an improvement in the protocol.

It is possible to pool phage collected from multiple organs after a first round of biopanning and inject the pooled sample into a new subject, where each of the multiple organs may be collected again for phage rescue. The polyorgan targeting protocol may be repeated for as many rounds of biopanning as desired. In this manner, it is possible to significantly reduce the number of subjects required for isolation of targeting peptides for multiple organs, while still achieving substantial enrichment of the organ-homing phage.

In preferred embodiments, phage are recovered from human organs, tissues or cell types after injection of a phage display library into a human subject. In certain embodiments, phage may be recovered by exposing a sample of the organ, tissue or cell type to a pilus positive bacterium, such as *E. coli* K91. In alternative embodiments, phage may be recovered by amplifying the phage inserts, ligating the inserts to phage DNA and producing new phage from the ligated DNA.

Proteins and Peptides

In certain embodiments, the present invention concerns novel compositions comprising at least one protein or peptide. As used herein, a protein or peptide generally refers, but is not limited to, a protein of greater than about 200 amino acids, up to a full length sequence translated from a gene; a polypeptide of greater than about 100 amino acids; and/or a peptide of from about 3 to about 100 amino acids. For convenience, the terms "protein," "polypeptide" and "peptide" are used interchangeably herein.

In certain embodiments the size of at least one protein or peptide may comprise, but is not limited to, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 925, about 950, about 975, about 1000, about 1100, about 1200, about 1300, about 1400, about 1500, about 1750, about 2000, about 2250, about 2500 or greater amino acid residues.

As used herein, an "amino acid residue" refers to any naturally occurring amino acid, any amino acid derivative or any amino acid mimic known in the art. In certain embodiments, the residues of the protein or peptide are sequential, without any non-amino acid interrupting the sequence of amino acid residues. In other embodiments, the sequence may comprise one or more non-amino acid moieties. In particular embodiments, the sequence of residues of the protein or peptide may be interrupted by one or more non-amino acid moieties.

Accordingly, the term "protein or peptide" encompasses amino acid sequences comprising at least one of the 20 common amino acids found in naturally occurring proteins, or at least one modified or unusual amino acid, including but not limited to those shown on Table 1 below.

TABLE 1

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

Proteins or peptides may be made by any technique known to those of skill in the art, including the expression of proteins, polypeptides or peptides through standard molecular biological techniques, the isolation of proteins or peptides from natural sources, or the chemical synthesis of proteins or peptides. The nucleotide and protein, polypeptide and peptide sequences corresponding to various genes have been previously disclosed, and may be found at computerized databases known to those of ordinary skill in the art. One such database is the National Center for Biotechnology Information's Genbank and GenPept databases (world wide web at ncbi.nlm.nih.gov/). The coding regions for known genes may be amplified and/or expressed using the techniques disclosed herein or as would be know to those of ordinary skill in the art. Alternatively, various commercial preparations of proteins, polypeptides and peptides are known to those of skill in the art.

Peptide Mimetics

Another embodiment for the preparation of polypeptides according to the invention is the use of peptide mimetics. Mimetics are peptide-containing molecules that mimic elements of protein secondary structure. See, for example, Johnson et al., "Peptide Turn Mimetics" in BIOTECHNOLOGY AND PHARMACY, Pezzuto et al., Eds., Chapman and Hall, New York (1993), incorporated herein by reference. The underlying rationale behind the use of peptide mimetics is that the peptide backbone of proteins exists chiefly to orient amino acid side chains in such a way as to facilitate molecular interactions, such as those of antibody and antigen. A peptide mimetic is expected to permit molecular interactions similar to the natural molecule. These principles may be used to engineer second generation molecules having many of the natural properties of the targeting peptides disclosed herein, but with altered and even improved characteristics.

Fusion Proteins

Other embodiments of the present invention concern fusion proteins. These molecules generally have all or a substantial portion of a targeting peptide, linked at the N- or C-terminus, to all or a portion of a second polypeptide or protein. For example, fusions may employ leader sequences from other species to permit the recombinant expression of a protein in a heterologous host. Another useful fusion includes the addition of an immunologically active domain, such as an antibody epitope, to facilitate purification of the fusion protein. Inclusion of a cleavage site at or near the fusion junction will facilitate removal of the extraneous polypeptide after purification. Other useful fusions include linking of functional domains, such as active sites from enzymes, glycosylation domains, cellular targeting signals or transmembrane regions. In preferred embodiments, the fusion proteins of the instant invention comprise a targeting peptide linked to a therapeutic protein or peptide. Examples of proteins or peptides that may be incorporated into a fusion protein include cytostatic proteins, cytocidal proteins, pro-apoptosis agents, anti-angiogenic agents, hormones, cytokines, growth factors, peptide drugs, antibodies, Fab fragments antibodies, antigens, receptor proteins, enzymes, lectins, MHC proteins, cell adhesion proteins and binding proteins. These examples are not meant to be limiting and it is contemplated that within the scope of the present invention virtually and protein or peptide could be incorporated into a fusion protein comprising a targeting peptide. Methods of generating fusion proteins are well known to those of skill in the art. Such proteins can be produced, for example, by chemical attachment using bifunctional cross-linking reagents, by de novo synthesis of the complete fusion protein, or by attachment of a DNA sequence encoding the targeting peptide to a DNA sequence encoding the second peptide or protein, followed by expression of the intact fusion protein.

Protein Purification

In certain embodiments a protein or peptide may be isolated or purified. Protein purification techniques are well known to those of skill in the art. These techniques involve, at one level, the homogenization and crude fractionation of the cells, tissue or organ to polypeptide and non-polypeptide fractions. The protein or polypeptide of interest may be further purified using chromatographic and electrophoretic techniques to achieve partial or complete purification (or purification to homogeneity). Analytical methods particularly suited to the preparation of a pure peptide are ion-exchange chromatography, gel exclusion chromatography, polyacrylamide gel electrophoresis, affinity chromatography, immunoaffinity chromatography and isoelectric focusing. An example of receptor protein purification by affinity chromatography is disclosed in U.S. Pat. No. 5,206,347, the entire text of which is incorporated herein by reference. A particularly efficient method of purifying peptides is fast performance liquid chromatography (FPLC) or even high performance liquid chromatography (HPLC).

A purified protein or peptide is intended to refer to a composition, isolatable from other components, wherein the protein or peptide is purified to any degree relative to its naturally-obtainable state. An isolated or purified protein or peptide, therefore, also refers to a protein or peptide free from the environment in which it may naturally occur. Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95%, or more of the proteins in the composition.

Various methods for quantifying the degree of purification of the protein or peptide are known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity therein, assessed by a "-fold purification number." The actual units used to represent the amount of activity will, of course, be dependent upon the particular assay technique chosen to follow the purification, and whether or not the expressed protein or peptide exhibits a detectable activity.

Various techniques suitable for use in protein purification are well known to those of skill in the art. These include, for example, precipitation with ammonium sulphate, PEG, antibodies and the like, or by heat denaturation, followed by: centrifugation; chromatography steps such as ion exchange, gel filtration, reverse phase, hydroxylapatite and affinity chromatography; isoelectric focusing; gel electrophoresis; and combinations of these and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

Affinity chromatography is a chromatographic procedure that relies on the specific affinity between a substance to be isolated and a molecule to which it can specifically bind. This is a receptor-ligand type of interaction. The column material is synthesized by covalently coupling one of the binding partners to an insoluble matrix. The column material is then able to specifically adsorb the substance from the solution. Elution occurs by changing the conditions to those in which binding will not occur (e.g., altered pH, ionic strength, temperature, etc.). The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand.

Synthetic Peptides

Because of their relatively small size, the targeting peptides of the invention can be synthesized in solution or on a solid support in accordance with conventional techniques. Various automatic synthesizers are commercially available and can be used in accordance with known protocols. See, for example, Stewart and Young, Solid Phase Peptide Synthesis, 2d ed. Pierce Chemical Co., 1984; Tam et al., J. Am. Chem. Soc., 105:6442, 1983; Merrifield, Science, 232: 341-347, 1986; and Barany and Merrifield, The Peptides, Gross and Meienhofer, eds., Academic Press, New York, pp. 1-284, 1979, each incorporated herein by reference. Short peptide sequences, usually from about 6 up to about 35 to 50 amino acids, can be readily synthesized by such methods. Alternatively, recombinant DNA technology may be employed wherein a nucleotide sequence which encodes a peptide of the invention is inserted into an expression vector, transformed or transfected into an appropriate host cell, and cultivated under conditions suitable for expression.

Antibodies

In certain embodiments, it may be desirable to make antibodies against the identified targeting peptides or their receptors. The appropriate targeting peptide or receptor, or portions thereof, may be coupled, bonded, bound, conjugated, or chemically-linked to one or more agents via linkers, polylinkers, or derivatized amino acids. This may be performed such that a bispecific or multivalent composition or vaccine is produced. It is further envisioned that the methods used in the preparation of these compositions are familiar to those of skill in the art and should be suitable for administration to humans, i.e., pharmaceutically acceptable. Preferred agents are the carriers are keyhole limpet hemocyanin (KLH) or bovine serum albumin (BSA).

The term "antibody" is used to refer to any antibody-like molecule that has an antigen binding region, and includes antibody fragments such as Fab', Fab, F(ab')$_2$, single domain antibodies (DABs), Fv, scFv (single chain Fv), and the like. Techniques for preparing and using various antibody-based constructs and fragments are well known in the art. Means for preparing and characterizing antibodies are also well known in the art (See, e.g., Harlow and Lane, Antibodies: A Laboratory Manual, Cold Spring Harbor Laboratory, 1988; incorporated herein by reference).

Cytokines and Chemokines

In certain embodiments, it may be desirable to couple specific bioactive agents to one or more targeting peptides for targeted delivery to an organ, tissue or cell type. Such agents include, but are not limited to, cytokines, chemokines, pro-apoptosis factors and anti-angiogenic factors. The term "cytokine" is a generic term for proteins released by one cell population that act on another cell as intercellular mediators.

Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-.alpha. and -.beta.; mullerian-inhibiting substance; mouse gonadotropin-associated peptide; inhibin; activin; vascular endothelial growth factor; integrin; thrombopoietin (TPO); nerve growth factors such as NGF-.beta.; platelet-growth factor; transforming growth factors (TGFs) such as TGF-.alpha. and TGF-.beta.; insulin-like growth factor-I and -II; erythropoietin (EPO); osteoinductive factors; interferons such as interferon-α, -β, and -γ; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1.alpha., IL-2, IL-3, IL-4, IL-5, IL-6, IL-7, IL-8, IL-9, IL-10, IL-11, IL-12; IL-13, IL-14, IL-15, IL-16, IL-17, IL-18, LIF, G-CSF, GM-CSF, M-CSF, EPO, kit-ligand or FLT-3, angiostatin, thrombospondin, endostatin, tumor necrosis factor and LT. As used herein, the term cytokine includes proteins from natural sources or from recombinant cell culture and biologically active equivalents of the native sequence cytokines.

Chemokines generally act as chemoattractants to recruit immune effector cells to the site of chemokine expression. It may be advantageous to express a particular chemokine gene in combination with, for example, a cytokine gene, to enhance the recruitment of other immune system components to the site of treatment. Chemokines include, but are not limited to, RANTES, MCAF, MIP1-alpha, MIP1-Beta, and IP-10. The skilled artisan will recognize that certain cytokines are also known to have chemoattractant effects and could also be classified under the term chemokines.

Imaging Agents and Radioisotopes

In certain embodiments, the claimed peptides or proteins of the present invention may be attached to imaging agents of use for imaging and diagnosis of various diseased organs, tissues or cell types. Many appropriate imaging agents are known in the art, as are methods for their attachment to proteins or peptides (see, e.g., U.S. Pat. Nos. 5,021,236 and 4,472,509, both incorporated herein by reference). Certain attachment methods involve the use of a metal chelate complex employing, for example, an organic chelating agent such a DTPA attached to the protein or peptide (U.S. Pat. No. 4,472,509). Proteins or peptides also may be reacted with an enzyme in the presence of a coupling agent such as glutaraldehyde or periodate. Conjugates with fluorescein markers are prepared in the presence of these coupling agents or by reaction with an isothiocyanate.

Non-limiting examples of paramagnetic ions of potential use as imaging agents include chromium (III), manganese (II), iron (III), iron (II), cobalt (II), nickel (II), copper (II), neodymium (III), samarium (III), ytterbium (III), gadolinium (III), vanadium (II), terbium (III), dysprosium (III), holmium (III) and erbium (III), with gadolinium being particularly preferred. Ions useful in other contexts, such as X-ray imaging, include but are not limited to lanthanum (III), gold (III), lead (II), and especially bismuth (III).

Radioisotopes of potential use as imaging or therapeutic agents include astatine$^{211}$, $^{14}$carbon, $^{51}$chromium, $^{36}$chlorine, $^{57}$cobalt, $^{58}$cobalt, copper$^{67}$, $^{152}$Eu, gallium$^{67}$, $^{3}$hydrogen, iodine$^{123}$, iodine$^{125}$, iodine$^{131}$, indium$^{111}$, $^{59}$iron, $^{32}$phosphorus, rhenium$^{186}$, rhenium$^{188}$, $^{75}$selenium, $^{35}$sulphur, technicium$^{99m}$ and yttrium$^{90}$. $^{125}$I is often being preferred for use in certain embodiments, and technicium$^{99m}$ and indium$^{111}$ are also often preferred due to their low energy and suitability for long range detection.

Radioactively labeled proteins or peptides of the present invention may be produced according to well-known methods in the art. For instance, they can be iodinated by contact with sodium or potassium iodide and a chemical oxidizing agent such as sodium hypochlorite, or an enzymatic oxidizing agent, such as lactoperoxidase. Proteins or peptides according to the invention may be labeled with technetium-$^{99m}$ by ligand exchange process, for example, by reducing pertechnate with stannous solution, chelating the reduced technetium onto a Sephadex column and applying the peptide to this column or by direct labeling techniques, e.g., by incubating pertechnate, a reducing agent such as SNCl$_2$, a buffer solution such as sodium-potassium phthalate solution, and the peptide. Intermediary functional groups that are often used to bind radioisotopes that exist as metallic ions to peptides are diethylenetriaminepenta-acetic acid (DTPA) and ethylene diaminetetra-acetic acid (EDTA). Also contemplated for use are fluorescent labels, including rhodamine, fluorescein isothiocyanate and renographin.

In certain embodiments, the claimed proteins or peptides may be linked to a secondary binding ligand or to an enzyme (an enzyme tag) that will generate a colored product upon contact with a chromogenic substrate. Examples of suitable enzymes include urease, alkaline phosphatase, (horseradish) hydrogen peroxidase and glucose oxidase. Preferred secondary binding ligands are biotin and avidin or streptavidin compounds. The use of such labels is well known to those of skill in the art in light and is described, for example, in U.S. Pat. Nos. 3,817,837; 3,850,752; 3,939,350; 3,996,345; 4,277,437; 4,275,149 and 4,366,241; each incorporated herein by reference.

Cross-Linkers

Bifunctional cross-linking reagents have been extensively used for a variety of purposes including preparation of affinity matrices, modification and stabilization of diverse structures, identification of ligand and receptor binding sites, and structural studies. Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino, sulfhydryl, guanidino, indole, carboxyl specific groups. Of these, reagents directed to free amino groups have become especially popular because of their commercial availability, ease of synthesis and the mild reaction conditions under which they can be applied. A majority of heterobifunctional cross-linking reagents contains a primary amine-reactive group and a thiol-reactive group.

Exemplary methods for cross-linking ligands to liposomes are described in U.S. Pat. No. 5,603,872 and U.S. Pat. No. 5,401,511, each specifically incorporated herein by reference in its entirety). Various ligands can be covalently bound to liposomal surfaces through the cross-linking of amine residues. Liposomes, in particular, multilamellar vesicles (MLV) or unilamellar vesicles such as microemulsified liposomes (MEL) and large unilamellar liposomes (LUVET), each containing phosphatidylethanolamine (PE), have been prepared by established procedures. The inclusion of PE in the liposome provides an active functional residue, a primary amine, on the liposomal surface for cross-linking purposes. Ligands such as epidermal growth factor (EGF) have been successfully linked with PE-liposomes. Ligands are bound covalently to discrete sites on the liposome surfaces. The number and surface density of these sites are dictated by the liposome formulation and the liposome type. The liposomal surfaces may also have sites for non-covalent association. To form covalent conjugates of ligands and liposomes, cross-linking reagents have been studied for effectiveness and biocompatibility. Cross-linking reagents include glutaraldehyde (GAD), bifunctional oxirane (OXR), ethylene glycol diglycidyl ether (EGDE), and a water soluble carbodiimide, preferably 1-ethyl-3-(3-dimethylaminopropyl)carbodiimide (EDC). Through the complex chemistry of cross-linking, linkage of the amine residues of the recognizing substance and liposomes is established.

In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling in one example, of aldehydes to free thiols. The cross-linking reagent can be modified to cross-link various functional groups.

Nucleic Acids

Nucleic acids according to the present invention may encode a targeting peptide, a receptor protein, a fusion protein or other protein or peptide. The nucleic acid may be derived from genomic DNA, complementary DNA (cDNA) or synthetic DNA. Where incorporation into an expression vector is desired, the nucleic acid may also comprise a natural intron or an intron derived from another gene. Such engineered molecules are sometime referred to as "mini-genes."

A "nucleic acid" as used herein includes single-stranded and double-stranded molecules, as well as DNA, RNA, chemically modified nucleic acids and nucleic acid analogs. It is contemplated that a nucleic acid within the scope of the present invention may be of almost any size, determined in part by the length of the encoded protein or peptide.

It is contemplated that targeting peptides, fusion proteins and receptors may be encoded by any nucleic acid sequence that encodes the appropriate amino acid sequence. The design and production of nucleic acids encoding a desired amino acid sequence is well known to those of skill in the art, using standardized codon tables (see Table 2 below). In preferred embodiments, the codons selected for encoding each amino acid may be modified to optimize expression of the nucleic acid in the host cell of interest. Codon preferences for various species of host cell are well known in the art.

TABLE 2

| Amino Acid | | | Codons | | | | | |
|---|---|---|---|---|---|---|---|---|
| Alanine | Ala | A | GCA | GCC | GCG | GCU | | |
| Cysteine | Cys | C | UGC | UGU | | | | |
| Aspartic acid | Asp | D | GAC | GAU | | | | |
| Glutamic acid | Glu | E | GAA | GAG | | | | |
| Phenylalanine | Phe | F | UUC | UUU | | | | |
| Glycine | Gly | G | GGA | GGC | GGG | GGU | | |
| Histidine | His | H | CAC | CAU | | | | |
| Isoleucine | Ile | I | AUA | AUC | AUU | | | |
| Lysine | Lys | K | AAA | AAG | | | | |
| Leucine | Leu | L | UUA | UUG | CUA | CUC | CUG | CUU |
| Methionine | Met | M | AUG | | | | | |
| Asparagine | Asn | N | AAC | AAU | | | | |

TABLE 2-continued

| Amino Acid | | | Codons | | | | | |
|---|---|---|---|---|---|---|---|---|
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

In addition to nucleic acids encoding the desired peptide or protein, the present invention encompasses complementary nucleic acids that hybridize under high stringency conditions with such coding nucleic acid sequences. High stringency conditions for nucleic acid hybridization are well known in the art. For example, conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleotide content of the target sequence(s), the charge composition of the nucleic acid(s), and to the presence or concentration of formamide, tetramethylammonium chloride or other solvent(s) in a hybridization mixture.

Vectors for Cloning, Gene Transfer and Expression

In certain embodiments expression vectors are employed to express the targeting peptide or fusion protein, which can then be purified and used. In other embodiments, the expression vectors are used in gene therapy. Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are known.

Regulatory Elements

The terms "expression construct" or "expression vector" are meant to include any type of genetic construct containing a nucleic acid coding for a gene product in which part or all of the nucleic acid coding sequence is capable of being transcribed. In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The particular promoter employed to control the expression of a nucleic acid sequence of interest is not believed to be important, so long as it is capable of directing the expression of the nucleic acid in the targeted cell. Thus, where a human cell is targeted, it is preferable to position the nucleic acid coding region adjacent and under the control of a promoter that transcriptionally active in human cells. Generally speaking, such a promoter might include either a human or viral promoter.

In various embodiments, the human cytomegalovirus (CMV) immediate early gene promoter, the SV40 early promoter, the Rouse sarcoma virus long terminal repeat, rat insulin promoter, and glyceraldehyde-3-phosphate dehydrogenase promoter can be used to obtain high-level expression of the coding sequence of interest. The use of other viral or mammalian cellular or bacterial phage promoters that are well-known in the art to achieve expression of a coding sequence of interest is contemplated as well, provided that the levels of expression are sufficient for a given purpose.

Where a cDNA insert is employed, one will typically include a polyadenylation signal to effect proper polyadenylation of the gene transcript. The nature of the polyadenylation signal is not believed to be crucial to the successful practice of the invention, and any such sequence may be employed, such as human growth hormone and SV40 polyadenylation signals. Also contemplated as an element of the expression construct is a terminator. These elements can serve to enhance message levels and to minimize read through from the construct into other sequences.

Selectable Markers

In certain embodiments of the invention, the cells containing nucleic acid constructs of the present invention may be identified in vitro or in vivo by including a marker in the expression construct. Such markers would confer an identifiable change to the cell permitting easy identification of cells containing the expression construct. Usually the inclusion of a drug selection marker aids in cloning and in the selection of transformants. For example, genes that confer resistance to neomycin, puromycin, hygromycin, DHFR, GPT, zeocin, and histidinol are useful selectable markers. Alternatively, enzymes such as herpes simplex virus thymidine kinase (tk) or chloramphenicol acetyltransferase (CAT) may be employed. Immunologic markers also can be employed. The selectable marker employed is not believed to be important, so long as it is capable of being expressed simultaneously with the nucleic acid encoding a gene product. Further examples of selectable markers are well known to one of skill in the art.

Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome, and express viral genes stably and efficiently have made them attractive candidates for the transfer of foreign genes into mammalian cells (Ridgeway, 1988; Nicolas and Rubinstein, *In: Vectors: A survey of molecular cloning vectors and their uses,* Rodriguez and Denhardt, eds., Stoneham: Butterworth, pp. 494-513, 1988.; Baichwal and Sugden, Baichwal, *In: Gene Transfer,* Kucherlapati R, ed., New York, Plenum Press, pp. 117-148, 1986. 1986; Temin, In: Gene Transfer, Kucherlapati, R. ed., New York, Plenum Press, pp. 149-188, 1986). Preferred gene therapy vectors are generally viral vectors.

In using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

DNA viruses used as gene vectors include the papovaviruses (e.g., simian virus 40, bovine papilloma virus, and polyoma) (Ridgeway, pp 467-492, 1988; Baichwal and Sugden, 1986) and adenoviruses (Ridgeway, 1988; Baichwal and Sugden, 1986).

One of the preferred methods for in vivo delivery involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include, but is not limited to, constructs containing adenovirus sequences sufficient to (a) support packaging of the construct and (b) to express an antisense or a sense polynucleotide that has been cloned therein.

Generation and propagation of adenovirus vectors that are replication deficient depend on a unique helper cell line, designated 293, which is transformed from human embryonic kidney cells by Ad5 DNA fragments and constitutively expresses E1 proteins (Graham et al., *J. Gen. Virol.,* 36:59-72, 1977.). Since the E3 region is dispensable from the adenovirus genome (Jones and Shenk, *Cell,* 13:181-188, 1978), the current adenovirus vectors, with the help of 293 cells, carry foreign DNA in either the E1, the E3, or both regions (Graham and Prevec, *In: Methods in Molecular Biology: Gene Transfer and Expression Protocol,* E. J. Murray, ed., Humana Press, Clifton, N.J., 7:109-128, 1991.).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As discussed, the preferred helper cell line is 293. Racher et al., (*Biotechnol. Tech.* 9:169-174, 1995) disclosed improved methods for culturing 293 cells and propagating adenovirus.

Adenovirus vectors have been used in eukaryotic gene expression (Levrero et al., *Gene,* 101:195-202, 1991; Gomez-Foix et al., *J. Biol. Chem.,* 267:25129-25134,1992) and vaccine development (Grunhaus and Horwitz, 1992; Graham and Prevec, 1991). Animal studies have suggested that recombinant adenovirus could be used for gene therapy (Stratford-Perricaudet and Perricaudet, *In: Human Gene Transfer,* O. Cohen-Haguenauer et al, eds. John Libbey Eurotext, France, pp. 51-61, 1991; Stratford-Perricaudet et al., *Hum. Gene Ther.* 1:241-256, 1990; Rich et al., *Hum. Gene. Ther.* 4:461-476, 1993). Studies in administering recombinant adenovirus to different tissues include trachea instillation (Rosenfeld et al., *Science,* 252: 431-434, 1991; Rosenfeld et al., *Cell,* 68: 143-155, 1992), muscle injection (Ragot et al., *Nature,* 361: 647-650, 1993), peripheral intravenous injections (Herz and Gerard, *Proc. Natl. Acad. Sci. USA,* 90:2812-2816, 1993) and stereotactic innoculation into the brain (Le Gal La Salle et al., *Science,* 259:988-990,1993).

Other gene transfer vectors may be constructed from retroviruses. (Coffin, *In: Virology,* Fields et al., eds., Raven Press, New York, pp. 1437-1500, 1990.) The retroviral genome contains three genes, gag, pol, and env. that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences, and also are required for integration in the host cell genome (Coffin, 1990).

In order to construct a retroviral vector, a nucleic acid encoding protein of interest is inserted into the viral genome in the place of certain viral sequences to produce a virus that is replication-defective. In order to produce virions, a packaging cell line containing the gag, pol, and env genes, but without the LTR and packaging components, is constructed (Mann et al., *Cell,* 33:153-159, 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are capable of infecting a broad variety of cell types. However, integration and stable expression require the division of host cells (Paskind et al., *Virology,* 67:242-248, 1975).

Other viral vectors may be employed as expression constructs. Vectors derived from viruses such as vaccinia virus (Ridgeway, 1988; Baichwal and Sugden, 1986; Coupar et al., *Gene* 68:1-10, 1988), adeno-associated virus (AAV) (Ridgeway, 1988; Baichwal and Sugden, 1986; Hermonat and Muzycska, *Proc. Natl. Acad. Sci. USA,* 81: 6466-6470, 1984), and herpes viruses may be employed. They offer several attractive features for various mammalian cells (Friedmann, *Science,* 244:1275-1281, 1989; Ridgeway, 1988; Baichwal and Sugden, 1986; Coupar et al., 1988; Horwich et al., *J. Virol.,* 64:642-650,1990).

Several non-viral methods for the transfer of expression constructs into cultured mammalian cells also are contemplated by the present invention. These include calcium phosphate precipitation (Graham and van der Eb, *Virology,* 52:456-467, 1973.; Chen and Okayama, *Mol. Cell Biol.,* 7:2745-2752, 1987.; Rippe et al., *Mol. Cell Biol.* 10: 689-695, 1990; DEAE dextran (Gopal, et al. *Mol. Cell. Biol.,* 5:1188-1190,1985), electroporation (Tur-Kaspa et al., *Mol. Cell Biol.,* 6:716-718, 1986; Potter et al., *Proc. Natl. Acad. Sci. USA,* 81: 7161-7165, 1984), direct microinjection, DNA-loaded liposomes and lipofectamine-DNA complexes, cell sonication, gene bombardment using high velocity microprojectiles, and receptor-mediated transfection (Wu and Wu, *J. Biol. Chem.* 262:4429-4432, 1987; Wu and Wu, *Biochemistry,* 27:887-892, 1988). Some of these techniques may be successfully adapted for in vivo or ex vivo use.

In a further embodiment of the invention, the expression construct may be entrapped in a liposome. Liposome-mediated nucleic acid delivery and expression of foreign DNA in vitro has been very successful. Wong et al., (*Gene,* 10:87-94, 1980) demonstrated the feasibility of liposome-mediated delivery and expression of foreign DNA in cultured chick embryo, HeLa, and hepatoma cells. Nicolau et al., (*Methods Enzymol.,* 149:157-176, 1987.) accomplished successful liposome-mediated gene transfer in rats after intravenous injection.

Pharmaceutical Compositions

Where clinical applications are contemplated, it may be necessary to prepare pharmaceutical compositions—expression vectors, virus stocks, proteins, antibodies and drugs—in a form appropriate for the intended application. Generally, this will entail preparing compositions that are essentially free of impurities that could be harmful to humans or animals.

One generally will desire to employ appropriate salts and buffers to render delivery vectors stable and allow for uptake by target cells. Buffers also are employed when recombinant cells are introduced into a patient. Aqueous compositions of the present invention may comprise an effective amount of a protein, peptide, fusion protein, recombinant phage and/or expression vector, dissolved or dispersed in a pharmaceutically acceptable carrier or aqueous medium. Such compositions also are referred to as innocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the proteins or peptides of the present invention, its use in therapeutic compositions is contemplated. Supplementary active ingredients also can be incorporated into the compositions.

The active compositions of the present invention may include classic pharmaceutical preparations. Administration of these compositions according to the present invention are via any common route so long as the target tissue is available via that route. This includes oral, nasal, buccal, rectal, vaginal or topical. Alternatively, administration may be by orthotopic, intradermal, subcutaneous, intramuscular, intraperitoneal, intraarterial or intravenous injection. Such compositions normally would be administered as pharmaceutically acceptable compositions, described supra.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it is preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

Therapeutic Agents

In certain embodiments, therapeutic agents may be attached to a targeting peptide or fusion protein for selective delivery to, for example, white adipose tissue. Agents or factors suitable for use may include any chemical compound that induces apoptosis, cell death, cell stasis and/or anti-angiogenesis.

Regulators of Programmed Cell Death

Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins that share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death (e.g., Bax, Bak, Bik, Bim, Bid, Bad, Harakiri).

Non-limiting examples of pro-apoptosis agents contemplated within the scope of the present invention include gramicidin, magainin, mellitin, defensin, cecropin, (KLAKLAK)$_2$ (SEQ ID NO:1), (KLAKKLA)$_2$ (SEQ ID NO:2), (KAAKKAA)$_2$ (SEQ ID NO:3) or (KLGKKLG)$_3$ (SEQ ID NO:4).

Angiogenic Inhibitors

In certain embodiments the present invention may concern administration of targeting peptides attached to anti-angiogenic agents, such as angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU145156E, 16K prolactin fragment, Linomide, thalidomide, pentoxifylline, genistein, TNP470, endostatin, paclitaxel, accutin, angiostatin, cidofovir, vincristine, bleomycin, AGM-1470, platelet factor 4 or minocycline.

Proliferation of tumors cells relies heavily on extensive tumor vascularization, which accompanies cancer progression. Thus, inhibition of new blood vessel formation with anti-angiogenic agents and targeted destruction of existing blood vessels have been introduced as an effective and relatively non-toxic approach to tumor treatment. (Arap et al., Science 279:377-380, 1998; Arap et al., Curr. Opin. Oncol. 10:560-565, 1998; Ellerby et al., Nature Med. 5:1032-1038, 1999). A variety of anti-angiogenic agents and/or blood vessel inhibitors are known. (E.g., Folkman, In: Cancer: Principles and Practice, eds. De Vita et al., pp. 3075-3085, Lippincott-Raven, New York, 1997; Eliceiri and Cheresh, Curr. Opin. Cell. Biol. 13, 563-568, 2001).

White fat represents a unique tissue that, like tumors, can quickly proliferate and expand (Wasserman, In: Handbook of Physiology, eds. Renold and Cahill, pp. 87-100, American Physiological Society, Washington, D.C., 1965; Cinti, Eat. Weight. Disord. 5:132-142, 2000). Studies of adipose tissue reveal that it is highly vascularized. Multiple capillaries make contacts with every adipocyte, suggesting the importance of the vasculature for maintenance of the fat mass (Crandall et al., Microcirculation 4:211-232, 1997). A hypothesis underlying the present invention is that adipose tissue proliferation might rely on angiogenesis similarly to tumors. If so, destruction of fat neovasculature could prevent the development of obesity, whereas targeting existing adipose blood vessels could potentially result in fat regression. Methods of use of adipose targeting peptides may include induction of weight loss, treatment of obesity and/or treatment of HIV related lipodystrophy.

Cytotoxic Agents

Chemotherapeutic (cytotoxic) agents of potential use include, but are not limited to, 5-fluorouracil, bleomycin, busulfan, camptothecin, carboplatin, chlorambucil, cisplatin (CDDP), cyclophosphamide, dactinomycin, daunorubicin, doxorubicin, estrogen receptor binding agents, etoposide (VP16), farnesyl-protein transferase inhibitors, gemcitabine, ifosfamide, mechlorethamine, melphalan, mitomycin, navelbine, nitrosurea, plicomycin, procarbazine, raioxifene, tamoxifen, taxol, temazolomide (an aqueous form of DTIC), transplatinum, vinblastine and methotrexate, vincristine, or any analog or derivative variant of the foregoing. Most chemotherapeutic agents fall into the categories of alkylating agents, antimetabolites, antitumor antibiotics, corticosteroid hormones, mitotic inhibitors, and nitrosoureas, hormone agents, miscellaneous agents, and any analog or derivative variant thereof.

Chemotherapeutic agents and methods of administration, dosages, etc. are well known to those of skill in the art (see for example, the "Physicians Desk Reference", Goodman & Gilman's "The Pharmacological Basis of Therapeutics" and in "Remington's Pharmaceutical Sciences" $15^{th}$ ed., pp 1035-1038 and 1570-1580, incorporated herein by reference in relevant parts), and may be combined with the invention in light of the disclosures herein. Some variation in dosage will necessarily occur depending on the condition of the subject being treated. The person responsible for administration will, in any event, determine the appropriate dose for the individual subject. Examples of specific chemotherapeutic agents and dose regimes are also described herein. Of course, all of these dosages and agents described herein are exemplary rather than limiting, and other doses or agents may be used by a skilled artisan for a specific patient or application. Any dosage in-between these points, or range derivable therein is also expected to be of use in the invention.

Alkylating Agents

Alkylating agents are drugs that directly interact with genomic DNA to prevent cells from proliferating. This category of chemotherapeutic drugs represents agents that affect all phases of the cell cycle, that is, they are not phase-specific. An alkylating agent, may include, but is not limited to, a nitrogen mustard, an ethylenimene, a methylmelamine, an alkyl sulfonate, a nitrosourea or a triazines. They include but are not limited to: busulfan, chlorambucil, cisplatin, cyclophosphamide (cytoxan), dacarbazine, ifosfamide, mechlorethamine (mustargen), and melphalan.

Antimetabolites

Antimetabolites disrupt DNA and RNA synthesis. Unlike alkylating agents, they specifically influence the cell cycle during S phase. Antimetabolites can be differentiated into various categories, such as folic acid analogs, pyrimidine analogs and purine analogs and related inhibitory compounds. Antimetabolites include but are not limited to, 5-fluorouracil (5-FU), cytarabine (Ara-C), fludarabine, gemcitabine, and methotrexate.

Natural Products

Natural products generally refer to compounds originally isolated from a natural source, and identified as having a pharmacological activity. Such compounds, analogs and derivatives thereof may be, isolated from a natural source, chemically synthesized or recombinantly produced by any technique known to those of skill in the art. Natural products include such categories as mitotic inhibitors, antitumor antibiotics, enzymes and biological response modifiers.

Mitotic inhibitors include plant alkaloids and other natural agents that can inhibit either protein synthesis required for cell division or mitosis. They operate during a specific phase during the cell cycle. Mitotic inhibitors include, for example, docetaxel, etoposide (VP16), teniposide, paclitaxel, taxol, vinblastine, vincristine, and vinorelbine.

Taxoids are a class of related compounds isolated from the bark of the ash tree, *Taxus brevifolia*. Taxoids include but are not limited to compounds such as docetaxel and paclitaxel. Paclitaxel binds to tubulin (at a site distinct from that used by the vinca alkaloids) and promotes the assembly of microtubules.

Vinca alkaloids are a type of plant alkaloid identified to have pharmaceutical activity. They include such compounds as vinblastine (VLB) and vincristine.

Antibiotics

Certain antibiotics have both antimicrobial and cytotoxic activity. These drugs also interfere with DNA by chemically inhibiting enzymes and mitosis or altering cellular membranes. These agents are not phase specific so they work in all phases of the cell cycle. Examples of cytotoxic antibiotics include, but are not limited to, bleomycin, dactinomycin, daunorubicin, doxorubicin (Adriamycin), plicamycin (mithramycin) and idarubicin.

Miscellaneous Agents

Miscellaneous cytotoxic agents that do not fall into the previous categories include, but are not limited to, platinum coordination complexes, anthracenediones, substituted ureas, methyl hydrazine derivatives, amsacrine, L-asparaginase, and tretinoin. Platinum coordination complexes include such compounds as carboplatin and cisplatin (cis-DDP). An exemplary anthracenedione is mitoxantrone. An exemplary substituted urea is hydroxyurea. An exemplary methyl hydrazine derivative is procarbazine (N-methylhydrazine, MIH). These examples are not limiting and it is contemplated that any known cytotoxic, cytostatic or cytocidal agent may be attached to targeting peptides and administered to a targeted organ, tissue or cell type within the scope of the invention.

Dosages

The skilled artisan is directed to "Remington's Pharmaceutical Sciences" 15th Edition, chapter 33, and in particular to pages 624-652. Some variation in dosage will necessarily occur depending on the condition of the subject being treated. The person responsible for administration will, in any event, determine the appropriate dose for the individual subject. Moreover, for human administration, preparations should meet sterility, pyrogenicity, and general safety and purity standards as required by the FDA Office of Biologics standards.

EXAMPLES

The following examples are included to demonstrate preferred embodiments of the invention. It should be appreciated by those of skill in the art that the techniques disclosed in the examples which follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Identification of Mouse Placenta Targeting Peptides

Identification of Placenta Homing Peptides

Peptides homing to the mouse placenta were identified by a post-clearing protocol using a phage display library. A first round of biopanning was performed on pregnant mice. Samples of placenta were removed and phage rescued according to protocols described below, with one modification. In the typical biopanning protocol, thousands of phage may be recovered from a single organ, tissue or cell type. Typically, between 200 and 300 individual colonies are selected from plated phage and these are amplified and pooled to form the phage display library for the second or third rounds of biopanning. In the present Example, all phage rescued from the first round of biopanning were amplified in bulk on solid medium and then pooled to form the phage display library for the second round of biopanning. That is, there was no restriction of the rescued phage from the first round of biopanning. This in vivo biopanning without restriction was performed for three rounds (rounds I-III), then a post-clearing procedure was used.

In a post-clearing protocol (round IV), phage were administered to a non-pregnant mouse. Phage that bound to tissues other than placenta were absorbed from the circulation. Remaining phage were recovered from the plasma of the non-pregnant mouse. This protocol was designed to isolate phage that bound to placenta but not to other mouse organs, tissues or cell types. The following placenta-targeting peptides were identified, along with their frequencies. A search of the GenBank database disclosed that none of the sequences listed below was 100% homologous with any known peptide sequence.

TPKTSVT (SEQ ID NO:5) 7.4% in round III, 8.5% in round IV

RMDGPVR (SEQ ID NO:6) 3.1% in round III, 8.5% in round IV

RAPGGVR (SEQ ID NO:7)<1% in round III, 8.5% in round IV

VGLHARA (SEQ ID NO:8) 4.2% in round III, 7.4% in round IV

YIRPFIL (SEQ ID NO:9) 2.1% in round III, 5.3% in round IV

LGLRSVG (SEQ ID NO:10)<1% in round III, 5.3% in round IV

PSERSPS (SEQ ID NO:11) (data not available)

As can be seen, the use of a post-clearing procedure resulted in a substantial enrichment of phage bearing placenta targeting peptides. Although this procedure was used for placenta, the skilled artisan will realize that post-clearance can be performed for any organ, tissue or cell type where a phage library can be administered to a subject lacking that organ, tissue or cell type. For example, a post-clearing procedure for prostate or testicle targeting peptides could be performed in a female subject, and for ovary, vagina or uterus in a male subject.

A homology search identified several candidate proteins as endogenous analogs of the placental targeting peptides, including TCR gamma-1 (TPKTSVT, SEQ ID NO:5), tenascin (RMDGPVR, SEQ ID NO:6 and RAPGGVR, SEQ ID NO:7), angiotensin I (YIRPFTL, SEQ ID NO:9) and MHC H2-D-q alpha chain (VGLHARA, SEQ ID NO:8).

Validation of Placenta Homing Peptides and Inhibition of Pregnancy

Figure 1:
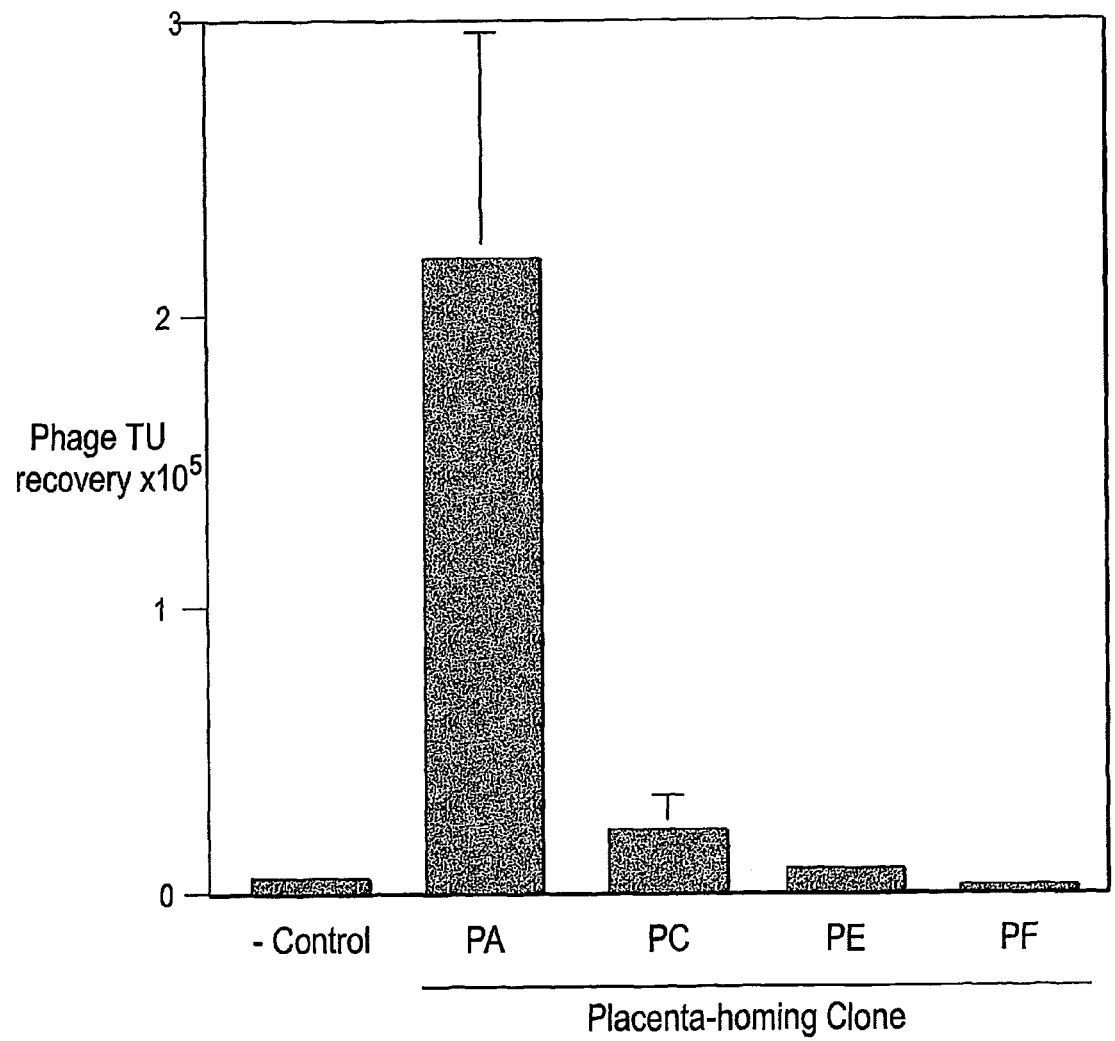
FIG. 1. Validation of placenta homing phage. Phage bearing targeting peptides were injected into pregnant mice and their recovery from placenta was compared to control fd-tet phage without targeting sequences. The placenta homing phage clones were: PA-TPKTSVT (SEQ ID NO:5), PC-RAPGGVR (SEQ ID NO:7), PE-LGLRSVG (SEQ ID NO:10), PF-YIRPFTL (SEQ ID NO:9).

The placenta homing peptides were validated in vivo by injection into pregnant mice and recovery from the placenta. FIG. 1 shows the results of the validation studies for selected placenta homing phage. The phage clones are identified as: PA-TPKTSVT (SEQ ID NO:5), PC-RAPGGVR (SEQ ID NO:7), PE-LGLRSVG (SEQ ID NO:10), PF-YIRPFTL (SEQ ID NO:9). It can be seen that the PA clone exhibited placental homing more than an order of magnitude greater than observed with control fd-tet phage. The PC clone also showed substantially higher placental localization, while the PE and PF clones were not substantially enriched in placenta compared to control phage.

Despite the absence of apparent enrichment of the PF clone in placental tissue, both the PA and PF peptides showed anti-placental activity. Table 3 shows the effects of the PA and PF placental targeting peptides injected into pregnant mice, attached to FITC (fluorescein isothiocyanate), GST (glutathion S-transferase) or to phage. At lower dosages (450 µg total), FITC conjugated PA and PF showed a slight effect on pregnancy (Table 3). At higher dosages (800 to 1000 µg protein or $4.5 \times 10^{10}$ phage), both protein and phage conjugated PA and PF peptides substantially interfered with fetal development (Table 3), apparently resulting in death of the fetuses in most cases. The CARAC peptide (SEQ ID NO:12), an adipose targeting peptide (FE, TREVHRS, SEQ ID NO:13) or fd-tet phage were used as non-placental targeting controls.

These results validate the placental targeting peptide sequences identified above. They further demonstrate that even in the absence of substantial enrichment of phage bearing the targeting sequence to the target organ (e.g. peptide PF, FIG. 1), the targeting peptide may nevertheless provide for targeted delivery of therapeutic agents to the target organ. In this study, it appeared that at lower dosages the PF peptide was more effective than the PA peptide at interfering with pregnancy, despite the observation that the PA peptide produced a many-fold higher level of phage localization to placenta.

The skilled artisan will realize that the disclosed methods and peptides may be of use for targeted delivery of therapeutic agents to the fetus through the placenta, as well as for novel approaches to terminating pregnancy and/or inducing labor.

Example 2

Localization of the TPKTSVT (SEQ ID NO:5) Peptide in Mouse Placenta

Material and Methods

Animals Staged pregnant 18 days postconception (dpc) C57BL/6 female mice were purchased from Harlan Teklad (Indianapolis, Ind.). Congenic pregnant β2m-null females (stock 002087) mice were purchased from The Jackson Laboratories (Bar Harbor, Me.). Anesthesia was performed with Avertin (0.015 ml/g) administered intraperitoneally (Pas-

TABLE 3

Effect of Placental Targeting Peptides on Fetal Development

| Peptide Injected | Pregnancy Outcome | Peptide Effect on Embryo |
|---|---|---|
| Inhibition with FITC conjugates - I  1 mouse injected iv (predominantly) or ip ~every other day, day 1-day 18, 9 times, Total 450 mM (~450 µg) | | |
| CARAC-FITC (- control) | Delivery: 18 d, 5 normal pups | No effect |
| PA-FITC (placenta homer) | Delivery: 19 d, 8 normal pups | No effect |
| PF-FITC (placenta homer) | Delivery: 21 d, 1 dead pup | Development delay, toxicity |
| Inhibition with FITC conjugates - II  1 mouse injected sc (predominantly) or iv ~every other day, day 4-day 17, 10 times, Total 1 M (~1 mg) | | |
| CARAC-FITC (- control) | Delivery: 20 d, 5 pups, 1-dead | Slight toxicity? |
| PA-FITC (placenta homer) | No fetuses inside after 21 d | Pregnancy termination |
| PF-FITC (placenta homer) | No fetuses inside after 21 d | Pregnancy termination |
| Inhibition with phage conjugates - I  1 mouse injected iv (predominantly) or ip ~every other day, day 1-day 18, 9 times, Total $4.5 \times 10^{10}$ TU | | |
| Fd-Tet (- control) | Avertin OD => death. fetuses-OK | ? |
| PA-phage (placenta homer) | Delivery: 24 d, 4 pups, 1-dead | Development delay, toxicity |
| PF-phage (placenta homer) | Delivery: 25 d, 8 pups, all dead | Development delay, toxicity |
| Inhibition with GST conjugates - I  1 mouse injected sc (predominantly) or iv ~every other day, day 4-day 17, 10 times, Total 800 µg | | |
| GST-FE (- control) | Delivery: 20 d, 2 pups, OK | No effect |
| GST-PA (placenta homer) | No delivery or fetuses after 21 d | Pregnancy termination |
| GST-PF (placenta homer) | Day 15: no fetuses inside, uterus necrotic | Pregnancy termination | qualini and Ruoslahti, 1996, *Nature* 380:364-366; Rajotte et al., 1998, *J. Clin. Invest.* 102: 430437).

Phage Library Screening In vivo screening of an M13 page-display $CX_7C$ library (Pasqualini et al., 2000, in *Phage Display: A Laboratory Manual*, eds. Barbas et al., Cold Spring Harbor Laboratory Press, New York, N.Y., pp. 22.1-24; Arap et al., 2002, *Nature Med.* 8:121-127), for placenta-homing peptides was performed as described (Pasqualini et al., 2000; Pasqualini and Ruoslahti, 1996) with novel modifications described below. In each biopanning round, an 18 dpc C57BL/6 female was injected intravenously (tail vein) with $10^{10}$ transducing units (FU) of the library. Increasing amounts of phage (from ~$10^3$ TU in round 1 to ~$10^4$ TU in round 4) were recovered from the placentas after 5 min of circulation. Recovered phage were bulk-amplified for subsequent rounds of screening. In a procedure introduced here for the first time, the sub-library that was amplified after the third round of panning was cleared of nonspecific binders in a subtraction step. A virgin C57BL/6 female was infused through the tail vein with $10^9$ TU of phage selected in round 3. After 5 min, the unbound circulating phage were recovered from plasma. The plasma contained approximately $10^7$ TU of pre-cleared phage. The precleared phage population, representing less than 1% of the injected pool, was recovered and amplified for the final round of biopanning.

Phage Recovery Mouse placentas and embryonic livers were individually weighed, ground with a glass Dounce homogenizer and suspended in 1 ml of Dulbecco's Modified Eagle's Medium (DMEM) containing proteinase inhibitors (DMEM-prin –1 mM PMSF, 20 µg/ml aprotinin, and 1 µg/ml leupeptin). The suspension was vortexed and washed three times with DMEM-prin. Tissue homogenates (or 10 ml of blood for normalization of phage titer in placenta against circulating phage titer) were incubated with 1 ml of host bacteria (log phase *E. coli* K91kan; OD600~2). Aliquots of the bacterial culture were plated onto Luria-Bertani agar plates containing 40 µg/ml tetracycline and 100 µg/ml kanamycin. Plates were incubated overnight at 37° C. Triplicate samples were processed for host bacterial infection, phage recovery, and histological analysis.

Fusion and Recombinant Peptides Carboxyfluorescein (FITC)-conjugated CTPKTSVTC (SEQ ID NO:144) or control peptide CARAC (SEQ ID NO:12), formed into cyclic peptides using the flanking cysteines, were chemically synthesized and HPLC-purified to >90% purity by Anaspec (San Jose, Calif.). The FITC-peptide stocks were made by dissolving lyophilized peptides in DMSO to a concentration of 20 mM, after which the peptides were diluted to 1 mM with PBS (phosphate buffered saline) and aliquots were frozen until use. The CTPKTSVTC (SEQ ID NO:144) peptide and an unrelated control peptide, CTREVHRSC (SEQ ID NO:87), fused in-frame with GST at the amino-terminus were purified to approximately 90% purity using the BugBuster GST Bind Kit (Novagen, Madison, Wis.). Purified peptides were buffer-exchanged into PBS using Centricon PL-10 columns (Millipore, Bedford, Mass.) and the aliquots were frozen until use. For in vivo peptide homing validation, 10 µl of FITC-peptide stocks diluted 20-fold with PBS or 250 µl of 5 mg/ml GST-peptides were injected. For phage homing competition and IgG transcytosis blocking experiments, 500 µl of 5 mg/ml GST-peptides were administered intravenously.

Peptide Localization in Tissues Immunohistochemistry on sections of formalin-fixed, paraffin-embedded mouse tissue was performed as described (Pasqualini et al., 2000; Pasqualini and Ruoslahti, 1996). For phage-peptide immunolocalization, a rabbit anti-fd phage antibody (Sigma Chemicals, St. Louis, Mo.) was used at 1:1,000 dilution and detected with a secondary horseradish peroxidase (HRP)-conjugated antibody. For GST-peptide immunolocalization, a goat anti-GST antibody (Amersham, Piscataway, N.J.) was used at 1:1,000 dilution and detected with a secondary alkaline phosphatase (AP)-conjugated antibody. For mouse IgG immunolocalization, the ARK Peroxidase Kit (DAKO, Carpinteria, Calif.) was used. All immunohistochemistry and FITC immunofluorescence images were captured using an Olympus IX70 microscope and digital camera setup.

Peptide Embryotoxicity For peptide embryotoxicity studies, agents were injected at the following daily doses: GST-peptides 0.1 mg (~3 nMoles), FITC-peptides 50 µg (~30 nMoles), and phage-peptides $10^{11}$ TU. All agents were dissolved in PBS. Mice were injected subcutaneously in the back (5-10 injections per course).

Results

Figure 3:
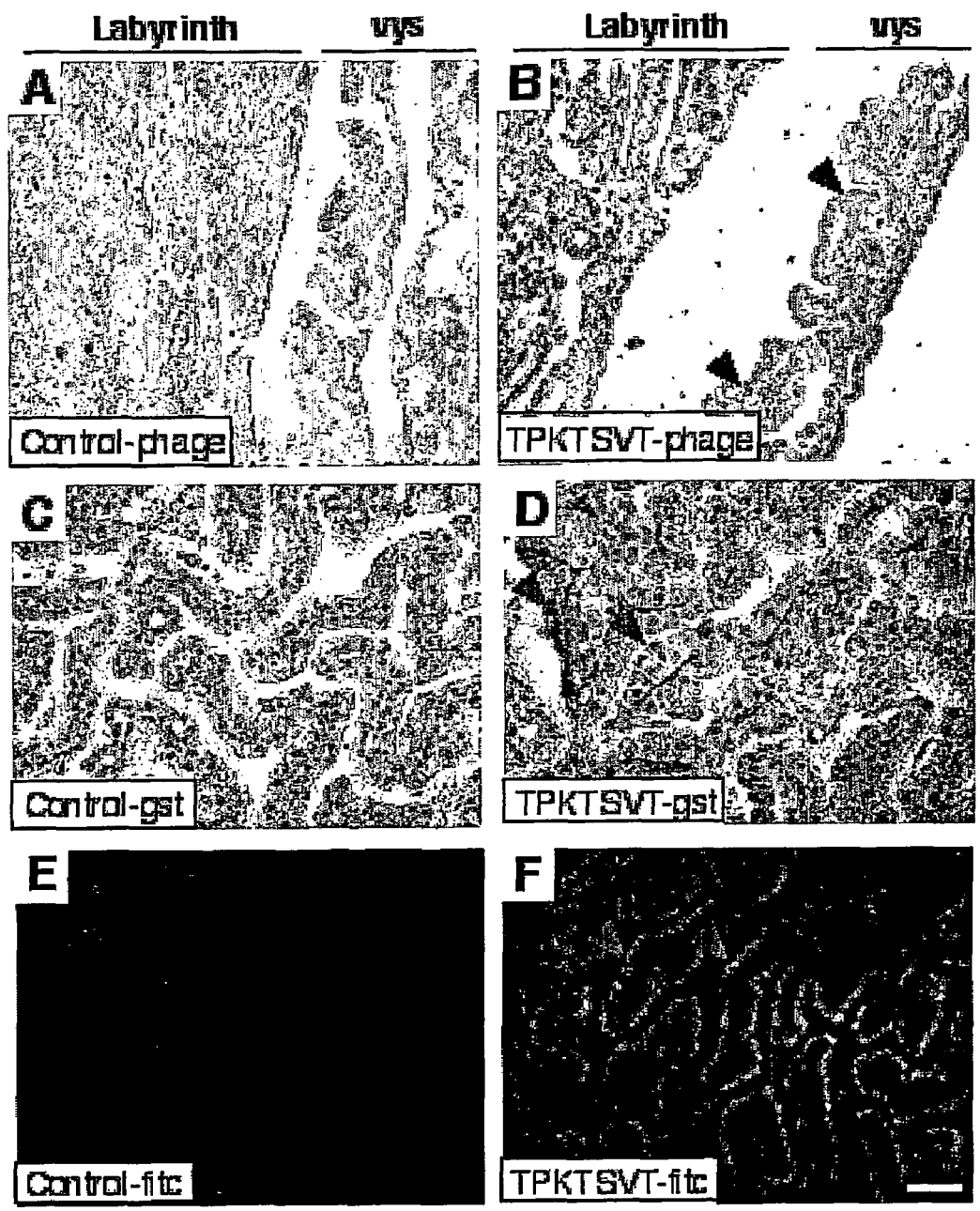
FIG. 3. In vivo homing of the TPKTSVT (SEQ ID NO:5) motif to the mouse villous yolk sac (vys). (A) and (B) anti-phage immunohistochemistry; (C) and (D) anti-GST immunohistochemistry; (E) and (F) FITC immunofluorescence in paraffin sections of placentas from 18 dpc (days post-conception) pregnant mice injected intravenously 6 h prior to tissue processing with: (A) control insertless phage, (B) TPKTSVT (SEQ ID NO:5) phage, (C) control GST peptide, (D) TPKTSVT (SEQ ID NO:5) linked to GST peptide, (E) control FITC-peptide, or (F) TPKTSVT (SEQ ID NO:5) linked to FITC peptide. Homing of the TPKTSVT (SEQ ID NO:5) peptide to the vys (dark arrows, D) and translocation to the embryonic capillaries (light arrow, D) are indicated. Only the vys is shown in (C-F). Bar: 100 µm (A-B); 20 µm (C-F).

Localization of the TPKTSVT (SEQ ID NO:5) Peptide in Mouse Placenta The tissue distribution of recombinant phage injected into pregnant mice was examined by immunohistochemistry (FIG. 3). While a control phage barely localized to placental tissues (FIG. 3A), the TPKTSVT (SEQ ID NO:5) phage homed to the placenta and showed marked localization to the villi of the visceral yolk sac (vys) endoderm (FIG. 3B, arrows). The vys is a layer of epithelial cells which surrounds the embryonic microvasculature and functions as the final barrier during transport of molecules, such as immunoglobulin G (IgG), from the labyrinth layer of the placenta into the fetus (Rugh, 1990; Beckman et al., 1990; Lyden et al., 2001, *J. Immunol.* 166:3882-3889; Jollie, 1990, *Teratology* 41:361-381).

To verify that targeting of the TPKTSVT (SEQ ID NO:5) motif to the vys endoderm also occurs if the peptide is outside of the context of the phage, the homing of TPKTSVT (SEQ ID NO:5) fused with glutathione S-transferase (GST) protein to placenta was also tested. GST fused to either TPKTSVT (SEQ ID NO:5) or a control peptide TREVHRS (SEQ ID NO:13) with a similar overall charge were injected into pregnant mice and the tissue distribution of each peptide was examined. No localization of the control GST fusion peptide to the placenta was observed (FIG. 3C). In contrast, accumulation of the TPKTSVT (SEQ ID NO:5) GST fusion peptide was readily detectable in the apical cytoplasm of the vys (FIG. 3D, arrows) and matched that observed for TPKTSVT (SEQ ID NO:5)-phage (FIG. 3B, arrows).

Similarly, fluorescein (FITC)-conjugated TPKTSVT (SEQ ID NO:5) injected intravenously into pregnant mice also specifically localized to the apical vys cytoplasm (FIG. 3F). A control peptide FITC conjugate was not detectable in the placenta (FIG. 3E). Localization of TPKTSVT (SEQ ID NO:5)-phage, TPKTSVT (SEQ ID NO:5)-GST, or TPKTSVT (SEQ ID NO:5)-FITC to control organs, such as brain and pancreas, was not detected (data not shown). Together, these data show that the TPKTSVT (SEQ ID NO:5) peptide targets the placenta, with the strongest homing noticed in the vys (FIG. 3B, FIG. 3D and FIG. 3F).

Figure 4:
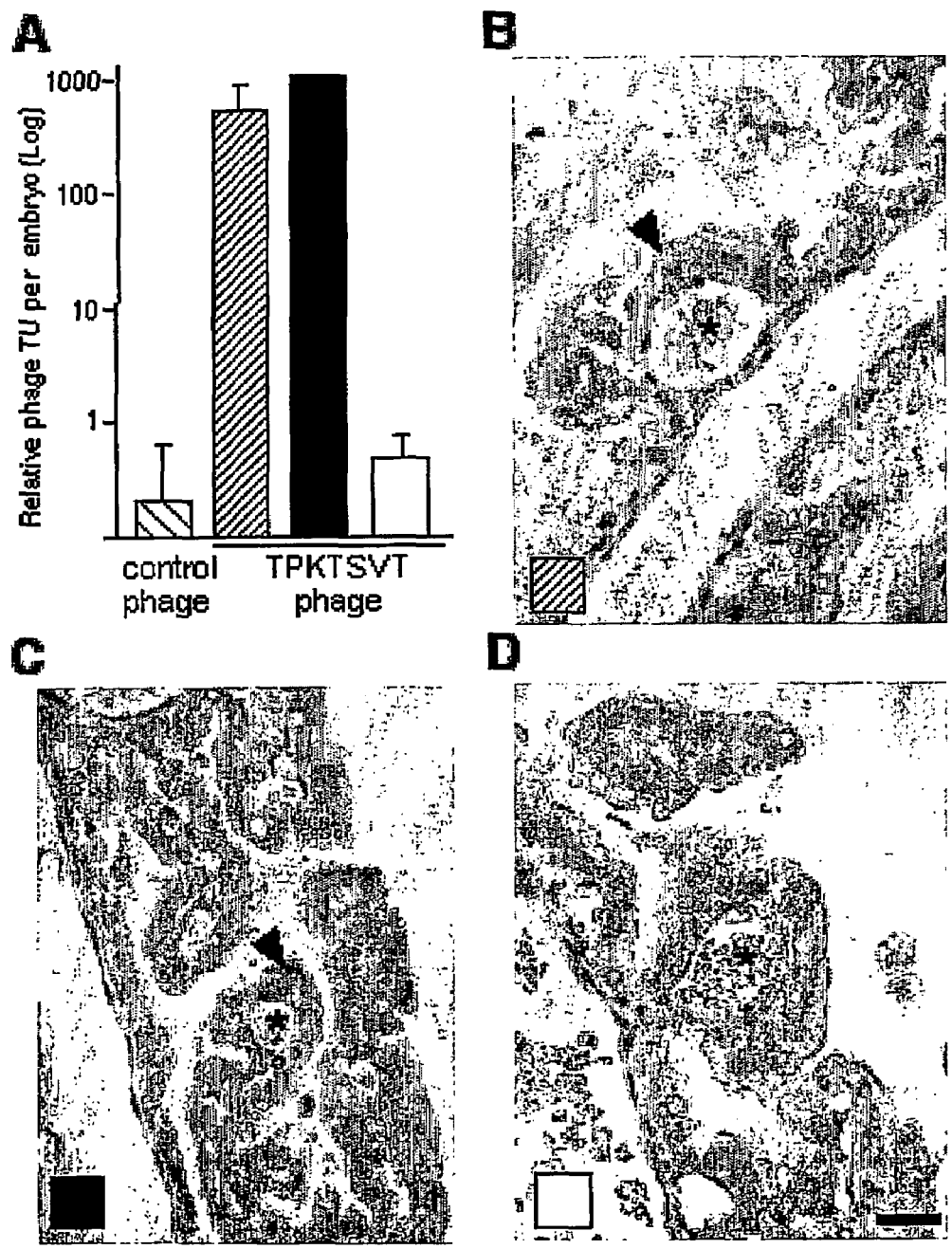
FIG. 4. The TPKTSVT (SEQ ID NO:5) peptide specifically binds a placental transporter. (A) Recovery of indicated phage from embryos carried by 18 dpc pregnant mice intravenously injected (tail vein) with $10^{10}$ TU of the indicated phage 6 h prior to phage recovery or immunohistochemistry. Control phage (light cross-hatch) showed no selective targeting of placenta. TPKTSVT (SEQ ID NO:5) phage were administered alone (dark cross-hatched) or co-administered with control-GST (black) or TPKTSVT (SEQ ID NO:5) linked to GST (white bar). Shown are mean +/− SEM (standard error) from different embryos. (B-D) Anti-phage HRP immunohistochemistry (arrowheads) in paraffin sections of the vys from the corresponding mice, as indicated. Asterisks mark embryonic capillaries. Bar: 20 µm.

The TPKTSVT (SEQ ID NO:5) Peptide Binds to a Placental Transporter The TPKTSVT (SEQ ID NO:5) peptide localizes to the vys (FIG. 3), which is the tissue primarily responsible for materno-fetal transport in mice. This motif was tested to see if it would promote phage transport into the embryo. Either TPKTSVT (SEQ ID NO:5)-phage or control phage were injected into pregnant mice and the recovery of phage from embryos was determined. Specific accumulation of TPKTSVT (SEQ ID NO:5)-phage in embryos was observed to be up to 1,000-fold greater than that of control phage (FIG. 4A). The TPKTSVT (SEQ ID NO:5) peptide was observed to apparently bind to a specific placental transporter.

The materno-fetal transfer of TPKTSVT (SEQ ID NO:5)-phage was blocked by an excess of co-injected TPKTSVT (SEQ ID NO:5) peptide, but not the control GST fusion peptide (FIG. 4A), suggesting transport by a specific receptor protein as opposed to non-specific uptake.

Phage immunocytochemistry confirmed that the uptake of TPKTSVT (SEQ ID NO:5)-phage by the vys cells was not affected by the control GST fusion peptide (FIG. 4A, FIG. 4B and FIG. 4C). FIG. 4B shows that TPKTSVT (SEQ ID NO:5)-phage administered alone are localized to the vys (arrows). FIG. 4C shows that in the presence of control-GST fusion peptides, the TPKTSVT (SEQ ID NO:5)-phage still localize to the vys (arrows). In contrast, the addition of TPKTSVT (SEQ ID NO:5)-GST fusion peptide prevented internalization of TPKTSVT (SEQ ID NO:5)-phage into the vys epithelium (FIG. 4D). Together, these results show that the TPKTSVT (SEQ ID NO:5) peptide is actively transported through the placenta into the embryo by binding to a receptor located on endothelial cells in the vys.

The TPKTSVT (SEQ ID NO:5) Peptide Blocks Placental IgG Transport The pattern of the TPKTSVT (SEQ ID NO:5) localization to the placenta (FIG. 3) is reminiscent of that observed for IgG in that tissue (Parr and Parr, 1985, *J. Reprod. Immunol.* 8: 153-171). Moreover, both IgG and TPKTSVT (SEQ ID NO:5) appear to undergo a receptor-mediated transport into the embryo during pregnancy. It was hypothesized that IgG and TPKTSVT (SEQ ID NO:5) bind to a common receptor in the placenta. The results presented herein show that the TPKTSVT (SEQ ID NO:5) peptide competes for the placental transport of IgG.

Figure 5:
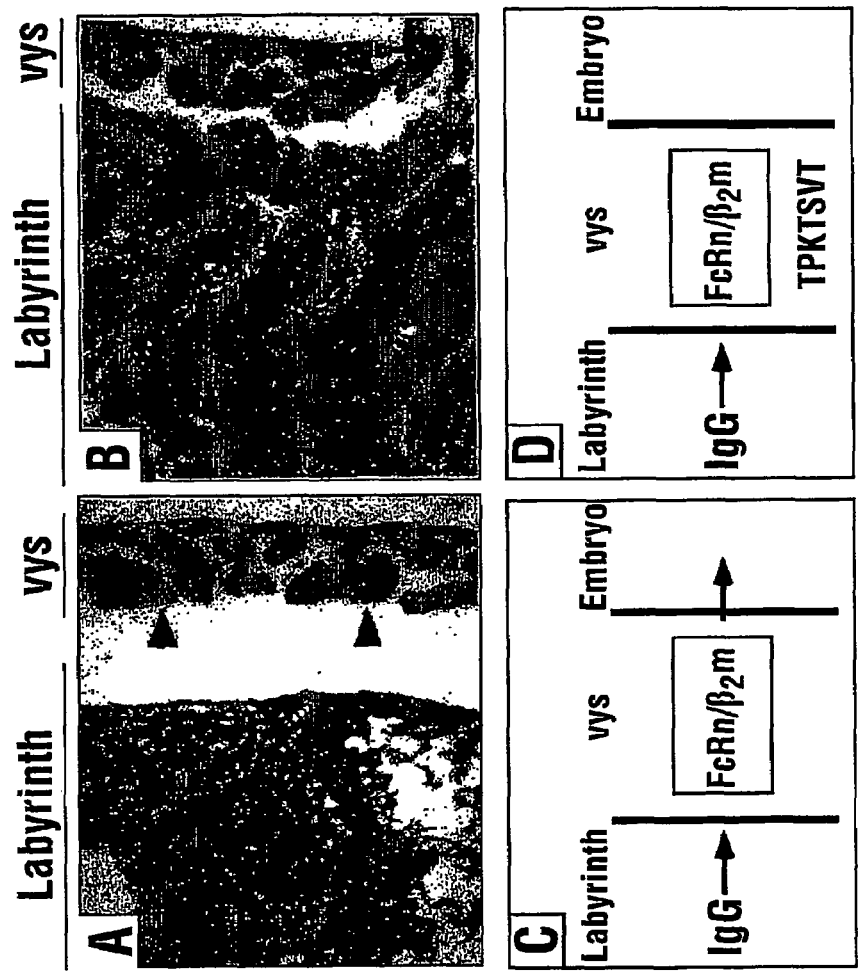
FIG. 5. The TPKTSVT (SEQ ID NO:5) peptide blocks placental IgG transcytosis. A 18 dpc pregnant mouse was intravenously injected with: (A) 100 mg of control GST fusion or (B) TPKTSVT (SEQ ID NO:5) linked to GST. The IgG distribution in the placenta after 6 h of peptide circulation was detected by anti-mouse IgG immunohistochemistry in paraffin sections. Strong immunostaining is noted in the vys of mice injected with a control GST fusion (arrowheads) and in the labyrinth of wild-type mice injected with either TPKTSVT (SEQ ID NO:5) linked to GST or control GST fusion (asterisks), but not in the vys of TPKTSVT (SEQ ID NO:5) linked to GST fusion. Bar: 100 µm. (C) and (D) A hypothetical model for the TPKTSVT (SEQ ID NO:5) peptide function. (C) Normally, the FcRn/$\beta_2$m complex transports IgG from maternal circulation through the labyrinth layer and then the yolk sac placenta (vys) and into the embryo. (D) Targeting of the FcRn/$\beta_2$m with TPKTSVT (SEQ ID NO:5) peptide can block the receptor complex and the transport of IgG or phage into the embryo.

Intravenous administration of a control GST-fusion peptide did not affect the placental transfer of IgG to the vys (FIG. 5A, arrowheads). In contrast, co-administration of an equimolar dose of TPKTSVT (SEQ ID NO:5)-GST blocked translocation of IgG through the placenta (FIG. 5B). Although IgG localization to the labyrinthine blood vessels in the embryo-distal placental compartments was still detectable (FIG. 5B, asterisks), IgG staining in the vys epithelium was markedly decreased (FIG. 5B). The vys levels of IgG in the presence of TPKTSVT (SEQ ID NO:5)-GST were similar to those observed in $\beta_2$m-null mice (not shown), which are genetically deficient in IgG transcytosis (Israel et al., 1995, *J. Immunol.* 154:6246-6251; Zijlstra, et al., 1990, *Nature* 344: 742-746). Based on these data, it is proposed that the TPKTSVT (SEQ ID NO:5) peptide selectively blocks transport through an immunoglobulin Fc receptor that mediates the uptake of IgG by the yolk sac (FIG. 5C and FIG. 5D).

The TPKTSVT (SEQ ID NO:5) Receptor is Associated with the $\beta_2$m Protein FcRn is a $\beta_2$m-associated Class I major histocompatibility complex (MHC-I) homologue. FcRN appears to regulate placental IgG transport (Ghetie and Ward, 2000, *Ann. Rev. Immunol.* 18:739-766; Simister and Story, 1997, *J. Reprod. Immunol.* 37:1-23). This is supported by the observation that IgG species which are incapable of binding to FcRn are not transported across the human placenta in an ex vivo model (Firan et al., 2001, *Int. Immunol.* 13:993-1002). In addition, FcRn expression patterns in the placenta resemble the pattern of placental IgG localization (Saji et al., 1999. *Rev. Reprod.* 4:81-89). A search of the mouse protein database using BLAST software (NCBI; http://www.ncbi.nlm.nih.gov/BLAST/) revealed the similarity of the TPKTSVT (SEQ ID NO:5) placental targeting peptide to the sequence PPKTTVT (amino acids 192-198 of the mouse MHC-I; Genbank accession AAD43175). Moreover, the corresponding conserved human MHC-I sequence, PPKTHVT, is exposed on the surface of the MHC-I $\alpha_3$ chain immediately adjacent to H-192 residue, a known $\beta_2$m contact site in the $\alpha_3$ domain of MHC-I homologues (Tysoe-Calnon et al., 1991, *Biochem. J.* 277:359-369). This makes the TPKTSVT (SEQ ID NO:5) motif an apparent mimeotope of FcRn. Homing of the TPKTSVT (SEQ ID NO:5) peptide to the placenta, despite expression of FcRn in other tissues, may be due to either differential association of additional receptor subunits, or by altered accessibility of the receptor to the circulating ligand in the placenta. This is consistent with previous reports of FcRn interacting with IgG in the placenta through a mechanism different from that in other tissues (Ghetie and Ward, *Ann. Rev. Immunol.* 18:739-766, 2000; Simister and Story, *J. Reprod. Immunol.* 37:1-23, 1997).

Figure 6:
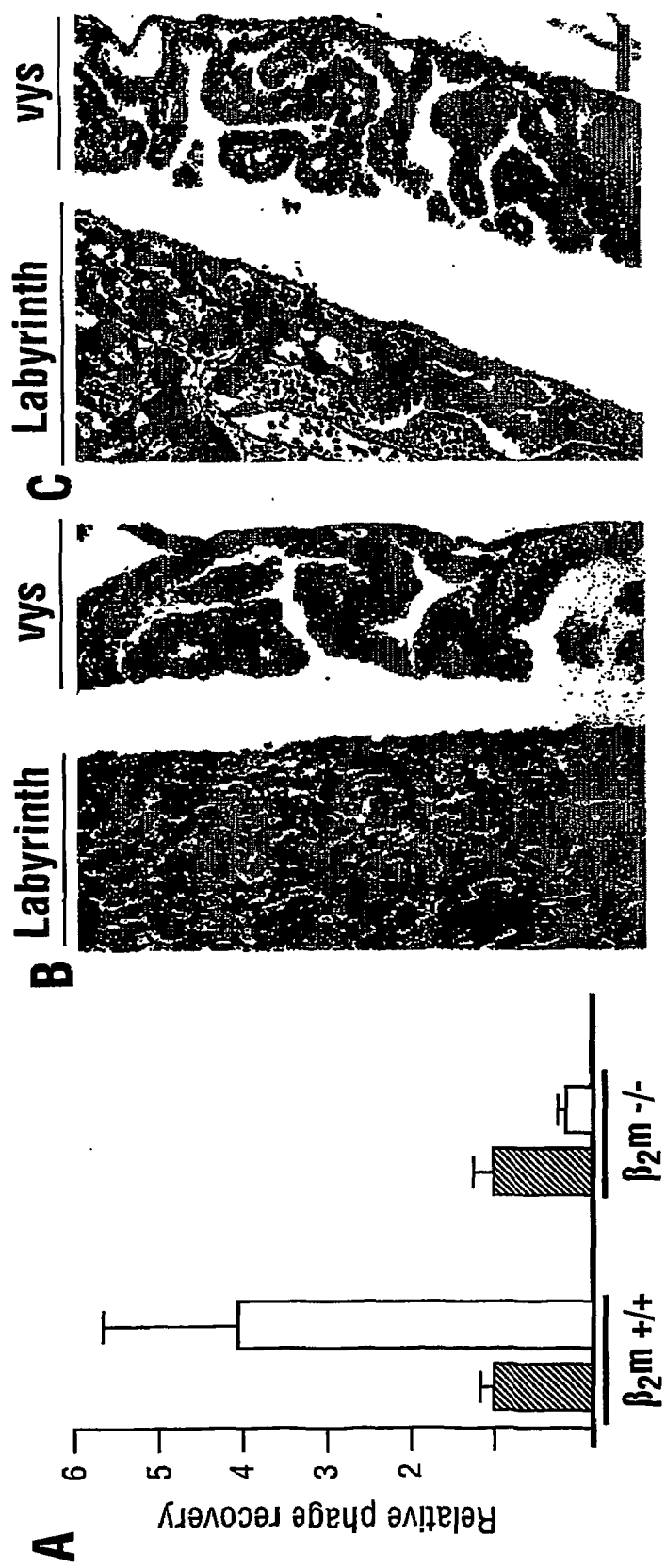
FIG. 6. Placental targeting by the TPKTSVT (SEQ ID NO:5) peptide requires a functional FcRn/$\beta_2$m receptor complex. (A) Relative phage recovery (placenta TU/ml to blood TU/ml ratio) from placentas derived from 18 dpc pregnant wild-type or $\beta_2$m-deficient mice injected with $10^{10}$ TU of control insertless phage (black) or TPKTSVT (SEQ ID NO:5) phage (white) 6 h prior to phage recovery or immunohistochemistry. Shown are mean +/− SEM from individual placentas. (B) and (C) Anti-phage immunohistochemistry in paraffin sections of the placenta from 18 dpc pregnant $\beta_2$m-null mice intravenously injected with (B) TPKTSVT (SEQ ID NO:5) phage or (C) control placenta-homing phage displaying the YIRPFTL (SEQ ID NO:9) peptide 6 h prior to tissue processing. Staining of a placenta-homing phage displaying the unrelated peptide YIRPFTL (SEQ ID NO:9) is detected in the labyrinth blood vessels (arrowheads). Bar: 100 µm.

The TPKTSVT (SEQ ID NO:5) motif was tested to determine if it targets the FcRn/$\beta_2$m receptor complex in the placenta. The $\beta_2$m-deficient mouse strain, in which FcRn is not functional (Isreal et al., 1995, *J. Immunol.* 154:6246-51; Zijlstra et al., 1990, *Nature* 344:742-746), was used as a model system to test whether the TPKTSVT (SEQ ID NO:5) peptide is a ligand for the FcRn/$\beta_2$m receptor complex. Phage displaying the TPKTSVT (SEQ ID NO:5) peptide were intravenously injected into pregnant $\beta_2$m-null mice and the recovery of phage from the placenta was assayed (FIG. 6). While the TPKTSVT (SEQ ID NO:5)-phage (FIG. 6A, white bars) homed to the wild-type (+/+) placenta relative to control phage (FIG. 6A, black bars), no such homing was detectable in $\beta_2$m-deficient mice (FIG. 6A). Immunohistochemical analysis of phage accumulation in $\beta_2$m wild-type (FIG. 3B) and $\beta_2$m-null (FIG. 6B) placentas confirmed that TPKTSVT (SEQ ID NO:5)-phage were not taken up by the vys epithelium in the $\beta_2$m-deficient mice. In contrast, in vivo localization of a control phage displaying a different placenta homing peptide, YIRPFTL (SEQ ID NO:9), which, unlike TPKTSVT (SEQ ID NO:5) peptide, homes to the vasculature of the labyrinthine placenta, rather than to the vys, was not affected in $\beta_2$m-null mice (FIG. 6C, arrowheads). Together, these observations strongly suggest that the TPKTSVT (SEQ ID NO:5) motif targets the placenta by binding to FcRn/$\beta_2$m.

The TPKTSVT (SEQ ID NO:5) Peptide Interferes with Mouse Pregnancy Because FcRn/$\beta_2$m regulates materno-fetal exchange, the above observations suggested that TPKTSVT (SEQ ID NO:5) might interfere with placental transport and embryonic development. TPKTSVT (SEQ ID NO:5) peptide was administered to pregnant mice in three different forms—displayed on the phage capsid, fused to GST or fused to FITC. The phage or fusion peptides were subcutaneously injected and the progression of pregnancy was compared with mice injected with control phage, control peptides, or saline. Multiple injections of the TPKTSVT (SEQ ID NO:5) peptide were administered, starting at midpregnancy (~12 days postconception, dpc) in doses non-toxic to the mother.

Figure 7:
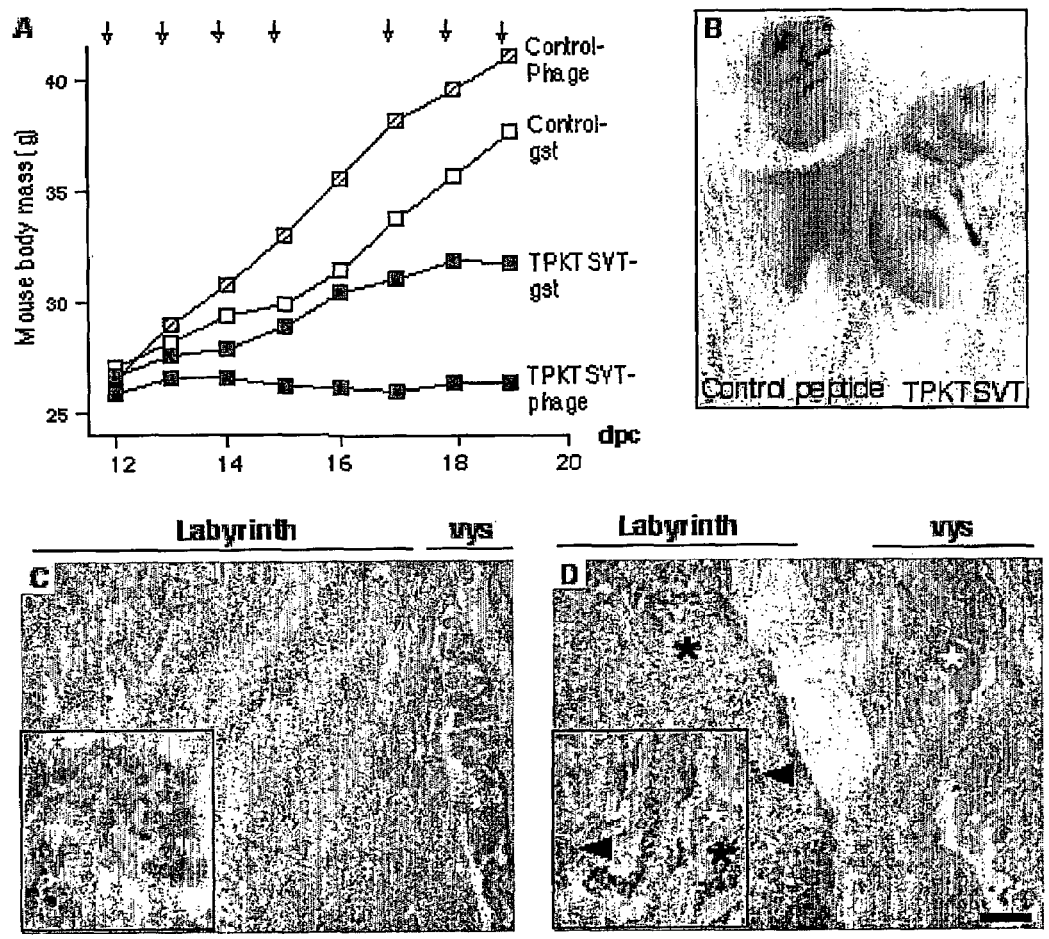
FIG. 7. TPKTSVT (SEQ ID NO:5) peptide inhibits mouse pregnancy and is teratogenic. (A) Pregnancy courses (representative from 5 independent experiments) in mice subcutaneously injected with the indicated phage or peptides were monitored by daily weighing of the mice upon each injection (arrows). (B) Appearance of a normally developed 20 dpc embryo (left) for control GST fusion treatment compared to a representative 20 dpc embryo (right) resulting from TPKTSVT (SEQ ID NO:5) linked to GST fusion treatment. A severely teratogenic phenotype is observed with the placental targeting fusion peptide. (C) and (D) Hematoxylin/eosin staining of 20 dpc paraffin-embedded placentas derived from mice injected for 7 days with (C) control GST fusion or (D) the TPKTSVT (SEQ ID NO:5) linked to GST fusion peptide. Note hemorrhage (black asterisks), necrosis (white asterisks), and fibrosis (arrowheads). Bar: 500 µm (50 µm for insets).

The effect of TPKTSVT (SEQ ID NO:5) peptide on fetal development is illustrated in FIG. 7A and FIG. 7B. TPKTSVT (SEQ ID NO:5) peptide inhibited the progression of pregnancy, as evidenced by diminished weight gain in mice injected with the TPKTSVT (SEQ ID NO:5) phage or GST fusion peptide compared to control phage or GST-peptide (FIG. 7A). The course of pregnancy courses in mice injected with control peptides were undistinguishable from those in saline-injected mice (data not shown).

Examination of embryos on the 20th day of pregnancy (the delivery day for the control) revealed that the TPKTSVT (SEQ ID NO:5) peptide has a severe effect on embryonic development. Growth-retarded, dead, or partially resorbed embryos were observed in mice injected with either TPKTSVT (SEQ ID NO:5)-phage, TPKTSVT (SEQ ID NO:5)-GST, or TPKTSVT (SEQ ID NO:5)-FITC (FIG. 7B, embryo to right of figure). The normal development of a mouse embryo injected with control peptide is shown on the left side of FIG. 7B. Administration of TPKTSVT (SEQ ID NO:5) fusion peptides to pregnant mice resulted in 43% complete embryo resorption and 21% dead or malformed conceptuses (FIG. 7B). The extent of embryo resorption and frequency of complete pregnancy abortion increased with prolonged TPKTSVT (SEQ ID NO:5) treatment (data not shown), suggesting that the peptide effect is dose-dependent. Embryo death or morbidity were not observed in any of the control groups.

Morphologic inspection of tissues from TPKTSVT (SEQ ID NO:5) peptide-injected mice revealed that, in contrast to controls, placentas were edematous and grossly deformed. Histopathological examination of the placentas showed that the TPKTSVT (SEQ ID NO:5) treatment induced massive dilation of blood vessels and intraplacental bleeding, as well as widespread hemorrhagic necrosis (FIG. 7D). Hematoxylin staining of the placental epithelium after seven days of peptide administration showed that most nuclei in the yolk sac and many in the labyrinthine compartment were degraded (FIG. 7D). Also, massive fibrosis was evident in the yolk sac cavity and in the labyrinthine portion of the placenta (FIG. 7D). In contrast, placentas from mice injected with control peptides (FIG. 7C) were indistinguishable from untreated placentas at corresponding stages of pregnancy. The effect of TPKTSVT (SEQ ID NO:5) peptide on the reproductive system was strikingly specific, as histological examination of control organs revealed no pathological changes or necrosis, and no signs of peptide toxicity to the mother were observed (data not shown).

The teratogenicity observed with TPKTSVT (SEQ ID NO:5) is probably not caused by the disruption of the FcRn/$\beta_2$M receptor function, as the fertility of mice is not significantly affected by $\beta_2$M deficiency (Zijlstra et al., Nature 344:74246, 1990). Rather, embryotoxicity is likely secondary to placental thrombosis and ischemia. An alternative mechanism could be activation of complement and an immune response against the targeting peptide itself.

These results have important implications for the development of pregnancy-safe therapeutics, as it appears that a substance can cause embryotoxicity by merely homing to a placental cell surface marker without inactivating the receptor function. This creates the basis for a high throughput identification system based on placental receptors prone to teratogen binding. Systematic screening of potential teratogens for binding to such receptors could be used to identify teratogenic activity and decrease the risk of teratogen induced birth defects.

Example 3

Identification of Mouse Adipose Targeting Peptides

Adipose Targeting Peptides

A similar protocol to that disclosed in Example 1 was used to isolate fat targeting peptides from a genetically obese mouse (Zhang et al., Nature, 372:425-432, 1994; Pelleymounter et al., Science 269:540-543, 1995). Phage that had been subjected to biopanning in obese mice were post-cleared in a normal mouse. The fat-targeting peptides isolated included TRNTGNI (SEQ ID NO:14), FDGQDRS (SEQ ID NO:15); WGPKRL (SEQ ID NO:16); WGESRL (SEQ ID NO:17); VMGSVTG (SEQ ID NO:18), KGGRAKD (SEQ ID NO:19), RGEVLWS (SEQ ID NO:20), TREVHRS (SEQ ID NO:13) and HGQGVRP (SEQ ID NO:21).

Homology searches identified several candidate proteins as the endogenous analogs of the fat targeting peptides, including stem cell growth factor (SCGF) (KGGRAKD, SEQ ID NO:19), attractin (mahogany) (RGEVLWS, SEQ ID NO:20), angiopoitin-related adipose factor (FIAF) (TREVHRS, SEQ ID NO:13), adipophilin (ADRP) (VMGSVTG, SEQ ID NO:18), Flt-1 or procollagen type XVII (TRNTGNI, SEQ ID NO:14) and fibrillin 2 or transferrin-like protein p97 (HGQGVRP, SEQ ID NO:21)

Validation of Adipose Targeting Peptides

Figure 2:
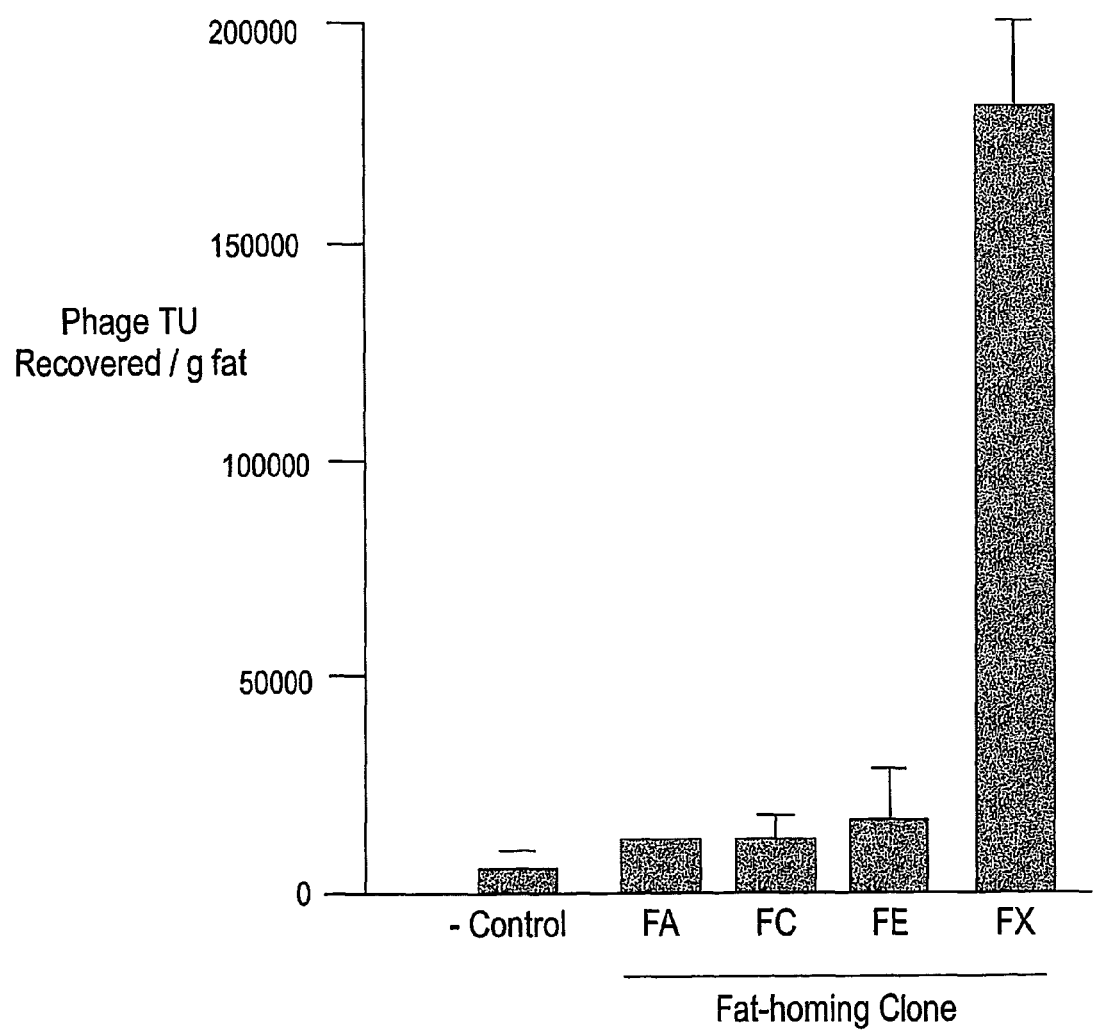
FIG. 2. Validation of adipose homing peptides. Phage bearing targeting peptides were injected into obese mice and their recovery from adipose tissue was compared to control fd-tet phage without targeting sequences.

The fat homing peptides were validated by in vivo homing, as shown in FIG. 2. The fat homing clones selected were: FA-KGGRAKD (SEQ ID NO:19), FC-RGEVLWS (SEQ ID NO:20), FE-TREVHRS (SEQ ID NO:13) and FX-VMGSVTG (SEQ ID NO:18). As seen in FIG. 2, all of these clones exhibited some elevation of homing to adipose tissue, with clone FX showing several orders of magnitude higher adipose localization than control fd-tet phage. Clone FX also exhibited substantially higher localization than the other selected fat homing clones. However, by analogy with the placental homing peptides disclosed above, the skilled artisan will realize that fat homing clones exhibiting lower levels of adipose tissue localization may still be of use for targeted delivery of therapeutic agents.

The skilled artisan will realize that targeting peptides selective for angiogenic vasculature in adipose tissue could be of use for weight reduction or for preventing weight gain. By attaching anti-angiogenic or toxic moieties to an adipose targeting peptide, the blood vessels supplying new fat tissue could be selectively inhibited, preventing the growth of new deposits of fat and potentially killing existing fat deposits.

Example 4

CKGGRAKDC (SEQ ID NO:22) Homes to White Fat in ob/ob Mice

Materials and Methods
Experimental Animals

C57BL/6 mice were purchased from Harlan Teklad. Leptin-deficient (ob/ob) (stock 000632) and leptin receptor-deficient (stock 000642) mice were purchased from Jackson Laboratories (Bar Harbor, Me.). Anesthesia was performed with Avertin (0.015 ml/g) administered intraperitoneally (Arap, et al., 1998; Pasqualini & Rouslahti, 1996).

In vivo Phage Library Screening

In vivo phage-display screening of the $CX_7C$ library (C, cysteine; X, any amino acid) (Pasqualini et al., 2000; Arap et al., Nature Med. 8:121-127, 2002) for fat-homing peptides was performed (Pasqualini & Rouslahti 1996, Pasqualini et al., 2000). In each biopanning round, an adult ob/ob mouse was injected intravenously (tail vein) with $10^{10}$ transducing units (TU) of the library. Phage (~300 TU/g in round 1 increased to ~$10^4$ TU/g in round 3) were recovered after 5 min of circulation by grinding subcutaneous white fat with a glass Dounce homogenizer, suspending the homogenate in 4° C. Dulbecco's Modified Eagle's medium (DMEM) containing proteinase inhibitors (DMEM-prin: 1 mM PMSF, 20 μg/ml aprotinin, and 1 μg/ml leupeptin) and washing with DMEM-prin. The lipid phase was discarded during the washes and only the solid-phase cellular material was used. Washed homogenates were incubated with host bacteria (log phase E. coli K91kan; $OD_{600}$~2). Bacterial cultures were plated onto Luria-Bertani agar plates containing 40 μg/ml tetracycline and 100 μg/ml kanamycin, incubated overnight at 37° C. and selected clones were bulk-amplified and used to precipitate phage for a subsequent round of biopanning. The sub-library amplified after the third round of panning was enriched for fat-specific binders using a subtraction step. A lean C57BL/6 female was injected (tail vein) with $10^9$ TU of phage selected in round 3. After 5 min of circulation, the unbound phage were recovered from plasma and amplified for the fourth and final round of biopanning. In this protocol, phage that bound to tissues other than adipose were removed from the sub-library, increasing the selectivity of the recovered phage for binding to adipose tissue.

Peptide Localization in Tissues

Staining of formalin-fixed, paraffin-embedded mouse tissue sections was performed (Pasqualini & Rouslahti, 1996; Pasqualini et al., 2000). For phage-peptide immunolocalization, $10^{10}$ TU of CKGGRAKDC (SEQ ID NO:22)-phage or a control insertless phage was injected intravenously. Phage immunohistochemistry was performed using a rabbit anti-fd phage antibody (Sigma Chemicals, St. Louis, Mo.) used at 1:1,000 dilution and a secondary horseradish peroxidase (HRP)-conjugated antibody. Apoptosis was detected using standard TUNEL immunohistochemistry and an HRP-conjugated antibody. For in vivo peptide homing validation, stocks of 5-carboxyfluorescein (FITC)-conjugated CKGGRAKDC (SEQ ID NO:22) or CARAC (SEQ ID NO:12) were chemically synthesized, cyclized using the terminal cysteines and HPLC-purified to >90% purity by Anaspec (San Jose, Calif.). Lyophilized peptides were dissolved in DMSO to a concentration of 20 mM. Ten µl of 1 mM peptide-FITC solution in PBS was injected 5 min prior to tissue extraction. For blood vessel localization, 10 µl of 2 mg/ml of rhodamine-conjugated lectin-I (RL-1102, Vector Laboratories, Burlingame, Calif.) was co-injected. All immunohistochemistry and FITC immunofluorescence images were captured using an Olympus IX70 microscope and digital camera setup (Melville, N.Y.).

Anti-Obesity Therapy

Stocks of CKGGRAKDC (SEQ ID NO:22) fused to (KLAKLAK)$_2$ (SEQ ID NO:1); (KLAKLAK)$_2$ (SEQ ID NO:1) alone; CARAC (SEQ ID NO:12) fused to (KLAKLAK)$_2$ (SEQ ID NO:1); and CKGGRAKDC (SEQ ID NO:22) peptide were chemically synthesized, cyclized using the terminal cysteines and HPLC-purified to >90% (Anaspec). Lyophilized peptides were dissolved in DMSO to a concentration of 65 mM to make stock solutions. A total of 150 µl of 0.65 mM peptide solution in PBS was subcutaneously injected daily in the back of C57BL/6 males, after body mass was measured each day. High-fat cafeteria diet for obesity induction (TD97366: 25.4% fat, 21.79% protein, 38.41% carbohydrate) was purchased from Harlan Teklad. Mice were pre-fed with TD97366 prior to the initiation of treatment with adipose targeting peptides to induce diet-related obesity. The high-fat diet resulted in an average weight of 50 g before treatment.

Results

In vivo phage display (Pasqualini and Ruoslahti, *Nature* 380:364-366, 1996; Kolonin et al., *Curr. Opin. Chem. Biol.* 5:308-313, 2001; Pasqualini et al., In Vivo Phage Display, In *Phage Display: A Laboratory Manual*, eds. Barbas et al., pp. 1-24. Cold Spring Harbor Laboratory Press, New York, 2000) was used as described above to obtain a peptide targeting the fat vasculature. A phage-display library was screened for peptide motifs that home to the vasculature of subcutaneous white fat in morbidly obese leptin-deficient (ob/ob) mice (Zhang et al. *Nature* 372:425-432, 1994). This model provides a convenient source of adipose tissue. Four rounds of panning were followed by a fat-specific in vivo subtraction to restrict ligands to those binding to adipose-specific endothelial receptors. The DNA encoding the corresponding phage-displayed peptides was then sequenced to obtain the targeting peptide amino acid sequences. Statistical analysis of selected motifs using SAS software (version 8, SAS Institute) revealed that the motif CKGGRAKDC (SEQ ID NO:22) constituted 4.5% of all clones identified in the screen. Intravenous administeration of this clone into ob/ob mice showed that CKGGRAKDC (SEQ ID NO:22)-phage accumulated in subcutaneous fat to a higher level than a control insertless phage (data not shown).

Figure 8:
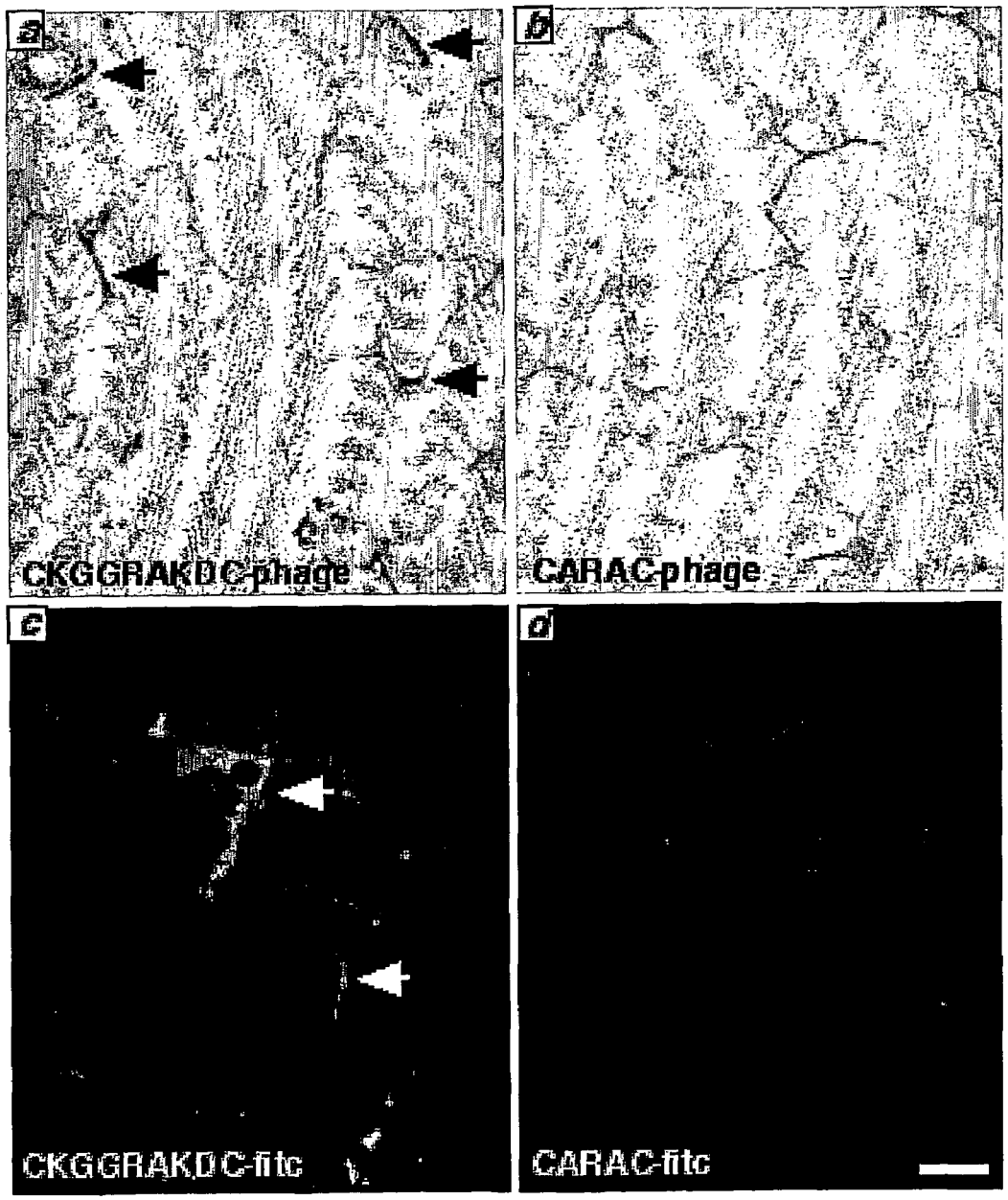
FIG. 8. In vivo fat homing of the CKGGRAKDC (SEQ ID NO:22) motif in genetically obese mice. (A) and (B) Anti-phage immunohistochemistry in paraffin sections of subcutaneous white fat from leptin-deficient mice intravenously injected 6 hr prior to tissue processing. (C) and (D) Peptide-FITC immunofluorescence in paraffin sections of subcutaneous white fat from leptin-deficient mice intravenously injected 6 hr prior to tissue processing. Mice were injected with (A) CKGGRAKDC (SEQ ID NO:22) phage, (B) control insertless phage, (C) CKGGRAKDC (SEQ ID NO:22) linked to FITC peptide, or (D) control CARAC (SEQ ID NO:12) linked to FITC peptide. Homing of the CKGGRAKDC (SEQ ID NO:22) peptide to fat blood vessels (arrows) and its uptake by fat endothelium are indicated. Bar: 10 µm.

The tropism of CKGGRAKDC (SEQ ID NO:22)-phage for adipose tissue was confirmed by immunohistochemistry: CKGGRAKDC (SEQ ID NO:22)-phage showed marked localization to the vasculature of subcutaneous and peritoneal white fat (FIG. 8*a*, arrows), whereas the control phage was undetectable in fat blood vessels (FIG. 8*b*). To test whether targeting of the CKGGRAKDC (SEQ ID NO:22) motif to the fat vasculature would also occur when the peptide is outside of the context of the phage, the in vivo distribution of intravenously injected CKGGRAKDC (SEQ ID NO:22) peptide fused to fluorescent (FITC) was determined. Immunofluorescence in subcutaneous and peritoneal fat from peptide-injected ob/ob mice showed that CKGGRAKDC (SEQ ID NO:22)-FITC localized to and was internalized by cells of white adipose vasculature (FIG. 8*c*, arrows), whereas a control CARAC (SEQ ID NO:12)-FITC conjugate was undetectable in adipose tissue (FIG. 8*d*).

CKGGRAKDC (SEQ ID NO:22) Homes to White Fat in Wild-Type Mice

The mutation in leptin that leads to the extreme proliferation of white adipose tissue in mice (Zhang et al., 1994) is not frequently encountered in humans (Ozata et al., *J. Clin. Endocrinol. Metab.* 84:3686-3695. 1999). Thus, this animal model may not be representative of the typical pattern of obesity in humans. To exclude the possibility that CKGGRAKDC (SEQ ID NO:22) homing to fat is limited to ob/ob mice and to demonstrate the general applicability of adipose-targeting peptides for naturally-occurring obesity, the CKGGRAKDC (SEQ ID NO:22) peptide was tested in wild-type mice.

Figure 9:
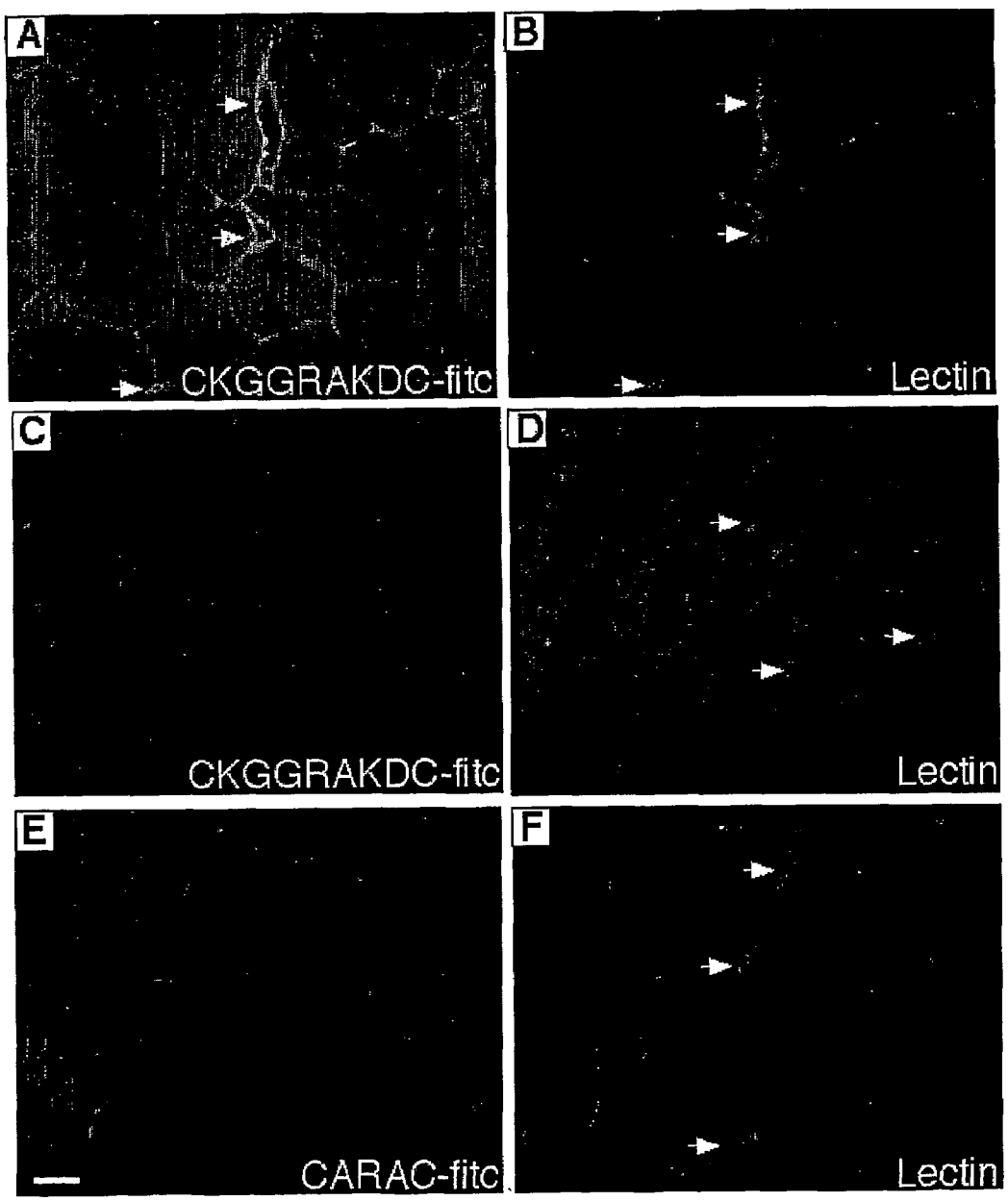
FIG. 9. In vivo fat homing of the CKGGRAKDC (SEQ ID NO:22) motif in wild-type mice. (A), (C) and (E) Peptide-FITC immunofluorescence or (B), (D) and (F) lectin-rhodamine immunofluorescence in blood vessels of (A), (B), (E) and (F) subcutaneous white fat or (C) and (D) pancreas controls detected in paraffin-sectioned tissues from c57bl/6 mice intravenously co-injected 5 min prior to tissue processing. Mice were injected with (A), (B), (C) and (D)) CKGGRAKDC (SEQ ID NO:22) linked to FITC peptide and lectin-rhodamine; or (E) and (F) control CARAC (SEQ ID NO:12) linked to FITC peptide and lectin-rhodamine. (B), (D) and (F) Arrows show endothelium marked with lectin.

FIG. 9 shows that the CKGGRAKDC (SEQ ID NO:22)-FITC fusion peptide intravenously injected into C57BL/6 (leptin +/+) mice specifically localized to blood vessels of subcutaneous and peritoneal white fat (FIG. 9A, FIG. 9B). A lectin-rhodamine peptide was used to visualize blood vessel endothelium (arrows, FIG. 9B, FIG. 9D, FIG. 9F). The CKGGRAKDC (SEQ ID NO:22)-FITC fusion peptide co-localized with lectin-rhodamine in adipose tissue (arrows, FIG. 9A and FIG. 9B). No such co-localization was observed in control pancreatic tissue (FIG. 9C and FIG. 9D) or other control organs (data not shown). The control CARAC (SEQ ID NO:12)-FITC peptide was not detectable in white fat vasculature (FIG. 9E and FIG. 9F). These in vivo localization data show that the adipose-targeting CKGGRAKDC (SEQ ID NO:22) peptide targets the white adipose vasculature in genetically normal obese mice as well as in leptin deficient mice, demonstrating the general applicability of adipose targeting using such peptides. The uptake of CKGGRAKDC (SEQ ID NO:22)-FITC by the endothelium of fat tissue suggests that the motif targets a receptor selectively expressed in the adipose vasculature that could provide a mechanism for directed delivery of therapeutic compounds to fat.

Design and Use of Fat-Targeted Pro-Apoptotic Peptide

It was next determined whether proliferation of adipose tissue could be controlled via targeted destruction of the fat vasculature. The pro-apoptotic peptide KLAKLAKKLAK-LAK (SEQ ID NO:1) (Ellerby et al., *Nature Med.* 5:1032-38, 1999) (designated KLAKLAK)$_2$), which disrupts mitochondrial membranes to induce apoptosis, has been targeted to receptors in tumor vasculature via a conjugated homing peptide (Ellerby et al 1999, Arap, et al., *Proc. Natl. Acad. Sci. U.S.A.* 99:1527-1531, 2002). The (KLAKLAK)$_2$ (SEQ ID NO:1) peptide was conjugated to the fat targeting CKGGRAKDC (SEQ ID NO:22) peptide for targeted delivery to fat vasculature in adipose tissue. The D enantiomer of (KLAKLAK)$_2$ (SEQ ID NO:1), which is resistant to proteolysis but still exhibits pro-apoptotic activity, was conjugated to the CKGGRAKDC (SEQ ID NO:22) peptide via a glycinylglycine bridge. The conjugated fat-targeting, pro-apoptotic peptide was administered to mice and the effect on adipose tissue was monitored.

A non-genetic mouse obesity model was initially used. A cohort of C57BL/6 (wild-type) mice, in which obesity had been induced by a high-fat cafeteria diet, were subcutaneously injected with CKGGRAKDC (SEQ ID NO:22)-(KLAKLAK)$_2$ (SEQ ID NO:1) peptide and weighed daily over a period of two weeks. Cafeteria dieting continued throughout the experiment. As shown in FIG. 10A, injections of CKGGRAKDC (SEQ ID NO:22) conjugated to (KLAKLAK)$_2$ (SEQ ID NO:1) prevented obesity development and surprisingly caused a rapid decrease in body mass of up to 20%. In contrast, obese mice injected with two negative controls (an equimolar amount of either unconjugated CKGGRAKDC (SEQ ID NO:22) and (KLAKLAK)$_2$ (SEQ ID NO:1) or a control CARAC (SEQ ID NO:12)-(KLAKLAK)$_2$ (SEQ ID NO:1) conjugate) did not show a significant body mass decrease and continued to increase in weight (FIG. 10A).

The effectiveness of the CKGGRAKDC (SEQ ID NO:22)-(KLAKLAK)$_2$ (SEQ ID NO:1) conjugate was also examined in wild-type mice fed on a regular diet (FIG. 10B). C57BL/6 mice that had developed a considerable amount of subcutaneous and peritoneal fat due to old age were subcutaneously injected with the CKGGRAKDC (SEQ ID NO:22)-(KLAKLAK)$_2$ (SEQ ID NO:1) conjugate or control peptides over a period of one month. As in the diet-induced obesity model, targeting of (KLAKLAK)$_2$ (SEQ ID NO:1) to fat by conjugation with CKGGRAKDC (SEQ ID NO:22) resulted in greater than 35% reduction in body mass at a rate of 10% per week (FIG. 10B). No toxicity of the conjugated peptide was detected under these conditions (data not shown). In fact, the CKGGRAKDC (SEQ ID NO:22)-(KLAKLAK)$_2$ (SEQ ID NO:1) treated mice became more active and agile following body mass reduction and appeared healthier than prior to treatment (data not shown). The control untargeted (KLAKLAK)$_2$ (SEQ ID NO:1) treatments resulted in only a slight body mass reduction (FIG. 10B), possibly due to low levels of nonspecific toxicity. The control mice did not exhibit the increased activity and/or agility seen in treated mice (data not shown).

Fat Resorption with CKGGRAKDC (SEQ ID NO:22)-(KLAKLAK)$_2$ (SEQ ID NO:1) is Mediated by Apoptosis In both diet-induced and age-related obesity, the effect of CKGGRAKDC (SEQ ID NO:22)-(KLAKLAK)$_2$ (SEQ ID NO:1) treatment on body mass was due to fat resorption, which was visually apparent by the end of treatment (FIG. 11). Wild-type mice were fed on a high fat cafeteria diet (FIG. 11A). Alternatively, wild-type fed on a regular diet became obese as a consequence of old age (FIG. 11B, FIG. 11C, FIG. 11D). Mice were treated with CKGGRAKDC (SEQ ID NO:22) conjugated to (KLAKLAK)$_2$ (SEQ ID NO:1) (left side of FIG. 11), with CARAC (SEQ ID NO:12) conjugated to (KLAKLAK)$_2$ (SEQ ID NO:1) (middle of figure), or with unconjugated CKGGRAKDC (SEQ ID NO:22) and (KLAKLAK)$_2$ (right side of FIG. 11).

Gross inspection of mouse organs revealed that both subcutaneous (FIG. 11B) and visceral (FIG. 11C) fat exhibited marked resorption upon treatment with CKGGRAKDC (SEQ ID NO:22) conjugated to (KLAKLAK)$_2$ (SEQ ID NO:1) (right side of FIG. 11). Quantification of fat resorption after three weeks of treatment by weighing a specific fat depot (epididymal fat, FIG. 11D) showed a greater than 3-fold reduction in fat mass compared with controls (FIG. 11D, left side of figure compared to middle and right side).

Histopathological analysis of tissues from mice treated with CKGGRAKDC (SEQ ID NO:22) conjugated to (KLAKLAK)$_2$ (SEQ ID NO:1) showed vascular apoptosis (FIG. 12A, arrows) and resulting fat necrosis with lymphocyte infiltration (FIG. 12C, arrows) in adipose tissue following treatment. In contrast, mice treated with a control fusion peptide comprising CARAC (SEQ ID NO:12) conjugated to (KLAKLAK)$_2$ (SEQ ID NO:1) showed no vascular apoptosis or fat necrosis (FIG. 12D). No abnormalities in other organs treated with CKGGRAKDC (SEQ ID NO:22) conjugated to (KLAKLAK)$_2$ (SEQ ID NO:1) (data not shown).

Injection of CKGGRAKDC (SEQ ID NO:22) conjugated to (KLAKLAK)$_2$ (SEQ ID NO:1) into genetically obese mice, but not into normal obese mice, was occasionally observed to result in mortality within a few days of injection. It is not clear what the mechanism might be for inducing death in genetically obese mice, although development of pulmonary or cardiac fat embolism or rapid drop of serum calcium due to saponification by released lipids are possibilities. However, these results suggest that treatment of grossly obese subjects might result in sufficient adipose cell death and necrosis to adversely affect the health of the subject, indicating that lower dosages and/or use of a time release formulation of the adipose targeting conjugate may be preferred in cases of excessive obesity.

Adipose Receptor Protein for CKGGRAKDC (SEQ ID NO:22)

A band of approximately 35,000 Daltons (35 kDa) was isolated from mouse adipose tissue extract that bound to CKGGRAKCDC (SEQ ID NO:22) conjugated to (KLAKLAK)$_2$ (SEQ ID NO:1). There was much less binding of the 35 kDa fraction to the control peptide CARAC (SEQ ID NO:12) conjugated to (KLAKAK)$_2$ (SEQ ID NO:1) (data not shown). The 35 kDa band was analyzed by mass spectrometry, which identified three proteins present in the sample.

The three proteins included predominately a B cell receptor associated protein (prohibitin), apolipoprotein E, and the voltage dependent anion channel (VDAC). Further studies were performed by immunoprecipitation, using either CKGGRAKDC (SEQ ID NO:22) or CARAC (SEQ ID NO:12) conjugated to (KLAKAK)$_2$ (SEQ ID NO:1) and precipitating with commercially available antibodies.

SDS-polyacrylamide gel electrophoresis of the immunoprecipitated protein showed that only the prohibitin receptor protein complex was substantially enriched by binding to CKGGRAKDC (SEQ ID NO:22) (data not shown), with over a ten-fold enrichment in the CKGGRAKDC (SEQ ID NO:22) precipitated fraction compared to the CARAC (SEQ ID NO:12) precipitated fraction (data not shown). The CARAC (SEQ ID NO:12)-(KLAKAK)$_2$ (SEQ ID NO:1) fusion peptide exhibited low levels of non-specific binding to all three proteins (VDAC, prohibitin and apolipoprotein E). It is unknown whether those proteins bound to the CARAC (SEQ ID NO:12) moiety or to (KLAKAK)$_2$ (SEQ ID NO:1).

It is concluded that the adipose tissue endothelial receptor for CKGGRAKDC (SEQ ID NO:22) is prohibitin (Genbank Accession No. NM_008831). Probitin is expressed in mitochrondria of various cell types and in the cell membrane of B lymphocytes. Immunohistochemical analysis shows that prohibitin is expressed in blood vessels of adipose tissues but not of other organs (data not shown). Based on these results, it is concluded that pro-apoptosis agents conjugated to targeting peptides that bind to a prohibitin receptor protein complex are effective to induce adipose cell death and weight loss in obese subjects. The skilled artisan will realize that other prohibitin-binding targeting peptides, antibodies, etc. may be used within the scope of the claimed methods and compositions to control weight and/or to induce weight loss. Further, other known cytocidal, cytotoxic and/or cytostatic agents may be used in place of $(KLAKAK)_2$ (SEQ ID NO:1) to control weight or induce weight loss within the scope of the claimed subject matter.

Example 5

Screening an Alpha-Spleen Antibody Library in vivo by BRASIL

The following Examples are illustrative of general techniques that may be of use in various embodiments of the claimed invention. As part of the reticulo-endothelial system, biopanning against spleen tissue is complicated by the high background of non-specific phage localization to spleen. The decreased background observed in biopanning with the BRASIL method is advantageous for identifying targeting peptides against tissues such as spleen.

This example demonstrates an illustrative embodiment of the BRASIL method. A phage library based on immunoglobulins derived against the target organ (mouse spleen) was developed and then subjected to in vivo biopanning. To construct the immunoglobulin library, mouse spleen was injected into a chicken. After boosting, the chicken spleen was collected and immunoglobulin variable domain sequences were obtained by PCR™ amplification of chicken spleen mRNA. The amplified immunoglobulin variable sequences were inserted into a phage display library (α-library) that was then used for in vivo biopanning against mouse spleen. Thus, the spleen targeting peptide sequences obtained from phage localized to mouse spleen in vivo were derived from antibody fragments produced in the chicken in response to mouse spleen antigens. The success of this example further shows the broad utility of the BRASIL method. The skilled artisan will realize that the present invention is not limited to the embodiments disclosed herein and that many further developments of the BRASIL methodology are included in the scope of the present invention.

Materials and Methods

Library Construction

A white leghorn chicken was immunized with spleen homogenate (about 150 mg per injection) from a perfused (10 ml MEM) Balb/c mouse. The chicken received spleen homogenate boosters at 4 weeks and 8 weeks after the initial immunization. Immune response to mouse spleen by FACS analysis showed that the chicken immune serum contained antibodies against a mouse cell-line (TRAMP-C1). The chicken was sacrificed and its spleen was removed to TRI Reagent (Molecular Research Center, Inc., Cincinnati, Ohio) 12 weeks after the first immunization.

Total RNA was prepared from the chicken spleen using the manufacturer's protocol for the TRI reagent. cDNA was prepared from the total RNA using oligo (dT)-primers and Superscript enzyme (Life Technologies, Gaithersburg, Md.). cDNAs encoding chicken spleen immunoglobulin variable regions were amplified by CHybVH and ChybIgB ($V_{heavy}$) or by CSCVK and CHHybL-B ($V_{kappa}$) primers according to standard techniques. Light chain variable regions and constant regions were PCR™ amplified together using CSC-F and lead-B primers and $V_{kappa}$ and $C_{kappa}$ templates. Heavy chain variable regions and constant regions were PCR™ amplified together using dp-seq and lead-F primers and $V_{heavy}$ and $C_{heavy}$ templates. Heavy- and light-chain fragments were PCR™ amplified together with CSC-P and dp-Ex primers. PCR primers were purchased from Genosys (The Woodlands, TX) or GenBase (St. Lucia, Queensland, Australia), using primer sequences listed in the Cold Spring Harbor laboratory course manual, "Phage Display of Combinatorial Antibody Libraries" (Barbas et al., 2000), the relevant text of which is incorporated herein by reference.

After digestion with Sfi I, the amplification products were ligated to SfiI-digested pComb3x for insertion into the phage library. Ligated pComb3-123 plasmid was electroporated into ER2537-*E. coli* and phage production was started with subsequent VCM13 (helper phage) infection. The resulting library size was about $5 \times 10^6$ cfu.

In vivo Screening of α-Spleen Library Using BRASIL

Four rounds of in vivo screening in mice were performed using the chicken α-spleen library. About 0.8 to $2.0 \times 10^{10}$ TU were injected into a Balb/c mouse. The library was allowed to circulate for 5 minutes. After sacrifice, the mouse spleen was recovered and a single cell suspension was prepared by pressing the spleen through a 70 µm cell strainer nylon mesh. The single cell suspension was centrifuged over oil (9:1 dibutyl phtalate:cyclohexane) using the BRASIL technique and 200 µl of log phase ER2537 *E. coli* were infected with the pellet. Amplified phage recovered from the mouse spleen was used for the subsequent round of screening. No obvious enrichment in the screening rounds was seen in the number of phage homing to spleen and brain compared with the conventional biopanning method, using a piece of spleen obtained prior to BRASIL.

Phage localized in mouse spleen from the fourth round of screening of the chicken Fab inserts were PCR™ amplified and the PCR product was digested with Bst I. Half of the clones out of 90 analyzed produced a similar restriction pattern. Of those, 20 clones were sequenced from which only two had an identical restriction pattern. Four of the antibody based phage clones (numbers 2, 6, 10 and 12) were subjected to further analysis using binding and localization assays.

Testing the Clones in vitro Using BRASIL

A singe cell suspension was prepared from two mouse spleens. The suspension was divided into five tubes and incubated on ice with $3 \times 10^9$ TU of Fab clones #2, #6, #10, #12 and $2 \times 10^9$ TU tet-phage. Phage bound to mouse spleen cells were recovered by BRASIL. 200 µl of log phase ER2537 *E. coli* was infected with the pellet and serial dilutions were plated on LB/carbenicillin and LB/tetracycline plates for assessment of phage binding. Fd-tet was used as an internal control to normalize all the phage homing experiments.

Testing Clones in vivo with BRASIL

Phage ($3 \times 10^9$) of Fab clones #2, #6, #10, #12 and $2 \times 10^9$ TU tet-phage were injected into the tail veins of Balb/c mice and allowed to circulate for 5 minutes. The spleens were recovered and single cell suspensions were prepared on ice from whole spleens. Cell bound phage were recovered by BRASIL. 200 µl of log phase ER2537 *E. coli* was infected with the pellet and serial dilutions were plated on LB/carbenicillin and LB/tetracycline plates for assessment of the phage recovery.

Testing Clone #10 Versus, Control Phage NPC-3TT in vivo with BRASIL

Phage ($3 \times 10^9$ TU) of Fab clone #10 and NPC-3TT (control Fab phage) and $1 \times 10^9$ TU of control Fd-tet-phage were injected to mice (2 mice for NPC-3TT, 2 mice for clone #10)

and allowed to circulate for 5 minutes. Spleens were recovered and single cell suspensions were prepared on ice. Cell-bound phage were recovered by BRASIL. 200 μl of log phase ER2537 E. coli was infected with the pellet and serial dilutions were plated on LB/carbenicillin and LB/tetracycline plates. The NPC-3TT phage is a human anti-tetanus toxin Fab fragment displaying phage.

Homing of Fab Clone #10 to Spleen Versus Bone Marrow

Phage ($3\times10^9$ TU) of Fab clone #10 and NPC-3tt control and $1\times10^9$ TU of Fd-tet control phage were injected into mice (2 mice for NPC-3TT, 2 mice for clone #10) and allowed to circulate for 5 minutes. The spleens were recovered and single cell suspensions were prepared. Bone marrow was recovered from the same mice (both femurs) as a control for organ specific homing. Cell-bound phage were recovered by BRASIL.

Fab-Fragment Production

The plasmid pComb3 containing the chicken Fab inserts was electroporated into ER2537 bacteria. Serial dilutions were plated onto LB/carbenicillin plates and incubated overnight at 37° C. Fab production culture (in super broth with 100 μg/ml carbenicillin) was started from a single plated colony. Fab production was induced with 1 mM IPTG for 7 hours at 30° C. The Fab fragment was purified from the periplasmic fraction SN2 by affinity purification after determination of the Fab concentration in bacteria supernatant, periplasmic fractions SN1 and SN2 and in the bacteria lysate by ELISA. An α-Fab-Protein G-column was coupled (2 mg/ml) with dimethylpimelimidate (DMP) using standard protocols (Harlow and Lane, Antibodies: A Laboratory Manual, Cold Spring Harbor Laboratory Press, New York, N.Y., 1988).

For purifying Fab fragments the following method was used. The SN2 fraction was loaded into a 1 ml HiTrap-protein G-α-Fab-column (Amersham Pharmacia Biotech, Piscataway, N.J.) either over 2 hours (if using lower than 50 ml volume with superloop) or overnight (with more than 50 ml volume using a peristaltic pump). The column was washed with 10-20 ml of PBS (phosphate buffered saline). The Fab fragments were eluted with 10 ml of 20 mM glycine buffer, pH 2.2, 150 mM NaCl and 1 ml fractions were collected. Fractions are neutralized with 1 M Tris immediately after elution. Protein concentrations were quantified by $A_{280}$.

Intravascular Staining

To determine in vivo distribution of the recovered Fab fragments, 50 to 60 μg of Fab fragment (Fab#10, NPC3-tt or R#16) was injected into the tail vein of a Balb/c mouse and allowed to circulate for 8 minutes. 50 μg of L. esculentum lectin-FITC was injected into the mouse and the mouse tissues were fixed by perfusion with 25 to 30 ml of 4% paraformaldehyde/PBS after 2 minutes of lectin circulation. Tissues were removed and post-fixed in 4% paraformaldehyde for 1 hour. Fixed tissues were incubated in 30% sucrose/PBS overnight at 4° C., changing the solution at least twice. The tissues were embedded in the freezing media and frozen on dry ice.

Fixed tissue sections were stained for Fab as follows. Frozen tissue sections (55 μm) were cut on a microtome and washed 3× with PBS. The thin sections were blocked with PBS/0.3% TritonX-100/5% goat serum for 1 hr at room temperature. Sections were incubated overnight at room temperature with 1:400 Cy3 conjugated α-human anti-Fab antibody. The conjugated sections were washed 6× with PBS/0.3% Triton X-100, 3× with PBS, and fixed with 4% paraformaldehyde for 15 minutes. After fixation the sections were washed again 2× with PBS and 2× with distilled water, then mounted on slides using VectorShield.

Results

The in vitro localization to mouse spleen cells of phage clones expressing chicken Fab fragments was examined by BRASIL. As shown in FIG. 13, the Fab phage clones isolated by BRASIL showed differential binding to mouse spleen cells compared to Fd-tet insertless control phage. Clone #6 showed the lowest degree of binding, similar to the control phage NPC-3TT, which contained a Fab fragment but was not isolated from mouse spleen. Clones #2, #10 and #12 all showed selective binding to mouse spleen cells compared to the Fd-tet control, with at least a two-fold increased binding observed for clones #2 and #10 (FIG. 13). The amino acid sequences determined for the clone inserts were:

```
Clone #2:                                 (SEQ ID NO:23)

CQPAMAAVTLDESGGGLQTPGGALSLVCKASGFTFNSYPMGWVRQAPG
KGLEWVAVISSSGTTWYAPAVKGRATISRDNGQSTVRLQLSNLRAED

Clone #6:                                 (SEQ ID NO:24)

CQPAMAAVTLDESGGGLQTPGGTLSLVCKASGISIGYGMNWVRQAPGK
GLEYVASISGDGNFAHYGAPVKGRATISRDDGQNTVTLQLNNLR

Clone #10:                                (SEQ ID NO:25)

CQPAMAAVTLDESGGGLQTPGGTLSLVCKGSGFIFSRYDMAWVRQAPG
KGLEWVAGIDDGGGYTTLYAPAVKGRATITSRDNGQSTVRLQLNNLR

Clone #12:                                (SEQ ID NO:26)

ANQPWPPLTLDESGGGLQTPGGALSLVCKASGFTMSSYDMFWVRQAPG
KGLEFVAGISSSGSSTEYGAAVKGRATISRDNGQSTVRLQLNNLRAED
```

A direct comparison was made of in vitro phage binding for the Fab clones compared to NPC-3TT. As shown in FIG. 14, clones #2 and #10 exhibited the highest levels of binding to mouse spleen cells in vitro. Clones #6 and #12 showed levels of binding to mouse spleen that were only slightly higher than the binding of phage NPC-3TT.

The preferential binding of the chicken Fab phage clones was confirmed by in vivo studies using BRASIL. As shown in FIG. 15, selective localization to mouse spleen was even more dramatic in vivo, with Fab clones #2, #6 and #10 showing many-fold increased binding to spleen compared to Fd-tet phage. In contrast, Fab clone #12 did not exhibit significantly elevated binding to mouse spleen compared to Fd-tet phage. These results show that in vitro results obtained with spleen targeting phage are confirmed in vivo.

Fab clone #10 was selected for additional characterization by in vivo localization to mouse spleen. The results, shown in FIG. 16, confirm that Fab clone #10 exhibited 3 to 10 fold enrichment in spleen compared to Fd-tet. This effect was not due to general Fab binding, since the Fab control phage NPC-3TT did not exhibit selective localization in spleen compared to Fd-tet insertless phage.

Binding of Fab clone #10 was organ specific, as demonstrated in FIG. 17. Phage from Fab clone #10 and NPC-3TT control were recovered from spleen and bone marrow tissue from the same injected mice. It can be seen in FIG. 17 that Fab clone #10 exhibited selective localization to spleen but not to bone marrow tissue. The control phage did not exhibit selective localization to bone marrow (FIG. 17) or spleen (not shown).

These results show that Fab phage clone #10 selectively targets mouse spleen tissue for binding both in vitro and in vivo. These results were further validated by vascular staining for in vivo phage distribution. Control phage used for this study were clones NPC-3TT (Fab fragment) and clone R#16 (isolated from angiogenic retina screening).

Fab clone #10 was observed to bind to mouse spleen tissue in vivo by fluorescent staining (not shown). The control phage NPC-3TT and R#16 did not stain spleen tissue under identical conditions (not shown). The clone #10 and NPC-3TT phage were observed to intensively stain kidneys of injected animals, perhaps due to glomerular filtration (not shown). Other control organs (lung, brain, liver, heart and skeletal muscle) did not show staining with clone #10 (not shown).

These results demonstrate that spleen targeting phage peptides can be identified by the BRASIL method. They further show the feasibility of the phage display technique using antibody fragments against a target organ, tissue or cell type to obtain a starting phage library. The ability to obtain targeting peptides against spleen, a tissue that has proven refractory to biopanning using standard phage display protocols because of the high non-specific background, shows the advantages of the BRASIL method.

Example 6

Identification of Receptor/Ligand Pairs: Targeting Peptides Against Integrin Receptors Certain embodiments of the present invention concern the identification of receptor/ligand pairs for various applications. Targeting peptides selective for organs, tissues or cell types bind to receptors (as defined above), normally located on the lumenal surface of blood vessels within the target. In certain embodiments, targeting peptides may be used to identify or characterize such receptors, either directly or indirectly. In addition to their use as targets for delivery of gene therapy vectors, other therapeutic agents or imaging agents for in vivo imaging, such naturally occurring receptors are of use as potential targets for development of new therapeutic agents directed against the receptor itself, for development of vaccines directed against the receptor, and for understanding the molecular mechanisms underlying various disease states. Naturally, the targeting peptides themselves may serve as the basis for new therapeutic agents directed against the receptors.

Targeting peptides may frequently act as mimeotopes of endogenous ligands that bind to the targeted receptor. In other embodiments, the endogenous ligands may be identified and characterized using the disclosed methods. Such ligands are also of potential use as targets for development of new therapeutic agents, etc.

The present example illustrates one embodiment related to identification of receptor/ligand pairs, in this case, integrin receptors. Non-limiting examples of applications of targeting peptides directed against integrins include regulation of cell proliferation and chemotaxis, pro-apoptosis and anti-angiogenesis. In this embodiment, purified integrins attached to a solid substrate were used to screen phage display libraries to identify targeting peptides directed against integrins.

Background

Integrin function is regulated by cytokines and other soluble factors in a variety of biological systems. Most commonly, exposure to such factors leads to conformational alterations that result in changes in the activation state of the receptors (i.e., increased or decreased affinity for a given ligand and/or receptor clustering in the plasma membrane). Changes in integrin-dependent adhesion ultimately activate various complex signal transduction pathways. At the molecular level, the induced co-localization of cytoskeleton proteins with integrin cytoplasmic domains controls signal transduction.

Cytoplasmic domains are key regulators of integrin function (reviewed in Hynes, *Cell* 69:11-25, 1992; Ruoslahti, *Ann. Rev. Cell Dev. Biol.* 12:697-715, 1996). Individual α and β subunit cytoplasmic domains are highly conserved among different species (Hemler et al., *In: Integrins: The Biological Problems*, ed. Takada, CRC Press, Inc. Boca Raton, Fla., pp. 1-35, 1994). Although the cytoplasmic domains of various β subunits share similar primary structures, they differ in certain functional characteristics. Experiments with chimeric integrins have shown that the cytoplasmic domains of β chains are responsible for regulating receptor distribution and recruitment to focal adhesion sites (Pasqualini and Hemler, *J. Cell. Biol.* 125:447-460, 1994). Thus, certain cytoplasmic domains are critical for integrin-mediated signaling into the cell (outside-in signaling) and activation of integrin-ligand binding activity (inside-out signaling) (Hemler et al., 1994).

The integrins αvβ3 and αvβ5 are selectively expressed in angiogenic vasculature but not in normal vasculature (Brooks et al., 1994a, 1994b; Pasqualini et al., 1997; Arap et al., 1998). Moreover, αv integrin antagonists have been shown to block the growth of neovessels (Brooks et al., 1994a, 1994b, 1995; Hammes et al., 1996). In these experiments, endothelial cell apoptosis was identified as the mechanism for the inhibition of angiogenesis (Brooks et al., 1994a, 1994b, 1995). Angiogenesis initiated by bFGF can be inhibited by an anti-αvβ3 blocking antibody, whereas VEGF-mediated angiogenesis can be prevented by a blocking antibody against αvβ5. The integrins αvβ3 and αvβ5 have been reported to be preferentially displayed in different types of ocular neovascular disease (Friedlander et al., 1995, 1996). Thus, distinct cytokine-induced pathways that lead to angiogenesis seem to depend on specific αv integrins.

The search for αv integrin-associated molecules has been hampered by technical difficulties. First, the physical associations involved are likely to rely on an assembly of multimeric ligands that no longer occurs when cells are not intact. Second, their association to integrins is usually of low affinity. Finally, changes in the conformation and phosphorylation states of the associating proteins may add a further level of complexity in these transiently modulated interactions. Because of these problems, only a limited number of proteins that bind to integrin cytoplasmic domains have been identified. These proteins, such as paxillin and ICAP-1, mainly associate with the β1 chain (Shattil and Ginsberg, 1997). Cytohesin-1 and filamin associate with the cytoplasmic domain of β2.

The disclosed methods have several advantages over previous approaches: (i) the ability to characterize the intracellular molecules that directly or indirectly interact with integrin cytoplasmic domains; (ii) the development of antibodies against molecules that bind to integrin cytoplasmic domains in very low amounts; and (iii) the phage display library screenings will lead to the identification of peptides that mimic cytoplasmic-domain binding proteins.

Methods

Two Dimensional Cell Culture

Three human endothelial cell lines that express β3 and β5 integrins were used: KS1767 cells (Herndier et al., 1996), HUVECs (ATCC), and BCE cells (Solowska et al., 1991). Sterile glass coverslips covered with different proteins (i.e. vitronectin, fibronectin, collagen, or laminin) were used as substrates. After cells attached and spread, the monolayers were rendered quiescent by a 12-hour incubation in medium containing 0.05% fetal calf serum. Peptides were introduced into the cells using the penetratin membrane-permeable tag (see below). The cells were plated onto ECM proteins for adhesion and spreading. The monolayer was stimulated for 6 hours with each of the growth factors involved in αv-mediated angiogenesis, including bFGF, TNFα, VEGF, and TGFβ. Untreated cells were the negative controls.

Three-Dimensional Cell Culture:

150 µl of Matrigel were added per well of 24-well tissue culture plates and allowed to gel at 37° C. for 10 min. HUVECs starved for 24 h in M199 medium supplemented with 2% FCS before being trypsinized were used. $10^4$ cells were gently added to each of the triplicate wells and allowed to adhere to the gel coating for 30 min at 37° C. Then, medium was replaced with peptides in complete medium. The plates were monitored and photographed after 24 h with an inverted microscope (Canon).

Chemotaxis Assay:

Cell migration assays were performed as follows: 48-well microchemotaxis chambers were used. Polyvinylpyrrolidone-free polycarbonate filters (Nucleopore, Cambridge, Mass.) with 8-µm pores were coated with 1% gelatin for 10 min at room temperature and equilibrated in M199 medium supplemented with 2% FCS. Peptides were placed in the lower compartment of a Boyden chamber in M199 supplemented with 2% FCS, 20 ng/ml VEGF-A (R&D System), and 1 U/ml heparin. Overnight-starved subconfluent cultures were quickly trypsinized, and resuspended in M199 containing 2% FCS at a final concentration of $2 \times 10^6$ cells/ml. After the filter was placed between lower and upper chambers, 50 µl of the cell suspension was seeded in the upper compartment. Cells were allowed to migrate for 5 h at 37° C. in a humidified atmosphere with 5% $CO_2$. The filter was then removed, and cells on the upper side were scraped with a rubber policeman. Migrated cells were fixed in methanol and stained with Giemsa solution (Diff-Quick, Baxter Diagnostics, Rome, Italy). Five random high-power fields (magnitude 40×) were counted in each well.

Proliferation Assay:

Cell proliferation was measured as described (Pasqualini and Hemler, 1994). Briefly, $4 \times 10^4$ HUVECs were incubated in 24-wells plates. The cells were starved for 24 h, and then the medium was removed and replaced in the presence of VEGF and 15 µM of each peptide and incubated for 18 h. Then, 50 µl of media containing [$^3$H]thymidine (1 µCi/ml) was added to the wells, and after 6 additional hours of incubation at 37° C., the medium was removed and the cells were fixed in 10% TCA for 30 min at 4° C., washed with ethanol, and solubilized in 0.5 N NaOH. Radioactivity was counted by liquid scintillation with an LS 6000SC Beckman scintillation counter. Each experiment was performed three times with triplicates, and the results are expressed as the mean ±SD.

Apoptosis Assay (Propidium Iodide Staining Subdiploid Population)

Approximately $1 \times 10^6$ cells were harvested in complete media and 15 µM of peptide added for 4, 8, or 12 h. The cells were then washed in PBS and resuspended in 0.5 ml propidium iodide solution (50 µg/ml PI, 0.1% Triton X-100, 0.1% sodium citrate). After a 24-h incubation at 4° C., cells were counted with a XL Coulter (Coulter Corporation) with a 488-nm laser; 12,000 cells were counted for each histogram, and cell cycle distributions were analyzed with Multicycle program.

After microinjection or penetratin-mediated internalization of the peptides and appropriate controls, cell apoptosis was monitored using the ApopTag kit. Experiments were performed in the presence of caspase inhibitors and antibodies against specific caspases.

Cytokine- and Tumor-Induced Angiogenesis Assays

Angiogenic factors and tumor cells implanted into CAM stimulate growth of new capillaries. Angiogenesis was induced in CAMs from 10-day chicken embryos by VEGF or bFGF filters implanted in regions that were previously avascular. Different treatments (penetratin peptides and controls) were applied topically, and after 3 days, the filters and surrounding CAMs were resected and fixed in formalin. The number of blood vessels entering the disk was quantified within the focal plane of the CAM with a stereomicroscope. The mean number of vessels and standard errors from 8 CAMs in each group were compared.

Phosphorylation and Panning of Phosphorylated Phage Libraries

Phosphorylation of peptide libraries with src family protein kinases (Fyn, c-Src, Lyn, and Syc) and serine/threonine kinases such as a MAP kinase were performed as described previously (Schmitz et al., 1996; Dente et al., 1997; Gram et al., 1997). Briefly, phage particles were collected from culture supernatants by double precipitation with 20% polyethylene glycol 8000 in 2.5 M NaCl. Particles were dissolved at $10^{12}$ particles/ml. Purified phage (10 µl) were incubated for 3 hours at room temperature with different concentrations (35 to 3,500 units) of protein kinases in a reaction buffer volume of 50 µl. The reaction mixtures were transferred to tubes containing 10 µg of agarose-conjugated anti-P-Tyr, anti-P-Ser, or anti-P-Thr monoclonal antibodies to select phage displaying phosphorylated peptides. Bound phage were eluted by washing the column with 0.3 ml of elution buffer (0.1 M NaCl/glycine/1 mg/ml BSA, pH 2.35). The eluates were neutralized with 2 M Tris-base and incubated with 2 ml of a mid-log bacteria culture. Aliquots of 20 µl were removed for plating, and phage were harvested as described. The phosphorylation-selection step was repeated. Phosphorylated peptides binding to β3 and β5 cytoplasmic domains were analyzed as described in the previous section.

Matrix-assisted laser desorption time-of-flight (MALDI-TOF) mass spectrometry was used to map in vitro phosphorylation sites on the β3 and β5 cytoplasmic domains and cytoplasmic domain-binding peptides. The fusion proteins or peptides were phosphorylated in vitro as described and purified by RP-HPLC or RP microtip columns. Phosphorylated peptides were identified by three methods: (1) 80-Da mass shifts after kinase reactions; (2) loss of 80 Da after phosphatase treatment; or (3) loss of 80 Da or 98 Da in reflector vs. linear mode for tyrosine phosphorylated or serine, threonine phosphorylated peptides, respectively. Where needed, peptides were purified by RP-HPLC and subjected to carboxypeptidase and aminopeptidase digestions to produce sequence ladders. This was particularly useful where one peptide may harbor two or more phosphorylation sites.

Panning on Phosphorylated GST-fusion Proteins.

GST fusion proteins were phosphorylated in vitro as described (Schmitz et al., 1996; Dente et al., 1997; Gram et al., 1997). Briefly, 10 µg/ml was incubated for 3 h at room temperature with 5.5 units of Fyn protein kinase in reaction buffer (50 MM Tris, 5 mM $MgCl_2$, 500 µM $Na_3VO_4$, 500 µM ATP in a total volume of 50 µl). The reaction was stopped by adding 40% of TCA. After the kinase substrate protein was precipitated, it was resuspended in PBS and coated on microtiter wells at 10 µg/well. An aliquot of $CX_7C$ library ($2.5 \times 10^{11}$ transducing units) was incubated on the GST fusion proteins. Phage were sequenced from randomly selected clones.

Mass Spectrometry Studies

Mass spectrometric peptide mass mapping was used to identify novel ligands for β3 and/or β5 cytoplasmic domains. Polyclonal and monoclonal antibodies raised against the cytoplasmic domain-binding peptides were used to purify target proteins (cytoskeletal or signaling molecules). These proteins were resolved by SDS-PAGE, cut out from the SDS gels, and digested in-gel with trypsin. After extraction of the peptides, MALDI-TOF mass spectrometry analysis was performed to produce a list of peptide masses. This list of peptide masses, in combination with protease specificity, produces a relatively specific "signature" that can be used to search sequence databases. If the protein sequence is present in a database, the protein can be identified with high confidence by this method. The lower detection limit for this approach is currently 1 pmol, at least 10-20-fold better than N-terminal Edman sequencing methods.

Results

Panning of Phage Peptide Libraries on β3 or β5 Cytoplasmic Domains.

β3 and β5 cytoplasmic domain-binding peptides were isolated by screening multiple phage libraries with recombinant GST fusion proteins that contained either GST-β3cyto or GST-β5cyto coated onto microtiter wells. Immobilized GST was used as a negative control for enrichment during the panning of each cytoplasmic domain. Phage were sequenced from randomly selected clones after three rounds of panning as disclosed elsewhere (Koivunen et al., Biotechnology 13:265-270, 1995; Pasqualini et al., 1995). Distinct sequences were isolated that interacted specifically with the β3 or with the β5 cytoplasmic domains (Table 4). Randomly selected clones from panning rounds II and III were sequenced. Amino acid sequences of the phagemid encoded peptides were deduced from nucleotide sequences. The most frequent motifs found after panning with the indicated libraries are shown in Table 4. The ratios were calculated by dividing the number of colonies recovered from β3-GST-coated wells and those recovered from GST or BSA.

TABLE 4

Sequences displayed by phage binding to
β3 or β5 integrin cytoplasmic domain

| Peptide motif | SEQ ID NO | β3/GST Ratio | β3/BSA Ratio |
|---|---|---|---|
| CX₉ Library | | | |
| CEQRQTQEGC | SEQ ID NO:27 | 4.3 | 14 |
| CARLEVLLPC | SEQ ID NO:28 | 2.8 | 18.7 |
| X₄YX₄ Library | | | |
| YDWWYPWSW | SEQ ID NO:29 | 5.6 | 163 |
| GLDTYRGSP | SEQ ID NO:30 | 4.1 | 48 |
| SDNRYIGSW | SEQ ID NO:31 | 3.3 | 32 |
| YEWWYWSWA | SEQ ID NO:32 | 2.2 | 28.1 |
| KVSWYLDNG | SEQ ID NO:33 | 2.1 | 20 |
| SDWYYPWSW | SEQ ID NO:34 | 2.1 | 157 |
| AGWLYMSWK | SEQ ID NO:35 | 1.8 | 2.4 |
| Pool Cyclic Libraries | | | |
| CFQNRC | SEQ ID NO:36 | 3.1 | 16 |
| CNLSSEQC | SEQ ID NO:37 | 2.7 | 62 |
| CLRQSYSYNC | SEQ ID NO:38 | 2.4 | 3.2 |

TABLE 4-continued

Sequences displayed by phage binding to
β3 or β5 integrin cytoplasmic domain

| Peptide motif | SEQ ID NO | β5/GST Ratio | β5/BSA Ratio |
|---|---|---|---|
| Pool Cyclic Libraries | | | |
| CYIWPDSGLC | SEQ ID NO:39 | 5.2 | 193 |
| CEPYWDGWFC | SEQ ID NO:40 | 3.1 | 400 |
| CKEDGWLMTC | SEQ ID NO:41 | 2.3 | 836 |
| CKLWQEDGY | SEQ ID NO:42 | 1.8 | 665 |
| CWDQNYLDDC | SEQ ID NO:43 | 1.5 | 100 |
| X₄YX₄ Library | | | |
| DEEGYYMMR | SEQ ID NO:44 | 11.5 | 29 |
| KQFSYRYLL | SEQ ID NO:45 | 4.5 | 8 |
| VVISYSMPD | SEQ ID NO:46 | 3.8 | 28 |
| SDWYYPWSW | SEQ ID NO:34 | 2.4 | 304 |

The specificity of the interaction with β3 or β5 cytoplasmic domains was determined by calculating the ratios of phage bound to the cytoplasmic domain containing-fusion proteins (β3 or β5) versus GST alone (negative control). FIG. 18 shows the results from binding assays performed with the GST-β3cyto binding phage. Six phage were tested that displayed the motifs most frequently found during the second and third rounds of panning. Each panel shows the results from binding assays for the phage displaying different peptides that bind to the β3 cytoplasmic domain, as indicated. Insertless phage or unselected libraries were used as negative controls and did not show binding above background. Two plating dilutions were shown for each assay.

A similar strategy was used to determine the specificity of the phage isolated in the screenings involving the β5 cytoplasmic domain fusion protein. The binding assays were performed with individually amplified phage, shown in FIG. 19. Five phage were tested that displayed the motifs found most frequently during the second and third rounds of panning. Each panel shows the binding assays for the phage displaying peptides that bind to the β5 cytoplasmic domain. Insertless phage or unselected libraries were used as negative controls and did not show binding above background in these assays.

To determine whether the binding of the selected motifs was specific for each cytoplasmic domain, binding assays were performed comparing the interaction of individual phage motifs with β1, β3, or β5 cytoplasmic domain fusion proteins. ELISA with anti-GST antibodies showed that the three proteins can be coated onto plastic at equivalent efficiency, and thus the differences in binding do not reflect differences in coating concentrations (not shown). Both the β3- and β5-selected phage selectively interacted with the proteins on which they were originally selected, with average binding selectivities observed of β3/β1=3.9, β3/β5=3.7, β5/β1=4.8, and β5/β3=6.9 (not shown). The average selectivity for integrin cytoplasmic domains versus BSA was about one to two orders of magnitude (not shown). None of the phage tested seemed to bind strongly to the β1 cytoplasmic domain (not shown).

Characterization of Synthetic Peptides Corresponding to the Sequences Displayed by the Integrin-Cytoplasmic Domain-Binding Phage.

Specific phage were selected for further studies on the basis of their binding properties. Synthetic peptides corresponding to the sequence displayed by each phage were used to perform binding inhibition studies. This assay determined whether phage binding was entirely mediated by the targeting peptide displayed by the phage or whether it also included a non-specific component. As expected, the synthetic peptides inhibited the binding of the corresponding phage in a dose-dependent manner (FIG. 20 and FIG. 21). A control peptide containing unrelated amino acids had no effect on phage binding when tested at identical concentrations.

Phosphorylation Events Modulate the Interaction of the Selected Peptides with Cytoplasmic Domains Events involving phosphorylation are important in regulating signal transduction. The phage display system was used to evaluate the effect of tyrosine phosphorylation at two levels. First, recombinant fusion proteins containing β3 or β5 cytoplasmic domains were used for panning of phage libraries displaying tyrosine-containing peptides. Second, the cytoplasmic domains themselves were phosphorylated before phage selection was performed. Experiments were performed to investigate the capacity of specific tyrosine kinases to modulate the interaction of the selected peptides with the cytoplasmic domains. The results obtained in the panning of phage libraries displaying tyrosine-containing peptides are shown in Table 5.

Randomly selected clones from rounds III and IV were sequenced from a $X_4YX_4$ phosphorylated library with Fyn. Amino acid sequences of the phagemid encoded peptides were deduced from nucleotide sequences. Table 5 shows the motifs found most frequently after the indicated libraries were panned with β3 or β5. The ratio of binding to β3 or β5 was calculated by dividing the number of β3 or β5 colonies by GST or BSA colonies found after panning. The ratio of binding to β3 or β5 with phosphorylated phage by Fyn versus unphosphorylated phage was calculated by dividing the number of colonies found after the panning.

TABLE 5

Sequences displayed by phosphorylated phage binding to integrin cytoplasmic domains.

| Peptide Motif | | Phos/ Unphos | β3 or β5/GST | β3 or β5/BSA |
|---|---|---|---|---|
| β3 cytoplasmic | | | | |
| GGGSYRHVE | SEQ ID NO:49 | 13.2 | 1.5 | 5.3 |
| RAILYRLAN | SEQ ID NO:50 | 2.8 | 1.3 | 20 |
| MLLGYRFEK | SEQ ID NO:51 | 2.5 | 3.5 | 2.7 |
| β5 cytoplasmic | | | | |
| TMLRYTVRL | SEQ ID NO:52 | 14.3 | 3.4 | 2.2 |
| TMLRYFMFP | SEQ ID NO:53 | 4.2 | 2.3 | 3.8 |
| TLRKYFHSS | SEQ ID NO:54 | 3.8 | 3.8 | 15.2 |

The effect of phosphorylation on the affinity and specificity of the cytoplasmic domain-binding was examined. Phage displaying the β3 and β5 cytoplasmic domain-binding peptides were phosphorylated in vitro as previously described (Schmitz et al., 1996; Dente et al., 1997; Gram et al., 1997), using Fyn kinase. Specific phosphorylation of the tyrosine-containing peptide on the surface of the phage was confirmed by using $^{32}$P-gamma dATP in the kinase reaction and by separating the phage pIII protein by SDS-PAGE.

Phage phosphorylated in vitro showed increased binding affinity and specificity to the β3 integrin cytoplasmic domain (FIG. 22). The TLRKYFHSS (SEQ ID NO:54) phage was also tested in assays that included other GST-cytoplasmic domain fusion proteins to determine specificity (FIG. 23).

Sequence Similarity of Integrin Binding Peptides with Known Cytoskeletal and Signaling Proteins.

The peptides displayed by integrin cytoplasmic domain-binding phage were similar to certain regions found within cytoskeletal proteins and proteins involved in signal transduction (Table 6). The similarity of some of the isolated peptides to a region of mitogen-activated protein kinase 5 (MAPK5, amino acids 227-234) was particularly interesting. A connection involving the MAPK cascade, cell adhesion, migration and proliferation has been proposed (Lin et al., 1997)

TABLE 6

Sequence similarity of integrin binding peptides with known cytoskeletal and signaling proteins.

| Isolated Motif | Candidate Proteins | Region (AA #) | Homology % |
|---|---|---|---|
| β3 cytoplasmic | | | |
| GLDTYRGSP (SEQ ID NO:30) | Ras-related protein Ser/Thr kinase (K-11) | 124-133 18-25 | 75 75 |
| SDNRYIGSW (SEQ ID NO:31) | PDGF receptor Phosphatidylinositol 4 phosphatase 5 Receptor protein kinase Protein kinase clk2 | 985-992 233-241 185-191 71-79 | 85 85 85 63 |
| CEQRQTQEGC (SEQ ID NO:27) | MAPK5 Phosphatidylinositol 3-kinase | 227-234 494-503 | 75 78 |
| CLRQSYSYNC (SEQ ID NO:38) | Cyclin-dependent kinase 5 (cdk5) | 230-239 | 75 |

TABLE 6-continued

Sequence similarity of integrin binding peptides with known cytoskeletal and signaling proteins.

| Isolated Motif | Candidate Proteins | Region (AA #) | Homology % |
|---|---|---|---|
| β5 cytoplasmic | | | |
| VVISYSMPD (SEQ ID NO:46) | Ser/Thr kinase | 479-485 | 83 |
| | IFN (β chain) | 27-35 | 70 |
| | Actin | 240-248 | 67 |
| DEEGYYMMR (SEQ ID NO:44) | Focal adhesion kinase | 43-51 | 75 |
| | Tubulin | 60-66 | 100 |
| | Putative Ser/Thr kinase | 292-299 | 86 |

Membrane-Permeable Peptides

Penetratin is a peptide that can translocate hydrophilic compounds across the plasma membrane. Fusion to the penetrating moiety allows oligopeptides to be targeted directly to the cytoplasm, nucleus, or both without apparent degradation (Derossi et al., 1994). This membrane-permeable peptide consists of 16 residues (RQIKIWFQNRRMKWKK, SEQ ID NO:55) corresponding to amino acids 43-58 of the homeodomain of Antennapedia, a Drosophila transcription factor (Joliet et al., 1991a, 1991b; Le Roux et al., 1993). Internalization mediated by penetratin occurs at both 37° C. and 4° C., and the internalized peptide can be retrieved intact from cells.

Peptides were designed containing penetratin sequences fused to the sequences of motifs found to bind β3 or β5 cytoplasmic domains. The peptides were synthesized on a 431 Applied Biosystems peptide synthesizer using p-hydroxymethylphenoxy methyl polystyrene (HMP) resin and standard Fmoc chemistry. Peptide internalization and visualization was performed as described (Derossi et al., 1994; Hall et al., 1996; Theodore et al., 1995).

Briefly, 10-50 μg/ml of the biotinylated peptide was added to cells in culture. Peptides were incubated with plated cells. After 2-4 hours, the cultures were washed three times with tissue culture media, fixed and permeabilized using ethanol:acetic acid (9:1) for 5 min at −20° C. Nonspecific protein binding sites were blocked by incubating the cultures for 30 min with Tris-buffered saline (TBS) containing 10% fetal calf serum (FCS) and 0.02% Tween. The cultures were incubated in the same buffer containing FITC-conjugated Streptavidin (1:200 dilution) and washed with TBS before being mounted for viewing by confocal microscopy. The penetratin-linked peptides were internalized quite efficiently (data not shown).

Functional data showed that the cytoplasmic domain-binding peptides selected on β3 or β5 can interfere with integrin-mediated signaling and subsequent cellular responses (i.e., endothelial cell adhesion, spreading, proliferation, migration). A commercial panel of "internalizable" versions of the synthetic motifs found by phage screenings (SDNRYIGSW (SEQ ID NO:31); CEQRQTQEGC (SEQ ID NO:27); β3 binding peptides and VVISYSMPD (SEQ ID NO:46); a β5-binding peptide) were obtained. These complex chimeric peptides consist of the most selective of the β3 or β5-cytoplasmic domain-binding peptides coupled to penetratin, plus a biotin moiety to allow the peptides to be tracked once they were internalized into intact cells. These membrane-permeable forms of the peptides are internalized, may affect β3 and β5 post-ligand binding cellular events and can induce massive apoptosis (data not shown).

Endothelial Cell Proliferation, Chemotaxis and Apoptosis

The effect of β3 and β5 integrin cytoplasmic domain-binding motifs on endothelial cell proliferation was evaluated after stimulation with factors that activate endothelial cells (FIG. 24). Cell proliferation was measured according to Pasqualini and Hemler (1994). Briefly, 4×10⁴ HUVECs were incubated in 24-well plates and starved for 24 h, after which the medium was removed and replaced in the presence of VEGF and 15 μM of each peptide. After another 18 h of incubation, 50 μl of medium containing [³H]thymidine (1 μCi/ml) was added to the wells. After 6 additional hours of incubation at 37° C., the medium was removed and the cells were fixed in 10% TCA for 30 min at 4° C., washed with ethanol and solubilized in 0.5 N NaOH. Radioactivity was counted by liquid scintillation by using a LS 6000SC Beckman scintillation counter. Each experiment was performed three times with triplicates, and the results were expressed as the mean ±SD.

The effect of β3 and β5 integrin cytoplasmic domain-binding motifs in endothelial cell migration was evaluated after stimulation with factors that activate endothelial cells. The peptides tested affected cell function in a dose-dependent and specific way. Their properties seem to be intrinsic to the β3 or to the β5 cytoplasmic domain (FIG. 25).

Chemotaxis Assay.

Cell migration was assayed in a 48-well microchemotaxis chamber. Polyvinylpyrrolidone-free polycarbonate filters with 8-μm pores were coated with 1% gelatin for 10 min at room temperature and equilibrated in M199 medium supplemented with 2% FCS. Peptides were placed in the lower compartment of a Boyden chamber in M199 supplemented with 2% FCS, 20 ng/ml VEGF-A (R&D System), and 1 U/ml heparin. Overnight-starved subconfluent cultures were quickly trypsinized, and resuspended in M199 containing 2% FCS at a final concentration of 2×10⁶ cells/ml. After the filter was placed between lower and upper chambers, 50 μl of the cell suspension was seeded in the upper compartment. Cells were allowed to migrate for 5 h at 37° C. in a humidified atmosphere with 5% CO₂. The filter was then removed, and cells on the upper side were scraped with a rubber policeman. Migrated cells were fixed in methanol and stained with Giemsa solution. Five random high-power fields (magnitude 40×) were counted in each well. The results showed that both β3-integrin cytoplasmic domain binding peptides increased cell migration but penetratin did not affect the cells (data not shown).

Apoptosis Assay (Propidium Iodide (PI) Staining Subdiploid Population).

Approximately $1 \times 10^6$ cells were harvested in complete medium, and 15 μM of peptide was added for 4, 8, or 12 hours. The cells were then washed in PBS and resuspended in 0.5 ml propidium iodide solution (50 μg/ml PI, 0.1% Triton X-100, 0.1% sodium citrate). After a 24-h incubation at 4° C., the cells were counted with an XL Coulter (Coulter Corporation) with a 488 nm laser; 12,000 cells were counted for each histogram, and cell cycle distributions were analyzed with the Multicycle program.

Treatment of cells with VISY-penetratin chimera resulted in induction of apoptosis (FIG. 26, panel d). Pro-apoptotic effects were not observed when the cells were exposed to other growth factors (not shown). Penetratin alone and the other penetratin chimeras also could not induce similar effects (FIG. 26, panel c). This finding shows that novel approaches for inhibiting angiogenesis can be developed based on the use of integrin targeting peptides.

Immunization with Cytoplasmic Domain Binding Peptides and Characterization of the Resulting Antibodies Polyclonal antibodies that recognize αvβ3 and αvβ5-binding peptides were generated using KLH conjugates made with the synthetic peptides, according to standard techniques. Antibodies against two different synthetic peptides have been produced (FIG. 27). The sera not only recognize the immobilized peptides, but also recognize specific proteins in total cell extracts, as shown by western blot analysis (FIG. 28).

Rabbits were immunized with SDNRYIGSW (SEQ ID NO:31) or GLDTYRGSP (SEQ ID NO:30)-KLH conjugates. Each rabbit was injected with 200 μg of peptide conjugated with KLH in Complete Freund's Adjuvant. Between 20 and 60 days later, the rabbits were injected with 100 μg Incomplete Freund's Adjuvant. After the third immunization, sera was collected. Pre-immune serum obtained before the first immunization was used as an additional control in the experiments.

The polyclonal antibodies were tested by ELISA, Western blot and immunoprecipitation. In the ELISA assays, microtiter well plates were coated with 10 μg/ml of peptides. The plates were dried at 37° C., blocked with PBS+3% BSA, and incubated with different serum dilutions in PBS+1% BSA. After washing and incubation with the secondary antibody, an alkaline phosphate substrate was added and antibody binding detected colorimetrically at 405 nm. The reactivity observed both in the mouse and rabbit polyclonal sera was highly specific. In all cases, antibody binding could be abrogated by preincubation with the corresponding peptide that was used for immunization, but not by a control peptide (FIG. 27 and FIG. 28). Antibodies raised against two of the β3 cytoplasmic domain binding peptides recognize specific bands on total cell extracts and in immunoprecipitation experiments using 35S-labeled extracts. Similar results were obtained with polyclonal sera and purified IgGs (not shown).

The present example shows that targeting peptides against specific domains of cell receptors can be identified by phage display. Such peptides may be used to identify the endogenous ligands for cell receptors, such as endostatin. In addition, the peptides themselves may have therapeutic effects, or may serve as the basis for identification of more effective therapeutic agents. The endostatin targeting peptides identified herein, when introduced into cells, showed effects on cell proliferation, chemotaxis and apoptosis. The skilled artisan will realize that the present invention is not limited to the disclosed peptides or therapeutic effects. Other cell receptors and ligands, as well as inhibitors or activators thereof, may be identified by the disclosed methods.

Example 7

Induction of Apoptosis with Integrin Binding Peptides (Endothanos)

Example 6 showed that the VISY peptide (VVISYSMPD, SEQ ID NO:46), imported into cells by attachment to penetratin, could induce apoptosis in HUVEC cells. Antibodies raised against the VISY peptide were used to identify the endogenous cell analog of the peptide, identified herein as Annexin V. The results indicate that Annexin V is an endogenous ligand for the integrins that is involved in a novel pathway for apoptosis.

Methods

Protein Purification

Polyclonal antibodies against the VISY peptide (VVISYSMPD, SEQ ID NO:46) were prepared using the methods described in Example 6. MDA-MB-435 breast carcinoma cells were used for purification of the endogenous VISY peptide analog. Cells were washed three times with ice cold PBS and lysed with chilled water for 20 min. Cell extracts were centrifuged for 30 min at 100,000×g to separate the cytoplasmic fraction from the membrane fraction. The cytoplasmic fraction was subjected to column chromatography on a gel filtration column (10-50 kDa) and an anion exchange column (mono Q). The anion exchange column was eluted with a salt gradient from 50 mM to 1 M NaCl. One ml fractions were collected, run on SDS-PAGE and tested by Western blotting for the presence of endogenous proteins reactive with the anti-VISY antibody. The fraction of interest, containing a 36 kDa antibody reactive band, eluted at about 300 mM NaCl.

The 36 kDa always appeared in fractions that showed positive reactivity with the anti-VISY antibody. The fractions were analyzed by SDS-PAGE and 2-D gel electrophoresis, followed by Western blotting. A substantial enrichment of the 36 kDa protein was seen after column chromatography (not shown). The 36 kDa peptide was cut from the SDS-PAGE gel and analyzed by mass spectroscopy to obtain its sequence. All five peptide sequences that were obtained by mass spectroscopy showed 100% homology to the reported sequence of Annexin V (GenBank Accession No. GI_468888). In addition to its presence in 435 cells, the 36 kDa band was also seen in Kaposi sarcoma, SKOV and HUVEC cells (not shown).

Commercial antibodies against Annexin V were obtained (Santa Cruz Biologics, Santa Cruz, Calif.). Comparative Western blots were performed using the anti-VISY antibody and the anti-Annexin V antibody. Both antibodies showed reactivity with the 36 kDa protein (not shown). These results indicate that the endogenous protein analog of the VISY peptide is Annexin V.

Protein-Protein Interaction with Annexin V and β5 Cytoplasmic Domain.

Competitive binding assays were performed to examine the binding of Annexin V to β5 integrin and the effect of the VISY peptide. Plates were coated with GST fusion proteins of the cytoplasmic domains of various integrins and Annexin V was added to the plates. Binding of Annexin V was determined using anti-Annexin V antibodies. As shown in FIG. 29A, Annexin V did not bind to either the GST-β1 or GST-β3 integrins. Annexin V bound strongly to the GST-β5 integrin, but binding was dependent on the buffer used (FIG. 29A). Low binding was observed in Tris-buffered saline (TBS), while high binding was observed in "cytoplasmic buffer" (100 mM KCl, 3 mM NaCl, 3.5 mM MgCl$_2$, 10 mM PIPES, 3 mM DTT) with or without added calcium (2 mM) (FIG. 29A). Calcium was used because Annexin V activity has been reported to be modulated by calcium. Binding of Annexin V to GST-β5 was blocked by addition of the VISY peptide (FIG. 29A). FIG. 29B shows the relative levels of binding of anti-Annexin V antibody to purified Annexin V and to VISY peptide.

A reciprocal study was performed, using Annexin V to coat plates and adding GST fusion proteins of integrin cytoplasmic domains. Binding was assessed using anti-GST fusion protein antibodies. As expected, only GST-β5 showed substantial binding to Annexin V, while GST-β1 and GST-β3 showed low levels of Annexin V binding (not shown). In some studies, calcium ion appeared to interfere with the binding interaction between GST-β5 and Annexin V, with decreased binding observed in the presence of calcium (not shown). A greater degree of inhibition of Annexin V binding to GST-β5 by the VISY peptide was observed in the presence of calcium (67% inhibition) than in the absence of calcium (45%) (FIG. 29A).

Penetratin Peptide Chimera Binding to the β5 Cytoplasmic Domain Induces Programmed Cell Death.

The induction of apoptosis by VISY peptide was shown in Example 6 was confirmed. $10^6$ HUVEC were treated with 15 μM of VISY antennapedia (penetratin) chimera or 15 μM of antennapedia peptide (pentratin) alone for 2-4 hours and chromatin fragmentation was analyzed by electrophoresis in an agarose gel. FIG. 30 shows the induction of apoptosis by VISY-Ant (penetratin), as indicated by chromatin fragmentation. Neither VISY nor penetratin alone induced apoptosis. Induction of apoptosis was inhibited up to 70% when a caspase inhibitor (zVAD, caspase inhibitor I, Calbiochem #627610, San Diego, Calif.) was added to the media at the same time as the VISY chimeric peptide.

A distinction between the mechanism of cell death induced by VISY peptide and other pro-apoptosis agents is that other apoptotic mechanisms evaluated in cell culture typically involve detachment of the cells from the substrate, followed by cell death. In contrast, in VISY induced cell death, the cells do not detach from the substrate before dying. Thus, endothanos (death from inside) appears to differ from anoikis (homelessness).

The present results show that VISY peptides activate an integrin dependent apoptosis pathway. The present example shows that the endogenous analog for VISY peptide is Annexin V. These results demonstrate the existence of a novel apoptotic pathway, mediated through an interaction between Annexin V and β5 integrin and dependent on caspase activity. This novel apoptotic mechanism is termed endothanos. The skilled artisan will realize that the existence of a novel mechanism for inducing or inhibiting apoptosis is of use for a variety of applications, such as cancer therapy.

Example 8

Identification of Receptor/Ligand Pairs: Aminopeptidase A Regulates Endothelial Cell Function and Angiogenesis Endothelial cells in tumor vessels express specific angiogenic markers. Aminopeptidase A (APA, EC 3.4.11.7) is upregulated in microvessels undergoing angiogenesis. APA is a homodimeric, membrane-bound zinc metallopeptidase that hydrolyzes N-terminal glutamyl or aspartyl residues from oligopeptides (Nanus et al., 1993). In vivo, APA converts angiotensin II to angiotensin III. The renin-angiotensin system plays an important role in regulating several endocrine, cardiovascular, and behavioral functions (Ardaillou, 1997; Stroth and Unger, 1999). Recent studies also suggest a role for angiotensins in angiogenesis (Andrade et al., 1996), but the function of APA in the angiogenic process has not been investigated so far.

In the present example, targeting peptides capable of binding APA were identified by screening phage libraries on APA-expressing cells. APA-binding peptides containing the motif CPRECESIC (SEQ D NO:56) specifically inhibited APA enzyme activity. Soluble CPRECESIC (SEQ ID NO:56) peptide inhibited migration, proliferation, and morphogenesis of endothelial cells in vitro and interfered with in vivo angiogenesis in a chick embryo chorioallantoic membrane (CAM) assay. Furthermore, APA null mice had a decreased amount of retinal neovascularization compared to wild type (wt) mice in hypoxia-induced retinopathy in premature mice. These results may lead to a better understanding of the role of APA in angiogenesis and to development of new anti-tumor therapeutic strategies.

Materials and Methods

Cell Cultures

The renal carcinoma cell line SK-RC-49 was transfected with an expression vector encoding full-length APA cDNA (Geng et al., 1998). Cells were maintained in MEM (Irvine Scientific, Santa Ana, Calif.), supplemented with 2 mM glutamine, 1% nonessential amino acids, 1% vitamins (Gibco BRL), 100 U/ml streptomycin, 100 U/ml penicillin (Irvine Scientific), 10 mM sodium pyruvate (Sigma-Aldrich), and 10% fetal calf serum (FCS) C(issue Culture Biological, Tulare, Calif.). Stably transfected cells were maintained in G418-containing medium. HUVECs were isolated by collagenase treatment and used between passages 1 to 4. Cells were grown on gelatin-coated plastic in M199 medium (Sigma) supplemented with 20% FCS, penicillin (100 U/ml), streptomycin (50 μg/ml), heparin (50 μg/ml), and bovine brain extract (100 μg/ml). All media supplements were obtained commercially (Life Technologies, Inc., Milan, Italy).

Antibodies and Peptides

The anti-APA mAb RC38 (Schlingemann et al., 1996) was used to immunocapture APA from transfected cell lysates. CPRECESIC (SEQ ID NO:56) and GACVRLSACGA (SEQ ID NO:57) cyclic peptides were chemically synthesized, spontaneously cyclized in non-reducing conditions, and purified by mass spectrometry (AnaSpec San Jose, Calif.). The mass spectrometer analysis of the CPRECESIC (SEQ ID NO:56) peptide revealed six different peaks, possibly reflecting different positions of disulfide bounds and the formation of dimers. Due to the similar biochemical behavior of the different fractions on APA enzyme activity, a mix of the six peaks was used in all procedures described below.

APA Immunocapture

Cells were scraped from semi-confluent plates in cold PBS containing 100 mM N-octyl-β-glucopyranoside (Calbiochem), lysed on ice for 2 h, and centrifuged at 13,000×g for 15 min. Microtiter round-bottom wells (Falcon) were coated with 2 μg of RC38 for 4 h at room temperature and blocked with PBS/3% BSA (InterGen, Purchase, N.Y.) for 1 h at room temperature, after which 150 μl of cell lysate (1 mg/ml) was incubated on the mAb-coated wells overnight at 4° C., washed five times with PBS/0.1% Tween-20 (Sigma), and washed twice with PBS.

APA Enzyme Assay

Cells and immunocaptured proteins were tested for specific enzyme activity according to Liln et al. (1998). Briefly, adherent cells or RC38-immunocaptured cell extracts were incubated for 2 h at 37° C. with PBS containing 3 mM α-L-glutamyl-p-nitroanilide (Fluka) and 1 mM $CaCl_2$. Enzyme activity was determined by reading the optical absorbance (O.D.) at 405 nm in a microplate reader (Molecular Devices, Sunnyvale, Calif.).

Cell Panning

A $CX_3CX_3CX_3C$ (C, cysteine; X, any amino acid) library was prepared (Rajotte et al., 1998). Amplification and purification of phage particles and DNA sequencing of phage-displayed inserts were performed as described. Cells were detached by incubation with 2.5 mM EDTA in PBS, washed once in binding medium (DMEM high glucose supplemented with 20 mM HEPES and 2% FCS), and resuspended in the same medium at a concentration of $2 \times 10^6$ cells/ml. $10^{10}$ TU of phage were added to 500 µl of the cell suspension, and the mixture was incubated overnight (first round) or for 2 h (successive rounds) at 4° C. with gentle rotation. Cells were washed five times in binding medium at room temperature and resuspended in 100 µl of the same medium. Phage were rescued by adding 1 ml of exponentially growing K91Kan *Escherichia coli* bacteria and incubating the mixture for 1 h at room temperature. Bacteria were diluted in 10 ml of LB medium supplemented with 0.2 µg/ml tetracycline and incubated for another 20 min at room temperature. Serial dilutions were plated on LB plates containing 40 µg/ml tetracycline, and plates were incubated at 37° C. overnight before colonies were counted.

Phage Binding Specificity Assay

The cell binding assay was performed with an input of $10^9$ TU as described for the cell panning. The specificity was confirmed by adding CPRECESIC (SEQ ID NO:56) peptide to the binding medium in increasing concentrations. For phage binding on immunocaptured APA, wells were blocked for 1 h at room temperature with PBS/3% BSA and incubated with $10^9$ TU for 1 h at room temperature in 50 µl PBS/3% BSA. After eight washes in PBS/1% BSA/0.01% Tween-20 and two washes in PBS, phage were rescued by adding 200 µl of exponentially growing K91Kan *E. coli*. Each experiment was repeated at least three times.

In vivo Tumor Homing of APA-Binding Phage

MDA-MB-435-derived tumor xenografts were established in female nude mice 2 months old (Jackson Labs, Bar Harbor, Me.). Mice were anesthetized with Avertin and injected intravenously through the tail vein with $10^9$ TU of the phage in a 200 µl volume of DMEM. The phage were allowed to circulate for 5 min, and the animals were perfused through the heart with 5 ml of DMEM. The tumor and brain were dissected from each mouse, weighed, and equal amounts of tissue were homogenized. The tissue homogenates were washed three times with ice-cold DMEM containing a proteinase inhibitor cocktail and 0.1% BSA. Bound phage were rescued and counted as described for cell panning. Fd-tet phage was injected at the same input as a control. The experiment was repeated twice. In parallel, part of the same tissue samples were fixed in Bouin solution, and imbedded in paraffin for preparation of tissue sections. An antibody to M-13 phage (Amersham-Pharmacia) was used for the staining.

Cell Growth Assay

HUVECs were seeded in 48-well plates ($10^4$ cells/well) and allowed to attach for 24 h in complete M199 medium. The cells were then starved in M199 medium containing 2% FCS for 24 h. CPRECESIC (SEQ ID NO:56) or control GACVRLSACGA (SEQ ID NO:57) peptide (1 mM) was added to the wells in medium containing 2% FCS and 10 ng/ml VEGF-A (R&D System, Abingdom, UK). After incubation for the indicated times, cells were fixed in 2.5% glutaraldehyde, stained with 0.1% crystal violet in 20% methanol, and solubilized in 10% acetic acid. All treatments were done in triplicate. Cell growth was evaluated by measuring the O.D. at 590 nm in a microplate reader (Bio-Rad Laboratories, Hercules, Calif.). A calibration curve was established and a linear correlation between O.D. and cell counts was observed between $10^3$ and $10^5$ cells.

Chemotaxis Assay

A cell migration assay was performed in a 48-well microchemotaxis chamber (NeuroProbe, Gaithersburg, Md.) according to Bussolini et al. (1995). Polyvinylpyrrolidone-free polycarbonate filters (Nucleopore, Cambridge, Mass.) with 8-µm pores were coated with 1% gelatin for 10 min at room temperature and equilibrated in M199 medium supplemented with 2% FCS. CPRECESIC (SEQ ID NO:56) or control GACVRLSACGA (SEQ ID NO:57) peptide (1 mM) was placed in the lower compartment of a Boyden chamber in M199 medium supplemented with 2% FCS and 10 ng/ml VEGF-A (R&D System). Subconfluent cultures that had been starved overnight were harvested in PBS containing 2.5 mM EDTA, washed once in PBS, and resuspended in M199 medium containing 2% FCS at a final concentration of $2 \times 10^6$ cells/ml. After the filter was placed between the lower and upper chambers, 50 µl of the cell suspension was seeded in the upper compartment, and cells were allowed to migrate for 5 h at 37° C. in a humidified atmosphere with 5% $CO_2$. The filter was then removed, and cells on the upper side were scraped with a rubber policeman. Migrated cells were fixed in methanol and stained with Giemsa solution (Diff-Quick, Baxter Diagnostics, Rome, Italy). Five random high-power fields (magnitude 100×) were counted in each well. Each assay was run in triplicate.

Three-Dimensional Cell Culture

Matrigel (Collaborative Research, Bedford, Mass.) was added at 100 µl per well to 48-well tissue culture plates and allowed to solidify for 10 min at 37° C. HUVECs were starved for 24 h in M199 medium supplemented with 2% FCS before being harvested in PBS containing 2.5 mM EDTA. $10^4$ cells were gently added to each of the triplicate wells and allowed to adhere to the gel coating for 30 min at 37° C. Then, medium was replaced with indicated concentrations of CPRECESIC (SEQ ID NO:56) or GACVRLSACGA (SEQ ID NO:57) peptides in complete medium. The plates were photographed after 24 h with an inverted microscope (Canon). The assay was repeated three times.

CAM Assay

In vivo angiogenesis was evaluated by a CAM assay (Ribatti et al., 1994). Fertilized eggs from White Leghorn chickens were maintained in constant humidity at 37° C. On the third day of incubation, a square window was opened in the eggshell and 2-3 ml of albumen was removed to detach the developing CAM from the shell. The window was sealed with a glass plate of the same size and the eggs were returned to the incubator. At day 8, 1 $mm^3$ sterilized gelatin sponges (Gelfoam, Upjohn Co, Kalamazoo, Milan) were adsorbed with VEGF-A (20 ng, R&D System) and either CPRECESIC (SEQ ID NO:56) or control GACVRLSACGA (SEQ ID NO:57) peptide (1 mM) in 3 µl PBS and implanted on the top of the growing CAMs under sterile conditions. CAMs were examined daily until day 12 and photographed in ovo with a Leica stereomicroscope. Capillaries emerging from the sponge were counted. The assay was repeated twice.

Induction of Retinal Neovascularization

APA null mice have been described gin et al., 1998). Mice pups on P7 ($7^{th}$ day postpartum) with their nursing mothers were exposed to 75% oxygen for 5 days. Mice were brought back to normal oxygen (room air) on P12. For histological analysis mice were killed between P17 and P21 and eyes were enucleated and fixed in 4% paraformaldehyde in PBS overnight at 4° C. Fixed eyes were imbedded in paraffin and 5 µm serial sections were cut. Sections were stained with hematoxylin/eosin solution. Neovascular nuclei on the vitreous side of the internal limiting membrane were counted from 20 h/e-stained sections per each eye. The average number of neovascular nuclei per section was calculated and compared between animal groups using Student's t-test.

Results

Cell Panning with Phage Display Select an APA-Binding Motif

To identify a peptide capable of binding to APA, cells were screened with a random peptide phage library. First, SK-RC-49 renal carcinoma cells, which do not express APA, were transfected with full-length APA cDNA to obtain a model of APA expression in the native conformation. APA expressed as a result of transfection was functionally active, as evidenced by an APA enzyme assay (not shown), but parental SK-RC-49 cells showed neither APA expression nor activity (not shown).

The $CX_3CX_3CX_3C$ phage library ($10^{10}$ transducing units [TU]) was preadsorbed on parental SK-RC-49 cells to decrease nonspecific binding. Resuspended SK-RC49/APA cells were screened with phage that did not bind to the parent cells. SK-RC-49/APA-bound phage were amplified and used for two consecutive rounds of selection. An increase in phage binding to SK-RC-49/APA cells relative to phage binding to SK-RC-49 parental cells was observed in the second and third rounds (not shown).

Subsequent sequencing of the phage revealed a specific enrichment of a peptide insert, CYNLCIRECESICGADGACWTWCADGCSRSC (SEQ D NO:58), with a tandem repetition of the general library sequence $CX_3CX_3CX_3C$. This sequence represented 50% of 18 randomly selected phage inserts from round 2 and 100% of phage inserts from round 3. Four peptide inserts derived from round 2 shared sequence similarity with the tandem phage (Table 7, in bold font). Several other apparently conserved motifs were observed among round 2 peptides (Table 7, underlined or italicized). One of these overlapped in part with the tandem repeated sequence. A search for sequence homology of the selected peptides against human databases did not yield a significant match.

TABLE 7

APA-binding peptide sequences.

| Peptide sequences | Round 2 (%)/3 (%) |
|---|---|
| CYNLCIRECESICGADGACWTWCADGCSRSC (SEQ ID NO:58) | 50/100 |
| CLGQCASICVNDC (SEQ ID NO:59) | 5/— |
| CPKVCPRECESNC (SEQ ID NO:60) | 5/— |
| CGTGCAVECEVVC (SEQ ID NO:61) | 5/— |
| CAVACWADCQLGC (SEQ ID NO:62) | 5/— |
| CSGLCTVQCLEGC (SEQ ID NO:63) | 5/— |
| CSMMCLEGCDDWC (SEQ ID NO:64) | 5/— |
| OTHER | 20/— |

Selected Phage Inserts are Specific APA Ligands.

Phage displaying the peptide inserts CYNLCIRECESICGADGACWTWCADGCSRSC (SEQ ID NO:58), CPKVCPRECESNC (SEQ ID NO:60) or CLGQCASICVNDC (SEQ ID NO:59) were individually tested for APA binding. All three phage specifically bound to the surface of SK-RC-49/APA cells (not shown), with a similar pattern of 6-fold enrichment relative to SK-RC-49 parental cells. Control, insertless phage showed no binding preference (not shown). CGTGCAVECEVVC (SEQ ID NO:61) and the other phage selected in round 2 showed no selective binding to SK-RC-49/APA cells (data not shown). A soluble peptide, CPRECESIC (SEQ ID NO:56) containing a consensus sequence reproducing the APA-binding phage inserts was synthesized.

Binding assays were performed with CPKVCPRECESNC (SEQ ID NO:60) phage in the presence of the CPRECESIC (SEQ ID NO:56) peptide. Soluble CPRECESIC (SEQ ID NO:56) peptide competed with CPKVCPRECESNC (SEQ ID NO:60) phage for binding to SK-RC-49/APA cells, but had no effect on nonspecific binding to SK-RC-49 parental cells (not shown). The unrelated cyclic peptide GACVRLSACGA (SEQ ID NO:57) had no competitive activity (not shown). Binding of CYNLCIRECESICGADGACWTWCADGCSRSC (SEQ ID NO:58) phage was also displaced by CPRECESIC (SEQ ID NO:56) peptide, but the binding of CLGQCASICVNDC (SEQ ID NO:59) phage was not affected (data not shown).

To further confirm the substrate specificity of the selected peptide inserts, APA was partially purified from APA-transfected cell extracts by immunocapture with mAb RC38. The APA protein immobilized on RC38-coated microwells was functional, as confirmed by enzyme assay (not shown). The CYNLCIRECESICGADGACWTWCADGCSRSC (SEQ ID NO:58), CPKVCPRECESNC (SEQ ID NO:60), and CLGQCASICVNDC (SEQ ID NO:59) phage selectively bound immunocaptured APA, with a 10- to 12-fold enrichment compared to phage binding to RC38-immunocaptured cell lysates from SK-RC-49 parental cells (not shown).

APA-Binding Phage Target Tumors in vivo.

The ability of the identified peptide to home to tumors was evaluated, using nude mice implanted with human breast tumor xenografts as a model system. Phage were injected into the tail vein of tumor-bearing mice, and targeting was evaluated by phage recovery from tissue homogenates. CPKVCPRECESNC (SEQ ID NO:60) phage was enriched 4-fold in tumor xenografts compared to brain tissue, which was used as a control (FIG. 31). Insertless phage did not target the tumors (FIG. 31). Neither CYNLCIRECESICGADGACWTWCADGCSRSC (SEQ ID NO:58) nor CLGQCASICVNDC (SEQ ID NO:59) phage showed any tumor-homing preference (data not shown).

The homing of CPKVCPRECESNC (SEQ ID NO:60) was confirmed by anti-M13 immunostaining on tissue sections (not shown). Strong phage staining was apparent in tumor vasculature but not in normal vasculature (not shown). Insertless phage did not bind to tumor vessels.

CPRECESIC (SEQ ID NO:56) is a Specific Inhibitor of APA Activity.

To investigate the effect of CPRECESIC (SEQ ID NO:56) on APA enzyme activity, SK-RC-49/APA cells were incubated with the APA specific substrate α-glutamyl-p-nitroanilide in the presence of increasing concentrations of either CPRECESIC (SEQ ID NO:56) or control GACVRLSACGA (SEQ ID NO:57) peptides. Enzyme activity was evaluated by a colorimetric assay after 2 h incubation at 37° C. CPRECESIC (SEQ ID NO:56) inhibited APA enzyme activity, reducing the activity by 60% at the highest concentration tested (FIG. 32). The $IC_{50}$ of CPRECESIC (SEQ ID NO:56) for enzyme inhibition was calculated to be 800 μM. CPRECESIC (SEQ ID NO:56) did not affect the activity of a closely related protease, aminopeptidase N (data not shown).

CPRECESIC (SEQ ID NO:56) Inhibits Migration and Proliferation of Endothelial Cells.

The potential use of CPRECESIC (SEQ ID NO:56) peptide as an anti-angiogenic drug was determined. First, the effect of APA inhibition by CPRECESIC (SEQ ID NO:56) peptide in vitro on the migration and proliferation of human umbilical vein endothelial cells (HUVECs) stimulated with VEGF-A (10 ng/ml) was examined. The presence of functional APA on HUVECs was evaluated by enzyme assay (not shown). At the highest concentration tested (1 mM), CPRECESIC (SEQ ID NO:56) peptide inhibited chemotaxis of HUVECs by 70% in a Boyden chamber assay (FIG. 33). At the same peptide concentration, cell proliferation was inhibited by 50% (FIG. 34). Lower concentrations of CPRECESIC (SEQ ID NO:56) peptide or the GACVRLSACGA (SEQ ID NO:57) control peptide had no significant effect on cell migration or proliferation (not shown).

CPRECESIC (SEQ ID NO:56) Inhibits Angiogenesis in vitro and in vivo

The inhibitory effect of CPRECESIC (SEQ ID NO:56) peptide in different in vitro and in vivo models of angiogenesis was examined. HUVECs plated on a three-dimensional matrix gel differentiate into a capillary-like structure, providing an in vitro model for angiogenesis. Increasing concentrations of CPRECESIC (SEQ ID NO:56) peptide resulted in a progressive impairment of the formation of this network (not shown). At a peptide concentration of 1 mM, vessel-like branching structures were significantly fewer and shorter, and as a result, the cells could not form a complete network organization (not shown). The control peptide GACVRLSACGA (SEQ ID NO:57) did not affect HUVEC morphogenesis (not shown).

A commonly used model of simplified in vivo angiogenesis is the chicken chorioallantoic membrane (CAM), in which neovascularization can be stimulated during embryonic development. An appropriate stimulus, adsorbed on a gelatin sponge, induces microvessel recruitment to the sponge itself, accompanied by remodeling and ramification of the new capillaries. Eight-day-old chicken egg CAMs were stimulated with VEGF-A alone (20 ng) or with VEGF-A plus CPRECESIC (SEQ ID NO:56) or GACVRLSACGA (SEQ ID NO:57) (1 mM) peptides. The CAMs were photographed at day 12. Neovascularization induced by VEGF-A was inhibited by CPRECESIC (SEQ ID NO:56) by 40% based on the number of capillaries emerging from the sponge (Table 8). The neovessels did not show the highly branching capillary structures typically seen after VEGF-A stimulation (not shown). Treatment with control peptide GACVRLSACGA (SEQ ID NO:57) or with lower peptide concentrations of CPRECESIC (SEQ ID NO:56) had no effect on the number of growing vessels (not shown).

TABLE 8

CAM assay for angiogenesis

| TREATMENT | BLOOD VESSEL NUMBERS |
| --- | --- |
| No VEGF-A | 12.0 ± 2.82* |
| VEGF-A | 57.0 ± 1.41* |
| VEGF-A + control | 56.5 ± 2.12 |
| VEGF-A + CPRECESIC (SEQ ID NO: 56) | 5.5 ± 1.41* |

*$p < 0.01$ with the Student-Newman-Keuls test. The results are expressed as the mean and standard error from two independent experiments.

APA-Deficient Mice Show Impaired Neovascularization

The ability of $APA^{+/-}$ and $APA^{-/-}$ null mice to undergo neovascularization was examined in a model of hypoxic retinopathy in premature mice. Induction of retinal neovascularization by relative hypoxia was already present in $APA^{+/-}$ mice compared to wild type mice (not shown). Neovascularization was almost undetectable in APA null mice (not shown). Neovascularization was quantified by counting vitreous protruding neovascular nuclei from 20 sections of hypoxic eyes. Significant induction of retinal neovascularization (16.17±1.19 neovascular nuclei/eye section) was seen in the wild type mice on postnatal day 17 (P17) after 75% oxygen treatment from P7 to P12. Decreased amounts of neovascular nuclei were seen in the retinas of $APA^{+/-}$ (10.76±1.03 neovascular nuclei/eye section) and APA null (4.25±0.45 neovascular nuclei/eye section) mice on P17 after exposure to 75% oxygen from P7 to P12.

Discussion

In vivo, APA is overexpressed by activated microvessels, including those in tumors, but it is barely detectable in quiescent vasculature, making it a suitable target for vessel-directed tumor therapy. The present example identified a novel targeting peptide ligand for APA, CPRECESIC (SEQ ID NO:56). Soluble CPRECESIC (SEQ ID NO:56) peptide inhibited APA enzyme activity with an $IC_{50}$ of 800 µM.

Using cultured HUVECs as an in vitro model of angiogenesis, soluble CPRECESIC (SEQ ID NO:56) peptide inhibited VEGF-A-induced migration and proliferation of HUVECs. These data are consistent with a requirement for migration and proliferation of endothelial cells during angiogenesis. CPRECESIC (SEQ ID NO:56) also blocked the formation of capillary-like structures in a Matrigel model and inhibited angiogenesis in VEGF-A-stimulated CAMs.

APA was shown to be an important player in neovascularization induced by relative hypoxia, since APA null mice had significantly less retinal neovascularization compared to wt mice. These results strengthen the potential of using APA as a specific target for the inhibition of tumor angiogenesis.

In summary, the soluble peptide CPRECESIC (SEQ ID NO:56) is a selective APA ligand and inhibitor. The inhibition of APA by CPRECESIC (SEQ ID NO:56) led to the inhibition of angiogenesis in different in vitro and in vivo assays, demonstrating for the first time a prominent role for APA in the angiogenic process. Furthermore, APA-binding phage can home to tumor blood vessels, suggesting possible therapeutic uses of CPRECESIC (SEQ ID NO:56) as an inhibitor of tumor neovascularization. The endogenous analog of CPRECESIC (SEQ ID NO:56) may be identified by antibody based purification or identification methods, similar to those disclosed.

Example 9

Screening Phage Libraries by PALM

In certain embodiments, it is desirable to be able to select specific cell types from a heterogeneous sample of an organ or tissue. One method to accomplish such selective sampling is by PALM (Positioning and Ablation with Laser Microbeams).

The PALM Robot-Microbeam uses a precise, computer-guided laser for microablation. A pulsed ultra-violet (UV) laser is interfaced into a microscope and focused through an objective to a beam spot size of less than 1 micrometer in diameter. The principle of laser cutting is a locally restricted ablative photodecomposition process without heating (Hendrix, 1999). The effective laser energy is concentrated on the minute focal spot only and most biological objects are transparent for the applied laser wavelength. This system appears to be the tool of choice for recovery of homogeneous cell populations or even single cells or subcellular structures for subsequent phage recovery. Tissue samples may be retrieved by circumcising a selected zone or a single cell after phage administration to the subject. A clear-cut gap between selected and non-selected area is typically obtained. The isolated tissue specimen can be ejected from the object plane and catapulted directly into the cap of a common micro centrifuge tube in an entirely non-contact manner. The basics of this so called Laser Pressure Catapulting (LPC) method is believed to be the laser pressure force that develops under the specimen, caused by the extremely high photon density of the precisely focused laser microbeam. This tissue harvesting technique allows the phage to survive the microdissection procedure and be rescued.

PALM was used in the present example to select targeting phage for mouse pancreatic tissue, as described below.

Materials and Methods

In vivo and in situ Panning

A $CX_7C$ peptide phage library ($10^9$ TU) was injected into the tail vein of a C57BL/6 male mouse, and the pancreas was harvested to recover the phage by bacterial infection. Phage from 246 colonies were grown separately in 5 ml LB/kanamycin (100 µg/ml)/tetracycline (40 µg/ml) at 37° C. in the dark with agitation. Overnight cultures were pooled and the phage purified by NaCl/PEG precipitation for another round of in vivo bio-panning. Three hundred colonies were picked from the second round of panning, and the phage were recovered by precipitation. Phage from the second bio-panning round was then used for another round of in vivo panning and also was incubated with thawed frozen murine pancreatic sections for one in situ panning round.

For the third in vivo panning round, $10^9$ TU phage from the second round were injected into a third mouse and allowed to circulate for six minutes, followed by an intravenous injection of 50 µl of FITC-lectin (Vector Laboratories, Inc.). After a two-minute circulation, the mouse was perfused through the left ventricle with 3 ml MEM Earle salts. The pancreas was harvested, frozen at −80° C. in Tissue Tek (Sakura), and sectioned onto prepared slides.

For the third in situ round, purified phage, isolated from the second round, were incubated with 4-14 µm thawed murine pancreatic sections on ice for 30 minutes. Sections were rinsed with 100 µl ice-cold PBS 8× at room temperature (RT). Bound phage were recovered from each section by adding 100 µl K91 Kan$^R$ (OD$_{600}$=2.03) to infect at RT for 30-60 minutes. Infected K91 KanR were withdrawn from each section and allowed to recover in 10 ml LB/Kan/Tet (0.2 µg/ml) for 20 minutes in the dark. Aliquots from the each culture were plated out onto LB/Kan/Tet (40 µg/ml) plates and incubated overnight in the dark at 37° C. The tetracycline concentration of the remainder of each culture was increased to 40 µg/ml and the cultures were incubated overnight at 37° C. in the dark with agitation for phage amplification and purification.

DNA Amplification

Phage were recovered from cryo-preserved FITC-lectin stained mouse pancreatic islets and surrounding acinar cells that were microdissected from 14 µm sections using the PALM (Positioning and Ablation with Laser Microbeams) cold laser pressure catapulting system. Pancreatic islet and control sections were catapulted into 1 mM EDTA, pH 8, and frozen at −20° C. until enough material was collected for PCR amplification. Phage DNA was amplified with fUSE5 primers: forward primer 5' TAA TAC GAC TCA CTA TAG GGC AAG CTG ATA AAC CGA TAC AATT 3' (SEQ ID NO:65), reverse primer 5' CCC TCA TAG TTA GCG TAA CGA TCT 3' (SEQ ID NO:66). The PCR products were subjected to another round of PCR using a nested set of primers. The 3' end of the second primer set was tailed with the M13 reverse primer for sequencing purposes. The nested primer set used was: forward nested primer 5' CCTTTCTATTCTCACTCG-GCCG 3' (SEQ ID NO:67), reverse nested primer 5' CAG-GAAACAGCTATGACCGCTAAA-CAACTTTCAACAGTTTCGGC 3' (SEQ ID NO:68). To generate peptide insert sequence containing flanking SfiI restriction sites, two more primers were used: forward library primer 5' CACTCGGCCGACGGGGC 3' (SEQ ID NO:69), reverse primer 5' CAGTTTCGGCCCCAGCGGCCC 3' (SEQ ID NO:70). PCR products generated from the nested primers were gel purified (Qiagen), and confirmed for the presence of a $CX_7C$ peptide insert sequence using the M13 reverse primer by automated sequencing. PCR products generated from the library primers were gel purified (Qiagen), ligated into CsCl$_2$ purified fUSE5/SfiI, electroporated into electrocompetent MC1061 cells, and plated onto LB/streptomycin (100 µg/ml)/tetracycline (40 µg/ml) agar plates. Single colonies were subjected to colony PCR using the fUSE5 primers to verify the presence of a $CX_7C$ insert sequence by gel electrophoresis. Positive clones were sequenced using BigDye terminators (Perkin Elmer)

Phage Infection

Pancreatic islet and control sections were catapulted into 1 mM AEBSF, 20 µg/ml aprotinin, 10 µg/ml leupeptin, 1 mM elastase inhibitor I, 0.1 mM TPCK, 1 nM pepstatin A in PBS, pH 7.4, and frozen for 48 hours or less until enough material was collected. The sections were thawed on ice and the volume adjusted to 200 µl with PBS, pH 7.4. Samples were incubated with 1 ml K91 Kan$^R$ (OD=0.22) for two hours at RT on a nutator. Each culture was transferred to 1.2 ml LB/Kan/Tet (0.2 µg/ml) and incubated in the dark at RT for 40 minutes. The tetracycline concentration was increased to 40 µg/ml for each culture, and the cultures were incubated overnight at 37° C. with agitation. Each culture was plated out the following day onto LB/Kan/Tet agar plates and incubated for 14 hours at 37° C. in the dark. Positive clones were picked for colony PCR and automated sequencing.

Results

The general scheme for in vivo panning using PALM is illustrated in FIG. 35. After an initial round of in vivo selection, phage were either bulk amplified or else single colonies of phage from pancreas, kidney, lung and adrenal glands were amplified and subjected to additional rounds of in vivo screening. Both bulk amplified and colony amplified phage from mouse pancreas showed successive enrichment with increasing rounds of selection (not shown). After three rounds of selection, the colony amplified phage showed almost an order of magnitude higher enrichment than bulk amplified phage (not shown).

Table 9 lists selected targeting sequences and consensus motifs identified by pancreatic screening.

TABLE 9

Pancreatic targeting peptides and motifs

| Motif | Peptide Sequence |
|---|---|
| GGL (SEQ ID NO:111) | CVPGLGGLC (SEQ ID NO:71) |
|  | CGGLDVRMC (SEQ ID NO:72) |
|  | CDGGLDWVC (SEQ ID NO:73) |
| LGG (SEQ ID NO:112) | CVPGLGGLC (SEQ ID NO:71) |
|  | CTWLGGREC (SEQ ID NO:74) |
|  | CSRWGLGGC (SEQ ID NO:75) |
|  | CPPLGGSRC (SEQ ID NO:48) |

TABLE 9-continued

Pancreatic targeting peptides and motifs

| Motif | Peptide Sequence |
|---|---|
| VRG (SEQ ID NO:113) | CVGGVRGGC (SEQ ID NO:76) |
|  | CVGNDVRGC (SEQ ID NO:77) |
|  | CESRLVRGC (SEQ ID NO:78) |
|  | CGGRPVRGC (SEQ ID NO:79) |
| AGG (SEQ ID NO:114) | CTPFIAGGC (SEQ ID NO:80) |
|  | CREWMAGGC (SEQ ID NO:81) |
|  | CAGGSLRVC (SEQ ID NO:82) |
| VVG (SEQ ID NO:115) | CEGVVGIVC (SEQ ID NO:83) |
|  | CDSVVGAWC (SEQ ID NO:84) |
|  | CRTAVVGSC (SEQ ID NO:85) |
| VGG (SEQ ID NO:116) | CVGGARALC (SEQ ID NO:86) |
|  | CVGGVRGGC (SEQ ID NO:76) |
|  | CLAHRVGGC (SEQ ID NO:88) |
| GGL (SEQ ID NO:117) | CWALSGGLC (SEQ ID NO:89) |
|  | CGGLVAYGC (SEQ ID NO:90) |
|  | CGGLATTTC (SEQ ID NO:91) |
| GRV (SEQ ID NO:118) | CGRVNSVAC (SEQ ID NO:92) |
|  | CAGRVALRC (SEQ ID NO:93) |
| GGA (SEQ ID NO:119) | CWNGGARAC (SEQ ID NO:94) |
|  | CLDRGGAHC (SEQ ID NO:95) |
| GVV (SEQ ID NO:120) | CELRGVVVC (SEQ ID NO:96) |
| GGV (SEQ ID NO:121) | CIGGVHYAC (SEQ ID NO:97) |
|  | CGGVHALRC (SEQ ID NO:98) |
| GMWG (SEQ ID NO:122) | CIREGMWGC (SEQ ID NO:99) |
|  | CIRKGMWGC (SEQ ID NO:100) |
| ALR (SEQ ID NO:123) | CGGVHALRC (SEQ ID NO:98) |
|  | CAGRVALRC (SEQ ID NO:93) |
|  | CEALRLRAC (SEQ ID NO:101) |
| ALV (SEQ ID NO:124) | CALVNVHLC (SEQ ID NO:102) |
|  | CALVMVGAC (SEQ ID NO:103) |
| GGVH (SEQ ID NO:125) | CGGVHALRC (SEQ ID NO:98) |
|  | CIGGVHYAC (SEQ ID NO:97) |
| VSG (SEQ ID NO:126) | CMVSGVLLC (SEQ ID NO:104) |
|  | CGLVSGPWC (SEQ ID NO:105) |
|  | CLYDVSGGC (SEQ ID NO:106) |
| GPW (SEQ ID NO:127) | CSKVGPWWC (SEQ ID NO:107) |
|  | CGLVSGPWC (SEQ ID NO:108) |
| none | CAHHALMEC (SEQ ID NO:109) |
|  | CERPPFLDC (SEQ ID NO:110) |

FIG. 36 shows a general protocol for recovery of phage insert sequences from PALM selected thin section materials. As indicated, phage may be recovered by direct infection of E. coli host bacteria, after protease digestion of the thin section sample. Alternatively, phage inserts may be recovered by PCR amplification and cloned into new vector DNA, then electroporated or otherwise transformed into host bacteria for cloning.

Both methods of PALM recovery of phage were successful in retrieving pancreatic targeting sequences. Pancreatic sequences recovered by direct bacterial infection included CVPRRWDVC (SEQ ID NO:128), CQHTSGRGC (SEQ ID NO:129), CRARGWLLC (SEQ ID NO:130), CVSN-PRWKC (SEQ ID NO:131), CGGVHALRC (SEQ ID NO:98), CFNRTWIGC (SEQ ID NO:132) and CSRG-PAWGC (SEQ ID NO:133). Pancreatic targeting sequences recovered by amplification of phage inserts and cloning into phage include CWSRGQGGC (SEQ ID NO:134), CHVLW-STRC (SEQ ID NO:135), CLGLLMAGC (SEQ ID NO:136), CMSSPGVAC (SEQ ID NO:137), CLASGMDAC (SEQ ID NO:138), CHDERTGRC (SEQ ID NO:139), CAHHALMEC (SEQ ID NO:140), CMQGAATSC (SEQ ID NO:141), CMQ-GARTSC (SEQ ID NO:142) and CVRDLLTGC (SEQ ID NO:143).

FIG. 37 through FIG. 40 show sequence homologies identified for selected pancreatic targeting sequences. Several proteins known to be present in pancreatic tissues are identified. The results of this example show that the PALM method may be used for selecting cell types from tissue thin sections and recovering targeting phage sequences. The skilled artisan will realize that this method could be used with virtually any tissue to obtain targeting sequences directed to specific types of cells in heterologous organs or tissues.

All of the COMPOSITIONS, METHODS and APPARATUS disclosed and claimed herein can be made and executed without undue experimentation in light of the present disclosure. While the compositions and methods of this invention have been described in terms of preferred embodiments, it are apparent to those of skill in the art that variations maybe applied to the COMPOSITIONS, METHODS and APPARATUS and in the steps or in the sequence of steps of the methods described herein without departing from the concept, spirit and scope of the invention. More specifically, it are apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Anand-Apte B, Pepper M S, Voest E, Montesano R, Olsen B, Murphy G, Apte S S and Zetter B. Inhibition of angiogenesis by tissue inhibitor of metallopeinase-3. Invest. Opthamol. Vis. Sci. 38: 817-823, 1997

Arap W, Pasqualini R, and Ruoslahti E. Chemotherapy targeted to tumor vasculature. Curr. Opin. Oncol., 1998b.

Arap, W., Pasqualini R., and Ruoslahti, E. Cancer treatment by targeted drug delivery to tumor vasculature. Science 279:377-380, 1998a.

Arap, W., Pasqualini, R. & Ruoslahti, E. Chemotherapy targeted to tumor vasculature. *Curr Opin Oncol* 10, 560-565 (1998).

Baichwal and Sugden, *In: Gene Transfer,* Kucherlapati R, ed., New York, Plenum Press, pp. 117-148, 1986.

Baldwin, R. W. et al. Monoclonal antibody-defined antigens on tumor cells. *Biomembranes* 11, 285-312 (1983).

Barany and Merrifield, *The Peptides,* Gross and Meienhofer, eds., Academic Press, New York, pp. 1-284, 1979.

Bartlett, J. S., Kleinschmidt, J., Boucher, R. C. & Samulski, R. J. Targeted adeno-associated virus vector transduction of nonpermissive cells mediated by a bispecific Fab'gamma)2 antibody. Nat Biotechnol 17, 181-186, 1999.

BERGELSON, J. M., CUNNINGHAM, J. A., DROGUETT, G., KURT-JONES, E. A., KRITHIVAS, A.,

HONG, J. S., HORWITZ, M. S., CROWELL, R. L., and FINBERG, R. W. (1997). Isolation of a common receptor for coxsackie B viruses and adenoviruses 2 and 5. Science 275; 1320-1322.

Bielenberg, D. R., M. F. McCarty, C. D. Bucana, S. H. Yuspa, D. Morgan, J. M. Arbeit, L. M. Ellis, K. R. Cleary, and I. J. Fidler. 1999. Expression of interferon-beta is associated with growth arrest of murine and human epidermal cells. J Invest Dermatol 112:802-9.

Boehm T, Folkman J, Browder T, and O'Reilly M S. Anti-angiogenic therapy of experimental cancer does not induce acquired drug resistance. Nature 390:404-407, 1997

Boon, T. & Old, L. J. Cancer Tumor antigens. *Curr Opin Immunol* 9, 681-683 (1997).

Bossemeyer, D., Engh, R. A., Kinzel, V., Ponstingl, H. and Huber, R. Phosphotransferase and substrate binding mechanism of the cAMP-dependent protein kinase catalytic subunit from porcine heart as deduced from the 2.0 A structure of the complex with $Mn^{2+}$ adenylyn imidiophosphate and inhibitor peptide PKI(5-24). *EMBO J.* 12:849-859, 1993.

Brodt et. al, The role of marrow endothelium in the localization of metastastic cancer cells to bone. In Bone Metastasis-mechanisms and pathophysiology, pp 17-23, 1996. (Orr and Singh, eds.)

Brooks P C, Clark R A, Cheresh D A. Requirement of vascular integrin $\alpha v\beta 3$ for angiogenesis. Science 264:569-571, 1994a.

Brooks P C, Stromblad S, Klemle R, Visscher D, Sarkar F H, and Cheresh D A. Anti-integrin $\alpha v\beta 3$ blocks human breast cancer growth and angiogenesis in human skin. J. Clin. Invest. 96:1815-1822, 1995.

Brooks, P. C. et al. Localization of matrix metalloproteinase MMP-2 to the surface of invasive cells by interaction with integrin alpha v beta 3. Cell 85, 683-693, 1996.

Brooks, P. C., Montgomery A. M., Rosenfeld, M., Reisfeld, R. A., Hu, T., Klier, G., and Cheresh D. A. Integrin $\alpha v\beta 3$ antagonists promote tumor regression by inducing apoptosis of angiogenic blood vessels. Cell 79, 1157-1164, 1994b Brousset, P. S. Chittal, D. Schlaifer, J. Icart, C. Payen, F. Rigal-Huguet, J. J. Voigt, and G. Delsol. 1991. Detection of Epstein-Barr virus messenger RNA in Reed-Sternberg cells of Hodgkin's disease by in situ hybridization with biotinylated probes on specially processed modified acetone methyl benzoate xylene (ModAMeX) sections. Blood 77:1781-6.

Burg M, Pasqualini R, Arap W, Stallcup W, and Ruoslahti E. Identification of NG2 proteoglycan-binding peptides that home to tumor neovasculature. Cancer Res 58:2869-2874, 1999.

Burg, M. A., Pasqualini, R., Arap, W., Ruoslahti, E. & Stallcup, W. B. NG2 proteoglycan-binding peptides target tumor neovasculature. Cancer Res 59, 2869-2874, 1999.

Campbell et al., *Am. J. Pathol.*, 158:25-32, 2001.

Cao Y. O'Reilly M S. Marshall B. Flynn E. Ji R W and Folkman J. Expression of angiostatin cDNA in a murine fibrosarcoma suppresses primary tumor growth and produces long-term dormancy of metastases. J. Clin. Invest. 101:1055-1063, 1998.

Carter, H. B., Piantadosi, S. & Isaacs, J. T. Clinical evidence for and implications of the multistep development of prostate cancer. *J Urol* 143, 742-746 (1990).

Chang, K. L., and L. M. Weiss. 1996. The association of the Epstein-Barr virus with malignant lymphoma. Biomed Pharmacother 50:459-67.

Chen and Okayama, *Mol. Cell Biol.*, 7:2745-2752, 1987.

Chen et al., *J. Cell. Biochem.*, 78:404-416, 2000.

Chinni et al., *Clin. Cancer Res.* 3:1557-64, 1997.

Clark, E. A. and Brugge, J. S. Integrins and signal transduction pathways: the road taken. *Science* 268:233-238, 1995.

Coffin, In: *Virology,* Fields et al., eds., Raven Press, New York, pp. 1437-1500, 1990.

Cortese, I. et al. Identification of peptides specific for cerebrospinal fluid antibodies in multiple sclerosis by using phage libraries. *Proc Natl Acad Sci USA* 93, 11063-11067 (1996).

Couch et al., *Am. Rev. Resp. Dis.,* 88:394-403, 1963.

Coupar et al., *Gene,* 68:1-10, 1988.

Cox, D. R. Regression models and life tables. *Journal of the Royal Statistical Society* 74, 187-220 (1972).

Curiel, D. T. Strategies to adapt adenoviral vectors for targeted delivery. Ann N.Y. Acad Sci 886, 158-171, 1999.

Defilippi, P., Bozzo, C., Volpe, G., Romano, G., Venturino, M., Silengo, L. and Tarone, G. Integrin-mediated signal transduction in human endothelial cells: analysis of tyrosine phosphorylation events. *Cell Adh. Commun.* 87:75-86, 1994.

Delannet, M., Martin, F., Bossy, B., Cheresh, D. A., Reichardt, L. F. and Duband, J. L. Specific roles of the $\alpha v\beta 3$, $\alpha v\beta 3$, and $\alpha v\beta 5$ integrins in avian neural crest cell adhesion and migration on vitronectin. *Development.* 120:2687-702, 1994.

Delpino et al., *Mol. Membr. Biol.* 15:21-26, 1998.

Dente, L., Vetriani, C., Zucconi, A., Pelicci, G., Lanfrancone, L., Pelicci, P. G. and Cesareni, G. Modified phage peptide libraries as a tool to study specificity of phosphorylation and recognition of tyrosine containing peptides. *J. Mol. Biol.* 269:694-703, 1997.

Derossi, D., Chassaing, G. and Prochiantz, A. Trojan peptides: the penetratin system for intracellular delivery. *Trends Cell Biol.* 8:84-87, 1998.

Derossi, D., Joliot, A. H., Chassaing, G. and Prochiantz, A. The third helix of Antennapedia homeodomain translocates through biological membranes. *J. Biol. Chem.* 269:10444-10450, 1994

DMITRIEV, I., KRASNYKH, V., MILLER, C. R., WANG, M., KASHENTSEV, A. E., MIKHEEVA, G., BELOUSOVA, N., and CURIEL, D. T. (1998). An adenovirus vector with genetically modified fibers demonstrates expanded tropism via utilization of a coxsackie virus and adenovirus receptor-independent cell entry mechanism. J. Virol. 72; 9706-9713.

DOUGLAS, J. T., ROGERS, B. E., ROSENFELD, M. E., MICHAEL, S. I., FENG, M., and CURIEL, D. T. (1996). Targeted gene delivery by tropism-modified adenoviral vectors. Nature Biotechnol. 14; 1574-1578.

Dunn, I. S. Mammalian cell binding and transfection mediated by surface-modified bacteriophage lambda. Biochimie 78, 856-861, 1996.

Dybwad, A., Forre, O., Kjeldsen-Kragh, J., Natvig, J. B. & Sioud, M. Identification of new B cell epitopes in the sera of rheumatoid arthritis patients using a random nanopeptide phage library. *Eur J Immunol* 23, 3189-3193 (1993).

Eisen, T. et al. Continuous low dose Thalidomide: a phase II study in advanced melanoma, renal cell, ovarian and breast cancer. Br J Cancer 82, 812-817, 2000.

Ellerby H M, Arap W, Ellerby L, Kain R, Andrusiak R, Rio G, Krajeswki S, Lombardo C, Rao R, Ruoslahti E, Bredesen D, and Pasqualini R. Anti-cancer Activity of Targeted proapoptotic peptides. Nature Med 9:1032-1038, 1999

Enblad, G., K. Sandvej, E. Lennette, C. Sundstrom, G. Klein, B. Glimelius, and G. Pallesen. 1997. Lack of correlation between EBV serology and presence of EBV in the Hodgkin and Reed-Sternberg cells of patients with Hodgkin's disease. Int J Cancer 72:394-7.

Engelstädter M et al. Targeting human T cells by retroviral vectors displaying antibody domains selected from a phage display library. *Hum Gene Ther.* 2000; 11: 293-303.

Engerman, R. L. and Kern, T. S. (1986) Hyperglycemia as a cause of diabetic retinopathy. *Metabolism* 35(S1), 20-23.

Ferrara, N. and Davis-Smyth, T. (1997) The biology of vascular endothelial growth factor. *Endocr. Rev.*, 18, 4-25.

Filardo, E. J. and Cheresh, D. A. A β turn in the cytoplasmic tail of the integrin αv subunit influences conformation and ligand binding of αvβ3. *J. Biol. Chem.* 269:4641-4647, 1994a.

Filardo, E. J. and Cheresh, D. A. A structural basis for bidirectional integrin signalling. *Princess Takamatsu Symp.* 24:106-117, 1994b.

Filardo, E. J., Brooks, P. C., Deming, S. L., Damsky, C. and Cheresh, D. A. Requirement of the NPXY motif in the integrin β3 subunit cytoplasmic tail for melanoma cell migration in vitro and in vivo. *J. Cell Biol.* 130:441-450, 1995.

Folkman J. Addressing tumor blood vessels. Nature Biotechnol. 15: 510, 1997.

Folkman J. Angiogenesis in cancer, vascular, rheumatoid and other disease. Nature Med 1:27-31, 1995

Folkman, J. Antiangiogenic gene therapy. Proc Natl Acad Sci USA 95, 9064-9066, 1998.

Friedlander M, Brooks P C, Sharffer R W, Kincaid C M, Varner J A, and Cheresh D A. Definition of two angiogenic pathways by distinct αv integrins. Science, 270: 1500-1502, 1995.

Friedlander M, Theesfeld C L, Sugita M, Fruttiger M, Thomas M A, Chang S, Cheresh D A. Involvement of integrins αvβ3 and αvβ5 in ocular neovascular diseases. Proc. Natl. Acad. Sci. U.S.A. 93:9764-9769, 1996.

Friedmann, *Science,* 244:1275-1281, 1989.

Frisch S M. And Ruoslahti E. Integrins and anoikis. *Cur. Opin. in Cell Biol.* 9:701-706, 1997.

Furuya et al., *Cancer Res.* 54:6167-75, 1994.

Ghosh-Choudhury et al., *EMBO J.,* 6:1733-1739, 1987.

Gingrich J R, Barrios R J, Morton R A, Boyce B F, DeMayo F J, Finegold M J, Angelopoulou R, Rosen J M and Greenberg N M. Metastatic prostate cancer in a transgenic mouse. Cancer Res. 56:4096-4102, 1996.

Girod A et al. Genetic capsid modifications allow efficient re-targeting of adeno-associated virus type 2. *Nat Med* 1999; 5: 1052-1056.

Gold R. Differenitation between Cellular Apoptosis ad Necrosis by the Combined Use of In Situ Tailing Translation Techniques. Lab. Invest. 71: 219, 1994

Goldman C K et al. Targeted gene delivery to Karposi's sarcoma cells via the fibroblast growth factor receptor. *Cancer Res* 1997; 57: 1447-1451.

GOLDMAN, C. K., ROGERS, B. E., DOUGLAS, J. T., SOSNOWSKI, B. A., YING, W., SIEGAL, G. P., BAIRD, A., CAMPAIN, J. A., and CURIEL, D. T. (1997). Targeted gene delivery to Karposi's sarcoma cells via the fibroblast growth factor receptor. Cancer Res. 57; 1447-1451.

Gomez-Foix et al., *J. Biol. Chem.,* 267:25129-25134, 1992.

Gopal, *Mol. Cell Biol.,* 5:1188-1190, 1985.

Grace, M. J., L. Xie, M. L. Musco, S. Cui, M. Gurnani, R. DiGiacomo, A. Chang, S. Indelicato, J. Syed, R. Johnson, and L. L. Nielsen. 1999. The use of laser scanning cytometry to assess depth of penetration of adenovirus p53 gene therapy in human xenograft biopsies. Am J Pathol 155:1869-78.

Graham and Prevec, *In: Methods in Molecular Biology: Gene Transfer and Expression Protocol,* E. J. Murray, ed., Humana Press, Clifton, N.J., 7:109-128, 1991.

Graham and van der Eb., *Virology,* 52:456-467, 1973.

Graham et al., *J. Gen. Virol.,* 36:59-72, 1977.

Gram, H., Schmitz, R., Zuber, J. F. and Baumann, G. Identification of phosphopeptide ligands for Src-homology 2 (SH2) domain of Grb2 by phage display. *Eur. J. Biochem.* 246:633-637, 1997.

Greenberg N M, DeMayo F, Finegold M J, Medina D, Tilley W D, Aspinall J O, Cunha G R, Donjacour A A, Matusik R J and Rosen J M. Prostate cancer in a transgenic mouse. Proc. Natl. Acad. Sci. U.S.A. 92:3439-3443, 1995.

Griscelli F. Li H. Bennaceur-Griscelli A. Soria J. Opolon P. Soria C. Perricaudet M. Yeh P and Lu H. Angiostatin gene transfer: inhibition of tumor growth in vivo by blockage of endothelial cell proliferation associated with a mitosis arrest. Proc. Natl. Acad. Sci. U.S.A. 95:6367-72, 1998

Grunhaus and Horwitz, *Seminar in Virology,* 3:237-252, 1992.

Gunge, N., Takata, H., Fukuda, K., Iwao, S. & Miyakawa, I. Relocation of a cytoplasmic yeast linear plasmid to the nucleus is associated with circularization via nonhomologous recombination involving inverted terminal repeats. Mol Gen Genet 263, 846-853 (2000).

Hall, H., Williams, E J., Moore, S E., Walsh, F S., Prochiantz, A. and Doherty, P. Inhibition of FGF-stimulated phosphatidylinositol hydrolysis and neuron outgrowth by a cell -membrane permeable phosphopeptide. *Current Biology,* 6:580-587, 1996.

Hammes H P, Brownlee M, Jonczyk A, Sutter A, and Preissner K T. Subcutaneous injection of a cyclic peptide antagonist of vitronectin receptor-type integrins inhibits retinal neovascularization. Nature Med. 2: 529-533, 1996.

Hanahan, D. and Folkman, J. (1996) Patterns and Emerging Mechanisms of the Angiogenic Switch during Tumorogenesis. *Cell,* 86, 353-364.

Hansen, A. S., Norén, O., Sjöström, H. and Wedelin, O. (1993) A mouse aminopeptidase-N is a marker for antigen presenting cells and apears to be co-expressed with major histocompatibility complex class II molecules. *Eur. J. Immunol.,* 23, 2358-64.

HARLOW, E., and LANE, D. (1988). *Antibodies: A Laboratory Manual* (Cold Spring Harbor Laboratory Press, New York, N.Y.).

Hart S L et al. Cell binding and internalization by filamentous phage displaying a cyclic Arg-Gly-Asp-containing peptide. J. Biol. Chem. 269, 12468-12474, 1994

Hemler, M., Weitzman, J., Pasqualini, R., Kawaguchi, S., Kassner, P. and Berdichevsky, F. Structure, biochemical properties, and biological functions of integrin cytoplasmic domains. In: Integrins: The Biological Problems (ed. Yoshi Takada) CRC Press, Inc., Boca Raton, Fla., USA.; pp. 1-35, 1994.

Hendrix R W. Evolution: the long evolutionary reach of viruses. Current Biol. 9:914-917, 1999.

HENRY, L., XIA, D., WILKE, M., DEISENHOFER, J., and GERARD, R. (1994). Characterization of the knob domain of the adenovirus type 5 fiber protein expressed in *E. coli.* J. Virol. 68; 5239-5246.

Herbst, H., E. Steinbrecher, G. Niedobitek, L. S. Young, L. Brooks, N. Muller-Lantzsch, and H. Stein. 1992. Distribution and phenotype of Epstein-Barr virus-harboring cells in Hodgkin's disease. Blood 80:484-91.

Herbst, H., F. Dallenbach, M. Hummel, G. Niedobitek, S. Pileri, N. Muller-Lantzsch, and H. Stein. 1991. Epstein-Barr virus latent membrane protein expression in Hodgkin and Reed-Sternberg cells. Proc Natl Acad Sci USA 88:4766-70.

Hermonat and Muzycska, *Proc. Natl. Acad. Sci. USA,* 81:6466-6470, 1984.

Herndier B G, Werner A, Arnstein P, Abbey N W, Demartis F, Cohen R L, Shuman M A and Levy, J A Characterization of a human Kaposi's sarcoma cell line that induces angiogenic tumors in animals. AIDS 8:575-581, 1996.

Hersdorffer et al., *DNA Cell Biol.,* 9:713-723, 1990.

Herz and Gerard, *Proc. Natl Acad. Sci. USA,* 90:2812-2816, 1993.

HEYWOOD, S. P., and HOOPER, N. M. (1995). Development and application of a fluorometric assay for mammalian membrane dipeptidase. Anal. Biochem. 226; 10-14.

HONG, S. S., GALAUP, A., PEYTAVI, R., CHAZAL, N., and BOULANGER, P. A. (1999). Enhancement of adenovirus-mediated gene delivery by use of an oligopeptide with dual binding specificity. Hum. Gene Ther. 10; 2577-2586.

HONG, S. S., KARYAN, L., TOURNIER, J., CURIEL, D. T., and BOULANGER, P. A. (1997). Adenovirus type 5 fiber knob binds to MHC class I alpha-2 domain at the surface of human epithelial and B lymphoblastoid cells. EMBO J. 16; 2294-2306.

Horwich, et al., *J. Virol.,* 64:642-650, 1990.

Hughes et al., *Cancer Res.* 49:4452-54, 1989

Hynes, R. O. Integrins: versatility, modulation and signaling in cell adhesion. *Cell* 69:11-25, 1992.

Ivanenkov, V., Felici, F. & Menon, A. G. Uptake and intracellular fate of phage display vectors in mammalian cells. Biochim Biophys Acta 1448, 450-462, 1999a.

Ivanenkov, V. V., Felici, F. & Menon, A. G. Targeted delivery of multivalent phage display vectors into mammalian cells. Biochim Biophys Acta 1448, 463-472, 1999b.

*J. Natl. Cancer Inst.* 90:273-286, 1998.

Jarrett, A. F., A. A. Armstrong, and E. Alexander. 1996. Epidemiology of EBV and Hodgkin's lymphoma. Ann Oncol 7:5-10.

Jarrett, R. F., and J. MacKenzie. 1999. Epstein-Barr virus and other candidate viruses in the pathogenesis of Hodgkin's disease. Semin Hematol 36:260-9.

Johnson et al., "Peptide Turn Mimetics" in *BIOTECHNOLOGY AND PHARMACY,* Pezzuto et al., Eds., Chapman and Hall, New York (1993).

Joliot, A. H. Triller, A., Volovitch, M. Pernelle, C., and Prochiantz, A. alpha-2,8-Polysialic acid is the neuronal surface receptor of antennapedia homeobox peptide. *New Biol.* 3:1121-1131, 1991a.

Joliot, A. H., Pernelle, C., Deagostini-Bazin, H. and Prochiantz, A. Antennapedia homeobox peptide regulates neural morphogenesis *Proc. Natl. Acad. Sci. U.S.A.* 88:1864-1868, 1991b.

Jones and Shenk, *Cell,* 13:181-188, 1978.

Kaplan, E. L. a. M., P. Nonparametric estimation from incomplete observations. *Journal of the American Statistical Association* 53, 457-481 (1958).

Karlsson et al., *EMBO J.,* 5:2377-2385, 1986.

Kasono, K. et al. Selective gene delivery to head and neck cancer cells via an integrin targeted adenoviral vector. Clin Cancer Res 5, 2571-2579, 1999.

Kassner, P. D., Burg, M. A., Baird, A. & Larocca, D. Genetic selection of phage engineered for receptor-mediated gene transfer to mammalian cells. Biochem Biophys Res Commun 264, 921-928, 1999.

Kiang et al., *Chin. J. Physiol.* 40:213-219, 1997

Klemke, R. L., Yebra, M., Bayna, E. M. and Cheresh, D. A. Receptor tyrosine kinase signaling required for integrin $\alpha v\beta 5$-directed cell motility but not adhesion on vitronectin. *J. Cell Biol.* 127:859-866, 1994.

Koivunen E, Arap W, Valtanen H, Rainisalo A, Gahmberg C G, Salo T, Konttinen Y T, Sorsa T, Ruoslahti E, Pasqualini R. Tumor targeting with a selective gelatinase inhibitor. Nature Biotechnol 17:768-774, 1999a Koivunen E, Gay D A and Ruoslahti E. Selection of peptides binding to the $\alpha 5$ $\beta 1$ integrin from phage display library. J. Biol. Chem. 268:20205-20210, 1993.

Koivunen E, Wang B, and Ruoslahti E. Phage display libraries displaying cyclic peptides with different ring sizes: ligand specificities of the RGD-directed integrins. BioTechnology 13:265-270, 1995.

Koivunen, E. et al. Integrin-binding peptides derived from phage display libraries. *Methods Mol Biol* 129, 3-17 (1999b).

Kolanus, W. and Seed, B. Integrins and inside-out signal transduction: converging signals from PKC and PIP3. *Curr. Opin. Cell Biol.* 9:725-731, 1997.

Kolonin M G. Finley R L Jr. Targeting cyclin-dependent kinases in Drosophila with peptide aptamers. Proc. of the Natl. Acad. of Sci. USA 95:14266-71, 1998.

Kong H L and Crystal R G. Gene therapy strategies for tumor antiangiogenesis.

Kouzmitcheva G. A. et al. Identifying diagnostic peptides for lyme disease through epitope discovery. *Clin Diagn Lab Immunol* 8, 150-60 (2001).

KOZARSKY, K., JOOSS, K., DUNAHEE, M., STRAUSS, J. F., and WILSON, J. M. (1996). Effective treatment of familial hypercholesterolaemia in the mouse model using adenovirus-mediated transfer of the VLDL receptor gene. Nat. Genet. 13; 54-62.

KRASNYKH, V., DMITRIEV, I., MIKHEEV, A. G., MILLER, C. R., BELOUSOVA, N., and CURIEL, D. T. (1998). Characterization of an adenovirus vector containing a heterologous peptide epitope in the HI loop of the fiber knob. J. Virol. 72; 1844-1852.

KRASNYKH, V., MIKHEEVA, G. V., DOUGLAS, J. T., and CURIEL, D. T. (1996). Generation of recombinant adenovirus vectors with modified fibers for altering viral tropism. J. Virol. 70; 6839-6846.

Lane T. Shah J. Clinical features and management of benign prostatic hyperplasia. Hospital Medicine. 60(10):705-9, 1999.

Larocca D et al. Gene transfer to mammalian cells using genetically targeted filamentous bacteriophage. FASEB J 1999; 13:727-734.

Larocca, D., Witte, A., Johnson, W., Pierce, G. F. & Baird, A. Targeting bacteriophage to mammalian cell surface receptors for gene delivery. Hum Gene Ther 9, 2393-2399, 1998.

Le Gal La Salle et al., *Science,* 259:988-990, 1993.

Le Roux, I., Joliot, A. H., Bloch-Gallego, E., Prochiantz, A. and Volovitch, M. Neurotrophic activity of the Antennapedia homeodomain depends on its specific DNA-binding properties. *Proc. Natl. Acad. Sci. U.S.A.* 90:9120-9124, 1993

Levrero et al., *Gene,* 101:195-202, 1991.

Lewis, J. M., Cheresh, D. A. and Schwartz, M. A. Protein kinase C regulates $\alpha v\beta 5$-dependent cytoskeletal associations and focal adhesion kinase phosphorylation. *J. Cell Biol.* 134: 1323-1332, 1996.

Lin, T. H., Aplin, A. E., Shen, Y., Chen Q., Schaller, M. D., Romer L., Aukhil, I. and Juliano, R. L. Integrin-mediated activation of MAP kinase is independent of FAK: evidence for dual integrin signalling pathways in fibroblast. *J. Cell Biol.* 136:1385-1395, 1997.

Longhurst, C. M. and Jennings, L. K. Integrin-mediated signal transduction. *Cell Mol. Life Sci.* 54:514-526, 1998.

Look A T, Ashmun R A, Shapiro L H and Peiper S C. Human myeloid plasma membrane glycoprotein CD13 (gp150) is identical to aminopeptidase N. J. Clin. Invest. 83:1299-1307, 1989.

LOUIS, N., FENDER, P., BARGE, A., KITS, P., and CHROBOCZEK, J. (1994). Cell-binding domain of adenovirus serotype 2 fiber. J. Virol. 68; 4104-4106.

Lunardi, C. et al. Systemic sclerosis immunoglobulin G autoantibodies bind the human cytomegalovirus late protein UL94 and induce apoptosis in human endothelial cells [In Process Citation]. *Nat Med* 6, 1183-1186 (2000).

Lynch, C. M. et al. Adeno-associated virus vectors for vascular gene delivery. Circ Res 80, 497-505, 1997.

Lyons, S. F., and D. N. Liebowitz. 1998. The roles of human viruses in the pathogenesis of lymphoma. Semin Oncol 25:461-75.

MacGregor, G. R. & Caskey, C. T. Construction of plasmids that express *E. coli* beta-galactosidase in mammalian cells. Nucleic Acids Res 17, 2365, 1989.

Mahboubi et al, *J. Immunol.* 164:3837-3846, 2000.

Mann et al., *Cell,* 33:153-159, 1983.

Markowitz et al., *J. Virol.,* 62:1120-1124, 1988.

Martin F et al. Retrovirus targeting by tropism restriction to melanoma cells. *J Virol* 1999; 73: 6923-6929.

Martiny-Baron G, and Marme D. VEGF-mediated tumor angiogenesis: a new target for cancer therapy. Curr. Opin. Biotechnol. 6:675-680, 1995.

Mennuni, C. et al. Selection of phage-displayed peptides mimicking type 1 diabetes-specific epitopes. *J Autoimmun* 9, 431-436 (1996).

Merrifield, *Science,* 232: 341-347, 1986

MICHAEL, S. I., HONG, J. S., CURIEL, D. T., and ENGLER, J. A. (1995). Addition of a short peptide ligand to the adenovirus fiber protein. Gene Ther. 2; 660-668.

Mikolajczyk S D. Millar L S. Wang T J. Rittenhouse H G. Marks L S. Song W. Wheeler T M. Slawin K M. A precursor form of prostate-specific antigen is more highly elevated in prostate cancer compared with benign transition zone prostate tissue. Cancer Research. 60(3):756-9, 2000.

Miller C R et al. Differential susceptibility of primary and established human glioma cells to adenovirus infection: targeting via the epidermal growth factor receptor achieves fiber receptor independent gene transfer. *Cancer Res* 1998; 58: 5738-5748.

Motti, C. et al. Recognition by human sera and immunogenicity of HBsAg mimotopes selected from an M13 phage display library. *Gene* 146, 191-198 (1994).

Mulligan, *Science,* 260:926-932, 1993.

Mustonen T and Alitalo K. Endothelial receptor tyrosine kinases involved in angiogenesis. J. Cell Biol. 129:895-898, 1995.

Muzyczka N. Adeno-associated virus (AAV) vectors: will they work? J. Clin. Invest. 94:1351, 1994

Nicolas and Rubinstein, In: *Vectors: A survey of molecular cloning vectors and their uses,* Rodriguez and Denhardt, eds., Stoneham: Butterworth, pp. 494-513, 1988.

Nicolau et al., *Methods Enzymol.,* 149:157-176, 1987.

Old, L. J. Cancer immunology: the search for specificity— G. H. A. Clowes Memorial lecture. *Cancer Res* 41, 361-375 (1981).

Olofsson, B. Jeltsch, M., Eriksson, U. and Alitalo, K. (1999) Current Biology of VEGF-B and VEGF-C. *Curr Op Biotechnol,* 10, 528-535.

Olofsson, B., Pajusola, K., Kaipainen, A., Euler, G., Joukov, V., Saksela, O., Orpana, A., Pettersson, R. F., Alitalo, K. and Eriksson, U. (1996) Vascular Endothelial Growth factor B, a novel growth factor for endothelial cells. *Proc Natl Acad Sci USA,* 93, 2576-2581.

Owens, G. P., R. A. Williamson, M. P. Burgoon, O. Ghausi, D. R. Burton, and D. H. Gilden. 2000. Cloning the antibody response in humans with chronic inflammatory disease: immunopanning of subacute sclerosing panencephalitis (SSPE) brain sections with antibody phage libraries prepared from SSPE brain enriches for antibody recognizing measles virus antigens in situ. J Virol 74:1533-7.

Pallesen, G., S. J. Hamilton-Dutoit, M. Rowe, and L. S. Young. 1991. Expression of Epstein-Barr virus latent gene products in tumour cells of Hodgkin's disease [see comments]. Lancet 337:320-2.

Paskind et al., *Virology,* 67:242-248, 1975.

Pasqualini R and Ruoslahti E. Organ targeting in vivo using phage display peptide libraries. Nature 380:364-366, 1996.

Pasqualini R, Koivunen E, and Ruoslahti E. A peptide isolated from phage display libraries is a structural and functional mimic of an RGD-binding site on integrins. J. Cell Biol. 130:1189-1196, 1995.

Pasqualini R, Koivunen E, and Ruoslahti E. αv integrins as receptors for tumor targeting by circulating ligands. Nature Biotechnol 15:542-546, 1997

Pasqualini, R. and Hemler, M. E. Contrasting roles for integrin b1 and b5 cytoplasmic domains in subcellular localization, cell proliferation, and cell migration. *J. Cell Biol.* 125:447-60, 1994.

Pasqualini, R. Vascular Targeting with Phage Display Peptide Libraries. The Quart. J. Nucl. Med. 43:159-162, 1999.

Pasqualini, R., Arap W., Koivunen, E., Kain, R., Lahdenranta, J., Shapiro, L., Sakamoto, M., Stryn, A. and Ruoslahti, E. Aminopeptidase N is a receptor for tumor-homing peptides and a target for inhibiting angiogenesis. Cancer Res. 60: 722-727, 2000.

Pelleymounter et al. Effects of the obese gene product on body weight regulation in ob/ob mice. Science 269: 540-543, 1994.

Pereboeva, L. A., A. V. Pereboev, and G. E. Morris. 1998. Identification of antigenic sites on three hepatitis C virus proteins using phage-displayed peptide libraries. J Med Virol 56:105-11.

Pereboeva, L. A., A. V. Pereboev, L. F. Wang, and G. E. Morris. 2000. Hepatitis C epitopes from phage-displayed cDNA libraries and improved diagnosis with a chimeric antigen. J Med Virol 60:144-51.

Potter et al., *Proc. Nat. Acad. Sci. USA,* 81:7161-7165, 1984.

Poul, M. A. & Marks, J. D. Targeted gene delivery to mammalian cells by filamentous bacteriophage. J Mol Biol 288, 203-211, 1999.

Prezzi, C. et al. Selection of antigenic and immunogenic mimics of hepatitis C virus using sera from patients. *J Immunol* 156, 4504-4513 (1996).

Prezzi, C., M. Nuzzo, A. Meola, P. Delmastro, G. Galfre, R. Cortese, A. Nicosia, and P. Monaci. 1996. Selection of antigenic and immunogenic mimics of hepatitis C virus using sera from patients. J Immunol 156:4504-13.

PRICE, J. E., POLYZOS, A., ZHANG, R. D., and DANIELS, L. M. (1990). Tumorigenicity and metastasis of human breast carcinoma cells lines in nude mice. Cancer Res. 50; 717-721.

Puntoriero, G. et al. Towards a solution for hepatitis C virus hypervariability: mimotopes of the hypervariable region 1 can induce antibodies cross-reacting with a large number of viral variants. *Embo J* 17, 3521-3533 (1998).

Racher et al., *Biotechnology Techniques,* 9:169-174, 1995.

Ragot et al., *Nature,* 361:647-650, 1993.

Rajotte D and Ruoslahti E. Membrane dipeptidase is the receptor for a lung-targeting peptide identified by in vivo phage display. J Biol Chem 274:11593-11598, 1999

Rajotte D, Arap W, Hagedorn M, Koivunen E, Pasqualini R, and Ruoslahti E. Molecular heterogeneity of the vascular endothelium revealed by in vivo phage display. J Clin Invest 102:430-437, 1998

Rak J W, St. Croix B D, and Kerbel R S. Consequences of angiogenesis for tumor progression, metastasis and cancer. Anticancer Drugs 6:3-18, 1995.

Razzaque, A., Y. Francillon, P. N. Jilly, and F. Varricchio. 1996. Detection of human herpesvirus 6 sequences in lymphoma tissues by immunohistochemistry and polymerase chain reactions. Cancer Lett 106:221-6.

Remington's Pharmaceutical Sciences, 15th ed., pp. 1035-1038 and 1570-1580.

Renan, *Radiother. Oncol.*, 19:197-218, 1990.

Renata Pasqualini, W. A., Daniel Rajotte, and Erkki Ruoslahti. in *Phage Display: A Laboratory manual* (ed. Carlos F. Barbas III, D. R. B., Jamie K. Scott, and Gregg J. Silverman) 22.21-22.24 (Cold Spring Harbor Laboratory Press, N.Y., 2001).

Rich et al., *Hum. Gene Ther.*, 4:461-476, 1993.

Ridgeway, *In: Vectors: A Survey of Molecular Cloning Vectors and Their Uses*, Rodriguez et al., eds., Stoneham: Butterworth, pp. 467-492, 1988.

Rippe et al., *Mol. Cell Biol.*, 10:689-695, 1990.

ROELVINK, P. W., LEE, G. M., EINFELD, D. A., KOVESDI, I., and WICKHAM, T. J. (1999). Identification of a conserved receptor-binding site on the fiber proteins of CAR-recognizing adenoviridae. Science 286; 1568-1571.

ROMANCZUK, H., GALER, C. E., ZABNER, J., BARSOMIAN, G., WADSWORTH, S. C., and O'RIORDAN, C. R. (1999). Modification of an adenoviral vector with biologically selected peptides: a novel strategy for gene delivery to cells of choice. Hum. Gene Ther. 10; 2615-2626.

Rosenfeld et al., *Cell*, 68:143-155, 1992.

Rosenfeld et al., *Science*, 252:431-434, 1991.

Rowley, M. J. et al. Prediction of the immunodominant epitope of the pyruvate dehydrogenase complex E2 in primary biliary cirrhosis using phage display. *J Immunol* 164, 3413-3419 (2000).

Ruoslahti E. RGD and other sequence recognition sequences for integrins. Annu. Rev. Cell Dev. Biol. 12:697-715, 1996

Sahin, U. et al. Human neoplasms elicit multiple specific immune responses in the autologous host. *Proc Natl Acad Sci USA* 92, 11810-11813 (1995).

Sahin, U., Tureci, O. & Pfreundschuh, M. Serological identification of human tumor antigens. *Curr Opin Immunol* 9,709-716 (1997).

Scala, G. et al. Selection of HIV-specific immunogenic epitopes by screening random peptide libraries with HIV-1-positive sera. *J Immunol* 162, 6155-6161 (1999).

Schlingemann R O, Rietveld F J, de Waal R M, Ferrone S, Ruiter D J. Expression of the high molecular weight melanoma-associated antigen by pericytes during angiogenesis in tumors and in healing wounds. Am. J. Pathol. 136:1393-1405, 1990.

Schmitz, R., Baumann, G. and Gram, H. Catalytic specificity of phosphotyrosine kinase Blk, Lyn, c-Src and Syk as assessed by phage display *J. Mol. Biol.* 260: 664-677, 1996.

Shattil, S. J. and Ginsberg, M. H. Perspectives series: cell adhesion in vascular biology. Integrin signaling in vascular biology. *J. Clin. Invest.* 100:1-5, 1997.

Short S M, Talbott G A and Juliano R L. Integrin-mediated Signaling Events in Human Endothelial Cells. Mol. Biol. Cell 9: 1969-1980, 1998

Silverstein, *JCI* 74:1625-1633, 1984

Smith G. P. Surface presentation of protein epitopes using bacteriophage expression system. *Curr Opin Biotechnol* 2, 668-73 (1991).

Smith G P, and Scott J K. Libraries of peptides and proteins displayed in filamentous phage. Meth. Enzymol. 21:228-257, 1993.

Smith G P, and Scott J K. Searching for peptide ligands with an epitope library. Science 228:1315-1317, 1985

Smith, D. B., and K. S. Johnson. 1988. Single-step purification of polypeptides expressed in *Escherichia coli* as fusions with glutathione S-transferase. Gene 67:31-40.

Smith, G. P. 1985. Filamentous fusion phage: novel expression vectors that display cloned antigens on the virion surface. Science 228:1315-7.

Smith, G. P. Surface presentation of protein epitopes using bacteriophage expression systems. *Curr. Opin. Biotechnol.* 2:668-673, 1991.

Solowska J, Edelman J M, Albelda S M and Buck C A. (1991) Cytoplasmic and transmembrane domains of integrin $\beta 1$ and $\beta 3$ subunits are functionally interchangeable. J. Cell Biol. 114: 1079-1088.

Staratschek-Jox, A., S. Kotkowski, G. Belge, T. Rudiger, J. Bullerdiek, V. Diehl, and J. Wolf. 2000. Detection of Epstein-Barr virus in Hodgkin-Reed-Sternberg cells: no evidence for the persistence of integrated viral fragments inLatent membrane protein-1 (LMP-1)-negative classical Hodgkin's disease. Am J Pathol 156:209-16.

Sternberg, N. & Hoess, R. H. Display of peptides and proteins on the surface of bacteriophage lambda. Proc Natl Acad Sci USA 92, 1609-1613, 1995.

Stewart and Young, *Solid Phase Peptide Synthesis*, 2d. ed., Pierce Chemical Co., 1984.

Stoeckle et al., *Mol. Cell Biol.* 8:2675-80, 1988.

Stratford-Perricaudet and Perricaudet, *In: Human Gene Transfer*, O. Cohen-Haguenauer et al., eds., John Libbey Eurotext, France, pp. 51-61, 1991.

Stratford-Perricaudet et al., *Hum. Gene. Ther.*, 1:241-256, 1990.

Tam et al., *J. Am. Chem. Soc.*, 105:6442, 1983.

Tanaka T, Cao Y, Folkman J and Fine H A. Viral vector-targeted antiangiogenic gene therapy utilizing an angiostatin complementary DNA. Cancer Res. 58:3362-3369, 1998.

Temin, *In: Gene Transfer*, Kucherlapati R, ed., New York, Plenum Press, pp. 149-188, 1986.

Theodore, L., Derossi, D., Chassaing, G., Llirbat, B., Kubes, M., Jordan, P., Chneiweiss, H., Godement, P., and Prochiantz, A. Intraneuronal delivery of protein kinase C pseudosubstrate leads to growth cone collapse. *J. Neurosci.* 15:7158-7167, 1995.

Tischer, E., Mitchell, R., Hartman, T., Silvia, M., Gospodarowicz, D., Fiddes, J. C. and Abraham, J. (1991) the human Gene for Vascular Endothelial Growth Factor. *J. Biol. Chem.*, 226, 11947-11954.

Top et al., *J. Infect. Dis.*, 124:155-160, 1971.

Triantafilou et al., *Hum. Immunol.* 62:764-770, 2001.

Tureci, O., Sahin, U. & Pfreundschuh, M. Serological analysis of human tumor antigens: molecular definition and implications. *Mol Med Today* 3, 342-349 (1997).

Tur-Kaspa et al., *Mol. Cell Biol.*, 6:716-718, 1986.

U.S. Pat. No. 3,817,837
U.S. Pat. No. 3,850,752
U.S. Pat. No. 3,939,350
U.S. Pat. No. 3,996,345
U.S. Pat. No. 4,275,149
U.S. Pat. No. 4,277,437
U.S. Pat. No. 4,366,241
U.S. Pat. No. 4,472,509

U.S. Pat. No. 5,021,236
U.S. Pat. No. 5,206,347
U.S. Pat. No. 5,223,409
U.S. Pat. No. 5,401,511
U.S. Pat. No. 5,536,814
U.S. Pat. No. 5,622,699
U.S. Pat. No. 5,889,155
U.S. Pat. No. 6,068,829

Varmus et al., *Cell*, 25:23-36, 1981.

Veikkola, T. and Alitalo, K. (1999) VEGFs, receptors and angiogenesis. *Seminar Cancer Bio.l*, 9, 211-220.

VIGNE, E., MAHFOUZ, I., DEDIEU, J. F., BRIE, A., PERRICAUDET, M., and YEH, P. (1999). RGD inclusion in the hexon monomer provides adenovirus type 5-based vectors with a fiber knob-independent pathway for infection. J. Virol. 73; 5156-5161.

Vu, T. H. et al. MMP-9/gelatinase B is a key regulator of growth plate angiogenesis and apoptosis of hypertrophic chondrocytes. Cell 93, 411-422, 1998.

Vuori K. Ruoslahti E. Association of insulin receptor substrate-1 with integrins. *Science* 266:1576-1578, 1994

WATKINS, S. J., MESYANZHINOV, V. V., KUROCHKINA, L. P., and HAWKINS, R. E. (1997). The adenobody approach to viral targeting—specific and enhanced adenoviral gene delivery. Gene Ther. 4; 1004-1012.

Watson C A, Camera-Benson L, Palmer-Croker R and Pober J S. Variability among human umbilical vein endothelial cell cultures. Science 268: 447-448, 1995.

Weiss, L. M., J. G. Strickler, R. A. Warnke, D. T. Purtilo, and J. Sklar. 1987. Epstein-Barr viral DNA in tissues of Hodgkin's disease. Am J Pathol 129:86-91

Weiss, L. M., Y. Y. Chen, X. F. Liu, and D. Shibata. 1991. Epstein-Barr virus and Hodgkin's disease. A correlative in situ hybridization and polymerase chain reaction study. Am J Pathol 139:1259-65.

Weitzman M D, Wilson J M and Eck S L. Adenovirus vectors in cancer gene therapy. In: Gene Therapy and Vector Systems 2: 17-25, 1997.

Wells, J. A. and Lowman, H. B. Rapid evolution of peptide and protein binding properties in vitro. *Curr. Opin. Biotechnol.* 3:355-362, 1992.

Wickham T J. Haskard D. Segal D. Kovesdi I. Targeting endothelium for gene therapy via receptors up-regulated during angiogenesis and inflammation. Cancer Immunol. Immunother. 45:149-151, 1997c.

Wickham, T. J. Targeting adenovirus. Gene Ther 7, 110-114, 2000.

WICKHAM, T. J., CARRION, M. E., and KOVESDI, I. (1995). Targeting of adenovirus penton base to new receptors through replacement of its RGD motif with other receptor-specific peptide motifs. Gene Ther. 2; 750-756.

WICKHAM, T. J., LEE, G., TITUS, J., SCONOCCHIA, G., BAKACS, T., KOVESDI, I., and SEGAL, D. (1997a). Targeted adenovirus-mediated gene delivery to T-cells via CD3. J. Virol. 71; 7663-7669.

WICKHAM, T. J., MATHIAS, P., CHERESH, D. A., and NEMEROW, G. R. (1993). Integrins alpha v beta 3 and alpha v beta 5 promote adenovirus internalization but not attachment. Cell 73; 309-319.

WICKHAM, T. J., ROELVINK, P. W., BROUGH, D. E., and KOVESDI, I. (1996b). Adenovirus targeted to heparan-containing receptors increases its gene delivery efficiency to multiple cell types. Nature Biotechnol. 14; 1570-1573.

WICKHAM, T. J., SEGAL, D. M., ROELVINK, P. W., CARRION, M. E., LIZONOVA, A., LEE, G. M., and KOVESDI, I. (1996a). Targeted adenovirus gene transfer to endothelial and smooth muscle cells by using bispecific antibodies. J. Virol. 70; 6831-6838.

WICKHAM, T. J., TZENG, E., SHEARS II, L. L., ROELVINK, P. E., Li, Y., LEE, G. M., BROUGH,. D. E., LIZONOVA, A., and KOVESDI, I. (1997b). Increased in vitro and in vivo gene transfer by adenovirus vectors containing chimeric fiber proteins. J. Virol. 71; 8221-8229.

Wong et al., *Gene,* 10:87-94, 1980.

Wu and Wu, *Biochemistry,* 27: 887-892, 1988.

Wu and Wu, *J. Biol. Chem.,* 262: 4429-4432, 1987.

Zetter B R. Angiogenesis and tumor metastasis. Ann Rev Med 49:407-424, 1998

Zhang et al., J. Nature 372: 425, 1994.

Zhang J and Russell S. Vectors for cancer gene therapy. Cancer Met. Rev. 3:385-401, 1996.

ZHANG, W. (1999). Development and application of adenoviral vectors for gene therapy of cancer. Cancer Gene Ther. 6; 113-138.

Zini, S., Fournie-Zaluski, M. C., Chauvel, E., Roques, B., Corvol, P. and Cortes-Llorens, C. (1996) Identification of metabolic pathways of brain angiotensin II and III using specific aminopeptidase inhibitors: predominant role of angiotensin III in the control of vasopressin release. *Proc Natl Acad Sci USA,* 93, 11968-11973.

What is claimed is:

1. An isolated peptide of 100 amino acids or less in size, comprising at least the contiguous amino acids of SEQ ID NO:19, wherein the isolated peptide is a fat-targeting peptide.

2. The isolated peptide of claim 1, wherein said peptide is 50 amino acids or less in size.

3. The isolated peptide of claim 1, wherein said peptide is 25 amino acids or less in size.

4. The isolated peptide of claim 1, wherein said peptide is 10 amino acids or less in size.

5. The isolated peptide of claim 1, wherein said peptide is 7 amino acids in size.

6. The isolated peptide of claim 1, wherein said peptide comprises at least the contiguous amino acids of SEQ ID NO:22.

7. A target molecule comprising the isolated peptide of any one of claims 1, 5, or 6.

8. The target molecule of claim 7, wherein said molecule is a drug, a chemotherapeutic agent, a radioisotope, a pro-apoptosis agent, an anti-angiogenic agent, a hormone, a cytokine, a growth factor, a cytotoxic agent, a peptide, a protein, an antibiotic, an antibody, a Fab fragment of an antibody, an imaging agent, survival factor, an anti-apoptotic agent, a hormone antagonist or an antigen.

9. The target molecule of claim 8, wherein said pro-aptoptosis agent is selected from the group consisting of gramicidin, magainin, mellitin, defensin, cecropin, (KLAKLAK)$_2$ (SEQ ID NO:1), (KLAKKLA)$_2$ (SEQ ID NO:2), (KAAKKAA)$_2$ (SEQ ID NO:3) and (KLGKKLG)$_3$ (SEQ ID NO:4).

10. The target molecule of claim 8, wherein said anti-angiogenic agent is selected from the group consisting of thrombospondin, angiostatin5, pigment epithelium-derived factor, angiotensin, laminin peptides, fibronectin peptides, plasminogen activator inhibitors, tissue metalloproteinase inhibitors, interferons, interleukin 12, platelet factor 4, IP-10, Gro-β, thrombospondin, 2-methoxyoestradiol, proliferin-related protein, carboxiamidotriazole, CM101, Marimastat, pentosan polysulphate, angiopoietin 2 (Regeneron), interferon-alpha, herbimycin A, PNU 145156E, 16K prolactin fragment, Linomide, thalidomide, pentoxifylline, genistein, TNP-470, endostatin, paclitaxel, Docetaxel, polyamines, a proteasome inhibitor, a kinase inhibitor, a signaling peptide, accutin, cidofovir, vincristine, bleomycin, AGM-1470, platelet factor 4 and minocycline.

11. The target molecule of claim 8, wherein said cytokine is selected from the group consisting of interleukin 1 (IL-1), IL-2, IL-5, IL-10, IL-11, IL-12, IL-18, interferon-γ, (IF-γ), IF-α, IF-β, tumor necrosis factor-α (TNF-α), or GM-CSF (granulocyte macrophage colony stimulating factor).

12. A macromolecular complex comprising the isolated peptide of any one of claims 1-5 or 6.

13. The micromolecular complex of claim 12, wherein said complex is a virus, bacteriophage, a bacterium, a liposome, a microparticle or a magnetic bead.

14. The macromolecular complex of claim 12, wherein said peptide is attached to a eukaryotic expression vector.

15. The macromolecular complex of claim 14, wherein said vector is a gene therapy vector.

16. The macromolecular complex of claim 14, wherein said peptide is attached toa solid support.

* * * * *

UNITED STATES PATENT AND TRADEMARK OFFICE
CERTIFICATE OF CORRECTION

PATENT NO. : 7,452,964 B2  Page 1 of 1
APPLICATION NO. : 10/489071
DATED : November 18, 2008
INVENTOR(S) : Renata Pasqualini et al.

It is certified that error appears in the above-identified patent and that said Letters Patent is hereby corrected as shown below:

In claim 7, column 135, line 29, delete "1, 5" and insert -- 1-5 -- therefor.

In claim 13, column 136, line 33, delete "micromolecular" and insert --macromolecular-- therefor.

In claim 16, column 136, line 40, delete "14" and insert --12-- therefor.

In claim 16, column 136, line 41, delete "toa" and insert --to a-- therefor.

Signed and Sealed this

Tenth Day of February, 2009

JOHN DOLL
*Acting Director of the United States Patent and Trademark Office*

SEQUENCE LISTING

```
<160> NUMBER OF SEQ ID NOS: 144

<210> SEQ ID NO 1
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 1

Lys Leu Ala Lys Leu Ala Lys Lys Leu Ala Lys Leu Ala Lys
1               5                   10

<210> SEQ ID NO 2
<211> LENGTH: 14
<212> TYPE: PRT
<213> ORGANISM: Artificial Sequence
```

```
<220> FEATURE:
<223> OTHER INFORMATION: Synthetic Peptide

<400> SEQUENCE: 2

Lys Leu Ala Lys Lys Leu Ala Lys Leu Ala Lys Lys Leu Ala
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic Peptide

<400> SEQUENCE: 3

Lys Ala Ala Lys Lys Ala Ala Lys Ala Ala Lys Lys Ala Ala
1               5                   10

<210> SEQ ID NO 4
<211> LENGTH: 21
<212> TYPE: PRT
<213> ORGANISM: Artificial Sequence
<220> FEATURE:
<223> OTHER INFORMATION: Synthetic Peptide

<400> SEQUENCE: 4

Lys Leu Gly Lys Lys Leu Gly Lys Leu Gly Lys Lys Leu Gly Lys Leu
1               5                   10                  15

Gly Lys Lys Leu Gly
            20

<210> SEQ ID NO 5
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 5

Thr Pro Lys Thr Ser Val Thr
1               5

<210> SEQ ID NO 6
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 6

Arg Met Asp Gly Pro Val Arg
1               5

<210> SEQ ID NO 7
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 7

Arg Ala Pro Gly Gly Val Arg
1               5

<210> SEQ ID NO 8
<211> LENGTH: 7
```

```
<212> TYPE: PRT
<213> ORGANISM: Artificial Sequence
<220> FEATURE:
<223> OTHER INFORMATION: Synthetic Peptide

<400> SEQUENCE: 8

Val Gly Leu His Ala Arg Ala
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 9

Tyr Ile Arg Pro Phe Thr Leu
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 10

Leu Gly Leu Arg Ser Val Gly
1               5

<210> SEQ ID NO 11
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 11

Pro Ser Glu Arg Ser Pro Ser
1               5

<210> SEQ ID NO 12
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 12

Cys Ala Arg Ala Cys
1               5

<210> SEQ ID NO 13
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 13

Thr Arg Glu Val His Arg Ser
1               5

<210> SEQ ID NO 14
<211> LENGTH: 7
<212> TYPE: PRT
```

```
<213> ORGANISM: Artificial Sequence
<220> FEATURE:
<223> OTHER INFORMATION: Synthetic Peptide

<400> SEQUENCE: 14

Thr Arg Asn Thr Gly Asn Ile
1               5

<210> SEQ ID NO 15
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 15

Phe Asp Gly Gln Asp Arg Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 16

Trp Gly Pro Lys Arg Leu
1               5

<210> SEQ ID NO 17
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 17

Trp Gly Glu Ser Arg Leu
1               5

<210> SEQ ID NO 18
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 18

Val Met Gly Ser Val Thr Gly
1               5

<210> SEQ ID NO 19
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 19

Lys Gly Gly Arg Ala Lys Asp
1               5

<210> SEQ ID NO 20
<211> LENGTH: 7
<212> TYPE: PRT
<213> ORGANISM: Artificial Sequence
```

```
<220> FEATURE:
<223> OTHER INFORMATION: Synthetic Peptide

<400> SEQUENCE: 20

Arg Gly Glu Val Leu Trp Ser
1               5

<210> SEQ ID NO 21
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 21

His Gly Gln Gly Val Arg Pro
1               5

<210> SEQ ID NO 22
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 22

Cys Lys Gly Gly Arg Ala Lys Asp Cys
1               5

<210> SEQ ID NO 23
<211> LENGTH: 95
<212> TYPE: PRT
<213> ORGANISM: Mus musculus

<400> SEQUENCE: 23

Cys Gln Pro Ala Met Ala Ala Val Thr Leu Asp Glu Ser Gly Gly Gly
1               5                   10                  15

Leu Gln Thr Pro Gly Gly Ala Leu Ser Leu Val Cys Lys Ala Ser Gly
            20                  25                  30

Phe Thr Phe Asn Ser Tyr Pro Met Gly Trp Val Arg Gln Ala Pro Gly
        35                  40                  45

Lys Gly Leu Glu Trp Val Ala Val Ile Ser Ser Gly Thr Thr Trp
    50                  55                  60

Tyr Ala Pro Ala Val Lys Gly Arg Ala Thr Ile Ser Arg Asp Asn Gly
65                  70                  75                  80

Gln Ser Thr Val Arg Leu Gln Leu Ser Asn Leu Arg Ala Glu Asp
                85                  90                  95

<210> SEQ ID NO 24
<211> LENGTH: 92
<212> TYPE: PRT
<213> ORGANISM: Mus musculus

<400> SEQUENCE: 24

Cys Gln Pro Ala Met Ala Ala Val Thr Leu Asp Glu Ser Gly Gly Gly
1               5                   10                  15

Leu Gln Thr Pro Gly Gly Thr Leu Ser Leu Val Cys Lys Ala Ser Gly
            20                  25                  30

Ile Ser Ile Gly Tyr Gly Met Asn Trp Val Arg Gln Ala Pro Gly Lys
        35                  40                  45

Gly Leu Glu Tyr Val Ala Ser Ile Ser Gly Asp Gly Asn Phe Ala His
    50                  55                  60
```

```
Tyr Gly Ala Pro Val Lys Gly Arg Ala Thr Ile Ser Arg Asp Asp Gly
 65                  70                  75                  80

Gln Asn Thr Val Thr Leu Gln Leu Asn Asn Leu Arg
                 85                  90

<210> SEQ ID NO 25
<211> LENGTH: 95
<212> TYPE: PRT
<213> ORGANISM: Mus musculus

<400> SEQUENCE: 25

Cys Gln Pro Ala Met Ala Ala Val Thr Leu Asp Glu Ser Gly Gly Gly
  1               5                  10                  15

Leu Gln Thr Pro Gly Gly Thr Leu Ser Leu Val Cys Lys Gly Ser Gly
                 20                  25                  30

Phe Ile Phe Ser Arg Tyr Asp Met Ala Trp Val Arg Gln Ala Pro Gly
             35                  40                  45

Lys Gly Leu Glu Trp Val Ala Gly Ile Asp Asp Gly Gly Gly Tyr Thr
 50                  55                  60

Thr Leu Tyr Ala Pro Ala Val Lys Gly Arg Ala Thr Ile Thr Ser Arg
 65                  70                  75                  80

Asp Asn Gly Gln Ser Thr Val Arg Leu Gln Leu Asn Asn Leu Arg
                 85                  90                  95

<210> SEQ ID NO 26
<211> LENGTH: 96
<212> TYPE: PRT
<213> ORGANISM: Mus musculus

<400> SEQUENCE: 26

Ala Asn Gln Pro Trp Pro Pro Leu Thr Leu Asp Glu Ser Gly Gly Gly
  1               5                  10                  15

Leu Gln Thr Pro Gly Gly Ala Leu Ser Leu Val Cys Lys Ala Ser Gly
                 20                  25                  30

Phe Thr Met Ser Ser Tyr Asp Met Phe Trp Val Arg Gln Ala Pro Gly
             35                  40                  45

Lys Gly Leu Glu Phe Val Ala Gly Ile Ser Ser Gly Ser Ser Thr
 50                  55                  60

Glu Tyr Gly Ala Ala Val Lys Gly Arg Ala Thr Ile Ser Arg Asp Asn
 65                  70                  75                  80

Gly Gln Ser Thr Val Arg Leu Gln Leu Asn Asn Leu Arg Ala Glu Asp
                 85                  90                  95

<210> SEQ ID NO 27
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 27

Cys Glu Gln Arg Gln Thr Gln Glu Gly Cys
  1               5                  10

<210> SEQ ID NO 28
<211> LENGTH: 10
<212> TYPE: PRT
<213> ORGANISM: Artificial Sequence
<220> FEATURE:
<223> OTHER INFORMATION: Synthetic Peptide
```

```
<400> SEQUENCE: 28

Cys Ala Arg Leu Glu Val Leu Leu Pro Cys
1               5                   10

<210> SEQ ID NO 29
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 29

Tyr Asp Trp Trp Tyr Pro Trp Ser Trp
1               5

<210> SEQ ID NO 30
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 30

Gly Leu Asp Thr Tyr Arg Gly Ser Pro
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 31

Ser Asp Asn Arg Tyr Ile Gly Ser Trp
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 32

Tyr Glu Trp Trp Tyr Trp Ser Trp Ala
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 33

Lys Val Ser Trp Tyr Leu Asp Asn Gly
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 34

Ser Asp Trp Tyr Tyr Pro Trp Ser Trp
1               5

<210> SEQ ID NO 35
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 35

Ala Gly Trp Leu Tyr Met Ser Trp Lys
1               5

<210> SEQ ID NO 36
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 36

Cys Phe Gln Asn Arg Cys
1               5

<210> SEQ ID NO 37
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 37

Cys Asn Leu Ser Ser Glu Gln Cys
1               5

<210> SEQ ID NO 38
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 38

Cys Leu Arg Gln Ser Tyr Ser Tyr Asn Cys
1               5                   10

<210> SEQ ID NO 39
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 39

Cys Tyr Ile Trp Pro Asp Ser Gly Leu Cys
1               5                   10

<210> SEQ ID NO 40
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 40
```

```
Cys Glu Pro Tyr Trp Asp Gly Trp Phe Cys
1               5                   10

<210> SEQ ID NO 41
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 41

Cys Lys Glu Asp Gly Trp Leu Met Thr Cys
1               5                   10

<210> SEQ ID NO 42
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 42

Cys Lys Leu Trp Gln Glu Asp Gly Tyr
1               5

<210> SEQ ID NO 43
<211> LENGTH: 10
<212> TYPE: PRT
<213> ORGANISM: Artificial Sequence
<220> FEATURE:
<223> OTHER INFORMATION: Synthetic Peptide

<400> SEQUENCE: 43

Cys Trp Asp Gln Asn Tyr Leu Asp Asp Cys
1               5                   10

<210> SEQ ID NO 44
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 44

Asp Glu Glu Gly Tyr Tyr Met Met Arg
1               5

<210> SEQ ID NO 45
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 45

Lys Gln Phe Ser Tyr Arg Tyr Leu Leu
1               5

<210> SEQ ID NO 46
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 46
```

```
Val Val Ile Ser Tyr Ser Met Pro Asp
1               5
```

\<210\> SEQ ID NO 47
\<211\> LENGTH: 9
\<212\> TYPE: PRT
\<213\> ORGANISM: Artificial Sequence
\<220\> FEATURE:
\<223\> OTHER INFORMATION: Synthetic Peptide

\<400\> SEQUENCE: 47

```
Ser Asp Trp Tyr Tyr Pro Trp Ser Trp
1               5
```

\<210\> SEQ ID NO 48
\<211\> LENGTH: 9
\<212\> TYPE: PRT
\<213\> ORGANISM: Artificial Sequence
\<220\> FEATURE:
\<223\> OTHER INFORMATION: Synthetic Peptide

\<400\> SEQUENCE: 48

```
Cys Pro Pro Leu Gly Gly Ser Arg Cys
1               5
```

\<210\> SEQ ID NO 49
\<211\> LENGTH: 9
\<212\> TYPE: PRT
\<213\> ORGANISM: Artificial Sequence
\<220\> FEATURE:
\<223\> OTHER INFORMATION: Synthetic Peptide

\<400\> SEQUENCE: 49

```
Gly Gly Gly Ser Tyr Arg His Val Glu
1               5
```

\<210\> SEQ ID NO 50
\<211\> LENGTH: 9
\<212\> TYPE: PRT
\<213\> ORGANISM: Artificial Sequence
\<220\> FEATURE:
\<223\> OTHER INFORMATION: Synthetic Peptide

\<400\> SEQUENCE: 50

```
Arg Ala Ile Leu Tyr Arg Leu Ala Asn
1               5
```

\<210\> SEQ ID NO 51
\<211\> LENGTH: 9
\<212\> TYPE: PRT
\<213\> ORGANISM: Artificial Sequence
\<220\> FEATURE:
\<223\> OTHER INFORMATION: Synthetic Peptide

\<400\> SEQUENCE: 51

```
Met Leu Leu Gly Tyr Arg Phe Glu Lys
1               5
```

\<210\> SEQ ID NO 52
\<211\> LENGTH: 9
\<212\> TYPE: PRT
\<213\> ORGANISM: Artificial Sequence
\<220\> FEATURE:
\<223\> OTHER INFORMATION: Synthetic Peptide

\<400\> SEQUENCE: 52

```
Thr Met Leu Arg Tyr Thr Val Arg Leu
```

-continued

```
<210> SEQ ID NO 53
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 53

Thr Met Leu Arg Tyr Phe Met Phe Pro
1               5

<210> SEQ ID NO 54
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 54

Thr Leu Arg Lys Tyr Phe His Ser Ser
1               5

<210> SEQ ID NO 55
<211> LENGTH: 16
<212> TYPE: PRT
<213> ORGANISM: Artificial Sequence
<220> FEATURE:
<223> OTHER INFORMATION: Synthetic Peptide

<400> SEQUENCE: 55

Arg Gln Ile Lys Ile Trp Phe Gln Asn Arg Arg Met Lys Trp Lys Lys
1               5                   10                  15

<210> SEQ ID NO 56
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 56

Cys Pro Arg Glu Cys Glu Ser Ile Cys
1               5

<210> SEQ ID NO 57
<211> LENGTH: 11
<212> TYPE: PRT
<213> ORGANISM: Artificial Sequence
<220> FEATURE:
<223> OTHER INFORMATION: Synthetic Peptide

<400> SEQUENCE: 57

Gly Ala Cys Val Arg Leu Ser Ala Cys Gly Ala
1               5                   10

<210> SEQ ID NO 58
<211> LENGTH: 31
<212> TYPE: PRT
<213> ORGANISM: Artificial Sequence
<220> FEATURE:
<223> OTHER INFORMATION: Synthetic Peptide

<400> SEQUENCE: 58

Cys Tyr Asn Leu Cys Ile Arg Glu Cys Glu Ser Ile Cys Gly Ala Asp
1               5                   10                  15
```

```
Gly Ala Cys Trp Thr Trp Cys Ala Asp Gly Cys Ser Arg Ser Cys
            20                  25                  30

<210> SEQ ID NO 59
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 59

Cys Leu Gly Gln Cys Ala Ser Ile Cys Val Asn Asp Cys
1               5                   10

<210> SEQ ID NO 60
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 60

Cys Pro Lys Val Cys Pro Arg Glu Cys Glu Ser Asn Cys
1               5                   10

<210> SEQ ID NO 61
<211> LENGTH: 12
<212> TYPE: PRT
<213> ORGANISM: Artificial Sequence
<220> FEATURE:
<223> OTHER INFORMATION: Synthetic Peptide

<400> SEQUENCE: 61

Cys Gly Thr Gly Cys Ala Val Glu Cys Val Val Cys
1               5                   10

<210> SEQ ID NO 62
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 62

Cys Ala Val Ala Cys Trp Ala Asp Cys Gln Leu Gly Cys
1               5                   10

<210> SEQ ID NO 63
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 63

Cys Ser Gly Leu Cys Thr Val Gln Cys Leu Glu Gly Cys
1               5                   10

<210> SEQ ID NO 64
<211> LENGTH: 13
<212> TYPE: PRT
<213> ORGANISM: Artificial Sequence
<220> FEATURE:
<223> OTHER INFORMATION: Synthetic Peptide

<400> SEQUENCE: 64
```

```
Cys Ser Met Met Cys Leu Glu Gly Cys Asp Asp Trp Cys
1               5                   10
```

<210> SEQ ID NO 65
<211> LENGTH: 43
<212> TYPE: DNA
<213> ORGANISM: Artificial Sequence
<220> FEATURE:
<223> OTHER INFORMATION: Synthetic Oligonucleotide

<400> SEQUENCE: 65
taatacgact cactataggg caagctgata aaccgataca att                43

<210> SEQ ID NO 66
<211> LENGTH: 24
<212> TYPE: DNA
<213> ORGANISM: Artificial Sequence
<220> FEATURE:
<223> OTHER INFORMATION: Synthetic Oligonucleotide

<400> SEQUENCE: 66
ccctcatagt tagcgtaacg atct                                     24

<210> SEQ ID NO 67
<211> LENGTH: 22
<212> TYPE: DNA
<213> ORGANISM: Artificial Sequence
<220> FEATURE:
<223> OTHER INFORMATION: Synthetic Oligonucleotide

<400> SEQUENCE: 67
cctttctatt ctcactcggc cg                                       22

<210> SEQ ID NO 68
<211> LENGTH: 44
<212> TYPE: DNA
<213> ORGANISM: Artificial Sequence
<220> FEATURE:
<223> OTHER INFORMATION: Synthetic Oligonucleotide

<400> SEQUENCE: 68
caggaaacag ctatgaccgc taaacaactt tcaacagttt cggc               44

<210> SEQ ID NO 69
<211> LENGTH: 17
<212> TYPE: DNA
<213> ORGANISM: Artificial Sequence
<220> FEATURE:
<223> OTHER INFORMATION: Synthetic Oligonucleotide

<400> SEQUENCE: 69
cactcggccg acggggc                                             17

<210> SEQ ID NO 70
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 70
cagtttcggc cccagcggcc c                                        21

<210> SEQ ID NO 71
<211> LENGTH: 9
<212> TYPE: PRT

```
<213> ORGANISM: Artificial Sequence
<220> FEATURE:
<223> OTHER INFORMATION: Synthetic Peptide

<400> SEQUENCE: 71

Cys Val Pro Gly Leu Gly Gly Leu Cys
1               5

<210> SEQ ID NO 72
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 72

Cys Gly Gly Leu Asp Val Arg Met Cys
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 73

Cys Asp Gly Gly Leu Asp Trp Val Cys
1               5

<210> SEQ ID NO 74
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 74

Cys Thr Trp Leu Gly Gly Arg Glu Cys
1               5

<210> SEQ ID NO 75
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 75

Cys Ser Arg Trp Gly Leu Gly Gly Cys
1               5

<210> SEQ ID NO 76
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 76

Cys Val Gly Gly Val Arg Gly Gly Cys
1               5

<210> SEQ ID NO 77
<211> LENGTH: 9
<212> TYPE: PRT
<213> ORGANISM: Artificial Sequence
```

```
<220> FEATURE:
<223> OTHER INFORMATION: Synthetic Peptide

<400> SEQUENCE: 77

Cys Val Gly Asn Asp Val Arg Gly Cys
1               5

<210> SEQ ID NO 78
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 78

Cys Glu Ser Arg Leu Val Arg Gly Cys
1               5

<210> SEQ ID NO 79
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 79

Cys Gly Gly Arg Pro Val Arg Gly Cys
1               5

<210> SEQ ID NO 80
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 80

Cys Thr Pro Phe Ile Ala Gly Gly Cys
1               5

<210> SEQ ID NO 81
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 81

Cys Arg Glu Trp Met Ala Gly Gly Cys
1               5

<210> SEQ ID NO 82
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 82

Cys Ala Gly Gly Ser Leu Arg Val Cys
1               5

<210> SEQ ID NO 83
<211> LENGTH: 9
<212> TYPE: PRT
<213> ORGANISM: Artificial Sequence
<220> FEATURE:
```

```
<223> OTHER INFORMATION: Synthetic Peptide

<400> SEQUENCE: 83

Cys Glu Gly Val Val Gly Ile Val Cys
1               5

<210> SEQ ID NO 84
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 84

Cys Asp Ser Val Val Gly Ala Trp Cys
1               5

<210> SEQ ID NO 85
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 85

Cys Arg Thr Ala Val Val Gly Ser Cys
1               5

<210> SEQ ID NO 86
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 86

Cys Val Gly Gly Ala Arg Ala Leu Cys
1               5

<210> SEQ ID NO 87
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 87

Cys Thr Arg Glu Val His Arg Ser Cys
1               5

<210> SEQ ID NO 88
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 88

Cys Leu Ala His Arg Val Gly Gly Cys
1               5

<210> SEQ ID NO 89
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 89

Cys Trp Ala Leu Ser Gly Gly Leu Cys
1               5

<210> SEQ ID NO 90
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 90

Cys Gly Gly Leu Val Ala Tyr Gly Cys
1               5

<210> SEQ ID NO 91
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 91

Cys Gly Gly Leu Ala Thr Thr Thr Cys
1               5

<210> SEQ ID NO 92
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 92

Cys Gly Arg Val Asn Ser Val Ala Cys
1               5

<210> SEQ ID NO 93
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 93

Cys Ala Gly Arg Val Ala Leu Arg Cys
1               5

<210> SEQ ID NO 94
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 94

Cys Trp Asn Gly Gly Ala Arg Ala Cys
1               5

<210> SEQ ID NO 95
<211> LENGTH: 9
<212> TYPE: PRT
<213> ORGANISM: Artificial Sequence
<220> FEATURE:
<223> OTHER INFORMATION: Synthetic Peptide
```

```
<400> SEQUENCE: 95

Cys Leu Asp Arg Gly Gly Ala His Cys
1               5

<210> SEQ ID NO 96
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 96

Cys Glu Leu Arg Gly Val Val Val Cys
1               5

<210> SEQ ID NO 97
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 97

Cys Ile Gly Gly Val His Tyr Ala Cys
1               5

<210> SEQ ID NO 98
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 98

Cys Gly Gly Val His Ala Leu Arg Cys
1               5

<210> SEQ ID NO 99
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 99

Cys Ile Arg Glu Gly Met Trp Gly Cys
1               5

<210> SEQ ID NO 100
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 100

Cys Ile Arg Lys Gly Met Trp Gly Cys
1               5

<210> SEQ ID NO 101
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 101
```

```
Cys Glu Ala Leu Arg Leu Arg Ala Cys
1               5

<210> SEQ ID NO 102
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 102

Cys Ala Leu Val Asn Val His Leu Cys
1               5

<210> SEQ ID NO 103
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 103

Cys Ala Leu Val Met Val Gly Ala Cys
1               5

<210> SEQ ID NO 104
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 104

Cys Met Val Ser Gly Val Leu Leu Cys
1               5

<210> SEQ ID NO 105
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 105

Cys Gly Leu Val Ser Gly Pro Trp Cys
1               5

<210> SEQ ID NO 106
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 106

Cys Leu Tyr Asp Val Ser Gly Gly Cys
1               5

<210> SEQ ID NO 107
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 107
```

```
Cys Ser Lys Val Gly Pro Trp Trp Cys
1               5

<210> SEQ ID NO 108
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 108

Cys Gly Leu Val Ser Gly Pro Trp Cys
1               5

<210> SEQ ID NO 109
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 109

Cys Ala His His Ala Leu Met Glu Cys
1               5

<210> SEQ ID NO 110
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 110

Cys Glu Arg Pro Pro Phe Leu Asp Cys
1               5

<210> SEQ ID NO 111
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 111

Gly Gly Leu
1

<210> SEQ ID NO 112
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 112

Leu Gly Gly
1

<210> SEQ ID NO 113
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 113

Val Arg Gly
```

-continued

```
<210> SEQ ID NO 114
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 114

Ala Gly Gly
1

<210> SEQ ID NO 115
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 115

Val Val Gly
1

<210> SEQ ID NO 116
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 116

Val Gly Gly
1

<210> SEQ ID NO 117
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 117

Gly Gly Leu
1

<210> SEQ ID NO 118
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 118

Gly Arg Val
1

<210> SEQ ID NO 119
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 119

Gly Gly Ala
1
```

```
<210> SEQ ID NO 120
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 120

Gly Val Val
1

<210> SEQ ID NO 121
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 121

Gly Gly Val
1

<210> SEQ ID NO 122
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 122

Gly Met Trp Gly
1

<210> SEQ ID NO 123
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 123

Ala Leu Arg
1

<210> SEQ ID NO 124
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 124

Ala Leu Val
1

<210> SEQ ID NO 125
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 125

Gly Gly Val His
1
```

```
<210> SEQ ID NO 126
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 126

Val Ser Gly
1

<210> SEQ ID NO 127
<211> LENGTH: 3
<212> TYPE: PRT
<213> ORGANISM: Artificial Sequence
<220> FEATURE:
<223> OTHER INFORMATION: Synthetic Peptide

<400> SEQUENCE: 127

Gly Pro Trp
1

<210> SEQ ID NO 128
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 128

Cys Val Pro Arg Arg Trp Asp Val Cys
1               5

<210> SEQ ID NO 129
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 129

Cys Gln His Thr Ser Gly Arg Gly Cys
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 130

Cys Arg Ala Arg Gly Trp Leu Leu Cys
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 131

Cys Val Ser Asn Pro Arg Trp Lys Cys
1               5
```

```
<210> SEQ ID NO 132
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 132

Cys Phe Asn Arg Thr Trp Ile Gly Cys
1               5

<210> SEQ ID NO 133
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 133

Cys Ser Arg Gly Pro Ala Trp Gly Cys
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 134

Cys Trp Ser Arg Gly Gln Gly Gly Cys
1               5

<210> SEQ ID NO 135
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 135

Cys His Val Leu Trp Ser Thr Arg Cys
1               5

<210> SEQ ID NO 136
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 136

Cys Leu Gly Leu Leu Met Ala Gly Cys
1               5

<210> SEQ ID NO 137
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 137

Cys Met Ser Ser Pro Gly Val Ala Cys
1               5

<210> SEQ ID NO 138
```

```
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 138

Cys Leu Ala Ser Gly Met Asp Ala Cys
1               5

<210> SEQ ID NO 139
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 139

Cys His Asp Glu Arg Thr Gly Arg Cys
1               5

<210> SEQ ID NO 140
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 140

Cys Ala His His Ala Leu Met Glu Cys
1               5

<210> SEQ ID NO 141
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 141

Cys Met Gln Gly Ala Ala Thr Ser Cys
1               5

<210> SEQ ID NO 142
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 142

Cys Met Gln Gly Ala Arg Thr Ser Cys
1               5

<210> SEQ ID NO 143
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 143

Cys Val Arg Asp Leu Leu Thr Gly Cys
1               5

<210> SEQ ID NO 144
<211> LENGTH: 9
```

```
<212> TYPE: PRT
<213> ORGANISM: Artificial Sequence
<220> FEATURE:
<223> OTHER INFORMATION: Synthetic Peptide

<400> SEQUENCE: 144

Cys Thr Pro Lys Thr Ser Val Thr Cys
1               5
```